(12) United States Patent
Schreck et al.

(10) Patent No.: US 12,121,461 B2
(45) Date of Patent: Oct. 22, 2024

(54) HEART VALVE PROSTHESIS DELIVERY SYSTEM AND METHOD FOR DELIVERY OF HEART VALVE PROSTHESIS WITH INTRODUCER SHEATH

(71) Applicant: JenaValve Technology, Inc., Irvine, CA (US)

(72) Inventors: Stefan Schreck, San Clemente, CA (US); Teodoro S. Jimenez, Jr., Aliso Viejo, CA (US); Eileen Charlton, Garden Grove, CA (US); William Gould, Santa Fe, NM (US)

(73) Assignee: JenaValve Technology, Inc., Irvine, CA (US)

( * ) Notice: Subject to any disclaimer, the term of this patent is extended or adjusted under 35 U.S.C. 154(b) by 379 days.

(21) Appl. No.: 15/559,498

(22) PCT Filed: Mar. 17, 2016

(86) PCT No.: PCT/EP2016/055783
§ 371 (c)(1),
(2) Date: Sep. 19, 2017

(87) PCT Pub. No.: WO2016/150806
PCT Pub. Date: Sep. 29, 2016

(65) Prior Publication Data
US 2018/0116843 A1    May 3, 2018

Related U.S. Application Data

(60) Provisional application No. 62/136,092, filed on Mar. 20, 2015.

(51) Int. Cl.
*A61F 2/966* (2013.01)
*A61F 2/07* (2013.01)
(Continued)

(52) U.S. Cl.
CPC ............... *A61F 2/966* (2013.01); *A61F 2/07* (2013.01); *A61F 2/2418* (2013.01);
(Continued)

(58) Field of Classification Search
CPC ...... A61F 2/966; A61F 2/2427; A61F 2/2436; A61F 2002/9505
See application file for complete search history.

(56) References Cited

U.S. PATENT DOCUMENTS

| 15,192 A | 6/1856 | Peale |
|---|---|---|
| 388,776 A | 8/1888 | Hall |

(Continued)

FOREIGN PATENT DOCUMENTS

| AU | 757647 B2 | 2/2003 |
|---|---|---|
| AU | 776895 B2 | 9/2004 |

(Continued)

OTHER PUBLICATIONS

US 6,331,185 B1, 12/2001, Gambale et al. (withdrawn)
(Continued)

*Primary Examiner* — Sarah A Long
(74) *Attorney, Agent, or Firm* — Greenberg Traurig, LLP; Christopher C. Bolten; Robert D. Ward

(57) ABSTRACT

The present disclosure relates to a delivery system, a catheter system and a method for the minimally invasive application of prostheses to an individual in need thereof and a method for loading a prosthesis onto a catheter system and/or a delivery system.

21 Claims, 24 Drawing Sheets

(51) Int. Cl.
   *A61F 2/24* (2006.01)
   *A61F 2/86* (2013.01)
   *A61F 2/95* (2013.01)
   *A61F 2/958* (2013.01)
   *A61M 25/01* (2006.01)
   *A61M 25/06* (2006.01)

(52) U.S. Cl.
   CPC .......... *A61F 2/2427* (2013.01); *A61F 2/2433* (2013.01); *A61F 2/2436* (2013.01); *A61F 2/86* (2013.01); *A61F 2002/9505* (2013.01); *A61F 2/9517* (2020.05); *A61F 2/9522* (2020.05); *A61F 2002/9583* (2013.01); *A61F 2250/0006* (2013.01); *A61M 25/0136* (2013.01); *A61M 2025/0681* (2013.01)

(56) References Cited

U.S. PATENT DOCUMENTS

| | | |
|---|---|---|
| 944,214 A | 12/1909 | Rydquist |
| 2,121,182 A | 6/1938 | Benjamin |
| 2,669,896 A | 2/1954 | Clough |
| 2,682,057 A | 6/1954 | Lord |
| 2,701,559 A | 2/1955 | Cooper |
| 2,832,078 A | 4/1958 | Williams |
| 3,029,819 A | 4/1962 | Starks et al. |
| 3,099,016 A | 7/1963 | Edwards et al. |
| 3,113,586 A | 12/1963 | Edmark, Jr. et al. |
| 3,130,418 A | 4/1964 | Head et al. |
| 3,143,742 A | 8/1964 | Cromie |
| 3,210,836 A | 10/1965 | Johanson et al. |
| 3,221,006 A | 11/1965 | Moore et al. |
| 3,334,629 A | 8/1967 | Cohn |
| 3,365,728 A | 1/1968 | Edwards et al. |
| 3,367,364 A | 2/1968 | Cruz, Jr. et al. |
| 3,409,013 A | 11/1968 | Berry et al. |
| 3,445,916 A | 5/1969 | Schulte et al. |
| 3,540,431 A | 11/1970 | Mobin-Uddin et al. |
| 3,548,417 A | 12/1970 | Kischer et al. |
| 3,570,014 A | 3/1971 | Hancock et al. |
| 3,574,865 A | 4/1971 | Hamaker |
| 3,587,115 A | 6/1971 | Shiley et al. |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,078,268 A | 3/1978 | Possis |
| 4,084,268 A | 4/1978 | Ionescu et al. |
| 4,106,126 A | 8/1978 | Traenkle |
| 4,106,129 A | 8/1978 | Carpentier et al. |
| 4,118,806 A | 10/1978 | Porier et al. |
| 4,164,046 A | 8/1979 | Cooley |
| 4,182,446 A | 1/1980 | Penny |
| 4,191,218 A | 3/1980 | Clark et al. |
| 4,214,587 A | 7/1980 | Sakura, Jr. |
| 4,215,871 A | 8/1980 | Hirsch et al. |
| 4,222,126 A | 9/1980 | Boretos et al. |
| 4,233,690 A | 11/1980 | Akins |
| 4,261,342 A | 4/1981 | Aranguren Duo |
| 4,263,680 A | 4/1981 | Reul et al. |
| 4,265,694 A | 5/1981 | Boretos et al. |
| 4,291,420 A | 9/1981 | Reul |
| 4,297,749 A | 11/1981 | Davis et al. |
| 4,319,831 A | 3/1982 | Matsui et al. |
| RE30,912 E | 4/1982 | Hancock |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,350,492 A | 9/1982 | Wright et al. |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Simon |
| 4,441,215 A | 4/1984 | Kaster |
| 4,441,216 A | 4/1984 | Ionescu et al. |
| 4,470,157 A | 9/1984 | Love |
| 4,484,579 A | 11/1984 | Meno et al. |
| 4,485,816 A | 12/1984 | Krumme |
| 4,491,986 A | 1/1985 | Gabbay |
| 4,501,030 A | 2/1985 | Lane |
| 4,502,488 A | 3/1985 | Degironimo et al. |
| 4,531,943 A | 7/1985 | Van Tassel et al. |
| 4,535,483 A | 8/1985 | Klawitter et al. |
| 4,546,499 A | 10/1985 | Possis et al. |
| 4,562,597 A | 1/1986 | Possis et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,619,246 A | 10/1986 | Molgaard-Nielsen et al. |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,665,918 A | 5/1987 | Garza et al. |
| 4,680,031 A | 7/1987 | Alonso |
| 4,681,908 A | 7/1987 | Broderick et al. |
| 4,687,483 A | 8/1987 | Fisher et al. |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,769,029 A | 9/1988 | Patel |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,806,595 A | 2/1989 | Noishiki et al. |
| 4,819,751 A | 4/1989 | Shimada et al. |
| 4,829,990 A | 5/1989 | Thuroff et al. |
| 4,834,755 A | 5/1989 | Silvestrini et al. |
| 4,846,830 A | 7/1989 | Knoch et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,950,227 A | 8/1990 | Savin et al. |
| 4,953,553 A | 9/1990 | Tremulis |
| 4,954,126 A | 9/1990 | Wallsten |
| 4,966,604 A | 10/1990 | Reiss |

(56) References Cited

U.S. PATENT DOCUMENTS

| | | |
|---|---|---|
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,002,566 A | 3/1991 | Carpentier et al. |
| 5,007,896 A | 4/1991 | Shiber |
| 5,026,366 A | 6/1991 | Leckrone |
| 5,026,377 A | 6/1991 | Burton et al. |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,053,008 A | 10/1991 | Bajaj |
| 5,059,177 A | 10/1991 | Towne et al. |
| 5,061,273 A | 10/1991 | Yock |
| 5,061,277 A | 10/1991 | Carpentier et al. |
| 5,064,435 A | 11/1991 | Porter |
| 5,078,720 A | 1/1992 | Burton et al. |
| 5,080,668 A | 1/1992 | Bolz et al. |
| 5,085,635 A | 2/1992 | Cragg |
| 5,089,015 A | 2/1992 | Ross |
| 5,094,661 A | 3/1992 | Levy et al. |
| 5,104,399 A | 4/1992 | Lazarus |
| 5,104,407 A | 4/1992 | Lam et al. |
| 5,108,425 A | 4/1992 | Hwang |
| 5,122,154 A | 6/1992 | Rhodes |
| 5,132,473 A | 7/1992 | Furutaka et al. |
| 5,141,494 A | 8/1992 | Danforth et al. |
| 5,143,987 A | 9/1992 | Hansel et al. |
| 5,147,388 A | 9/1992 | Yamazaki |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,178,632 A | 1/1993 | Hanson |
| 5,192,301 A | 3/1993 | Kamiya et al. |
| 5,193,546 A | 3/1993 | Shaknovich |
| 5,197,979 A | 3/1993 | Quintero et al. |
| 5,201,757 A | 4/1993 | Heyn et al. |
| 5,207,695 A | 5/1993 | Trout, III |
| 5,209,741 A | 5/1993 | Spaeth |
| 5,211,183 A | 5/1993 | Wilson |
| 5,215,541 A | 6/1993 | Nashef et al. |
| 5,217,481 A | 6/1993 | Barbara |
| 5,217,483 A | 6/1993 | Tower |
| 5,232,445 A | 8/1993 | Bonzel |
| 5,234,447 A | 8/1993 | Kaster et al. |
| 5,234,456 A | 8/1993 | Silvestrini |
| 5,238,004 A | 8/1993 | Sahatjian et al. |
| 5,258,008 A | 11/1993 | Wilk |
| 5,258,023 A | 11/1993 | Reger |
| 5,258,042 A | 11/1993 | Mehta |
| 5,272,909 A | 12/1993 | Nguyen et al. |
| 5,275,580 A | 1/1994 | Yamazaki |
| 5,279,612 A | 1/1994 | Eberhardt |
| 5,282,847 A | 2/1994 | Trescony et al. |
| 5,287,861 A | 2/1994 | Wilk |
| 5,295,958 A | 3/1994 | Shturman |
| 5,327,774 A | 7/1994 | Nguyen et al. |
| 5,330,486 A | 7/1994 | Wilk |
| 5,330,500 A | 7/1994 | Song |
| 5,332,402 A | 7/1994 | Teitelbaum |
| 5,336,258 A | 8/1994 | Quintero et al. |
| 5,342,348 A | 8/1994 | Kaplan |
| 5,344,426 A | 9/1994 | Lau et al. |
| 5,344,427 A | 9/1994 | Cottenceau et al. |
| 5,344,442 A | 9/1994 | Deac |
| 5,350,398 A | 9/1994 | Pavcnik et al. |
| 5,350,399 A | 9/1994 | Erlebacher et al. |
| 5,352,240 A | 10/1994 | Ross |
| 5,354,330 A | 10/1994 | Hanson et al. |
| 5,360,444 A | 11/1994 | Kusuhara |
| 5,368,608 A | 11/1994 | Levy et al. |
| 5,370,685 A | 12/1994 | Stevens |
| 5,380,054 A | 1/1995 | Galvis |
| 5,387,235 A | 2/1995 | Chuter |
| 5,389,096 A | 2/1995 | Aita et al. |
| 5,389,106 A | 2/1995 | Tower |
| 5,397,351 A | 3/1995 | Pavcnik et al. |
| 5,397,355 A | 3/1995 | Marin et al. |
| 5,409,019 A | 4/1995 | Wilk |
| 5,411,552 A | 5/1995 | Andersen et al. |
| 5,415,633 A | 5/1995 | Lazarus et al. |
| 5,425,739 A | 6/1995 | Jessen |
| 5,425,762 A | 6/1995 | Muller |
| 5,429,144 A | 7/1995 | Wilk |
| 5,431,676 A | 7/1995 | Dubrul et al. |
| 5,433,723 A | 7/1995 | Lindenberg et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,449,384 A | 9/1995 | Johnson |
| 5,456,712 A | 10/1995 | Maginot |
| 5,456,713 A | 10/1995 | Chuter |
| 5,464,449 A | 11/1995 | Ryan et al. |
| 5,469,868 A | 11/1995 | Reger |
| 5,470,320 A | 11/1995 | Tiefenbrun et al. |
| 5,476,506 A | 12/1995 | Lunn |
| 5,476,508 A | 12/1995 | Amstrup |
| 5,476,510 A | 12/1995 | Eberhardt et al. |
| 5,480,423 A | 1/1996 | Ravenscroft et al. |
| 5,480,424 A | 1/1996 | Cox |
| 5,486,193 A | 1/1996 | Bourne et al. |
| 5,487,760 A | 1/1996 | Villafana |
| 5,489,294 A | 2/1996 | McVenes et al. |
| 5,489,297 A | 2/1996 | Duran |
| 5,489,298 A | 2/1996 | Love et al. |
| 5,496,346 A | 3/1996 | Horzewski et al. |
| 5,499,995 A | 3/1996 | Teirstein |
| 5,500,014 A | 3/1996 | Quijano et al. |
| 5,500,015 A | 3/1996 | Deac |
| 5,507,767 A | 4/1996 | Maeda et al. |
| 5,509,930 A | 4/1996 | Love |
| 5,522,881 A | 6/1996 | Lentz |
| 5,527,337 A | 6/1996 | Stack et al. |
| 5,530,949 A | 6/1996 | Koda et al. |
| 5,534,007 A | 7/1996 | St. Germain et al. |
| 5,540,712 A | 7/1996 | Kleshinski et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,549,666 A | 8/1996 | Hata et al. |
| 5,554,119 A | 9/1996 | Harrison et al. |
| 5,554,185 A | 9/1996 | Block et al. |
| 5,569,274 A | 10/1996 | Rapacki et al. |
| 5,571,167 A | 11/1996 | Maginot |
| 5,571,174 A | 11/1996 | Love et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,580,922 A | 12/1996 | Park et al. |
| 5,591,185 A | 1/1997 | Kilmer et al. |
| 5,591,195 A | 1/1997 | Taheri et al. |
| 5,593,434 A | 1/1997 | Williams |
| 5,595,571 A | 1/1997 | Jaffe et al. |
| 5,596,471 A | 1/1997 | Hanlin |
| 5,607,464 A | 3/1997 | Trescony et al. |
| 5,607,465 A | 3/1997 | Camilli |
| 5,609,626 A | 3/1997 | Quijano et al. |
| 5,613,982 A | 3/1997 | Goldstein |
| 5,618,299 A | 4/1997 | Khosravi et al. |
| 5,626,553 A | 5/1997 | Frassica et al. |
| 5,628,784 A | 5/1997 | Strecker |
| 5,632,778 A | 5/1997 | Goldstein |
| 5,634,942 A | 6/1997 | Chevillon et al. |

(56) References Cited

U.S. PATENT DOCUMENTS

| | | |
|---|---|---|
| 5,643,278 A | 7/1997 | Wijay |
| 5,645,559 A | 7/1997 | Hachtman et al. |
| 5,653,684 A | 8/1997 | Laptewicz et al. |
| 5,653,745 A | 8/1997 | Trescony et al. |
| 5,653,749 A | 8/1997 | Love et al. |
| 5,655,548 A | 8/1997 | Nelson et al. |
| 5,662,124 A | 9/1997 | Wilk |
| 5,662,671 A | 9/1997 | Barbut et al. |
| 5,662,703 A | 9/1997 | Yurek et al. |
| 5,665,115 A | 9/1997 | Cragg |
| 5,667,523 A | 9/1997 | Bynon et al. |
| 5,674,277 A | 10/1997 | Freitag |
| 5,674,298 A | 10/1997 | Levy et al. |
| 5,679,112 A | 10/1997 | Levy et al. |
| 5,681,345 A | 10/1997 | Euteneuer |
| 5,682,906 A | 11/1997 | Sterman et al. |
| 5,683,451 A | 11/1997 | Lenker et al. |
| 5,690,644 A | 11/1997 | Yurek et al. |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,697,972 A | 12/1997 | Kim et al. |
| 5,700,269 A | 12/1997 | Pinchuk et al. |
| 5,702,368 A | 12/1997 | Stevens et al. |
| 5,709,713 A | 1/1998 | Evans et al. |
| 5,713,917 A | 2/1998 | Leonhardt et al. |
| 5,713,950 A | 2/1998 | Cox |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,718,725 A | 2/1998 | Sterman et al. |
| 5,720,391 A | 2/1998 | Dohm et al. |
| 5,720,776 A | 2/1998 | Chuter et al. |
| 5,725,549 A | 3/1998 | Lam |
| 5,725,550 A | 3/1998 | Nadal |
| 5,728,068 A | 3/1998 | Leone et al. |
| 5,728,151 A | 3/1998 | Garrison et al. |
| 5,733,267 A | 3/1998 | Del Toro |
| 5,733,325 A | 3/1998 | Robinson et al. |
| 5,735,842 A | 4/1998 | Krueger et al. |
| 5,746,476 A | 5/1998 | Novak et al. |
| 5,746,709 A | 5/1998 | Rom et al. |
| 5,746,765 A | 5/1998 | Kleshinski et al. |
| 5,746,775 A | 5/1998 | Levy et al. |
| 5,749,890 A | 5/1998 | Shaknovich |
| 5,749,921 A | 5/1998 | Lenker et al. |
| 5,755,682 A | 5/1998 | Knudson et al. |
| 5,755,777 A | 5/1998 | Chuter |
| 5,755,783 A | 5/1998 | Stobie et al. |
| 5,756,476 A | 5/1998 | Epstein et al. |
| 5,758,663 A | 6/1998 | Wilk et al. |
| 5,766,151 A | 6/1998 | Valley et al. |
| 5,769,780 A | 6/1998 | Hata et al. |
| 5,769,812 A | 6/1998 | Stevens et al. |
| 5,769,882 A | 6/1998 | Fogarty et al. |
| 5,769,887 A | 6/1998 | Brown et al. |
| 5,772,609 A | 6/1998 | Nguyen et al. |
| 5,776,188 A | 7/1998 | Shepherd et al. |
| 5,782,809 A | 7/1998 | Umeno et al. |
| 5,782,904 A | 7/1998 | White et al. |
| 5,795,331 A | 8/1998 | Cragg et al. |
| 5,797,946 A | 8/1998 | Chin |
| 5,797,960 A | 8/1998 | Stevens et al. |
| 5,799,661 A | 9/1998 | Boyd et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,327 A | 9/1998 | Green et al. |
| 5,807,384 A | 9/1998 | Mueller |
| 5,807,405 A | 9/1998 | Vanney et al. |
| 5,810,836 A | 9/1998 | Hussein et al. |
| 5,814,016 A | 9/1998 | Valley et al. |
| 5,817,113 A | 10/1998 | Gifford, III et al. |
| 5,817,126 A | 10/1998 | Imran |
| 5,823,956 A | 10/1998 | Roth et al. |
| 5,824,037 A | 10/1998 | Fogarty et al. |
| 5,824,038 A | 10/1998 | Wall |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,063 A | 10/1998 | Cox |
| 5,824,064 A | 10/1998 | Taheri |
| 5,824,071 A | 10/1998 | Nelson et al. |
| 5,824,080 A | 10/1998 | Lamuraglia |
| 5,829,447 A | 11/1998 | Stevens et al. |
| 5,830,222 A | 11/1998 | Makower |
| 5,836,869 A | 11/1998 | Kudo et al. |
| 5,840,081 A | 11/1998 | Andersen et al. |
| 5,841,382 A | 11/1998 | Walden et al. |
| 5,843,158 A | 12/1998 | Lenker et al. |
| 5,843,161 A | 12/1998 | Solovay |
| 5,843,181 A | 12/1998 | Jaffe et al. |
| 5,851,232 A | 12/1998 | Lois |
| 5,853,419 A | 12/1998 | Imran |
| 5,853,420 A | 12/1998 | Chevillon et al. |
| 5,855,210 A | 1/1999 | Sterman et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,865,723 A | 2/1999 | Love |
| 5,868,783 A | 2/1999 | Tower |
| 5,873,812 A | 2/1999 | Ciana et al. |
| 5,873,906 A | 2/1999 | Lau et al. |
| 5,876,373 A | 3/1999 | Giba et al. |
| 5,876,419 A | 3/1999 | Carpenter et al. |
| 5,876,434 A | 3/1999 | Flomenblit et al. |
| 5,876,448 A | 3/1999 | Thompson et al. |
| 5,878,751 A | 3/1999 | Hussein et al. |
| 5,880,242 A | 3/1999 | Hu et al. |
| 5,885,228 A | 3/1999 | Rosenman et al. |
| 5,885,238 A | 3/1999 | Stevens et al. |
| 5,885,259 A | 3/1999 | Berg |
| 5,888,201 A | 3/1999 | Stinson et al. |
| 5,891,160 A | 4/1999 | Williamson, IV et al. |
| 5,891,191 A | 4/1999 | Stinson |
| 5,895,399 A | 4/1999 | Barbut et al. |
| 5,895,420 A | 4/1999 | Mirsch, II et al. |
| 5,899,936 A | 5/1999 | Goldstein |
| 5,906,619 A | 5/1999 | Olson et al. |
| 5,907,893 A | 6/1999 | Zadno-Azizi et al. |
| 5,908,028 A | 6/1999 | Wilk |
| 5,908,029 A | 6/1999 | Knudson et al. |
| 5,908,451 A | 6/1999 | Yeo |
| 5,908,452 A | 6/1999 | Bokros et al. |
| 5,910,144 A | 6/1999 | Hayashi |
| 5,910,154 A | 6/1999 | Tsugita et al. |
| 5,911,734 A | 6/1999 | Tsugita et al. |
| 5,911,752 A | 6/1999 | Dustrude et al. |
| 5,913,842 A | 6/1999 | Boyd et al. |
| 5,916,193 A | 6/1999 | Stevens et al. |
| 5,922,022 A | 7/1999 | Nash et al. |
| 5,924,424 A | 7/1999 | Stevens et al. |
| 5,925,012 A | 7/1999 | Murphy-Chutorian et al. |
| 5,925,063 A | 7/1999 | Khosravi |
| 5,928,281 A | 7/1999 | Huynh et al. |
| 5,931,848 A | 8/1999 | Saadat |
| 5,935,119 A | 8/1999 | Guy et al. |
| 5,935,161 A | 8/1999 | Robinson et al. |
| 5,935,163 A | 8/1999 | Gabbay |
| 5,938,632 A | 8/1999 | Ellis |
| 5,938,697 A | 8/1999 | Killion et al. |
| 5,941,908 A | 8/1999 | Goldsteen et al. |
| 5,944,019 A | 8/1999 | Knudson et al. |
| 5,944,738 A | 8/1999 | Amplatz et al. |

(56) References Cited

U.S. PATENT DOCUMENTS

| | | | |
|---|---|---|---|
| 5,104,407 B1 | 9/1999 | Lam et al. |
| 5,948,017 A | 9/1999 | Taheri |
| 5,954,764 A | 9/1999 | Parodi |
| 5,954,766 A | 9/1999 | Zadno-Azizi et al. |
| 5,957,949 A | 9/1999 | Leonhardt et al. |
| 5,961,549 A | 10/1999 | Nguyen et al. |
| 5,964,405 A | 10/1999 | Benary et al. |
| 5,964,798 A | 10/1999 | Imran |
| 5,968,064 A | 10/1999 | Selmon et al. |
| 5,968,068 A | 10/1999 | Dehdashtian et al. |
| 5,968,070 A | 10/1999 | Bley et al. |
| 5,971,993 A | 10/1999 | Hussein et al. |
| 5,975,949 A | 11/1999 | Holliday et al. |
| 5,976,153 A | 11/1999 | Fischell et al. |
| 5,976,155 A | 11/1999 | Foreman et al. |
| 5,976,174 A | 11/1999 | Ruiz |
| 5,976,178 A | 11/1999 | Goldsteen et al. |
| 5,976,192 A | 11/1999 | McIntyre et al. |
| 5,976,650 A | 11/1999 | Campbell et al. |
| 5,979,455 A | 11/1999 | Maginot |
| 5,980,455 A | 11/1999 | Daniel et al. |
| 5,980,533 A | 11/1999 | Holman |
| 5,980,548 A | 11/1999 | Evans et al. |
| 5,984,956 A | 11/1999 | Tweden et al. |
| 5,984,957 A | 11/1999 | Laptewicz, Jr. et al. |
| 5,984,959 A | 11/1999 | Robertson et al. |
| 5,984,964 A | 11/1999 | Roberts et al. |
| 5,987,344 A | 11/1999 | West |
| 5,989,276 A | 11/1999 | Houser et al. |
| 5,989,287 A | 11/1999 | Yang et al. |
| 5,993,469 A | 11/1999 | McKenzie et al. |
| 5,993,481 A | 11/1999 | Marcade et al. |
| 5,997,525 A | 12/1999 | March et al. |
| 5,997,557 A | 12/1999 | Barbut et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,001,126 A | 12/1999 | Nguyen-Thien-Nhon |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,010,449 A | 1/2000 | Selmon et al. |
| 6,010,522 A | 1/2000 | Barbut et al. |
| 6,010,530 A | 1/2000 | Goicoechea |
| 6,010,531 A | 1/2000 | Donlon et al. |
| 6,012,457 A | 1/2000 | Lesh |
| 6,013,854 A | 1/2000 | Moriuchi |
| 6,015,431 A | 1/2000 | Thornton et al. |
| 5,061,277 B1 | 2/2000 | Carpentier et al. |
| 6,019,777 A | 2/2000 | Mackenzie |
| 6,019,778 A | 2/2000 | Wilson et al. |
| 6,022,370 A | 2/2000 | Tower |
| 6,026,814 A | 2/2000 | LaFontaine et al. |
| 6,027,476 A | 2/2000 | Sterman et al. |
| 6,027,520 A | 2/2000 | Tsugita et al. |
| 6,027,525 A | 2/2000 | Suh et al. |
| 6,029,671 A | 2/2000 | Stevens et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,042,554 A | 3/2000 | Rosenman et al. |
| 6,042,581 A | 3/2000 | Ryan et al. |
| 6,042,589 A | 3/2000 | Marianne |
| 6,042,598 A | 3/2000 | Tsugita et al. |
| 6,042,607 A | 3/2000 | Williamson, IV et al. |
| 6,045,565 A | 4/2000 | Ellis et al. |
| 6,051,014 A | 4/2000 | Jang |
| 6,051,104 A | 4/2000 | Oriaran et al. |
| 6,053,924 A | 4/2000 | Hussein |
| 6,053,942 A | 4/2000 | Eno et al. |
| 6,056,743 A | 5/2000 | Ellis et al. |
| 6,059,809 A | 5/2000 | Amor et al. |
| 6,059,827 A | 5/2000 | Fenton, Jr. |
| 6,066,160 A | 5/2000 | Colvin et al. |
| 6,067,988 A | 5/2000 | Mueller |
| 6,068,638 A | 5/2000 | Makower |
| 6,071,292 A | 6/2000 | Makower et al. |
| 6,074,416 A | 6/2000 | Berg et al. |
| 6,074,417 A | 6/2000 | Peredo |
| 6,074,418 A | 6/2000 | Buchanan et al. |
| 6,076,529 A | 6/2000 | Vanney et al. |
| 6,076,742 A | 6/2000 | Benary |
| 6,077,297 A | 6/2000 | Robinson et al. |
| 6,079,414 A | 6/2000 | Roth |
| 6,080,163 A | 6/2000 | Hussein et al. |
| 6,080,170 A | 6/2000 | Nash et al. |
| 6,083,257 A | 7/2000 | Taylor et al. |
| 6,091,042 A | 7/2000 | Benary |
| 6,092,526 A | 7/2000 | LaFontaine et al. |
| 6,092,529 A | 7/2000 | Cox |
| 6,093,166 A | 7/2000 | Knudson et al. |
| 6,093,177 A | 7/2000 | Javier, Jr. et al. |
| 6,093,185 A | 7/2000 | Ellis et al. |
| 6,093,203 A | 7/2000 | Uflacker |
| 6,093,530 A | 7/2000 | McIlroy et al. |
| 6,096,074 A | 8/2000 | Pedros |
| 6,102,941 A | 8/2000 | Tweden et al. |
| 6,102,944 A | 8/2000 | Huynh et al. |
| 6,106,550 A | 8/2000 | Magovern et al. |
| 6,110,191 A | 8/2000 | Dehdashtian et al. |
| 6,110,198 A | 8/2000 | Fogarty et al. |
| 6,110,201 A | 8/2000 | Quijano et al. |
| 6,113,612 A | 9/2000 | Swanson et al. |
| 6,113,630 A | 9/2000 | Vanney et al. |
| 6,113,823 A | 9/2000 | Eno |
| 6,117,169 A | 9/2000 | Moe |
| 6,120,520 A | 9/2000 | Saadat et al. |
| 6,120,534 A | 9/2000 | Ruiz |
| 6,123,682 A | 9/2000 | Knudson et al. |
| 6,123,723 A | 9/2000 | Konya et al. |
| 6,125,852 A | 10/2000 | Stevens et al. |
| 6,126,649 A | 10/2000 | Vantassel et al. |
| 6,126,654 A | 10/2000 | Giba et al. |
| 6,126,685 A | 10/2000 | Lenker et al. |
| 6,126,686 A | 10/2000 | Badylak et al. |
| 6,132,451 A | 10/2000 | Payne et al. |
| 6,132,473 A | 10/2000 | Williams et al. |
| 6,132,986 A | 10/2000 | Pathak et al. |
| 6,139,510 A | 10/2000 | Palermo |
| 6,139,541 A | 10/2000 | Vanney et al. |
| 6,142,987 A | 11/2000 | Tsugita |
| 6,143,021 A | 11/2000 | Staehle |
| 6,143,987 A | 11/2000 | Makita |
| 6,146,366 A | 11/2000 | Schachar |
| 6,146,415 A | 11/2000 | Fitz |
| 6,146,417 A | 11/2000 | Ischinger |
| 6,152,937 A | 11/2000 | Peterson et al. |
| 6,152,956 A | 11/2000 | Pierce |
| 6,155,264 A | 12/2000 | Ressemann et al. |
| 6,156,031 A | 12/2000 | Aita et al. |
| 6,156,055 A | 12/2000 | Ravenscroft |
| 6,156,531 A | 12/2000 | Pathak et al. |
| 6,157,852 A | 12/2000 | Selmon et al. |
| 6,159,225 A | 12/2000 | Makower |
| 6,159,239 A | 12/2000 | Greenhalgh |
| 6,162,208 A | 12/2000 | Hipps |
| 6,162,245 A | 12/2000 | Jayaraman |
| 6,165,185 A | 12/2000 | Shennib et al. |
| 6,165,188 A | 12/2000 | Saadat et al. |
| 6,165,200 A | 12/2000 | Tsugita et al. |
| 6,165,209 A | 12/2000 | Patterson et al. |
| 6,167,605 B1 | 1/2001 | Morales |
| 6,168,579 B1 | 1/2001 | Tsugita |
| 6,168,614 B1 | 1/2001 | Andersen et al. |
| 6,168,616 B1 | 1/2001 | Brown, III |
| 6,171,251 B1 | 1/2001 | Mueller et al. |
| 6,171,327 B1 | 1/2001 | Daniel et al. |
| 6,171,335 B1 | 1/2001 | Wheatley et al. |
| 6,177,514 B1 | 1/2001 | Pathak et al. |
| 6,179,859 B1 | 1/2001 | Bates et al. |

(56) References Cited

U.S. PATENT DOCUMENTS

| | | |
|---|---|---|
| 6,182,664 B1 | 2/2001 | Cosgrove |
| 6,182,668 B1 | 2/2001 | Tweden et al. |
| 6,183,481 B1 | 2/2001 | Lee et al. |
| 6,186,972 B1 | 2/2001 | Nelson et al. |
| 6,187,016 B1 | 2/2001 | Hedges et al. |
| 6,190,353 B1 | 2/2001 | Makower et al. |
| 6,190,393 B1 | 2/2001 | Bevier et al. |
| 6,190,405 B1 | 2/2001 | Culombo et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,053 B1 | 3/2001 | Cosgrove et al. |
| 6,197,296 B1 | 3/2001 | Davies et al. |
| 6,197,324 B1 | 3/2001 | Crittenden |
| 6,200,311 B1 | 3/2001 | Danek et al. |
| 6,200,336 B1 | 3/2001 | Pavcnik et al. |
| 6,203,550 B1 | 3/2001 | Olson |
| 6,203,556 B1 | 3/2001 | Evans et al. |
| 6,206,888 B1 | 3/2001 | Bicek et al. |
| 6,206,911 B1 | 3/2001 | Milo |
| 6,210,408 B1 | 4/2001 | Chandrasekaran et al. |
| 6,210,957 B1 | 4/2001 | Carpentier et al. |
| 6,213,126 B1 | 4/2001 | LaFontaine et al. |
| 6,214,036 B1 | 4/2001 | Letendre et al. |
| 6,214,041 B1 | 4/2001 | Tweden et al. |
| 6,214,054 B1 | 4/2001 | Cunanan et al. |
| 6,214,055 B1 | 4/2001 | Simionescu et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,217,609 B1 | 4/2001 | Haverkost |
| 6,218,662 B1 | 4/2001 | Tchakarov et al. |
| 6,221,006 B1 | 4/2001 | Dubrul et al. |
| 6,221,049 B1 | 4/2001 | Selmon et al. |
| 6,221,091 B1 | 4/2001 | Khosravi |
| 6,221,096 B1 | 4/2001 | Aiba et al. |
| 6,221,100 B1 | 4/2001 | Strecker |
| 6,223,752 B1 | 5/2001 | Vanney et al. |
| 6,224,584 B1 | 5/2001 | March et al. |
| 6,231,544 B1 | 5/2001 | Tsugita et al. |
| 6,231,546 B1 | 5/2001 | Milo et al. |
| 6,231,551 B1 | 5/2001 | Barbut |
| 6,231,587 B1 | 5/2001 | Makower |
| 6,231,602 B1 | 5/2001 | Carpentier et al. |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,241,738 B1 | 6/2001 | Dereume |
| 6,241,741 B1 | 6/2001 | Duhaylongsod et al. |
| 6,241,757 B1 | 6/2001 | An et al. |
| 6,245,102 B1 | 6/2001 | Jayaraman |
| 6,245,103 B1 | 6/2001 | Stinson |
| 6,245,105 B1 | 6/2001 | Nguyen et al. |
| 6,248,112 B1 | 6/2001 | Gambale et al. |
| 6,248,116 B1 | 6/2001 | Chevillon et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,135 B1 | 6/2001 | Stinson et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,254,635 B1 | 7/2001 | Schroeder et al. |
| 6,254,636 B1 | 7/2001 | Peredo |
| 6,257,634 B1 | 7/2001 | Wei |
| 6,258,052 B1 | 7/2001 | Milo |
| 6,258,087 B1 | 7/2001 | Edwards et al. |
| 6,258,114 B1 | 7/2001 | Konya et al. |
| 6,258,115 B1 | 7/2001 | Dubrul |
| 6,258,119 B1 | 7/2001 | Hussein et al. |
| 6,258,120 B1 | 7/2001 | McKenzie et al. |
| 6,258,129 B1 | 7/2001 | Dybdal et al. |
| 6,258,150 B1 | 7/2001 | Mackellar |
| 6,261,304 B1 | 7/2001 | Hall et al. |
| 6,267,783 B1 | 7/2001 | Letendre et al. |
| 6,269,819 B1 | 8/2001 | Oz et al. |
| 6,270,513 B1 | 8/2001 | Tsugita et al. |
| 6,270,521 B1 | 8/2001 | Fischell et al. |
| 6,270,526 B1 | 8/2001 | Cox |
| 6,273,876 B1 | 8/2001 | Klima et al. |
| 6,273,895 B1 | 8/2001 | Pinchuk et al. |
| 6,276,661 B1 | 8/2001 | Laird |
| 6,277,555 B1 | 8/2001 | Duran et al. |
| 6,283,127 B1 | 9/2001 | Sterman et al. |
| 6,283,951 B1 | 9/2001 | Flaherty et al. |
| 6,283,983 B1 | 9/2001 | Makower et al. |
| 6,283,995 B1 | 9/2001 | Moe et al. |
| 6,285,903 B1 | 9/2001 | Rosenthal et al. |
| 6,287,317 B1 | 9/2001 | Makower et al. |
| 6,287,334 B1 | 9/2001 | Moll et al. |
| 6,287,338 B1 | 9/2001 | Sarnowski et al. |
| 6,287,339 B1 | 9/2001 | Vazquez et al. |
| 6,290,709 B1 | 9/2001 | Ellis et al. |
| 6,290,728 B1 | 9/2001 | Phelps et al. |
| 6,296,662 B1 | 10/2001 | Caffey |
| 6,299,637 B1 | 10/2001 | Shaolian et al. |
| 6,302,875 B1 | 10/2001 | Makower et al. |
| 6,302,892 B1 | 10/2001 | Wilk |
| 6,302,906 B1 | 10/2001 | Goicoechea et al. |
| 6,306,164 B1 | 10/2001 | Kujawski |
| 6,309,382 B1 | 10/2001 | Garrison et al. |
| 6,309,417 B1 | 10/2001 | Spence et al. |
| 6,311,693 B1 | 11/2001 | Sterman et al. |
| 6,312,465 B1 | 11/2001 | Griffin et al. |
| 6,319,281 B1 | 11/2001 | Patel |
| 6,322,548 B1 | 11/2001 | Payne et al. |
| 6,322,593 B1 | 11/2001 | Pathak et al. |
| 6,325,067 B1 | 12/2001 | Sterman et al. |
| 6,327,772 B1 | 12/2001 | Zadno-Azizi et al. |
| 6,330,884 B1 | 12/2001 | Kim |
| 6,331,189 B1 | 12/2001 | Wolinsky et al. |
| 6,334,873 B1 | 1/2002 | Lane et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,346,074 B1 | 2/2002 | Roth |
| 6,346,116 B1 | 2/2002 | Brooks et al. |
| 6,348,063 B1 | 2/2002 | Yassour et al. |
| 6,350,248 B1 | 2/2002 | Knudson et al. |
| 6,350,277 B1 | 2/2002 | Kocur |
| 6,350,278 B1 | 2/2002 | Lenker et al. |
| 6,352,547 B1 | 3/2002 | Brown et al. |
| 6,352,554 B2 | 3/2002 | De Paulis |
| 6,352,708 B1 | 3/2002 | Duran et al. |
| 6,357,104 B1 | 3/2002 | Myers |
| 6,358,277 B1 | 3/2002 | Duran |
| 6,361,519 B1 | 3/2002 | Knudson et al. |
| 6,361,545 B1 | 3/2002 | Macoviak et al. |
| 6,363,938 B2 | 4/2002 | Saadat et al. |
| 6,363,939 B1 | 4/2002 | Wilk |
| 6,364,895 B1 | 4/2002 | Greenhalgh |
| 6,368,338 B1 | 4/2002 | Konya et al. |
| 6,371,970 B1 | 4/2002 | Khosravi et al. |
| 6,371,983 B1 | 4/2002 | Lane |
| 6,375,615 B1 | 4/2002 | Flaherty et al. |
| 6,378,221 B1 | 4/2002 | Ekholm, Jr. et al. |
| 6,379,319 B1 | 4/2002 | Garibotto et al. |
| 6,379,365 B1 | 4/2002 | Diaz |
| 6,379,372 B1 | 4/2002 | Dehdashtian et al. |
| 6,379,383 B1 | 4/2002 | Palmaz et al. |
| 6,379,740 B1 | 4/2002 | Rinaldi et al. |
| 6,380,457 B1 | 4/2002 | Yurek et al. |
| 6,383,193 B1 | 5/2002 | Cathcart et al. |
| 6,387,119 B2 | 5/2002 | Wolf et al. |
| 6,387,122 B1 | 5/2002 | Cragg |
| 6,390,098 B1 | 5/2002 | LaFontaine et al. |
| 6,391,051 B2 | 5/2002 | Sullivan, III et al. |

(56) References Cited

U.S. PATENT DOCUMENTS

| | | |
|---|---|---|
| 6,391,538 B1 | 5/2002 | Vyavahare et al. |
| 6,395,208 B1 | 5/2002 | Herweck et al. |
| 6,398,807 B1 | 6/2002 | Chouinard et al. |
| 6,401,720 B1 | 6/2002 | Stevens et al. |
| 6,402,736 B1 | 6/2002 | Brown et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,406,493 B1 | 6/2002 | Tu et al. |
| 6,409,697 B2 | 6/2002 | Eno et al. |
| 6,409,750 B1 | 6/2002 | Hyodoh et al. |
| 6,409,751 B1 | 6/2002 | Hall et al. |
| 6,409,755 B1 | 6/2002 | Vrba |
| 6,409,759 B1 | 6/2002 | Peredo |
| 6,413,275 B1 | 7/2002 | Nguyen et al. |
| 6,416,490 B1 | 7/2002 | Ellis et al. |
| 6,416,510 B1 | 7/2002 | Altman et al. |
| 6,423,089 B1 | 7/2002 | Gingras et al. |
| 6,425,916 B1 | 7/2002 | Garrison et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,440,164 B1 | 8/2002 | DiMatteo et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,451,025 B1 | 9/2002 | Jervis |
| 6,451,054 B1 | 9/2002 | Stevens |
| 6,454,760 B2 | 9/2002 | Vanney |
| 6,454,794 B1 | 9/2002 | Knudson et al. |
| 6,454,799 B1 | 9/2002 | Schreck |
| 6,458,092 B1 | 10/2002 | Gambale et al. |
| 6,458,140 B2 | 10/2002 | Akin et al. |
| 6,458,153 B1 | 10/2002 | Bailey et al. |
| 6,458,323 B1 | 10/2002 | Boekstegers |
| 6,461,382 B1 | 10/2002 | Cao |
| 6,464,709 B2 | 10/2002 | Shennib et al. |
| 6,468,303 B1 | 10/2002 | Amplatz et al. |
| 6,468,660 B2 | 10/2002 | Ogle et al. |
| 6,471,723 B1 | 10/2002 | Ashworth et al. |
| 6,475,169 B2 | 11/2002 | Ferrera |
| 6,475,226 B1 | 11/2002 | Belef et al. |
| 6,475,239 B1 | 11/2002 | Campbell et al. |
| 6,475,244 B2 | 11/2002 | Herweck et al. |
| 6,478,819 B2 | 11/2002 | Moe |
| 6,479,079 B1 | 11/2002 | Pathak et al. |
| 6,482,220 B1 | 11/2002 | Mueller |
| 6,482,228 B1 | 11/2002 | Norred |
| 6,485,501 B1 | 11/2002 | Green |
| 6,485,502 B2 | 11/2002 | Don Michael et al. |
| 6,485,513 B1 | 11/2002 | Fan |
| 6,485,524 B2 | 11/2002 | Strecker |
| 6,487,581 B1 | 11/2002 | Spence et al. |
| 6,488,704 B1 | 12/2002 | Connelly et al. |
| 6,491,689 B1 | 12/2002 | Ellis et al. |
| 6,491,707 B2 | 12/2002 | Makower et al. |
| 6,494,211 B1 | 12/2002 | Boyd et al. |
| 6,494,897 B2 | 12/2002 | Sterman et al. |
| 6,494,909 B2 | 12/2002 | Greenhalgh |
| 6,503,272 B2 | 1/2003 | Duerig et al. |
| 6,508,496 B1 | 1/2003 | Huang |
| 6,508,803 B1 | 1/2003 | Horikawa et al. |
| 6,508,825 B1 | 1/2003 | Selmon et al. |
| 6,508,833 B2 | 1/2003 | Pavcnik et al. |
| 6,509,145 B1 | 1/2003 | Torrianni |
| 6,511,458 B2 | 1/2003 | Milo et al. |
| 6,511,491 B2 | 1/2003 | Grudem et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,517,573 B1 | 2/2003 | Pollock et al. |
| 6,521,179 B1 | 2/2003 | Girardot et al. |
| 6,524,323 B1 | 2/2003 | Nash et al. |
| 6,524,335 B1 | 2/2003 | Hartley et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,533,807 B2 | 3/2003 | Wolinsky et al. |
| 6,537,297 B2 | 3/2003 | Tsugita et al. |
| 6,537,310 B1 | 3/2003 | Palmaz et al. |
| 6,540,768 B1 | 4/2003 | Diaz et al. |
| 6,540,782 B1 | 4/2003 | Snyders |
| 6,544,230 B1 | 4/2003 | Flaherty et al. |
| 6,547,827 B2 | 4/2003 | Carpentier et al. |
| 6,551,303 B1 | 4/2003 | Van Tassel et al. |
| 6,558,318 B1 | 5/2003 | Daniel et al. |
| 6,558,417 B2 | 5/2003 | Peredo |
| 6,558,418 B2 | 5/2003 | Carpentier et al. |
| 6,558,429 B2 | 5/2003 | Taylor |
| 6,559,132 B1 | 5/2003 | Holmer |
| 6,561,998 B1 | 5/2003 | Roth et al. |
| 6,562,031 B2 | 5/2003 | Chandrasekaran et al. |
| 6,562,058 B2 | 5/2003 | Seguin et al. |
| 6,562,063 B1 | 5/2003 | Euteneuer et al. |
| 6,562,069 B2 | 5/2003 | Cai et al. |
| 6,564,805 B2 | 5/2003 | Garrison et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,569,196 B1 | 5/2003 | Vesely |
| 6,572,593 B1 * | 6/2003 | Daum ............... A61B 17/3417 604/164.13 |
| 6,572,642 B2 | 6/2003 | Rinaldi et al. |
| 6,572,643 B1 | 6/2003 | Gharibadeh |
| 6,572,652 B2 | 6/2003 | Shaknovich |
| 6,575,168 B2 | 6/2003 | LaFontaine et al. |
| 6,579,311 B1 | 6/2003 | Makower |
| 6,582,444 B2 | 6/2003 | Wilk |
| 6,582,460 B1 | 6/2003 | Cryer |
| 6,582,462 B1 | 6/2003 | Andersen et al. |
| 6,585,756 B1 | 7/2003 | Strecker |
| 6,585,758 B1 | 7/2003 | Chouinard et al. |
| 6,585,766 B1 | 7/2003 | Huynh et al. |
| 6,589,279 B1 | 7/2003 | Anderson et al. |
| 6,592,546 B1 | 7/2003 | Barbut et al. |
| 6,592,614 B2 | 7/2003 | Lenker et al. |
| 6,599,304 B1 | 7/2003 | Selmon et al. |
| 6,600,803 B2 | 7/2003 | Bruder et al. |
| 6,605,053 B1 | 8/2003 | Kamm et al. |
| 6,605,112 B1 | 8/2003 | Moll et al. |
| 6,605,113 B2 | 8/2003 | Wilk |
| 6,608,040 B1 | 8/2003 | Lin et al. |
| 6,610,077 B1 | 8/2003 | Hancock et al. |
| 6,610,085 B1 | 8/2003 | Lazarus |
| 6,610,100 B2 | 8/2003 | Phelps et al. |
| 6,613,069 B2 | 9/2003 | Boyd et al. |
| 6,613,077 B2 | 9/2003 | Gilligan et al. |
| 6,613,079 B1 | 9/2003 | Wolinsky et al. |
| 6,613,081 B2 | 9/2003 | Kim et al. |
| 6,613,086 B1 | 9/2003 | Moe et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,626,939 B1 | 9/2003 | Burnside et al. |
| 6,632,241 B1 | 10/2003 | Hancock et al. |
| 6,632,243 B1 | 10/2003 | Zadno-Azizi et al. |
| 6,632,470 B2 | 10/2003 | Morra et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,635,085 B1 | 10/2003 | Caffey et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,651,672 B2 | 11/2003 | Roth |

(56) References Cited

U.S. PATENT DOCUMENTS

| | | |
|---|---|---|
| 6,652,540 B1 | 11/2003 | Cole et al. |
| 6,652,546 B1 | 11/2003 | Nash et al. |
| 6,652,555 B1 | 11/2003 | Vantassel et al. |
| 6,652,571 B1 | 11/2003 | White et al. |
| 6,652,578 B2 | 11/2003 | Bailey et al. |
| 6,655,386 B1 | 12/2003 | Makower et al. |
| 6,656,213 B2 | 12/2003 | Solem |
| 6,660,003 B1 | 12/2003 | DeVore et al. |
| 6,660,024 B1 | 12/2003 | Flaherty et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,666,863 B2 | 12/2003 | Wentzel et al. |
| 6,669,709 B1 | 12/2003 | Cohn et al. |
| 6,669,724 B2 | 12/2003 | Park et al. |
| 6,673,089 B1 | 1/2004 | Yassour et al. |
| 6,673,101 B1 | 1/2004 | Fitzgerald et al. |
| 6,673,106 B2 | 1/2004 | Mitelberg et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,693 B1 | 1/2004 | Belding et al. |
| 6,676,698 B2 | 1/2004 | McGuckin, Jr. et al. |
| 6,679,268 B2 | 1/2004 | Stevens et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,648 B2 | 2/2004 | Flaherty et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,694,983 B2 | 2/2004 | Wolf et al. |
| 6,695,864 B2 | 2/2004 | Macoviak et al. |
| 6,695,865 B2 | 2/2004 | Boyle et al. |
| 6,695,875 B2 | 2/2004 | Stelter et al. |
| 6,695,878 B2 | 2/2004 | McGuckin, Jr. et al. |
| 6,699,274 B2 | 3/2004 | Stinson |
| 6,701,932 B2 | 3/2004 | Knudson et al. |
| 6,702,851 B1 | 3/2004 | Chinn et al. |
| 6,709,425 B2 | 3/2004 | Gambale et al. |
| 6,709,444 B1 | 3/2004 | Makower |
| 6,712,842 B1 | 3/2004 | Gifford, III et al. |
| 6,712,843 B2 | 3/2004 | Elliott |
| 6,714,841 B1 | 3/2004 | Wright et al. |
| 6,714,842 B1 | 3/2004 | Ito |
| 6,719,770 B2 | 4/2004 | Laufer et al. |
| 6,719,787 B2 | 4/2004 | Cox |
| 6,719,788 B2 | 4/2004 | Cox |
| 6,719,789 B2 | 4/2004 | Cox |
| 6,723,116 B2 | 4/2004 | Taheri |
| 6,723,122 B2 | 4/2004 | Yang et al. |
| 6,726,677 B1 | 4/2004 | Flaherty et al. |
| 6,729,356 B1 | 5/2004 | Baker et al. |
| 6,730,118 B2 | 5/2004 | Spenser et al. |
| 6,730,121 B2 | 5/2004 | Ortiz et al. |
| 6,730,377 B2 | 5/2004 | Wang |
| 6,733,513 B2 | 5/2004 | Boyle et al. |
| 6,733,525 B2 | 5/2004 | Yang et al. |
| 6,736,827 B1 | 5/2004 | McAndrew et al. |
| 6,736,839 B2 | 5/2004 | Cummings |
| 6,736,845 B2 | 5/2004 | Marquez et al. |
| 6,736,846 B2 | 5/2004 | Cox |
| 6,743,252 B1 | 6/2004 | Bates et al. |
| 6,746,464 B1 | 6/2004 | Makower |
| 6,752,828 B2 | 6/2004 | Thornton |
| 6,755,854 B2 | 6/2004 | Gillick et al. |
| 6,755,855 B2 | 6/2004 | Yurek et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,767,362 B2 | 7/2004 | Schreck |
| 6,769,434 B2 | 8/2004 | Liddicoat et al. |
| 6,773,454 B2 | 8/2004 | Wholey et al. |
| 6,773,455 B2 | 8/2004 | Allen et al. |
| 6,773,456 B1 | 8/2004 | Gordon et al. |
| 6,774,278 B1 | 8/2004 | Ragheb et al. |
| 6,776,791 B1 | 8/2004 | Stallings et al. |
| 6,786,925 B1 | 9/2004 | Schoon et al. |
| 6,786,929 B2 | 9/2004 | Gambale et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,000 B2 | 9/2004 | Simpson et al. |
| 6,797,002 B2 | 9/2004 | Spence et al. |
| 6,802,319 B2 | 10/2004 | Stevens et al. |
| 6,802,858 B2 | 10/2004 | Gambale et al. |
| 6,805,711 B2 | 10/2004 | Quijano et al. |
| 6,808,498 B2 | 10/2004 | Laroya et al. |
| 6,808,504 B2 | 10/2004 | Schorgl et al. |
| 6,808,529 B2 | 10/2004 | Fulkerson |
| 6,814,746 B2 | 11/2004 | Thompson et al. |
| 6,814,754 B2 | 11/2004 | Greenhalgh |
| 6,820,676 B2 | 11/2004 | Palmaz et al. |
| 6,821,211 B2 | 11/2004 | Otten et al. |
| 6,821,297 B2 | 11/2004 | Snyders |
| 6,824,041 B2 | 11/2004 | Grieder et al. |
| 6,824,970 B2 | 11/2004 | Vyavahare et al. |
| 6,830,568 B1 | 12/2004 | Kesten et al. |
| 6,830,575 B2 | 12/2004 | Stenzel et al. |
| 6,830,584 B1 | 12/2004 | Seguin |
| 6,830,585 B1 | 12/2004 | Artof et al. |
| 6,830,586 B2 | 12/2004 | Quijano et al. |
| 6,837,901 B2 | 1/2005 | Rabkin et al. |
| 6,837,902 B2 | 1/2005 | Nguyen et al. |
| 6,840,957 B2 | 1/2005 | DiMatteo et al. |
| 6,843,802 B1 | 1/2005 | Villalobos et al. |
| 6,846,325 B2 | 1/2005 | Liddicoat |
| 6,849,084 B2 | 2/2005 | Rabkin et al. |
| 6,849,085 B2 | 2/2005 | Marton |
| 6,854,467 B2 | 2/2005 | Boekstegers |
| 6,860,898 B2 | 3/2005 | Stack et al. |
| 6,861,211 B2 | 3/2005 | Levy et al. |
| 6,863,668 B2 | 3/2005 | Gillespie et al. |
| 6,863,684 B2 | 3/2005 | Kim et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,199 B2 | 4/2005 | Wilk et al. |
| 6,881,220 B2 | 4/2005 | Edwin et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,899,704 B2 | 5/2005 | Sterman et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,913,021 B2 | 7/2005 | Knudson et al. |
| 6,913,600 B2 | 7/2005 | Valley et al. |
| 6,916,304 B2 | 7/2005 | Eno et al. |
| 6,920,674 B2 | 7/2005 | Thornton |
| 6,920,732 B2 | 7/2005 | Mårtensson |
| 6,926,690 B2 | 8/2005 | Renati |
| 6,926,732 B2 | 8/2005 | Derus et al. |
| 6,929,009 B2 | 8/2005 | Makower et al. |
| 6,929,011 B2 | 8/2005 | Knudson et al. |
| 6,929,653 B2 | 8/2005 | Strecter |
| 6,936,058 B2 | 8/2005 | Forde et al. |
| 6,936,066 B2 | 8/2005 | Palmaz et al. |
| 6,936,067 B2 | 8/2005 | Buchanan |
| 6,939,352 B2 | 9/2005 | Buzzard et al. |
| 6,939,359 B2 | 9/2005 | Tu et al. |

(56) References Cited

U.S. PATENT DOCUMENTS

| | | |
|---|---|---|
| 6,939,365 B1 | 9/2005 | Fogarty et al. |
| 6,939,370 B2 | 9/2005 | Hartley et al. |
| 6,942,682 B2 | 9/2005 | Vrba et al. |
| 6,945,949 B2 | 9/2005 | Wilk |
| 6,945,997 B2 | 9/2005 | Huynh et al. |
| 6,949,080 B2 | 9/2005 | Wolf et al. |
| 6,949,118 B2 | 9/2005 | Kohler et al. |
| 6,951,571 B1 | 10/2005 | Srivastava |
| 6,953,332 B1 | 10/2005 | Kurk et al. |
| 6,953,481 B2 | 10/2005 | Phelps et al. |
| 6,955,175 B2 | 10/2005 | Stevens et al. |
| 6,955,681 B2 | 10/2005 | Evans et al. |
| 6,964,652 B2 | 11/2005 | Guiles et al. |
| 6,964,673 B2 | 11/2005 | Tsugita et al. |
| 6,964,676 B1 | 11/2005 | Gerberding et al. |
| 6,969,395 B2 | 11/2005 | Eskuri |
| 6,972,025 B2 | 12/2005 | Wasdyke |
| 6,972,029 B2 | 12/2005 | Mayrhofer et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,990 B2 | 12/2005 | Mowry |
| 6,979,350 B2 | 12/2005 | Moll et al. |
| 6,984,242 B2 | 1/2006 | Campbell et al. |
| 6,984,244 B2 | 1/2006 | Perez et al. |
| 6,986,742 B2 | 1/2006 | Hart et al. |
| 6,986,784 B1 | 1/2006 | Weiser et al. |
| 6,988,949 B2 | 1/2006 | Wang |
| 6,989,027 B2 | 1/2006 | Allen et al. |
| 6,989,028 B2 | 1/2006 | Lashinski et al. |
| 6,991,649 B2 | 1/2006 | Sievers |
| 7,001,425 B2 | 2/2006 | McCullagh et al. |
| 7,004,176 B2 | 2/2006 | Lau |
| 7,008,397 B2 | 3/2006 | Tweden et al. |
| 7,011,095 B2 | 3/2006 | Wolf et al. |
| 7,011,681 B2 | 3/2006 | Vesely |
| 7,014,655 B2 | 3/2006 | Barbarash et al. |
| 7,018,401 B1 | 3/2006 | Hyodoh et al. |
| 7,018,406 B2 | 3/2006 | Seguin et al. |
| 7,018,408 B2 | 3/2006 | Bailey et al. |
| 7,022,134 B1 | 4/2006 | Quijano et al. |
| 7,025,773 B2 | 4/2006 | Gittings et al. |
| 7,025,780 B2 | 4/2006 | Gabbay |
| 7,025,791 B2 | 4/2006 | Levine et al. |
| 7,028,692 B2 | 4/2006 | Sterman et al. |
| 7,037,331 B2 | 5/2006 | Mitelberg et al. |
| 7,037,333 B2 | 5/2006 | Myers et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,048,757 B2 | 5/2006 | Shaknovich |
| 7,050,276 B2 | 5/2006 | Nishiyama |
| 7,074,236 B2 | 7/2006 | Rabkin et al. |
| 7,078,163 B2 | 7/2006 | Torrianni |
| 7,081,132 B2 | 7/2006 | Cook et al. |
| 7,097,658 B2 | 8/2006 | Oktay |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,108,715 B2 | 9/2006 | Lawrence-Brown et al. |
| 7,115,141 B2 | 10/2006 | Menz et al. |
| 7,118,585 B2 | 10/2006 | Addis |
| 7,122,020 B2 | 10/2006 | Mogul |
| 7,125,418 B2 | 10/2006 | Duran et al. |
| 7,128,759 B2 | 10/2006 | Osborne et al. |
| 7,137,184 B2 | 11/2006 | Schreck |
| 7,141,063 B2 | 11/2006 | White et al. |
| 7,141,064 B2 | 11/2006 | Scott et al. |
| 7,143,312 B1 | 11/2006 | Wang et al. |
| 7,147,662 B1 | 12/2006 | Pollock et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,163,556 B2 | 1/2007 | Xie et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,179,290 B2 | 2/2007 | Cao |
| 7,186,265 B2 | 3/2007 | Sharkawy et al. |
| 7,189,258 B2 | 3/2007 | Johnson et al. |
| 7,189,259 B2 | 3/2007 | Simionescu et al. |
| 7,191,018 B2 | 3/2007 | Gielen et al. |
| 7,191,406 B1 | 3/2007 | Barber et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,214,344 B2 | 5/2007 | Carpentier et al. |
| 7,217,287 B2 | 5/2007 | Wilson et al. |
| 7,235,092 B2 | 6/2007 | Banas et al. |
| 7,235,093 B2 | 6/2007 | Gregorich |
| 7,238,200 B2 | 7/2007 | Lee et al. |
| 7,241,257 B1 | 7/2007 | Ainsworth et al. |
| 7,252,682 B2 | 8/2007 | Seguin |
| 7,258,696 B2 | 8/2007 | Rabkin et al. |
| 7,258,891 B2 | 8/2007 | Pacetti et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,285,130 B2 | 10/2007 | Austin |
| 7,297,150 B2 | 11/2007 | Cartledge et al. |
| 7,300,457 B2 | 11/2007 | Palmaz |
| 7,300,463 B2 | 11/2007 | Liddicoat |
| 7,311,730 B2 | 12/2007 | Gabbay |
| 7,314,449 B2 | 1/2008 | Pfeiffer et al. |
| 7,314,485 B2 | 1/2008 | Mathis |
| 7,314,880 B2 | 1/2008 | Chang et al. |
| 7,316,706 B2 | 1/2008 | Bloom et al. |
| 7,316,712 B2 | 1/2008 | Peredo |
| 7,317,005 B2 | 1/2008 | Hoekstra et al. |
| 7,317,942 B2 | 1/2008 | Brown |
| 7,317,950 B2 | 1/2008 | Lee |
| 7,318,278 B2 | 1/2008 | Zhang et al. |
| 7,318,998 B2 | 1/2008 | Goldstein et al. |
| 7,319,096 B2 | 1/2008 | Malm et al. |
| 7,320,692 B1 | 1/2008 | Bender et al. |
| 7,320,704 B2 | 1/2008 | Lashinski et al. |
| 7,320,705 B2 | 1/2008 | Quintessenza |
| 7,320,706 B2 | 1/2008 | Al-Najjar |
| 7,322,932 B2 | 1/2008 | Xie et al. |
| 7,323,006 B2 | 1/2008 | Andreas et al. |
| 7,323,066 B1 | 1/2008 | Budron |
| 7,326,174 B2 | 2/2008 | Cox et al. |
| 7,326,219 B2 | 2/2008 | Mowry et al. |
| 7,326,236 B2 | 2/2008 | Andreas et al. |
| 7,327,862 B2 | 2/2008 | Murphy et al. |
| 7,329,278 B2 | 2/2008 | Seguin et al. |
| 7,329,279 B2 | 2/2008 | Haug et al. |
| 7,329,280 B2 | 2/2008 | Bolling et al. |
| 7,329,777 B2 | 2/2008 | Harter et al. |
| 7,331,991 B2 | 2/2008 | Kheradvar et al. |
| 7,331,993 B2 | 2/2008 | White |
| 7,333,643 B2 | 2/2008 | Murphy et al. |
| 7,335,158 B2 | 2/2008 | Taylor |
| 7,335,213 B1 | 2/2008 | Hyde et al. |
| 7,335,218 B2 | 2/2008 | Wilson et al. |
| 7,335,490 B2 | 2/2008 | Van Gilst et al. |
| 7,338,484 B2 | 3/2008 | Schoon et al. |
| 7,338,520 B2 | 3/2008 | Bailey et al. |
| 7,361,189 B2 | 4/2008 | Case et al. |
| 7,361,190 B2 | 4/2008 | Shaoulian et al. |
| 7,364,588 B2 | 4/2008 | Mathis et al. |
| 7,371,258 B2 | 5/2008 | Woo et al. |
| 7,374,560 B2 | 5/2008 | Ressemann et al. |
| 7,374,571 B2 | 5/2008 | Pease et al. |
| 7,377,895 B2 | 5/2008 | Spence et al. |
| 7,377,938 B2 | 5/2008 | Sarac et al. |
| 7,377,940 B2 | 5/2008 | Ryan et al. |
| 7,381,210 B2 | 6/2008 | Zarbatany et al. |

(56) References Cited

U.S. PATENT DOCUMENTS

| | | |
|---|---|---|
| 7,381,216 B2 | 6/2008 | Buzzard et al. |
| 7,381,218 B2 | 6/2008 | Schreck |
| 7,381,219 B2 | 6/2008 | Salahieh et al. |
| 7,381,220 B2 | 6/2008 | Macoviak et al. |
| 7,384,411 B1 | 6/2008 | Condado |
| 7,387,640 B2 | 6/2008 | Cummings |
| 7,389,874 B2 | 6/2008 | Quest et al. |
| 7,390,325 B2 | 6/2008 | Wang et al. |
| 7,393,358 B2 | 7/2008 | Malewicz |
| 7,393,360 B2 | 7/2008 | Spenser et al. |
| 7,396,364 B2 | 7/2008 | Moaddeb et al. |
| 7,399,315 B2 | 7/2008 | Lobbi |
| 7,402,171 B2 | 7/2008 | Osborne et al. |
| 7,404,792 B2 | 7/2008 | Spence et al. |
| 7,404,793 B2 | 7/2008 | Lau et al. |
| 7,405,259 B2 | 7/2008 | Frye et al. |
| 7,410,499 B2 | 8/2008 | Bicer |
| 7,412,274 B2 | 8/2008 | Mejia |
| 7,412,290 B2 | 8/2008 | Janke et al. |
| 7,415,861 B2 | 8/2008 | Sokel |
| 7,416,530 B2 | 8/2008 | Turner et al. |
| 7,422,603 B2 | 9/2008 | Lane |
| 7,422,606 B2 | 9/2008 | Ung-Chhun et al. |
| 7,423,032 B2 | 9/2008 | Ozaki et al. |
| 7,426,413 B2 | 9/2008 | Balczewski et al. |
| 7,427,279 B2 | 9/2008 | Frazier et al. |
| 7,427,287 B2 | 9/2008 | Turovskiy et al. |
| 7,427,291 B2 | 9/2008 | Liddicoat et al. |
| 7,429,269 B2 | 9/2008 | Schwammenthal et al. |
| 7,430,448 B1 | 9/2008 | Zimmer et al. |
| 7,430,484 B2 | 9/2008 | Ohara |
| 7,431,691 B1 | 10/2008 | Wilk |
| 7,431,733 B2 | 10/2008 | Knight |
| 7,435,059 B2 | 10/2008 | Smith et al. |
| 7,435,257 B2 | 10/2008 | Lashinski et al. |
| 7,442,204 B2 | 10/2008 | Schwammenthal et al. |
| RE40,570 E | 11/2008 | Carpentier et al. |
| 7,445,630 B2 | 11/2008 | Lashinski et al. |
| 7,445,631 B2 | 11/2008 | Salahieh et al. |
| 7,445,632 B2 | 11/2008 | McGuckin, Jr. et al. |
| 7,452,371 B2 | 11/2008 | Pavcnik et al. |
| 7,455,689 B2 | 11/2008 | Johnson |
| 7,462,156 B2 | 12/2008 | Mitrev |
| 7,462,184 B2 | 12/2008 | Worley et al. |
| 7,462,191 B2 | 12/2008 | Spenser et al. |
| 7,468,050 B1 | 12/2008 | Kantrowitz |
| 7,470,284 B2 | 12/2008 | Lambrecht et al. |
| 7,470,285 B2 | 12/2008 | Nugent et al. |
| 7,473,271 B2 | 1/2009 | Gunderson |
| 7,473,275 B2 | 1/2009 | Marquez |
| 7,473,417 B2 | 1/2009 | Zeltinger et al. |
| 7,476,196 B2 | 1/2009 | Spence et al. |
| 7,476,199 B2 | 1/2009 | Spence et al. |
| 7,476,200 B2 | 1/2009 | Tal |
| 7,476,244 B2 | 1/2009 | Buzzard et al. |
| 7,481,838 B2 | 1/2009 | Carpentier et al. |
| 7,485,088 B2 | 2/2009 | Murphy et al. |
| 7,485,143 B2 | 2/2009 | Webler et al. |
| 7,488,346 B2 | 2/2009 | Navia |
| 7,491,232 B2 | 2/2009 | Bolduc et al. |
| 7,493,869 B1 | 2/2009 | Foster et al. |
| 7,497,824 B2 | 3/2009 | Taylor |
| 7,500,949 B2 | 3/2009 | Gottlieb et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,507,199 B2 | 3/2009 | Wang et al. |
| 7,510,572 B2 | 3/2009 | Gabbay |
| 7,510,574 B2 | 3/2009 | Le et al. |
| 7,510,575 B2 | 3/2009 | Spenser et al. |
| 7,510,577 B2 | 3/2009 | Moaddeb et al. |
| 7,513,863 B2 | 4/2009 | Bolling et al. |
| 7,513,909 B2 | 4/2009 | Lane et al. |
| 7,522,950 B2 | 4/2009 | Fuimaono et al. |
| 7,524,330 B2 | 4/2009 | Berreklouw |
| 7,530,253 B2 | 5/2009 | Spenser et al. |
| 7,530,995 B2 | 5/2009 | Quijano et al. |
| 7,534,261 B2 | 5/2009 | Friedman |
| 7,544,206 B2 | 6/2009 | Cohn |
| 7,547,322 B2 | 6/2009 | Sarac et al. |
| 7,553,324 B2 | 6/2009 | Andreas et al. |
| 7,556,386 B2 | 7/2009 | Smith |
| 7,556,646 B2 | 7/2009 | Yang et al. |
| 7,569,071 B2 | 8/2009 | Haverkost et al. |
| 7,578,828 B2 | 8/2009 | Gittings et al. |
| 7,585,321 B2 | 9/2009 | Cribier |
| 7,591,848 B2 | 9/2009 | Allen |
| 7,594,974 B2 | 9/2009 | Cali et al. |
| 7,601,159 B2 | 10/2009 | Ewers et al. |
| 7,601,195 B2 | 10/2009 | Ichikawa |
| 7,608,099 B2 | 10/2009 | Johnson et al. |
| 7,611,534 B2 | 11/2009 | Kapadia et al. |
| 7,618,446 B2 | 11/2009 | Andersen et al. |
| 7,622,276 B2 | 11/2009 | Cunanan et al. |
| 7,625,403 B2 | 12/2009 | Krivoruchko |
| 7,628,802 B2 | 12/2009 | White et al. |
| 7,628,803 B2 | 12/2009 | Pavcnik et al. |
| 7,632,296 B2 | 12/2009 | Malewicz |
| 7,632,298 B2 | 12/2009 | Hijlkema et al. |
| 7,635,386 B1 | 12/2009 | Gammie |
| 7,641,687 B2 | 1/2010 | Chinn et al. |
| 7,651,519 B2 | 1/2010 | Dittman |
| 7,655,034 B2 | 2/2010 | Mitchell et al. |
| 7,674,282 B2 | 3/2010 | Wu et al. |
| 7,682,390 B2 | 3/2010 | Seguin |
| 7,704,222 B2 | 4/2010 | Wilk et al. |
| 7,704,277 B2 | 4/2010 | Zakay et al. |
| 7,712,606 B2 | 5/2010 | Salahieh et al. |
| 7,715,903 B2 | 5/2010 | Hartley et al. |
| 7,717,955 B2 | 5/2010 | Lane et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,722,671 B1 | 5/2010 | Carlyle et al. |
| 7,731,742 B2 | 6/2010 | Schlick et al. |
| 7,735,493 B2 | 6/2010 | Van Der Burg et al. |
| 7,736,327 B2 | 6/2010 | Wilk et al. |
| 7,736,388 B2 | 6/2010 | Goldfarb et al. |
| 7,743,481 B2 | 6/2010 | Lafont et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,771,463 B2 | 8/2010 | Ton et al. |
| 7,771,467 B2 | 8/2010 | Svensson |
| 7,776,083 B2 | 8/2010 | Vesely |
| 7,780,725 B2 | 8/2010 | Haug et al. |
| 7,780,726 B2 | 8/2010 | Seguin |
| 7,785,360 B2 | 8/2010 | Freitag |
| 7,794,487 B2 | 9/2010 | Majercak et al. |
| 7,799,046 B2 | 9/2010 | White et al. |
| 7,799,065 B2 | 9/2010 | Pappas |
| 7,803,185 B2 | 9/2010 | Gabbay |
| 7,806,919 B2 | 10/2010 | Bloom et al. |
| 7,823,267 B2 | 11/2010 | Bolduc |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,837,727 B2 | 11/2010 | Goetz et al. |
| 7,846,203 B2 | 12/2010 | Cribier |
| 7,846,204 B2 | 12/2010 | Letac et al. |
| 7,854,758 B2 | 12/2010 | Taheri |
| 7,857,845 B2 | 12/2010 | Stacchino et al. |
| 7,862,602 B2 | 1/2011 | Licata et al. |
| 7,867,274 B2 | 1/2011 | Hill et al. |
| 7,887,583 B2 | 2/2011 | Macoviak |
| 7,892,276 B2 | 2/2011 | Stocker et al. |
| 7,892,292 B2 | 2/2011 | Stack et al. |
| 7,896,913 B2 | 3/2011 | Damm et al. |
| 7,896,915 B2 | 3/2011 | Guyenot et al. |
| 7,914,569 B2 | 3/2011 | Nguyen et al. |
| 7,914,574 B2 | 3/2011 | Schmid et al. |
| 7,914,575 B2 | 3/2011 | Guyenot et al. |
| 7,918,880 B2 | 4/2011 | Austin |
| 7,927,363 B2 | 4/2011 | Perouse |

(56) References Cited

U.S. PATENT DOCUMENTS

| | | |
|---|---|---|
| 7,938,851 B2 | 5/2011 | Olson et al. |
| 7,947,071 B2 | 5/2011 | Schmid et al. |
| 7,947,075 B2 | 5/2011 | Goetz et al. |
| 7,951,189 B2 | 5/2011 | Haverkost et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |
| 7,972,359 B2 | 7/2011 | Kreidler |
| 7,972,376 B1 | 7/2011 | Dove et al. |
| 7,972,378 B2 | 7/2011 | Tabor et al. |
| 7,988,724 B2 | 8/2011 | Salahieh et al. |
| 7,993,386 B2 | 8/2011 | Elliott |
| 8,002,824 B2 | 8/2011 | Jenson et al. |
| 8,002,825 B2 | 8/2011 | Letac et al. |
| 8,012,198 B2 | 9/2011 | Hill et al. |
| 8,021,421 B2 | 9/2011 | Fogarty et al. |
| RE42,818 E | 10/2011 | Cali et al. |
| RE42,857 E | 10/2011 | Cali et al. |
| 8,038,704 B2 | 10/2011 | Sherburne |
| 8,038,709 B2 | 10/2011 | Palasis et al. |
| 8,043,450 B2 | 10/2011 | Cali et al. |
| 8,048,153 B2 | 11/2011 | Salahieh et al. |
| 8,052,715 B2 | 11/2011 | Quinn et al. |
| 8,052,749 B2 | 11/2011 | Salahieh et al. |
| 8,052,750 B2 | 11/2011 | Tuval et al. |
| 8,057,540 B2 | 11/2011 | Letac et al. |
| 8,062,355 B2 | 11/2011 | Figulla et al. |
| 8,062,536 B2 | 11/2011 | Liu et al. |
| 8,062,537 B2 | 11/2011 | Tuominen et al. |
| 8,062,749 B2 | 11/2011 | Shelestak et al. |
| 8,070,799 B2 | 12/2011 | Righini et al. |
| 8,075,641 B2 | 12/2011 | Aravanis et al. |
| 8,083,788 B2 | 12/2011 | Acosta et al. |
| 8,092,518 B2 | 1/2012 | Schreck |
| 8,092,520 B2 | 1/2012 | Quadri |
| 8,092,521 B2 | 1/2012 | Figulla et al. |
| 8,128,676 B2 | 3/2012 | Cummings |
| 8,128,681 B2 | 3/2012 | Shoemaker et al. |
| 8,133,217 B2 | 3/2012 | Stokes et al. |
| 8,133,270 B2 | 3/2012 | Kheradvar et al. |
| 8,136,659 B2 | 3/2012 | Salahieh et al. |
| 8,137,394 B2 | 3/2012 | Stocker et al. |
| 8,137,398 B2 | 3/2012 | Tuval et al. |
| 8,147,534 B2 | 4/2012 | Berez et al. |
| 8,157,853 B2 | 4/2012 | Laske et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,206,437 B2 | 6/2012 | Bonhoeffer et al. |
| 8,211,107 B2 | 7/2012 | Parks et al. |
| 8,216,174 B2 | 7/2012 | Wilk et al. |
| 8,216,301 B2 | 7/2012 | Bonhoeffer et al. |
| 8,221,493 B2 | 7/2012 | Boyle et al. |
| 8,226,707 B2 | 7/2012 | White |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,236,241 B2 | 8/2012 | Carpentier et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,287,584 B2 | 10/2012 | Salahieh et al. |
| 8,303,653 B2 | 11/2012 | Bonhoeffer et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,136 B2 | 1/2013 | Howat et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,999 B2 | 1/2013 | Kheradvar et al. |
| 8,357,387 B2 | 1/2013 | Dove et al. |
| 8,366,767 B2 | 2/2013 | Zhang |
| 8,372,134 B2 | 2/2013 | Schlick et al. |
| 8,376,865 B2 | 2/2013 | Forster et al. |
| 8,377,117 B2 | 2/2013 | Keidar et al. |
| 8,382,822 B2 | 2/2013 | Pavcnik et al. |
| 8,398,704 B2 | 3/2013 | Straubinger et al. |
| 8,398,708 B2 | 3/2013 | Meiri et al. |
| 8,403,983 B2 | 3/2013 | Quadri et al. |
| 8,414,641 B2 | 4/2013 | Stocker et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,439,961 B2 | 5/2013 | Jagger et al. |
| 8,445,278 B2 | 5/2013 | Everaerts et al. |
| 8,460,365 B2 | 6/2013 | Haverkost et al. |
| 8,465,540 B2 | 6/2013 | Straubinger et al. |
| 8,468,667 B2 | 6/2013 | Straubinger et al. |
| 8,470,023 B2 | 6/2013 | Eidenschink et al. |
| 8,491,650 B2 | 7/2013 | Wiemeyer et al. |
| 8,512,394 B2 | 8/2013 | Schmid et al. |
| 8,512,399 B2 | 8/2013 | Lafontaine |
| 8,512,400 B2 | 8/2013 | Tran et al. |
| 8,512,401 B2 | 8/2013 | Murray, III et al. |
| 8,523,936 B2 | 9/2013 | Schmid et al. |
| 8,535,368 B2 | 9/2013 | Headley, Jr. et al. |
| 8,540,762 B2 | 9/2013 | Schmid et al. |
| 8,545,547 B2 | 10/2013 | Schmid et al. |
| 8,545,552 B2 | 10/2013 | Garrison et al. |
| 8,551,160 B2 | 10/2013 | Figulla et al. |
| 8,556,880 B2 | 10/2013 | Freyman et al. |
| 8,556,966 B2 | 10/2013 | Jenson |
| 8,568,475 B2 | 10/2013 | Nguyen et al. |
| 8,579,936 B2 | 11/2013 | Abbott et al. |
| 8,579,962 B2 | 11/2013 | Salahieh et al. |
| 8,579,965 B2 | 11/2013 | Bonhoeffer et al. |
| 8,585,756 B2 | 11/2013 | Bonhoeffer et al. |
| 8,585,759 B2 | 11/2013 | Bumbalough |
| 8,591,570 B2 | 11/2013 | Revuelta et al. |
| 8,597,226 B2 | 12/2013 | Wilk et al. |
| 8,603,159 B2 | 12/2013 | Seguin et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,074 B2 | 1/2014 | Ryan |
| 8,623,075 B2 * | 1/2014 | Murray, III ........... A61F 2/2418 623/1.11 |
| 8,623,076 B2 | 1/2014 | Salahieh et al. |
| 8,623,078 B2 | 1/2014 | Salahieh et al. |
| 8,628,562 B2 | 1/2014 | Cummings |
| 8,628,571 B1 | 1/2014 | Hacohen et al. |
| 8,647,381 B2 | 2/2014 | Essinger et al. |
| 8,668,733 B2 | 3/2014 | Haug et al. |
| 8,672,997 B2 | 3/2014 | Drasler et al. |
| 8,679,174 B2 | 3/2014 | Ottma et al. |
| 8,685,077 B2 | 4/2014 | Laske et al. |
| 8,696,743 B2 | 4/2014 | Holecek et al. |
| 8,721,713 B2 | 5/2014 | Tower et al. |
| 8,721,717 B2 | 5/2014 | Shoemaker et al. |
| 8,734,508 B2 | 5/2014 | Hastings et al. |
| 8,758,430 B2 | 6/2014 | Ferrari et al. |
| 8,764,818 B2 | 7/2014 | Gregg |
| 8,778,020 B2 | 7/2014 | Gregg et al. |
| 8,790,395 B2 | 7/2014 | Straubinger et al. |
| 8,795,305 B2 | 8/2014 | Martin et al. |
| 8,795,356 B2 | 8/2014 | Quadri et al. |
| 8,808,356 B2 | 8/2014 | Braido et al. |
| 8,808,364 B2 | 8/2014 | Palasis et al. |
| RE45,130 E | 9/2014 | Figulla et al. |
| 8,828,078 B2 | 9/2014 | Salahieh et al. |
| 8,828,079 B2 | 9/2014 | Thielen et al. |
| 8,840,662 B2 | 9/2014 | Salahieh et al. |
| 8,840,663 B2 | 9/2014 | Salahieh et al. |
| 8,845,721 B2 | 9/2014 | Braido et al. |
| 8,851,286 B2 | 10/2014 | Chang et al. |
| 8,852,272 B2 | 10/2014 | Gross et al. |
| 8,858,620 B2 | 10/2014 | Salahieh et al. |
| 8,894,703 B2 | 11/2014 | Salahieh et al. |
| 8,932,349 B2 | 1/2015 | Jenson et al. |

(56) References Cited

U.S. PATENT DOCUMENTS

| | | |
|---|---|---|
| 8,940,014 B2 | 1/2015 | Gamarra et al. |
| 8,951,243 B2 | 2/2015 | Crisostomo et al. |
| 8,951,299 B2 | 2/2015 | Paul et al. |
| 8,956,383 B2 | 2/2015 | Aklog et al. |
| 8,992,608 B2 | 3/2015 | Haug et al. |
| 8,998,976 B2 | 4/2015 | Gregg et al. |
| 9,005,273 B2 | 4/2015 | Salahieh et al. |
| 9,011,521 B2 | 4/2015 | Haug et al. |
| 9,023,099 B2 | 5/2015 | Duffy et al. |
| 9,028,542 B2 | 5/2015 | Hill et al. |
| 9,039,756 B2 | 5/2015 | White |
| 9,044,318 B2 | 6/2015 | Straubinger et al. |
| 9,131,926 B2 | 9/2015 | Crisostomo et al. |
| 9,138,315 B2 | 9/2015 | Straubinger et al. |
| 9,149,358 B2 | 10/2015 | Tabor et al. |
| 9,168,130 B2 | 10/2015 | Straubinger et al. |
| 9,168,131 B2 | 10/2015 | Yohanan et al. |
| 9,168,136 B2 | 10/2015 | Yang et al. |
| RE45,790 E | 11/2015 | Figulla et al. |
| 9,180,005 B1 | 11/2015 | Lashinski et al. |
| 9,186,482 B2 | 11/2015 | Dorn |
| 9,211,266 B2 | 12/2015 | Iwazawa et al. |
| 9,216,082 B2 | 12/2015 | Von Segesser et al. |
| 9,248,037 B2 | 2/2016 | Roeder et al. |
| 9,265,608 B2 | 2/2016 | Miller et al. |
| 9,277,991 B2 | 3/2016 | Salahieh et al. |
| 9,277,993 B2 | 3/2016 | Gamarra et al. |
| 9,295,551 B2 | 3/2016 | Straubinger et al. |
| 9,301,840 B2 | 4/2016 | Nguyen et al. |
| 9,301,843 B2 | 4/2016 | Richardson et al. |
| 9,308,085 B2 | 4/2016 | Salahieh et al. |
| 9,320,599 B2 | 4/2016 | Salahieh et al. |
| 9,326,853 B2 | 5/2016 | Olson et al. |
| 9,358,106 B2 | 6/2016 | Salahieh et al. |
| 9,358,110 B2 | 6/2016 | Paul et al. |
| 9,370,419 B2 | 6/2016 | Hill et al. |
| 9,370,421 B2 | 6/2016 | Crisostomo et al. |
| 9,387,076 B2 | 7/2016 | Paul et al. |
| 9,393,094 B2 | 7/2016 | Salahieh et al. |
| 9,393,113 B2 | 7/2016 | Salahieh et al. |
| 9,393,114 B2 | 7/2016 | Sutton et al. |
| 9,393,115 B2 | 7/2016 | Tabor et al. |
| 9,415,567 B2 | 8/2016 | Sogard et al. |
| 9,421,083 B2 | 8/2016 | Eidenschink et al. |
| 9,439,759 B2 | 9/2016 | Straubinger et al. |
| 9,463,084 B2 | 10/2016 | Stinson |
| 9,474,598 B2 | 10/2016 | Gregg et al. |
| 9,474,609 B2 | 10/2016 | Haverkost et al. |
| 9,492,276 B2 | 11/2016 | Lee et al. |
| 9,510,945 B2 | 12/2016 | Sutton et al. |
| 9,510,947 B2 | 12/2016 | Straubinger et al. |
| 9,526,609 B2 | 12/2016 | Salahieh et al. |
| 9,532,872 B2 | 1/2017 | Salahieh et al. |
| 9,539,091 B2 | 1/2017 | Yang et al. |
| 9,554,924 B2 | 1/2017 | Schlick et al. |
| 9,597,432 B2 | 3/2017 | Nakamura |
| 9,649,212 B2 | 5/2017 | Fargahi |
| 9,717,593 B2 | 8/2017 | Alkhatib et al. |
| 9,744,031 B2 | 8/2017 | Girard et al. |
| D800,908 S | 10/2017 | Hariton et al. |
| 9,775,709 B2 | 10/2017 | Miller et al. |
| 9,788,945 B2 | 10/2017 | Ottma et al. |
| 9,861,476 B2 | 1/2018 | Salahieh et al. |
| 9,867,694 B2 | 1/2018 | Girard et al. |
| 9,867,699 B2 | 1/2018 | Straubinger et al. |
| 9,872,768 B2 | 1/2018 | Paul et al. |
| 9,878,127 B2 | 1/2018 | Damm et al. |
| 9,889,002 B2 | 2/2018 | Bonhoeffer et al. |
| 9,901,445 B2 | 2/2018 | Backus et al. |
| 9,949,824 B2 | 4/2018 | Bonhoeffer et al. |
| 9,956,075 B2 | 5/2018 | Salahieh et al. |
| 9,968,761 B2 | 5/2018 | Brecker |
| 9,987,133 B2 | 6/2018 | Straubinger et al. |
| 10,092,324 B2 | 10/2018 | Gillespie et al. |
| 10,143,552 B2 | 12/2018 | Wallace et al. |
| 10,154,901 B2 | 12/2018 | Straubinger et al. |
| 10,321,987 B2 | 6/2019 | Wang et al. |
| 10,363,134 B2 | 7/2019 | Figulla et al. |
| 10,543,084 B2 | 1/2020 | Guyenot et al. |
| 10,575,947 B2 | 3/2020 | Straubinger et al. |
| 10,638,918 B2 | 5/2020 | Atarot et al. |
| 10,702,382 B2 | 7/2020 | Straubinger et al. |
| 10,709,555 B2 | 7/2020 | Schreck et al. |
| 10,856,978 B2 | 12/2020 | Straubinger et al. |
| 10,856,987 B2 | 12/2020 | Cabiri et al. |
| 11,065,138 B2 | 7/2021 | Schreck et al. |
| 11,147,669 B2 | 10/2021 | Straubinger et al. |
| 11,154,398 B2 | 10/2021 | Straubinger et al. |
| 11,197,754 B2 | 12/2021 | Saffari et al. |
| 11,266,497 B2 | 3/2022 | Cao et al. |
| 2001/0000041 A1 | 3/2001 | Selmon et al. |
| 2001/0001314 A1 | 5/2001 | Davison et al. |
| 2001/0002445 A1 | 5/2001 | Vesely |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0007956 A1 | 7/2001 | Letac et al. |
| 2001/0008969 A1 | 7/2001 | Evans et al. |
| 2001/0010017 A1 | 7/2001 | Letac et al. |
| 2001/0011187 A1 | 8/2001 | Pavcnik et al. |
| 2001/0011189 A1 | 8/2001 | Drasler et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0021872 A1 | 9/2001 | Bailey et al. |
| 2001/0025196 A1 | 9/2001 | Chinn et al. |
| 2001/0025643 A1 | 10/2001 | Foley |
| 2001/0027287 A1 | 10/2001 | Shmulewitz et al. |
| 2001/0027338 A1 | 10/2001 | Greenberg |
| 2001/0027339 A1 | 10/2001 | Boatman et al. |
| 2001/0029385 A1 | 10/2001 | Shennib et al. |
| 2001/0032013 A1 | 10/2001 | Marton |
| 2001/0034547 A1 | 10/2001 | Hall et al. |
| 2001/0037117 A1 | 11/2001 | Gambale et al. |
| 2001/0037141 A1 | 11/2001 | Yee et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0039450 A1 | 11/2001 | Pavcnik et al. |
| 2001/0041902 A1 | 11/2001 | Lepulu et al. |
| 2001/0041928 A1 | 11/2001 | Pavcnik et al. |
| 2001/0041930 A1 | 11/2001 | Globerman et al. |
| 2001/0044631 A1 | 11/2001 | Akin et al. |
| 2001/0044634 A1 | 11/2001 | Don Michael et al. |
| 2001/0044647 A1 | 11/2001 | Pinchuk et al. |
| 2001/0044652 A1 | 11/2001 | Moore |
| 2001/0044656 A1 | 11/2001 | Williamson, IV et al. |
| 2001/0047165 A1 | 11/2001 | Makower et al. |
| 2001/0049523 A1 | 12/2001 | DeVore et al. |
| 2001/0051822 A1 | 12/2001 | Stack et al. |
| 2001/0053932 A1 | 12/2001 | Phelps et al. |
| 2002/0002349 A1 | 1/2002 | Flaherty et al. |
| 2002/0002396 A1 | 1/2002 | Fulkerson |
| 2002/0002401 A1 | 1/2002 | McGuckin, Jr. et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0010489 A1 | 1/2002 | Grayzel et al. |
| 2002/0010508 A1 | 1/2002 | Chobotov |
| 2002/0026233 A1 | 2/2002 | Shaknovich |
| 2002/0029014 A1 | 3/2002 | Jayaraman |
| 2002/0029079 A1 | 3/2002 | Kim et al. |
| 2002/0029981 A1 | 3/2002 | Nigam |
| 2002/0032476 A1 | 3/2002 | Gambale et al. |
| 2002/0032478 A1 | 3/2002 | Boekstegers et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |

(56) References Cited

U.S. PATENT DOCUMENTS

| | | |
|---|---|---|
| 2002/0045928 A1 | 4/2002 | Boeksteger |
| 2002/0045929 A1 | 4/2002 | Diaz |
| 2002/0049486 A1 | 4/2002 | Knudson et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055772 A1 | 5/2002 | McGuckin, Jr. et al. |
| 2002/0055774 A1 | 5/2002 | Liddicoat |
| 2002/0055775 A1 | 5/2002 | Carpentier et al. |
| 2002/0058897 A1 | 5/2002 | Renati |
| 2002/0058987 A1 | 5/2002 | Butaric et al. |
| 2002/0058993 A1 | 5/2002 | Landau et al. |
| 2002/0058995 A1 | 5/2002 | Stevens |
| 2002/0062146 A1 | 5/2002 | Makower et al. |
| 2002/0065478 A1 | 5/2002 | Knudson et al. |
| 2002/0065485 A1 | 5/2002 | DuBois et al. |
| 2002/0072699 A1 | 6/2002 | Knudson et al. |
| 2002/0072789 A1 | 6/2002 | Hackett et al. |
| 2002/0077566 A1 | 6/2002 | Laroya et al. |
| 2002/0077654 A1 | 6/2002 | Javier, Jr. et al. |
| 2002/0077696 A1 | 6/2002 | Zadno-Azizi et al. |
| 2002/0082584 A1 | 6/2002 | Rosenman et al. |
| 2002/0082609 A1 | 6/2002 | Green |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095173 A1 | 7/2002 | Mazzocchi et al. |
| 2002/0095206 A1 | 7/2002 | Addonizio et al. |
| 2002/0095209 A1 | 7/2002 | Zadno-Azizi et al. |
| 2002/0099439 A1 | 7/2002 | Schwartz et al. |
| 2002/0100484 A1 | 8/2002 | Hall et al. |
| 2002/0103533 A1 | 8/2002 | Langberg et al. |
| 2002/0107565 A1 | 8/2002 | Greenhalgh |
| 2002/0111627 A1 | 8/2002 | Vincent-Prestigiacomo |
| 2002/0111665 A1 | 8/2002 | Lauterjung |
| 2002/0111668 A1 | 8/2002 | Smith |
| 2002/0111672 A1 | 8/2002 | Kim et al. |
| 2002/0111674 A1 | 8/2002 | Chouinard et al. |
| 2002/0117789 A1 | 8/2002 | Childers et al. |
| 2002/0120322 A1 | 8/2002 | Thompson et al. |
| 2002/0120323 A1 | 8/2002 | Thompson et al. |
| 2002/0120328 A1 | 8/2002 | Pathak et al. |
| 2002/0123698 A1 | 9/2002 | Garibotto et al. |
| 2002/0123786 A1 | 9/2002 | Gittings et al. |
| 2002/0123790 A1 | 9/2002 | White et al. |
| 2002/0123802 A1 | 9/2002 | Snyders |
| 2002/0128552 A1 | 9/2002 | Nowlin et al. |
| 2002/0133183 A1 | 9/2002 | Lentz et al. |
| 2002/0133226 A1 | 9/2002 | Marquez et al. |
| 2002/0138087 A1 | 9/2002 | Shennib et al. |
| 2002/0138138 A1 | 9/2002 | Yang |
| 2002/0143285 A1 | 10/2002 | Eno et al. |
| 2002/0143289 A1 | 10/2002 | Ellis et al. |
| 2002/0143387 A1 | 10/2002 | Soetikno et al. |
| 2002/0144696 A1 | 10/2002 | Sharkawy et al. |
| 2002/0151913 A1 | 10/2002 | Berg et al. |
| 2002/0151970 A1 | 10/2002 | Garrison et al. |
| 2002/0156522 A1 | 10/2002 | Ivancev et al. |
| 2002/0161377 A1 | 10/2002 | Rabkin |
| 2002/0161383 A1 | 10/2002 | Akin et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0161424 A1 | 10/2002 | Rapacki et al. |
| 2002/0161426 A1 | 10/2002 | Iancea |
| 2002/0165479 A1 | 11/2002 | Wilk |
| 2002/0165576 A1 | 11/2002 | Boyle et al. |
| 2002/0165606 A1 | 11/2002 | Wolf et al. |
| 2002/0173842 A1 | 11/2002 | Buchanan |
| 2002/0177766 A1 | 11/2002 | Mogul |
| 2002/0177772 A1 | 11/2002 | Altman et al. |
| 2002/0177840 A1 | 11/2002 | Farnholtz |
| 2002/0177894 A1 | 11/2002 | Acosta et al. |
| 2002/0179098 A1 | 12/2002 | Makower et al. |
| 2002/0183716 A1 | 12/2002 | Herweck et al. |
| 2002/0183781 A1 | 12/2002 | Casey et al. |
| 2002/0186558 A1 | 12/2002 | Plank et al. |
| 2002/0188341 A1 | 12/2002 | Elliott |
| 2002/0188344 A1 | 12/2002 | Bolea et al. |
| 2002/0193782 A1 | 12/2002 | Ellis et al. |
| 2002/0193871 A1 | 12/2002 | Beyersdorf et al. |
| 2002/0198594 A1 | 12/2002 | Schreck |
| 2003/0004541 A1 | 1/2003 | Linder et al. |
| 2003/0004560 A1 | 1/2003 | Chobotov et al. |
| 2003/0009189 A1 | 1/2003 | Gilson et al. |
| 2003/0014104 A1 | 1/2003 | Cribier |
| 2003/0018377 A1 | 1/2003 | Berg et al. |
| 2003/0018379 A1 | 1/2003 | Knudson et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0028213 A1 | 2/2003 | Thill et al. |
| 2003/0028247 A1 | 2/2003 | Cali |
| 2003/0033001 A1 | 2/2003 | Igaki |
| 2003/0036791 A1 | 2/2003 | Philipp et al. |
| 2003/0036795 A1 | 2/2003 | Andersen et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0042186 A1 | 3/2003 | Boyle |
| 2003/0044315 A1 | 3/2003 | Boeksteger |
| 2003/0045828 A1 | 3/2003 | Wilk |
| 2003/0050694 A1 | 3/2003 | Yang et al. |
| 2003/0055371 A1 | 3/2003 | Wolf et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0065386 A1 | 4/2003 | Weadock |
| 2003/0069492 A1 | 4/2003 | Abrams et al. |
| 2003/0069646 A1 | 4/2003 | Stinson |
| 2003/0070944 A1 | 4/2003 | Nigam |
| 2003/0073973 A1 | 4/2003 | Evans et al. |
| 2003/0074058 A1 | 4/2003 | Sherry |
| 2003/0078561 A1 | 4/2003 | Gambale et al. |
| 2003/0078652 A1 | 4/2003 | Sutherland |
| 2003/0083730 A1 | 5/2003 | Stinson |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0100920 A1 | 5/2003 | Akin et al. |
| 2003/0105514 A1 | 6/2003 | Phelps et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0120195 A1 | 6/2003 | Milo et al. |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0130746 A1 | 7/2003 | Ashworth et al. |
| 2003/0135257 A1 | 7/2003 | Taheri |
| 2003/0139796 A1 | 7/2003 | Sequin et al. |
| 2003/0139798 A1 | 7/2003 | Brown et al. |
| 2003/0139803 A1 | 7/2003 | Sequin et al. |
| 2003/0139804 A1 | 7/2003 | Hankh et al. |
| 2003/0144657 A1 | 7/2003 | Bowe et al. |
| 2003/0144732 A1 | 7/2003 | Cosgrove et al. |
| 2003/0149474 A1 | 8/2003 | Becker |
| 2003/0149475 A1 | 8/2003 | Hyodoh et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0153971 A1 | 8/2003 | Chandrasekaran |
| 2003/0153974 A1 | 8/2003 | Spenser et al. |
| 2003/0158573 A1 | 8/2003 | Gittings et al. |
| 2003/0158595 A1 | 8/2003 | Randall et al. |
| 2003/0163193 A1 | 8/2003 | Widenhouse |
| 2003/0163198 A1 | 8/2003 | Morra et al. |
| 2003/0165352 A1 | 9/2003 | Ibrahim et al. |
| 2003/0171803 A1 | 9/2003 | Shimon |
| 2003/0171805 A1 | 9/2003 | Berg et al. |

(56) References Cited

U.S. PATENT DOCUMENTS

| | | |
|---|---|---|
| 2003/0176884 A1 | 9/2003 | Berrada et al. |
| 2003/0181850 A1 | 9/2003 | Diamond et al. |
| 2003/0181938 A1 | 9/2003 | Roth et al. |
| 2003/0181942 A1 | 9/2003 | Sutton et al. |
| 2003/0187495 A1 | 10/2003 | Cully et al. |
| 2003/0191449 A1 | 10/2003 | Nash et al. |
| 2003/0191516 A1 | 10/2003 | Weldon et al. |
| 2003/0191519 A1 | 10/2003 | Lombardi et al. |
| 2003/0191526 A1 | 10/2003 | Van Tassel et al. |
| 2003/0195457 A1 | 10/2003 | LaFontaine et al. |
| 2003/0195458 A1 | 10/2003 | Phelps et al. |
| 2003/0195609 A1 | 10/2003 | Berenstein et al. |
| 2003/0195620 A1 | 10/2003 | Huynh et al. |
| 2003/0198722 A1 | 10/2003 | Johnston, Jr. et al. |
| 2003/0199759 A1 | 10/2003 | Richard |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0204160 A1 | 10/2003 | Kamm et al. |
| 2003/0204249 A1 | 10/2003 | Letort |
| 2003/0208224 A1 | 11/2003 | Broome |
| 2003/0212410 A1 | 11/2003 | Stenzel et al. |
| 2003/0212413 A1 | 11/2003 | Wilk |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216678 A1 | 11/2003 | March et al. |
| 2003/0216679 A1 | 11/2003 | Wolf et al. |
| 2003/0216774 A1 | 11/2003 | Larson |
| 2003/0220661 A1 | 11/2003 | Mowry et al. |
| 2003/0220667 A1 | 11/2003 | Van Der Burg et al. |
| 2003/0225445 A1 | 12/2003 | Derus et al. |
| 2003/0229366 A1 | 12/2003 | Reggie et al. |
| 2003/0229390 A1 | 12/2003 | Ashton et al. |
| 2003/0233117 A1 | 12/2003 | Adams et al. |
| 2003/0236542 A1 | 12/2003 | Makower |
| 2003/0236567 A1 | 12/2003 | Elliot |
| 2003/0236568 A1 | 12/2003 | Hojeibane et al. |
| 2003/0236570 A1 | 12/2003 | Cook et al. |
| 2004/0004926 A1 | 1/2004 | Maeda |
| 2004/0006298 A1 | 1/2004 | Wilk |
| 2004/0006380 A1 | 1/2004 | Buck et al. |
| 2004/0015225 A1 | 1/2004 | Kim et al. |
| 2004/0015228 A1 | 1/2004 | Lombardi et al. |
| 2004/0018651 A1 | 1/2004 | Nadeau |
| 2004/0019348 A1 | 1/2004 | Stevens et al. |
| 2004/0019374 A1 | 1/2004 | Hojeibane et al. |
| 2004/0026389 A1 | 2/2004 | Kessler et al. |
| 2004/0033364 A1 | 2/2004 | Spiridigliozzi et al. |
| 2004/0034411 A1 | 2/2004 | Quijano et al. |
| 2004/0037946 A1 | 2/2004 | Morra et al. |
| 2004/0039343 A1 | 2/2004 | Eppstein et al. |
| 2004/0039436 A1 | 2/2004 | Spenser et al. |
| 2004/0044350 A1 | 3/2004 | Martin et al. |
| 2004/0044361 A1 | 3/2004 | Frazier et al. |
| 2004/0044392 A1 | 3/2004 | Von Oepen |
| 2004/0044400 A1 | 3/2004 | Cheng et al. |
| 2004/0044402 A1 | 3/2004 | Jung et al. |
| 2004/0049204 A1 | 3/2004 | Harari et al. |
| 2004/0049207 A1 | 3/2004 | Goldfarb et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0058097 A1 | 3/2004 | Weder |
| 2004/0059280 A1 | 3/2004 | Makower et al. |
| 2004/0059407 A1 | 3/2004 | Escamilla et al. |
| 2004/0059409 A1 | 3/2004 | Stenzel |
| 2004/0059429 A1 | 3/2004 | Amin et al. |
| 2004/0073157 A1 | 4/2004 | Knudson et al. |
| 2004/0073198 A1 | 4/2004 | Gilson et al. |
| 2004/0073238 A1 | 4/2004 | Makower |
| 2004/0073289 A1 | 4/2004 | Hartley |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0078950 A1 | 4/2004 | Schreck |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088042 A1 | 5/2004 | Kim et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093016 A1 | 5/2004 | Root et al. |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0102855 A1 | 5/2004 | Shank |
| 2004/0106931 A1 | 6/2004 | Guiles et al. |
| 2004/0106976 A1 | 6/2004 | Bailey et al. |
| 2004/0106990 A1 | 6/2004 | Spence et al. |
| 2004/0107004 A1 | 6/2004 | Levine et al. |
| 2004/0111096 A1 | 6/2004 | Tu et al. |
| 2004/0113306 A1 | 6/2004 | Rapacki et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127847 A1 | 7/2004 | DuBois et al. |
| 2004/0127912 A1 | 7/2004 | Rabkin et al. |
| 2004/0127936 A1 | 7/2004 | Salahieh et al. |
| 2004/0127979 A1 | 7/2004 | Wilson et al. |
| 2004/0127982 A1 | 7/2004 | Machold et al. |
| 2004/0133154 A1 | 7/2004 | Flaherty et al. |
| 2004/0133225 A1 | 7/2004 | Makower |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0138745 A1 | 7/2004 | Macoviak et al. |
| 2004/0147868 A1 | 7/2004 | Bardsley et al. |
| 2004/0147869 A1 | 7/2004 | Wolf et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0153145 A1 | 8/2004 | Simionescu et al. |
| 2004/0153146 A1 | 8/2004 | Lashinski et al. |
| 2004/0158143 A1 | 8/2004 | Flaherty et al. |
| 2004/0158277 A1 | 8/2004 | Lowe et al. |
| 2004/0163094 A1 | 8/2004 | Matsui et al. |
| 2004/0167444 A1 | 8/2004 | Laroya et al. |
| 2004/0167565 A1 | 8/2004 | Beulke et al. |
| 2004/0167573 A1 | 8/2004 | Williamson, IV et al. |
| 2004/0167620 A1 | 8/2004 | Ortiz et al. |
| 2004/0168691 A1 | 9/2004 | Sharkawy et al. |
| 2004/0176791 A1 | 9/2004 | Lim et al. |
| 2004/0181140 A1 | 9/2004 | Falwell et al. |
| 2004/0186507 A1 | 9/2004 | Hall et al. |
| 2004/0186557 A1 | 9/2004 | Gambale et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0186587 A1 | 9/2004 | Ahern |
| 2004/0193180 A1 | 9/2004 | Buzzard et al. |
| 2004/0193244 A1 | 9/2004 | Hartley et al. |
| 2004/0193252 A1 | 9/2004 | Perez et al. |
| 2004/0193261 A1 | 9/2004 | Berreklouw |
| 2004/0197695 A1 | 10/2004 | Aono |

(56) References Cited

U.S. PATENT DOCUMENTS

| | | |
|---|---|---|
| 2004/0199245 A1 | 10/2004 | Lauterjung |
| 2004/0204683 A1 | 10/2004 | McGuckin, Jr. et al. |
| 2004/0204755 A1 | 10/2004 | Robin |
| 2004/0206363 A1 | 10/2004 | McCarthy et al. |
| 2004/0210104 A1 | 10/2004 | Lau et al. |
| 2004/0210190 A1 | 10/2004 | Kohler et al. |
| 2004/0210240 A1 | 10/2004 | Saint |
| 2004/0210301 A1 | 10/2004 | Obermiller |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215317 A1 | 10/2004 | Cummings |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0219180 A1 | 11/2004 | Gambale et al. |
| 2004/0220598 A1 | 11/2004 | Bolduc et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0236411 A1 | 11/2004 | Sarac et al. |
| 2004/0236418 A1 | 11/2004 | Stevens |
| 2004/0243143 A1 | 12/2004 | Corcoran et al. |
| 2004/0243221 A1 | 12/2004 | Fawzi et al. |
| 2004/0249343 A1 | 12/2004 | Cioanta |
| 2004/0254594 A1 | 12/2004 | Alfaro |
| 2004/0254636 A1 | 12/2004 | Flagle et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0000858 A1 | 1/2005 | Roovers |
| 2005/0004505 A1 | 1/2005 | Phelps et al. |
| 2005/0004558 A1 | 1/2005 | Gambale et al. |
| 2005/0004648 A1 | 1/2005 | Boekstegers |
| 2005/0008589 A1 | 1/2005 | Legrand et al. |
| 2005/0009000 A1 | 1/2005 | Wilhelm et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021136 A1 | 1/2005 | Xie et al. |
| 2005/0025857 A1 | 2/2005 | Schoenherr et al. |
| 2005/0027305 A1 | 2/2005 | Shiu et al. |
| 2005/0027348 A1 | 2/2005 | Case et al. |
| 2005/0033220 A1 | 2/2005 | Wilk et al. |
| 2005/0033398 A1 | 2/2005 | Seguin |
| 2005/0033402 A1 | 2/2005 | Cully et al. |
| 2005/0038495 A1 | 2/2005 | Greenan |
| 2005/0038509 A1 | 2/2005 | Ashe |
| 2005/0043585 A1 | 2/2005 | Datta et al. |
| 2005/0043711 A1 | 2/2005 | Corcoran et al. |
| 2005/0043757 A1 | 2/2005 | Arad et al. |
| 2005/0043759 A1 | 2/2005 | Chanduszko |
| 2005/0043760 A1 | 2/2005 | Fogarty et al. |
| 2005/0043781 A1 | 2/2005 | Foley |
| 2005/0043790 A1 | 2/2005 | Seguin |
| 2005/0049674 A1 | 3/2005 | Berra et al. |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060018 A1 | 3/2005 | Dittman |
| 2005/0060029 A1 | 3/2005 | Le et al. |
| 2005/0060030 A1 | 3/2005 | Lashinski et al. |
| 2005/0065594 A1 | 3/2005 | DiMatteo et al. |
| 2005/0070794 A1 | 3/2005 | Deal et al. |
| 2005/0070957 A1 | 3/2005 | Das |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0075776 A1 | 4/2005 | Cho |
| 2005/0084595 A1 | 4/2005 | Shukla et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0090846 A1 | 4/2005 | Pedersen et al. |
| 2005/0090890 A1 | 4/2005 | Wu et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096726 A1 | 5/2005 | Sequin et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0096768 A1 | 5/2005 | Huang et al. |
| 2005/0098547 A1 | 5/2005 | Cali et al. |
| 2005/0100580 A1 | 5/2005 | Osborne et al. |
| 2005/0101903 A1 | 5/2005 | Kohler et al. |
| 2005/0101904 A1 | 5/2005 | Wilk |
| 2005/0101968 A1 | 5/2005 | Dadourian |
| 2005/0107822 A1 | 5/2005 | Wasdyke |
| 2005/0107871 A1 | 5/2005 | Realyvasquez et al. |
| 2005/0113902 A1 | 5/2005 | Geiser et al. |
| 2005/0113904 A1 | 5/2005 | Shank et al. |
| 2005/0113910 A1 | 5/2005 | Paniagua et al. |
| 2005/0119688 A1 | 6/2005 | Bergheim |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0131438 A1 | 6/2005 | Cohn |
| 2005/0137499 A1 | 6/2005 | Sheets et al. |
| 2005/0137609 A1 | 6/2005 | Guiraudon |
| 2005/0137681 A1 | 6/2005 | Shoemaker et al. |
| 2005/0137682 A1 | 6/2005 | Justino |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143804 A1 | 6/2005 | Haverkost |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149159 A1 | 7/2005 | Andreas et al. |
| 2005/0149166 A1 | 7/2005 | Schaeffer et al. |
| 2005/0149181 A1 | 7/2005 | Eberhardt |
| 2005/0150775 A1 | 7/2005 | Zhang et al. |
| 2005/0159726 A1 | 7/2005 | Evans et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0171597 A1 | 8/2005 | Boatman et al. |
| 2005/0171598 A1 | 8/2005 | Schaeffer |
| 2005/0177227 A1 | 8/2005 | Heim et al. |
| 2005/0182483 A1 | 8/2005 | Osborne et al. |

(56) References Cited

U.S. PATENT DOCUMENTS

| | | |
|---|---|---|
| 2005/0182486 A1 | 8/2005 | Gabbay |
| 2005/0186349 A1 | 8/2005 | Loper et al. |
| 2005/0187616 A1 | 8/2005 | Realyvasquez |
| 2005/0192527 A1 | 9/2005 | Gharib et al. |
| 2005/0192665 A1 | 9/2005 | Spenser et al. |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0214342 A1 | 9/2005 | Tweden et al. |
| 2005/0222664 A1 | 10/2005 | Parker |
| 2005/0222668 A1 | 10/2005 | Schaeffer et al. |
| 2005/0222674 A1 | 10/2005 | Paine |
| 2005/0228334 A1 | 10/2005 | Knudson et al. |
| 2005/0228472 A1 | 10/2005 | Case et al. |
| 2005/0228495 A1 | 10/2005 | Macoviak |
| 2005/0228496 A1 | 10/2005 | Mensah et al. |
| 2005/0234546 A1 | 10/2005 | Nugent et al. |
| 2005/0240200 A1 | 10/2005 | Bergheim |
| 2005/0240262 A1 | 10/2005 | White |
| 2005/0240263 A1 | 10/2005 | Fogarty et al. |
| 2005/0251243 A1 | 11/2005 | Seppala et al. |
| 2005/0251250 A1 | 11/2005 | Verhoeven et al. |
| 2005/0251251 A1 | 11/2005 | Cribier |
| 2005/0251252 A1 | 11/2005 | Stobie |
| 2005/0256532 A1 | 11/2005 | Nayak et al. |
| 2005/0261759 A1 | 11/2005 | Lambrecht et al. |
| 2005/0267523 A1 | 12/2005 | Devellian et al. |
| 2005/0267560 A1 | 12/2005 | Bates |
| 2005/0267567 A1 | 12/2005 | Shalev |
| 2005/0267573 A9 | 12/2005 | Macoviak et al. |
| 2005/0283231 A1 | 12/2005 | Haug et al. |
| 2005/0283962 A1 | 12/2005 | Boudjemline |
| 2005/0288627 A1 | 12/2005 | Mogul |
| 2005/0288685 A1 | 12/2005 | Gulles et al. |
| 2005/0288706 A1 | 12/2005 | Widomski et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0009842 A1 | 1/2006 | Huynh et al. |
| 2006/0015168 A1 | 1/2006 | Gunderson |
| 2006/0025855 A1 | 2/2006 | Lashinski et al. |
| 2006/0025857 A1 | 2/2006 | Bergheim et al. |
| 2006/0028766 A1 | 2/2006 | Khizroev |
| 2006/0041218 A1 | 2/2006 | Phelps et al. |
| 2006/0047338 A1 | 3/2006 | Jenson et al. |
| 2006/0047343 A1 | 3/2006 | Oviatt et al. |
| 2006/0052736 A1 | 3/2006 | Tweden et al. |
| 2006/0052867 A1 | 3/2006 | Revuelta et al. |
| 2006/0058775 A1 | 3/2006 | Stevens et al. |
| 2006/0058864 A1 | 3/2006 | Schaeffer et al. |
| 2006/0058871 A1 | 3/2006 | Zakay et al. |
| 2006/0058872 A1 | 3/2006 | Salahieh et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0074484 A1 | 4/2006 | Huber |
| 2006/0074485 A1 | 4/2006 | Realyvasquez |
| 2006/0077447 A1 | 4/2006 | Sojian et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0111770 A1 | 5/2006 | Pavcnik et al. |
| 2006/0116757 A1 | 6/2006 | Lashinski et al. |
| 2006/0122692 A1 | 6/2006 | Gilad et al. |
| 2006/0135961 A1* | 6/2006 | Rosenman ......... A61M 25/0113 606/108 |
| 2006/0135964 A1 | 6/2006 | Vesely |
| 2006/0136034 A1 | 6/2006 | Modesitt et al. |
| 2006/0142846 A1 | 6/2006 | Pavcnik et al. |
| 2006/0142848 A1 | 6/2006 | Gabbay |
| 2006/0149360 A1 | 7/2006 | Schwammenthal et al. |
| 2006/0155312 A1 | 7/2006 | Levine et al. |
| 2006/0155366 A1 | 7/2006 | LaDuca et al. |
| 2006/0161248 A1 | 7/2006 | Case et al. |
| 2006/0161249 A1 | 7/2006 | Realyvasquez et al. |
| 2006/0161265 A1 | 7/2006 | Levine et al. |
| 2006/0167474 A1 | 7/2006 | Bloom et al. |
| 2006/0167543 A1 | 7/2006 | Bailey et al. |
| 2006/0173524 A1 | 8/2006 | Salahieh et al. |
| 2006/0178740 A1 | 8/2006 | Stacchino et al. |
| 2006/0190070 A1 | 8/2006 | Dieck et al. |
| 2006/0193885 A1 | 8/2006 | Leonard Neethling et al. |
| 2006/0195134 A1 | 8/2006 | Crittenden |
| 2006/0195183 A1 | 8/2006 | Navia et al. |
| 2006/0195186 A1 | 8/2006 | Drews et al. |
| 2006/0206192 A1 | 9/2006 | Tower et al. |
| 2006/0206202 A1 | 9/2006 | Bonhoeffer et al. |
| 2006/0210597 A1 | 9/2006 | Hiles |
| 2006/0212110 A1 | 9/2006 | Osborne et al. |
| 2006/0212111 A1 | 9/2006 | Case et al. |
| 2006/0217802 A1 | 9/2006 | Ruiz et al. |
| 2006/0224183 A1 | 10/2006 | Freudenthal |
| 2006/0229561 A1 | 10/2006 | Huszar |
| 2006/0229718 A1 | 10/2006 | Marquez |
| 2006/0229719 A1 | 10/2006 | Marquez et al. |
| 2006/0241745 A1 | 10/2006 | Solem |
| 2006/0246584 A1 | 11/2006 | Covelli |
| 2006/0247570 A1 | 11/2006 | Pokorney |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265043 A1 | 11/2006 | Mandrusov et al. |
| 2006/0265056 A1 | 11/2006 | Nguyen et al. |
| 2006/0270958 A1 | 11/2006 | George |
| 2006/0271149 A1 | 11/2006 | Berez et al. |
| 2006/0271161 A1 | 11/2006 | Meyer et al. |
| 2006/0271166 A1 | 11/2006 | Thill et al. |
| 2006/0271175 A1 | 11/2006 | Woolfson et al. |
| 2006/0276873 A1 | 12/2006 | Sato |
| 2006/0276874 A1 | 12/2006 | Wilson et al. |
| 2006/0276882 A1 | 12/2006 | Case et al. |
| 2006/0276887 A1 | 12/2006 | Brady et al. |
| 2006/0282161 A1 | 12/2006 | Huynh et al. |
| 2006/0287668 A1 | 12/2006 | Fawzi et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0010877 A1 | 1/2007 | Salahieh et al. |
| 2007/0010878 A1 | 1/2007 | Rafiee et al. |
| 2007/0010887 A1 | 1/2007 | Williams et al. |
| 2007/0016286 A1 | 1/2007 | Herrmann et al. |
| 2007/0016288 A1 | 1/2007 | Gurskis et al. |
| 2007/0020248 A1 | 1/2007 | Everaerts et al. |
| 2007/0021826 A1 | 1/2007 | Case et al. |
| 2007/0027518 A1 | 2/2007 | Case et al. |
| 2007/0027520 A1 | 2/2007 | Sherburne |
| 2007/0027533 A1 | 2/2007 | Douk |
| 2007/0027535 A1 | 2/2007 | Purdy, Jr. et al. |
| 2007/0032856 A1 | 2/2007 | Limon |
| 2007/0032879 A1 | 2/2007 | Levine et al. |
| 2007/0038291 A1 | 2/2007 | Case et al. |
| 2007/0038295 A1 | 2/2007 | Case et al. |
| 2007/0043420 A1 | 2/2007 | Lostetter |
| 2007/0043424 A1 | 2/2007 | Pryor |
| 2007/0043431 A1 | 2/2007 | Melsheimer |
| 2007/0043435 A1 | 2/2007 | Seguin et al. |
| 2007/0050014 A1 | 3/2007 | Johnson |

(56) References Cited

U.S. PATENT DOCUMENTS

| | | |
|---|---|---|
| 2007/0051377 A1 | 3/2007 | Douk et al. |
| 2007/0055340 A1 | 3/2007 | Pryor |
| 2007/0056346 A1 | 3/2007 | Spenser et al. |
| 2007/0060998 A1 | 3/2007 | Butterwick et al. |
| 2007/0061002 A1 | 3/2007 | Paul, Jr. et al. |
| 2007/0061008 A1 | 3/2007 | Salahieh et al. |
| 2007/0073389 A1 | 3/2007 | Bolduc et al. |
| 2007/0073392 A1 | 3/2007 | Heyninck-Jantz et al. |
| 2007/0078504 A1 | 4/2007 | Mialhe |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0100427 A1 | 5/2007 | Perouse |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0112355 A1 | 5/2007 | Salahieh et al. |
| 2007/0112358 A1 | 5/2007 | Abbott et al. |
| 2007/0112415 A1 | 5/2007 | Bartlett |
| 2007/0112422 A1 | 5/2007 | Dehdashtian |
| 2007/0118214 A1 | 5/2007 | Salahieh et al. |
| 2007/0123700 A1 | 5/2007 | Ueda et al. |
| 2007/0123979 A1 | 5/2007 | Perier et al. |
| 2007/0135889 A1 | 6/2007 | Moore et al. |
| 2007/0142906 A1 | 6/2007 | Figulla et al. |
| 2007/0142907 A1 | 6/2007 | Moaddeb et al. |
| 2007/0155010 A1 | 7/2007 | Farnsworth et al. |
| 2007/0156233 A1 | 7/2007 | Kapadia et al. |
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162113 A1 | 7/2007 | Sharkawy et al. |
| 2007/0173918 A1 | 7/2007 | Dreher et al. |
| 2007/0173932 A1 | 7/2007 | Cali et al. |
| 2007/0179592 A1 | 8/2007 | Schaeffer |
| 2007/0179600 A1 | 8/2007 | Vardi |
| 2007/0185513 A1 | 8/2007 | Woolfson et al. |
| 2007/0185565 A1 | 8/2007 | Schwammenthal et al. |
| 2007/0185571 A1 | 8/2007 | Kapadia et al. |
| 2007/0198078 A1 | 8/2007 | Berra et al. |
| 2007/0198097 A1 | 8/2007 | Zegdi |
| 2007/0203391 A1 | 8/2007 | Bloom et al. |
| 2007/0203503 A1 | 8/2007 | Salahieh et al. |
| 2007/0203560 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0225681 A1 | 9/2007 | House |
| 2007/0225802 A1 | 9/2007 | Forsell |
| 2007/0232898 A1 | 10/2007 | Huynh et al. |
| 2007/0233222 A1 | 10/2007 | Roeder et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1* | 10/2007 | Chia .................. A61F 2/2436 623/1.11 |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244543 A1 | 10/2007 | Mitchell |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244551 A1 | 10/2007 | Stobie |
| 2007/0244552 A1 | 10/2007 | Salahieh et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250151 A1 | 10/2007 | Pereira |
| 2007/0250160 A1 | 10/2007 | Rafiee |
| 2007/0255386 A1 | 11/2007 | Tenne |
| 2007/0255390 A1 | 11/2007 | Ducke et al. |
| 2007/0255394 A1 | 11/2007 | Ryan |
| 2007/0255396 A1 | 11/2007 | Douk et al. |
| 2007/0260301 A1 | 11/2007 | Chuter et al. |
| 2007/0260327 A1 | 11/2007 | Case et al. |
| 2007/0265701 A1 | 11/2007 | Gurskis et al. |
| 2007/0270751 A1 | 11/2007 | Stangenes et al. |
| 2007/0270943 A1 | 11/2007 | Solem et al. |
| 2007/0273813 A1 | 11/2007 | Yoshida et al. |
| 2007/0282436 A1 | 12/2007 | Pinchuk |
| 2007/0287717 A1 | 12/2007 | Fanning et al. |
| 2007/0288000 A1 | 12/2007 | Bonan |
| 2007/0288087 A1 | 12/2007 | Fearnot et al. |
| 2007/0288089 A1 | 12/2007 | Gurskis et al. |
| 2008/0004688 A1 | 1/2008 | Spenser et al. |
| 2008/0004696 A1 | 1/2008 | Vesely |
| 2008/0009934 A1 | 1/2008 | Schneider et al. |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0022504 A1 | 1/2008 | Melsheimer |
| 2008/0033534 A1 | 2/2008 | Cook et al. |
| 2008/0033541 A1 | 2/2008 | Gelbart et al. |
| 2008/0039925 A1 | 2/2008 | Ishimaru et al. |
| 2008/0039934 A1 | 2/2008 | Styrc |
| 2008/0045921 A1 | 2/2008 | Anderson et al. |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077227 A1 | 3/2008 | Ouellette et al. |
| 2008/0077234 A1 | 3/2008 | Styrc |
| 2008/0077236 A1 | 3/2008 | Letac et al. |
| 2008/0082165 A1 | 4/2008 | Wilson et al. |
| 2008/0082166 A1 | 4/2008 | Styrc et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0109070 A1 | 5/2008 | Wagner et al. |
| 2008/0125859 A1 | 5/2008 | Salahieh et al. |
| 2008/0127707 A1 | 6/2008 | Kokish et al. |
| 2008/0133002 A1 | 6/2008 | Gelbart et al. |
| 2008/0133003 A1 | 6/2008 | Seguin et al. |
| 2008/0140188 A1 | 6/2008 | Rahdert et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161909 A1 | 7/2008 | Kheradvar et al. |
| 2008/0161910 A1 | 7/2008 | Revuelta et al. |
| 2008/0161911 A1 | 7/2008 | Revuelta et al. |
| 2008/0172119 A1 | 7/2008 | Yamasaki et al. |
| 2008/0177381 A1 | 7/2008 | Navia et al. |
| 2008/0183273 A1 | 7/2008 | Mesana et al. |
| 2008/0188928 A1 | 8/2008 | Salahieh et al. |
| 2008/0195193 A1 | 8/2008 | Purdy et al. |
| 2008/0195199 A1 | 8/2008 | Kheradvar et al. |
| 2008/0200977 A1 | 8/2008 | Paul et al. |
| 2008/0208209 A1 | 8/2008 | Fischer et al. |
| 2008/0208327 A1 | 8/2008 | Rowe |
| 2008/0208328 A1 | 8/2008 | Antocci et al. |
| 2008/0208332 A1 | 8/2008 | Lamphere et al. |
| 2008/0215143 A1 | 9/2008 | Seguin |
| 2008/0215144 A1 | 9/2008 | Ryan et al. |
| 2008/0221672 A1 | 9/2008 | Lamphere et al. |

(56) References Cited

U.S. PATENT DOCUMENTS

| | | |
|---|---|---|
| 2008/0221703 A1 | 9/2008 | Que et al. |
| 2008/0228254 A1 | 9/2008 | Ryan |
| 2008/0228263 A1 | 9/2008 | Ryan |
| 2008/0234443 A1 | 9/2008 | Kiss et al. |
| 2008/0234797 A1 | 9/2008 | Styrc |
| 2008/0234814 A1 | 9/2008 | Salahieh et al. |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262590 A1 | 10/2008 | Murray |
| 2008/0262592 A1 | 10/2008 | Jordan et al. |
| 2008/0262593 A1 | 10/2008 | Ryan et al. |
| 2008/0262602 A1 | 10/2008 | Wilk et al. |
| 2008/0264102 A1 | 10/2008 | Berra |
| 2008/0269878 A1 | 10/2008 | Iobbi |
| 2008/0275549 A1 | 11/2008 | Rowe |
| 2008/0275550 A1 | 11/2008 | Kheradvar et al. |
| 2008/0288054 A1 | 11/2008 | Pulnev et al. |
| 2009/0005863 A1 | 1/2009 | Goetz et al. |
| 2009/0012356 A1 | 1/2009 | Dann et al. |
| 2009/0012600 A1 | 1/2009 | Styrc et al. |
| 2009/0030512 A1 | 1/2009 | Thielen et al. |
| 2009/0048656 A1 | 2/2009 | Wen |
| 2009/0054968 A1 | 2/2009 | Bonhoeffer et al. |
| 2009/0054969 A1 | 2/2009 | Salahieh et al. |
| 2009/0054976 A1 | 2/2009 | Tuval et al. |
| 2009/0062908 A1 | 3/2009 | Bonhoeffer et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0076598 A1 | 3/2009 | Salahieh et al. |
| 2009/0082844 A1 | 3/2009 | Zacharias et al. |
| 2009/0082858 A1 | 3/2009 | Nugent et al. |
| 2009/0085900 A1 | 4/2009 | Weiner |
| 2009/0093876 A1 | 4/2009 | Nitzan et al. |
| 2009/0093877 A1 | 4/2009 | Keidar et al. |
| 2009/0099640 A1 | 4/2009 | Weng |
| 2009/0099641 A1 | 4/2009 | Wu et al. |
| 2009/0099643 A1 | 4/2009 | Hyodoh et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0163951 A1 | 6/2009 | Simmons et al. |
| 2009/0164004 A1 | 6/2009 | Cohn |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192601 A1 | 7/2009 | Rafiee et al. |
| 2009/0198316 A1 | 8/2009 | Laske et al. |
| 2009/0198323 A1 | 8/2009 | Johnson et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222076 A1 | 9/2009 | Figulla et al. |
| 2009/0222082 A1 | 9/2009 | Lock et al. |
| 2009/0234407 A1 | 9/2009 | Hastings et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0248143 A1 | 10/2009 | Laham |
| 2009/0259306 A1 | 10/2009 | Rowe |
| 2009/0264759 A1 | 10/2009 | Byrd |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0287290 A1 | 11/2009 | Macaulay et al. |
| 2009/0287296 A1 | 11/2009 | Manasse |
| 2009/0287299 A1 | 11/2009 | Tabor et al. |
| 2009/0299462 A1 | 12/2009 | Fawzi et al. |
| 2009/0319037 A1 | 12/2009 | Rowe et al. |
| 2010/0004739 A1 | 1/2010 | Vesely |
| 2010/0004740 A1 | 1/2010 | Seguin et al. |
| 2010/0011564 A1 | 1/2010 | Millwee et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0049313 A1 | 2/2010 | Alon et al. |
| 2010/0057051 A1 | 3/2010 | Howat et al. |
| 2010/0057185 A1 | 3/2010 | Melsheimer et al. |
| 2010/0063573 A1 | 3/2010 | Hijlkema et al. |
| 2010/0069852 A1 | 3/2010 | Kelley |
| 2010/0069916 A1 | 3/2010 | Cully et al. |
| 2010/0070027 A1 | 3/2010 | Bonhoeffer et al. |
| 2010/0082089 A1 | 4/2010 | Quadri et al. |
| 2010/0082094 A1 | 4/2010 | Quadri et al. |
| 2010/0087913 A1 | 4/2010 | Rabkin et al. |
| 2010/0094399 A1 | 4/2010 | Dorn et al. |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0131057 A1 | 5/2010 | Subramanian et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0160725 A1 | 6/2010 | Kiser et al. |
| 2010/0161045 A1 | 6/2010 | Righini |
| 2010/0168839 A1 | 7/2010 | Braido et al. |
| 2010/0174362 A1 | 7/2010 | Straubinger et al. |
| 2010/0185275 A1 | 7/2010 | Richter et al. |
| 2010/0185277 A1 | 7/2010 | Braido et al. |
| 2010/0191320 A1 | 7/2010 | Straubinger et al. |
| 2010/0191326 A1 | 7/2010 | Alkhatib |
| 2010/0198346 A1 | 8/2010 | Keogh et al. |
| 2010/0210991 A1 | 8/2010 | Wilk et al. |
| 2010/0219092 A1 | 9/2010 | Salahieh et al. |
| 2010/0234932 A1 | 9/2010 | Arbefeuille et al. |
| 2010/0234940 A1 | 9/2010 | Dolan |
| 2010/0239917 A1 | 9/2010 | Lee et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1* | 9/2010 | Zhang ............... A61F 2/2427 623/2.11 |
| 2010/0256723 A1 | 10/2010 | Murray |
| 2010/0262231 A1 | 10/2010 | Tuval et al. |
| 2010/0268332 A1 | 10/2010 | Tuval et al. |
| 2010/0280459 A1 | 11/2010 | Werner |
| 2010/0280495 A1 | 11/2010 | Paul et al. |
| 2010/0286768 A1 | 11/2010 | Alkhatib |
| 2010/0292779 A1 | 11/2010 | Straubinger et al. |
| 2010/0292780 A1 | 11/2010 | Straubinger et al. |
| 2010/0292785 A1 | 11/2010 | Seguin et al. |
| 2010/0298931 A1 | 11/2010 | Quadri et al. |
| 2011/0004297 A1 | 1/2011 | Sogard et al. |
| 2011/0015616 A1 | 1/2011 | Straubinger et al. |
| 2011/0022157 A1 | 1/2011 | Essinger et al. |
| 2011/0029066 A1 | 2/2011 | Gilad et al. |
| 2011/0034852 A1 | 2/2011 | Hausler et al. |
| 2011/0040366 A1 | 2/2011 | Goetz et al. |
| 2011/0040374 A1 | 2/2011 | Goetz et al. |
| 2011/0071613 A1 | 3/2011 | Wood et al. |
| 2011/0093007 A1 | 4/2011 | Abbott et al. |
| 2011/0098805 A1 | 4/2011 | Dwork et al. |
| 2011/0106244 A1 | 5/2011 | Ferrari et al. |
| 2011/0118545 A1 | 5/2011 | Williams et al. |
| 2011/0137397 A1 | 6/2011 | Chau et al. |
| 2011/0166637 A1 | 7/2011 | Irwin et al. |
| 2011/0190862 A1 | 8/2011 | Bashiri et al. |
| 2011/0190874 A1 | 8/2011 | Celermajer et al. |
| 2011/0208290 A1 | 8/2011 | Straubinger et al. |
| 2011/0208297 A1 | 8/2011 | Tuval et al. |
| 2011/0224780 A1 | 9/2011 | Tabor et al. |
| 2011/0238159 A1 | 9/2011 | Guyenot et al. |

(56) References Cited

U.S. PATENT DOCUMENTS

| | | |
|---|---|---|
| 2011/0238167 A1 | 9/2011 | Dove et al. |
| 2011/0257729 A1 | 10/2011 | Spenser et al. |
| 2011/0257733 A1 | 10/2011 | Dwork |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264203 A1 | 10/2011 | Dwork et al. |
| 2011/0276121 A1 | 11/2011 | Levine |
| 2011/0276129 A1 | 11/2011 | Salahieh et al. |
| 2011/0288626 A1 | 11/2011 | Straubinger et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0035719 A1 | 2/2012 | Forster et al. |
| 2012/0035720 A1 | 2/2012 | Cali et al. |
| 2012/0041547 A1 | 2/2012 | Duffy et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059447 A1 | 3/2012 | Zilla et al. |
| 2012/0065464 A1 | 3/2012 | Ellis et al. |
| 2012/0078347 A1 | 3/2012 | Braido et al. |
| 2012/0078357 A1 | 3/2012 | Conklin |
| 2012/0078360 A1 | 3/2012 | Rafiee |
| 2012/0089224 A1 | 4/2012 | Haug et al. |
| 2012/0100182 A1 | 4/2012 | Mooney et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123515 A1 | 5/2012 | Hosford et al. |
| 2012/0123529 A1 | 5/2012 | Levi et al. |
| 2012/0130468 A1 | 5/2012 | Khosravi et al. |
| 2012/0132547 A1 | 5/2012 | Salahieh et al. |
| 2012/0136430 A1 | 5/2012 | Sochman et al. |
| 2012/0143084 A1 | 6/2012 | Shoham |
| 2012/0165957 A1 | 6/2012 | Everland et al. |
| 2012/0172982 A1 | 7/2012 | Stacchino et al. |
| 2012/0179244 A1 | 7/2012 | Schankereli et al. |
| 2012/0185030 A1 | 7/2012 | Igaki et al. |
| 2012/0197379 A1 | 8/2012 | Laske et al. |
| 2012/0209374 A1 | 8/2012 | Bonhoeffer et al. |
| 2012/0209376 A1 | 8/2012 | Hauser et al. |
| 2012/0221100 A1 | 8/2012 | Huber |
| 2012/0226341 A1 | 9/2012 | Schreck et al. |
| 2012/0283715 A1 | 11/2012 | Mihalik et al. |
| 2012/0283823 A1 | 11/2012 | Bonhoeffer et al. |
| 2012/0303113 A1 | 11/2012 | Benichou et al. |
| 2012/0303116 A1 | 11/2012 | Gorman, III et al. |
| 2012/0305441 A1 | 12/2012 | Murray et al. |
| 2012/0310332 A1 | 12/2012 | Murray et al. |
| 2012/0316637 A1 | 12/2012 | Holm et al. |
| 2012/0330408 A1 | 12/2012 | Hillukka et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030519 A1 | 1/2013 | Tran et al. |
| 2013/0030520 A1 | 1/2013 | Lee et al. |
| 2013/0046373 A1 | 2/2013 | Cartledge et al. |
| 2013/0053949 A1 | 2/2013 | Pintor et al. |
| 2013/0066342 A1 | 3/2013 | Dell et al. |
| 2013/0066419 A1 | 3/2013 | Gregg |
| 2013/0071441 A1 | 3/2013 | Iwazawa et al. |
| 2013/0073037 A1 | 3/2013 | Gregg et al. |
| 2013/0079867 A1 | 3/2013 | Hoffman et al. |
| 2013/0079869 A1 | 3/2013 | Straubinger et al. |
| 2013/0089655 A1 | 4/2013 | Gregg |
| 2013/0090728 A1 | 4/2013 | Solem |
| 2013/0090729 A1 | 4/2013 | Gregg et al. |
| 2013/0096664 A1 | 4/2013 | Goetz et al. |
| 2013/0116778 A1 | 5/2013 | Gregg et al. |
| 2013/0118949 A1 | 5/2013 | Chang et al. |
| 2013/0123757 A1 | 5/2013 | Crisostomo et al. |
| 2013/0123795 A1 | 5/2013 | Gamarra et al. |
| 2013/0123796 A1 | 5/2013 | Sutton et al. |
| 2013/0123898 A1 | 5/2013 | Tung et al. |
| 2013/0138207 A1 | 5/2013 | Quadri et al. |
| 2013/0144203 A1 | 6/2013 | Wilk et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0166017 A1 | 6/2013 | Cartledge et al. |
| 2013/0178930 A1 | 7/2013 | Straubinger et al. |
| 2013/0184813 A1 | 7/2013 | Quadri et al. |
| 2013/0190865 A1 | 7/2013 | Anderson |
| 2013/0204359 A1 | 8/2013 | Thubrikar et al. |
| 2013/0231735 A1 | 9/2013 | Deem et al. |
| 2013/0245752 A1 | 9/2013 | Goetz et al. |
| 2013/0253342 A1 | 9/2013 | Griswold et al. |
| 2013/0253635 A1 | 9/2013 | Straubinger et al. |
| 2013/0253640 A1 | 9/2013 | Meiri et al. |
| 2013/0268067 A1 | 10/2013 | Forster et al. |
| 2013/0274865 A1 | 10/2013 | Haverkost et al. |
| 2013/0274870 A1* | 10/2013 | Lombardi ............. A61F 2/2436 623/2.11 |
| 2013/0289698 A1 | 10/2013 | Wang et al. |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1 | 11/2013 | Kheradvar et al. |
| 2013/0310928 A1 | 11/2013 | Morriss et al. |
| 2013/0325101 A1 | 12/2013 | Goetz et al. |
| 2013/0338755 A1 | 12/2013 | Goetz et al. |
| 2013/0345799 A1 | 12/2013 | Lafontaine |
| 2014/0012368 A1 | 1/2014 | Sugimoto et al. |
| 2014/0012370 A1 | 1/2014 | Bonhoeffer et al. |
| 2014/0018911 A1 | 1/2014 | Zhou et al. |
| 2014/0052239 A1 | 2/2014 | Kong et al. |
| 2014/0058501 A1 | 2/2014 | Bonhoeffer et al. |
| 2014/0083190 A1 | 3/2014 | Kaack et al. |
| 2014/0088680 A1 | 3/2014 | Costello et al. |
| 2014/0094904 A1 | 4/2014 | Salahieh et al. |
| 2014/0114390 A1 | 4/2014 | Tobis et al. |
| 2014/0114405 A1 | 4/2014 | Paul et al. |
| 2014/0114406 A1 | 4/2014 | Salahieh et al. |
| 2014/0114407 A1 | 4/2014 | Rajamannan |
| 2014/0121766 A1 | 5/2014 | Salahieh et al. |
| 2014/0128969 A1 | 5/2014 | Hill et al. |
| 2014/0135912 A1 | 5/2014 | Salahieh et al. |
| 2014/0207229 A1 | 7/2014 | Shoemaker et al. |
| 2014/0222142 A1 | 8/2014 | Kovalsky et al. |
| 2014/0236287 A1 | 8/2014 | Clague et al. |
| 2014/0243962 A1 | 8/2014 | Wilson et al. |
| 2014/0243963 A1 | 8/2014 | Sheps et al. |
| 2014/0243967 A1 | 8/2014 | Salahieh et al. |
| 2014/0249621 A1 | 9/2014 | Eidenschink |
| 2014/0257473 A1 | 9/2014 | Rajamannan |
| 2014/0277414 A1 | 9/2014 | Kheradvar |
| 2014/0296962 A1 | 10/2014 | Cartledge et al. |
| 2014/0309732 A1 | 10/2014 | Solem |
| 2014/0316518 A1 | 10/2014 | Kheradvar et al. |
| 2014/0343669 A1 | 11/2014 | Lane et al. |
| 2014/0364799 A1* | 12/2014 | Beauvais ............. A61F 9/00736 604/28 |
| 2014/0379068 A1 | 12/2014 | Thielen et al. |
| 2015/0012085 A1 | 1/2015 | Salahieh et al. |
| 2015/0032056 A1* | 1/2015 | Okamura ............... A61B 90/94 604/164.1 |
| 2015/0032198 A1 | 1/2015 | Folk |
| 2015/0073540 A1 | 3/2015 | Salahieh et al. |
| 2015/0073541 A1 | 3/2015 | Salahieh et al. |
| 2015/0088252 A1 | 3/2015 | Jenson et al. |
| 2015/0094804 A1 | 4/2015 | Bonhoeffer et al. |
| 2015/0105857 A1 | 4/2015 | Bonhoeffer et al. |
| 2015/0127092 A1 | 5/2015 | Straubinger et al. |
| 2015/0127094 A1 | 5/2015 | Salahieh et al. |
| 2015/0142102 A1 | 5/2015 | Lafontaine et al. |
| 2015/0148894 A1 | 5/2015 | Damm et al. |

(56) References Cited

U.S. PATENT DOCUMENTS

| | | |
|---|---|---|
| 2015/0209142 A1 | 7/2015 | Paul et al. |
| 2015/0209146 A1 | 7/2015 | Hill et al. |
| 2015/0223933 A1 | 8/2015 | Haug et al. |
| 2015/0238315 A1 | 8/2015 | Rabito et al. |
| 2015/0245909 A1 | 9/2015 | Salahieh et al. |
| 2015/0272731 A1* | 10/2015 | Racchini ............ A61F 2/2418 623/2.11 |
| 2015/0320557 A1 | 11/2015 | Sutton et al. |
| 2015/0335423 A1 | 11/2015 | Gregg et al. |
| 2015/0352252 A1 | 12/2015 | Nakamura et al. |
| 2015/0359997 A1 | 12/2015 | Crisostomo et al. |
| 2016/0022418 A1 | 1/2016 | Salahieh et al. |
| 2016/0045306 A1 | 2/2016 | Agrawal et al. |
| 2016/0045307 A1 | 2/2016 | Yohanan et al. |
| 2016/0051362 A1 | 2/2016 | Cooper et al. |
| 2016/0067040 A1 | 3/2016 | Agrawal et al. |
| 2016/0120645 A1 | 5/2016 | Alon |
| 2016/0135951 A1 | 5/2016 | Salahieh et al. |
| 2016/0143731 A1 | 5/2016 | Backus et al. |
| 2016/0158003 A1 | 6/2016 | Wallace et al. |
| 2016/0166384 A1 | 6/2016 | Olson et al. |
| 2016/0199184 A1 | 7/2016 | Ma et al. |
| 2016/0206423 A1 | 7/2016 | O'Connor et al. |
| 2016/0213467 A1 | 7/2016 | Backus et al. |
| 2016/0220359 A1 | 8/2016 | Backus et al. |
| 2016/0220360 A1 | 8/2016 | Lin et al. |
| 2016/0220365 A1 | 8/2016 | Backus et al. |
| 2016/0250024 A1 | 9/2016 | Hill et al. |
| 2016/0256271 A1 | 9/2016 | Backus et al. |
| 2016/0262878 A1 | 9/2016 | Backus et al. |
| 2016/0346107 A1 | 12/2016 | Matthison-Hansen et al. |
| 2016/0354203 A1 | 12/2016 | Tuval et al. |
| 2016/0374793 A1 | 12/2016 | Lafontaine et al. |
| 2016/0376063 A1 | 12/2016 | Salahieh et al. |
| 2017/0000609 A1 | 1/2017 | Gross et al. |
| 2017/0007400 A1 | 1/2017 | Sogard et al. |
| 2017/0027654 A1 | 2/2017 | Frimer et al. |
| 2017/0027693 A1 | 2/2017 | Paul et al. |
| 2017/0049563 A1 | 2/2017 | Straubinger et al. |
| 2017/0049568 A1 | 2/2017 | Straubinger et al. |
| 2017/0056172 A1 | 3/2017 | Salahieh et al. |
| 2017/0065410 A1 | 3/2017 | Straubinger et al. |
| 2017/0087343 A1 | 3/2017 | Assaf et al. |
| 2017/0095595 A1 | 4/2017 | Nakamura |
| 2017/0212723 A1 | 7/2017 | Atarot et al. |
| 2017/0265849 A1 | 9/2017 | Assaf et al. |
| 2017/0333230 A1 | 11/2017 | Folan et al. |
| 2017/0348013 A1 | 12/2017 | Mottola et al. |
| 2018/0325604 A1 | 11/2018 | Atarot et al. |
| 2018/0368976 A1 | 12/2018 | Bonhoeffer et al. |
| 2019/0328522 A1 | 10/2019 | Straubinger et al. |
| 2020/0054449 A1 | 2/2020 | Min et al. |
| 2021/0038313 A1 | 2/2021 | Sholev et al. |
| 2021/0322153 A1 | 10/2021 | Tuval et al. |
| 2022/0192765 A1 | 6/2022 | Brasset et al. |
| 2022/0304803 A1 | 9/2022 | Guyenot et al. |

FOREIGN PATENT DOCUMENTS

| | | |
|---|---|---|
| AU | 777443 B2 | 10/2004 |
| AU | 778831 B2 | 12/2004 |
| AU | 2004231189 A1 | 12/2004 |
| AU | 2004242527 A1 | 1/2005 |
| AU | 2001281277 B2 | 9/2005 |
| AU | 2006308187 A1 | 5/2007 |
| AU | 2006310681 A1 | 5/2007 |
| AU | 2006328896 A1 | 6/2007 |
| AU | 2002329324 B2 | 7/2007 |
| AU | 2007294199 A1 | 3/2008 |
| AU | 2009200985 A1 | 4/2009 |
| AU | 2006328896 B2 | 8/2013 |
| CA | 2378589 A1 | 2/2001 |
| CA | 2381192 A1 | 2/2001 |
| CA | 2385662 A1 | 3/2001 |
| CA | 2407987 A1 | 11/2001 |
| CA | 2418958 A1 | 2/2002 |
| CA | 2435962 A1 | 8/2002 |
| CA | 2457755 A1 | 2/2003 |
| CA | 2436258 A1 | 1/2005 |
| CA | 2848485 A1 | 1/2005 |
| CA | 2848490 A1 | 1/2005 |
| CA | 2595233 A1 | 7/2006 |
| CA | 2627409 A1 | 5/2007 |
| CA | 2627555 | 5/2007 |
| CA | 2627555 A1 | 5/2007 |
| CA | 2634358 A1 | 6/2007 |
| CA | 2657839 A1 | 3/2008 |
| CA | 2659690 A1 | 3/2008 |
| CN | 1338951 A | 3/2002 |
| CN | 1342443 A | 4/2002 |
| CN | 1745727 A | 3/2006 |
| CN | 2762776 Y | 3/2006 |
| CN | 1897892 A | 1/2007 |
| CN | 2933337 Y | 8/2007 |
| CN | 101011298 A | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| CN | 102413793 A | 4/2012 |
| CN | 103118630 A | 5/2013 |
| DE | 2815756 A1 | 10/1979 |
| DE | 3640745 A1 | 6/1987 |
| DE | 3920657 A1 | 1/1991 |
| DE | 3640745 C2 | 3/1992 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 5/2000 |
| DE | 19857887 A1 | 7/2000 |
| DE | 19907646 A1 | 8/2000 |
| DE | 10010073 A1 | 9/2001 |
| DE | 10010074 A1 | 10/2001 |
| DE | 10034105 C1 | 4/2002 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 10048814 A1 | 5/2002 |
| DE | 10121210 A1 | 11/2002 |
| DE | 19546692 C2 | 11/2002 |
| DE | 10301026 A1 | 2/2004 |
| DE | 10048814 B4 | 4/2004 |
| DE | 10049812 B4 | 6/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10049815 B4 | 10/2005 |
| DE | 10010073 B4 | 12/2005 |
| DE | 102005003632 A1 | 8/2006 |
| DE | 10 2005 051 849 | 5/2007 |
| DE | 102005051849 A1 | 5/2007 |
| DE | 102005052628 A1 | 5/2007 |
| DE | 202007005491 U1 | 6/2007 |
| DE | 20221871 U1 | 9/2008 |
| DE | 69937568 T2 | 9/2008 |
| EP | 0084395 A1 | 7/1983 |
| EP | 0103546 A1 | 3/1984 |
| EP | 0103546 B1 | 5/1988 |
| EP | 0144167 B1 | 11/1989 |
| EP | 0402036 A1 | 12/1990 |
| EP | 0402176 A2 | 12/1990 |
| EP | 0411118 A1 | 2/1991 |
| EP | 0458877 A1 | 12/1991 |
| EP | 0515324 A1 | 11/1992 |
| EP | 0547135 A1 | 6/1993 |
| EP | 0579523 A1 | 1/1994 |
| EP | 0402176 B1 | 4/1994 |
| EP | 0592410 A1 | 4/1994 |

(56) References Cited

FOREIGN PATENT DOCUMENTS

| | | |
|---|---|---|
| EP | 0597967 A1 | 5/1994 |
| EP | 0597967 A4 | 12/1994 |
| EP | 0458877 B1 | 5/1995 |
| EP | 0657147 A2 | 6/1995 |
| EP | 0592410 B1 | 10/1995 |
| EP | 0696447 A2 | 2/1996 |
| EP | 0402036 B1 | 4/1996 |
| EP | 0729364 A1 | 9/1996 |
| EP | 0732088 A2 | 9/1996 |
| EP | 0756498 A1 | 2/1997 |
| EP | 0409929 B1 | 4/1997 |
| EP | 0778775 A1 | 6/1997 |
| EP | 0786970 A1 | 8/1997 |
| EP | 0792624 A1 | 9/1997 |
| EP | 0797957 A1 | 10/1997 |
| EP | 0797958 A1 | 10/1997 |
| EP | 0799604 A1 | 10/1997 |
| EP | 0801928 A1 | 10/1997 |
| EP | 0815798 A2 | 1/1998 |
| EP | 0826346 A1 | 3/1998 |
| EP | 0829239 A1 | 3/1998 |
| EP | 0836834 A2 | 4/1998 |
| EP | 0850607 A1 | 7/1998 |
| EP | 0853921 A2 | 7/1998 |
| EP | 0858779 A1 | 8/1998 |
| EP | 0871414 A1 | 10/1998 |
| EP | 0876796 A2 | 11/1998 |
| EP | 0876803 A2 | 11/1998 |
| EP | 0778775 B1 | 1/1999 |
| EP | 0888142 A1 | 1/1999 |
| EP | 0888750 A1 | 1/1999 |
| EP | 0895752 A1 | 2/1999 |
| EP | 0896813 A2 | 2/1999 |
| EP | 0903122 A2 | 3/1999 |
| EP | 0876796 A3 | 5/1999 |
| EP | 0928615 A1 | 7/1999 |
| EP | 0657147 B1 | 8/1999 |
| EP | 0934728 A2 | 8/1999 |
| EP | 0938877 A2 | 9/1999 |
| EP | 0943302 A2 | 9/1999 |
| EP | 0597967 B1 | 12/1999 |
| EP | 0696447 B1 | 1/2000 |
| EP | 0971649 A1 | 1/2000 |
| EP | 0986348 A1 | 3/2000 |
| EP | 1000590 A1 | 5/2000 |
| EP | 1011523 A1 | 6/2000 |
| EP | 1020166 A1 | 7/2000 |
| EP | 1027870 A1 | 8/2000 |
| EP | 1041942 A1 | 10/2000 |
| EP | 1041943 A1 | 10/2000 |
| EP | 1051204 A2 | 11/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 1089676 A2 | 4/2001 |
| EP | 1093771 A2 | 4/2001 |
| EP | 1097676 A1 | 5/2001 |
| EP | 1112042 A1 | 7/2001 |
| EP | 1112097 A1 | 7/2001 |
| EP | 1117446 A1 | 7/2001 |
| EP | 1158937 A1 | 12/2001 |
| EP | 0547135 B1 | 1/2002 |
| EP | 0729364 B1 | 1/2002 |
| EP | 1164976 A1 | 1/2002 |
| EP | 1166721 A2 | 1/2002 |
| EP | 1171061 A1 | 1/2002 |
| EP | 1206179 A1 | 5/2002 |
| EP | 0756498 B1 | 7/2002 |
| EP | 1233731 A1 | 8/2002 |
| EP | 0986348 B1 | 9/2002 |
| EP | 1235537 A1 | 9/2002 |
| EP | 1248655 A1 | 10/2002 |
| EP | 1251804 A1 | 10/2002 |
| EP | 1251805 A2 | 10/2002 |
| EP | 1255510 A1 | 11/2002 |
| EP | 1257305 A1 | 11/2002 |
| EP | 1259193 A1 | 11/2002 |
| EP | 1259195 A1 | 11/2002 |
| EP | 0959815 B1 | 12/2002 |
| EP | 0971649 B1 | 12/2002 |
| EP | 1262201 A1 | 12/2002 |
| EP | 1264582 A2 | 12/2002 |
| EP | 1281357 A2 | 2/2003 |
| EP | 1281375 A2 | 2/2003 |
| EP | 0888142 B1 | 5/2003 |
| EP | 1112097 B1 | 6/2003 |
| EP | 1330213 A1 | 7/2003 |
| EP | 0937439 B1 | 9/2003 |
| EP | 1017868 B1 | 9/2003 |
| EP | 1340473 A2 | 9/2003 |
| EP | 1347785 A1 | 10/2003 |
| EP | 1354569 A1 | 10/2003 |
| EP | 1356793 A2 | 10/2003 |
| EP | 1281375 A3 | 12/2003 |
| EP | 1340473 A3 | 2/2004 |
| EP | 1041943 B1 | 3/2004 |
| EP | 1356793 A3 | 3/2004 |
| EP | 1395208 A1 | 3/2004 |
| EP | 1401359 A2 | 3/2004 |
| EP | 0871414 B1 | 4/2004 |
| EP | 1406561 A2 | 4/2004 |
| EP | 1408882 A1 | 4/2004 |
| EP | 1042045 B1 | 5/2004 |
| EP | 1414295 A2 | 5/2004 |
| EP | 0819013 B1 | 6/2004 |
| EP | 1430853 A2 | 6/2004 |
| EP | 1347785 B1 | 7/2004 |
| EP | 1435878 A1 | 7/2004 |
| EP | 1435879 A1 | 7/2004 |
| EP | 1439800 A2 | 7/2004 |
| EP | 1441672 A1 | 8/2004 |
| EP | 0954248 B1 | 9/2004 |
| EP | 1452153 A1 | 9/2004 |
| EP | 0987998 B1 | 10/2004 |
| EP | 1206179 B1 | 10/2004 |
| EP | 1469797 A1 | 10/2004 |
| EP | 1087727 B1 | 11/2004 |
| EP | 1115452 A1 | 11/2004 |
| EP | 1117446 B1 | 11/2004 |
| EP | 1472996 A1 | 11/2004 |
| EP | 1477202 A2 | 11/2004 |
| EP | 1107710 B1 | 12/2004 |
| EP | 1233731 B1 | 12/2004 |
| EP | 1484081 A1 | 12/2004 |
| EP | 1494616 A2 | 1/2005 |
| EP | 1499366 A1 | 1/2005 |
| EP | 1143879 B1 | 3/2005 |
| EP | 1516599 A2 | 3/2005 |
| EP | 1518518 A2 | 3/2005 |
| EP | 1229864 B1 | 4/2005 |
| EP | 1253875 B1 | 4/2005 |
| EP | 1519697 A1 | 4/2005 |
| EP | 1521414 A1 | 4/2005 |
| EP | 1522278 A2 | 4/2005 |
| EP | 1088529 B1 | 6/2005 |
| EP | 1093771 B1 | 6/2005 |
| EP | 1251803 B1 | 6/2005 |
| EP | 1430853 A3 | 6/2005 |
| EP | 1539047 A2 | 6/2005 |
| EP | 1547533 A2 | 6/2005 |
| EP | 1059894 B1 | 7/2005 |
| EP | 1551274 A2 | 7/2005 |
| EP | 1551336 A1 | 7/2005 |
| EP | 1000590 B1 | 8/2005 |
| EP | 1027013 B1 | 8/2005 |
| EP | 1078610 B1 | 8/2005 |
| EP | 1560542 A1 | 8/2005 |
| EP | 1562515 A1 | 8/2005 |
| EP | 1570809 A1 | 9/2005 |
| EP | 1576937 A2 | 9/2005 |
| EP | 0943302 B1 | 10/2005 |
| EP | 1267753 B1 | 10/2005 |
| EP | 1582178 A2 | 10/2005 |

(56) References Cited

FOREIGN PATENT DOCUMENTS

| | | |
|---|---|---|
| EP | 1582179 A2 | 10/2005 |
| EP | 1011523 B1 | 11/2005 |
| EP | 1067869 B1 | 11/2005 |
| EP | 1469797 B1 | 11/2005 |
| EP | 1589902 A1 | 11/2005 |
| EP | 1598031 A2 | 11/2005 |
| EP | 1600110 A1 | 11/2005 |
| EP | 1600121 A1 | 11/2005 |
| EP | 0786970 B1 | 12/2005 |
| EP | 1156757 B1 | 12/2005 |
| EP | 1603493 A2 | 12/2005 |
| EP | 1605871 A1 | 12/2005 |
| EP | 1021141 B1 | 1/2006 |
| EP | 1614400 A2 | 1/2006 |
| EP | 1616531 A2 | 1/2006 |
| EP | 1616536 A2 | 1/2006 |
| EP | 1041942 B1 | 6/2006 |
| EP | 1441672 A4 | 6/2006 |
| EP | 1663070 A2 | 6/2006 |
| EP | 1667614 A1 | 6/2006 |
| EP | 1494616 A4 | 7/2006 |
| EP | 1690515 A1 | 8/2006 |
| EP | 1702247 A2 | 9/2006 |
| EP | 1051204 B1 | 12/2006 |
| EP | 1734902 A1 | 12/2006 |
| EP | 1395208 B1 | 1/2007 |
| EP | 1251805 B1 | 3/2007 |
| EP | 1255510 B1 | 4/2007 |
| EP | 1499366 B1 | 7/2007 |
| EP | 1600121 B1 | 7/2007 |
| EP | 1835948 A1 | 9/2007 |
| EP | 1112042 B1 | 11/2007 |
| EP | 1251797 B1 | 11/2007 |
| EP | 1616531 B1 | 12/2007 |
| EP | 1863545 A2 | 12/2007 |
| EP | 1878407 A1 | 1/2008 |
| EP | 1886649 A2 | 2/2008 |
| EP | 1406561 A4 | 3/2008 |
| EP | 1893132 A2 | 3/2008 |
| EP | 1900343 A2 | 3/2008 |
| EP | 1901681 A1 | 3/2008 |
| EP | 1435878 B1 | 4/2008 |
| EP | 1886649 A3 | 4/2008 |
| EP | 1251804 B1 | 7/2008 |
| EP | 1605871 B1 | 7/2008 |
| EP | 1968491 A2 | 9/2008 |
| EP | 1259195 B1 | 10/2008 |
| EP | 1980220 A1 | 10/2008 |
| EP | 1994913 A2 | 11/2008 |
| EP | 1994913 A3 | 12/2008 |
| EP | 2000115 A2 | 12/2008 |
| EP | 1560542 A4 | 1/2009 |
| EP | 1408882 B1 | 2/2009 |
| EP | 1255510 B3 | 3/2009 |
| EP | 1330213 B1 | 3/2009 |
| EP | 2033593 A1 | 3/2009 |
| EP | 2047824 A1 | 4/2009 |
| EP | 2059192 A1 | 5/2009 |
| EP | 2074964 A1 | 7/2009 |
| EP | 1401359 B1 | 8/2009 |
| EP | 1968491 B1 | 7/2010 |
| EP | 1259193 B1 | 11/2010 |
| EP | 2257242 A1 | 12/2010 |
| EP | 2266503 A2 | 12/2010 |
| EP | 2266504 A2 | 12/2010 |
| EP | 1893132 B1 | 3/2011 |
| EP | 2266503 A3 | 4/2011 |
| EP | 2266504 A3 | 4/2011 |
| EP | 2059192 B1 | 7/2011 |
| EP | 1441672 B1 | 9/2011 |
| EP | 2364669 A2 | 9/2011 |
| EP | 2387977 A1 | 11/2011 |
| EP | 1603493 B1 | 12/2011 |
| EP | 1281375 B1 | 2/2012 |
| EP | 2364669 A3 | 3/2012 |
| EP | 2047824 B1 | 5/2012 |
| EP | 2474287 A1 | 7/2012 |
| EP | 2387977 B1 | 11/2013 |
| EP | 1551274 B1 | 12/2014 |
| EP | 2874812 A1 | 5/2015 |
| EP | 2749254 B1 | 6/2015 |
| EP | 1702247 B1 | 8/2015 |
| EP | 2926766 A1 | 10/2015 |
| EP | 1519697 B1 | 11/2015 |
| EP | 1863545 B1 | 11/2015 |
| EP | 1835948 B1 | 2/2016 |
| EP | 1734902 B1 | 6/2016 |
| EP | 3028668 A1 | 6/2016 |
| EP | 1539047 B1 | 11/2016 |
| EP | 1667614 B1 | 12/2016 |
| EP | 3181096 A1 | 6/2017 |
| EP | 1667614 B2 | 4/2020 |
| FR | 2788217 A1 | 7/2000 |
| FR | 2815844 A1 | 5/2002 |
| FR | 2828263 A1 | 2/2003 |
| GB | 2433700 A | 7/2007 |
| GB | 2440809 A | 2/2008 |
| JP | 52-86296 | 7/1977 |
| JP | S5286296 A | 7/1977 |
| JP | S54137896 U | 9/1979 |
| JP | 62-227352 | 10/1987 |
| JP | S62227352 A | 10/1987 |
| JP | 1049571 A | 2/1989 |
| JP | S6449571 A | 2/1989 |
| JP | H0447576 B2 | 8/1992 |
| JP | H04505866 A | 10/1992 |
| JP | H06505187 A | 6/1994 |
| JP | H06343703 A | 12/1994 |
| JP | 7-504091 | 5/1995 |
| JP | H07504091 A | 5/1995 |
| JP | H07505803 A | 6/1995 |
| JP | H07265339 A | 10/1995 |
| JP | H0833715 A | 2/1996 |
| JP | H1049571 A | 2/1998 |
| JP | H10507673 A | 7/1998 |
| JP | 2001000460 A | 1/2001 |
| JP | 2001504016 A | 3/2001 |
| JP | 2001526574 A | 12/2001 |
| JP | 2002525168 A | 8/2002 |
| JP | 2002525169 A | 8/2002 |
| JP | 2002536115 A | 10/2002 |
| JP | 2003515386 A | 5/2003 |
| JP | 2003518984 A | 6/2003 |
| JP | 2003-523262 | 8/2003 |
| JP | 2003-524504 | 8/2003 |
| JP | 2003523262 A | 8/2003 |
| JP | 2003524504 A | 8/2003 |
| JP | 2004504111 A | 2/2004 |
| JP | 2004130068 A | 4/2004 |
| JP | 2004514467 A | 5/2004 |
| JP | 2004255186 A | 9/2004 |
| JP | 2004267750 A | 9/2004 |
| JP | 2004283461 A | 10/2004 |
| JP | 2005505343 A | 2/2005 |
| JP | 2005-118585 | 5/2005 |
| JP | 2005118585 A | 5/2005 |
| JP | 2007516055 A | 6/2007 |
| JP | 2007521125 A | 8/2007 |
| JP | 2007-296375 | 11/2007 |
| JP | 2007296375 A | 11/2007 |
| JP | 2007298375 A | 11/2007 |
| JP | 2007534381 A | 11/2007 |
| JP | 2007536003 A | 12/2007 |
| JP | 2008506497 A | 3/2008 |
| JP | 2008514345 A | 5/2008 |
| JP | 2008535572 A | 9/2008 |
| JP | 2008539305 A | 11/2008 |
| JP | 2008539985 A | 11/2008 |
| JP | 2008541865 A | 11/2008 |
| JP | 2009034529 A | 2/2009 |
| JP | 2009061293 A | 3/2009 |
| JP | 2009509635 A | 3/2009 |
| JP | 4246433 B2 | 4/2009 |
| JP | 2009520535 A | 5/2009 |

(56) References Cited

FOREIGN PATENT DOCUMENTS

| | | |
|---|---|---|
| JP | 2009131397 A | 6/2009 |
| JP | 4295460 B2 | 7/2009 |
| JP | 2009528905 A | 8/2009 |
| JP | 2009534157 A | 9/2009 |
| JP | 2010525896 A | 7/2010 |
| JP | 2010526609 A | 8/2010 |
| JP | 4636794 B2 | 2/2011 |
| JP | 2011509805 A | 3/2011 |
| JP | 4739223 B2 | 8/2011 |
| JP | 2012500665 A | 1/2012 |
| JP | 4904362 B2 | 3/2012 |
| JP | 4912395 B2 | 4/2012 |
| JP | 2012518446 A | 8/2012 |
| JP | 2013520260 A | 6/2013 |
| JP | 2013521884 A | 6/2013 |
| JP | 2013526388 A | 6/2013 |
| JP | 5341455 B2 | 11/2013 |
| JP | 2013540495 A | 11/2013 |
| JP | 6144009 B2 | 6/2017 |
| JP | 6449571 B2 | 1/2019 |
| WO | WO 92/12690 | 8/1982 |
| WO | WO-8402266 A1 | 6/1984 |
| WO | WO-90/09102 | 8/1990 |
| WO | WO-9009102 A1 | 8/1990 |
| WO | WO-9014804 A1 | 12/1990 |
| WO | WO-9117720 A1 | 11/1991 |
| WO | WO-9203990 A1 | 3/1992 |
| WO | WO-9212690 A1 | 8/1992 |
| WO | WO-9214419 A1 | 9/1992 |
| WO | WO-9217118 A1 | 10/1992 |
| WO | WO-9301768 A1 | 2/1993 |
| WO | WO-9315693 A1 | 8/1993 |
| WO | WO-9320757 A2 | 10/1993 |
| WO | WO-9504556 A2 | 2/1995 |
| WO | WO-9504556 A3 | 4/1995 |
| WO | WO-9511055 A1 | 4/1995 |
| WO | WO-95/24873 | 9/1995 |
| WO | WO-9524873 A1 | 9/1995 |
| WO | WO-95/28183 | 10/1995 |
| WO | WO-9528183 A1 | 10/1995 |
| WO | WO-9528899 A1 | 11/1995 |
| WO | WO-9529640 A1 | 11/1995 |
| WO | WO-9529713 A1 | 11/1995 |
| WO | WO-96/13227 | 5/1996 |
| WO | WO-9613227 A1 | 5/1996 |
| WO | WO-9614032 A1 | 5/1996 |
| WO | WO-9624306 A1 | 8/1996 |
| WO | WO-9630072 A1 | 10/1996 |
| WO | WO-9632972 A1 | 10/1996 |
| WO | WO-9635469 A1 | 11/1996 |
| WO | WO-9639962 A1 | 12/1996 |
| WO | WO-9639964 A1 | 12/1996 |
| WO | WO-9639965 A1 | 12/1996 |
| WO | WO-9640012 A1 | 12/1996 |
| WO | WO-9713463 A1 | 4/1997 |
| WO | WO-9713471 A1 | 4/1997 |
| WO | WO-9724082 A1 | 7/1997 |
| WO | WO-9727893 A1 | 8/1997 |
| WO | WO-9727897 A1 | 8/1997 |
| WO | WO-9727898 A1 | 8/1997 |
| WO | WO-9728839 A1 | 8/1997 |
| WO | WO-97/32615 | 9/1997 |
| WO | WO-9732551 A1 | 9/1997 |
| WO | WO-9732615 A1 | 9/1997 |
| WO | WO-9743961 A1 | 11/1997 |
| WO | WO-9748350 A1 | 12/1997 |
| WO | WO-9803118 A1 | 1/1998 |
| WO | WO-9806356 A1 | 2/1998 |
| WO | WO-9808456 A1 | 3/1998 |
| WO | WO-9810714 A1 | 3/1998 |
| WO | WO-9811846 A1 | 3/1998 |
| WO | WO-9814137 A1 | 4/1998 |
| WO | WO-9816161 A1 | 4/1998 |
| WO | WO-9819633 A1 | 5/1998 |
| WO | WO-9824373 A1 | 6/1998 |
| WO | WO-9825533 A1 | 6/1998 |
| WO | WO-9825549 A1 | 6/1998 |
| WO | WO-9829057 A1 | 7/1998 |
| WO | WO-9836790 A1 | 8/1998 |
| WO | WO-9838916 A1 | 9/1998 |
| WO | WO-9838925 A1 | 9/1998 |
| WO | WO-9838939 A1 | 9/1998 |
| WO | WO-9838941 A1 | 9/1998 |
| WO | WO-9839038 A1 | 9/1998 |
| WO | WO 98/43556 | 10/1998 |
| WO | WO-98/46165 | 10/1998 |
| WO | WO-9843556 A1 | 10/1998 |
| WO | WO-9844869 A1 | 10/1998 |
| WO | WO-9846115 A2 | 10/1998 |
| WO | WO-9846119 A1 | 10/1998 |
| WO | WO-9846165 A1 | 10/1998 |
| WO | WO-9849964 A1 | 11/1998 |
| WO | WO-9850103 A1 | 11/1998 |
| WO | WO-9853759 A2 | 12/1998 |
| WO | WO-9853761 A1 | 12/1998 |
| WO | WO-9855027 A2 | 12/1998 |
| WO | WO-9855047 A1 | 12/1998 |
| WO | WO-9857590 A1 | 12/1998 |
| WO | WO-9857591 A1 | 12/1998 |
| WO | WO-9857592 A1 | 12/1998 |
| WO | WO-9857599 A2 | 12/1998 |
| WO | WO-9907296 A1 | 2/1999 |
| WO | WO-9908624 A1 | 2/1999 |
| WO | WO-9915112 A1 | 4/1999 |
| WO | WO-9915220 A1 | 4/1999 |
| WO | WO-9917671 A1 | 4/1999 |
| WO | WO-9917683 A1 | 4/1999 |
| WO | WO-9921490 A1 | 5/1999 |
| WO | WO-9921510 A1 | 5/1999 |
| WO | WO-9922655 A1 | 5/1999 |
| WO | WO-9922656 A1 | 5/1999 |
| WO | WO-9922658 A1 | 5/1999 |
| WO | WO-9925273 A1 | 5/1999 |
| WO | WO-9927985 A1 | 6/1999 |
| WO | WO-99/37337 | 7/1999 |
| WO | WO-9933414 A1 | 7/1999 |
| WO | WO-9935977 A1 | 7/1999 |
| WO | WO-9935979 A1 | 7/1999 |
| WO | WO-9935980 A1 | 7/1999 |
| WO | WO-9936000 A1 | 7/1999 |
| WO | WO-9936001 A1 | 7/1999 |
| WO | WO-9937337 A2 | 7/1999 |
| WO | WO-9938459 A2 | 8/1999 |
| WO | WO-9940853 A1 | 8/1999 |
| WO | WO-9940868 A1 | 8/1999 |
| WO | WO-9940963 A1 | 8/1999 |
| WO | WO-9940964 A1 | 8/1999 |
| WO | WO-9942058 A1 | 8/1999 |
| WO | WO-9944524 A2 | 9/1999 |
| WO | WO-9944540 A2 | 9/1999 |
| WO | WO-9944542 A2 | 9/1999 |
| WO | WO-9947071 A1 | 9/1999 |
| WO | WO-9947075 A1 | 9/1999 |
| WO | WO-9948545 A1 | 9/1999 |
| WO | WO-9948549 A2 | 9/1999 |
| WO | WO-9949793 A1 | 10/1999 |
| WO | WO-9949910 A2 | 10/1999 |
| WO | WO-9951162 A1 | 10/1999 |
| WO | WO-9951165 A1 | 10/1999 |
| WO | WO-9953863 A1 | 10/1999 |
| WO | WO-9953987 A1 | 10/1999 |
| WO | WO-9955406 A1 | 11/1999 |
| WO | WO-99/66863 | 12/1999 |
| WO | WO-9960941 A1 | 12/1999 |
| WO | WO-9962430 A1 | 12/1999 |
| WO | WO-9966863 A2 | 12/1999 |
| WO | WO 00/02503 A1 | 1/2000 |
| WO | WO-0002503 A1 | 1/2000 |
| WO | WO-0009059 A2 | 2/2000 |
| WO | WO-0009195 A1 | 2/2000 |
| WO | WO 00/15148 | 3/2000 |
| WO | WO-0010623 A1 | 3/2000 |
| WO | WO-0012029 A1 | 3/2000 |
| WO | WO-0013722 A1 | 3/2000 |

(56) References Cited

FOREIGN PATENT DOCUMENTS

| | | |
|---|---|---|
| WO | WO-0015146 A1 | 3/2000 |
| WO | WO-0015147 A1 | 3/2000 |
| WO | WO-0015148 A1 | 3/2000 |
| WO | WO-0015149 A1 | 3/2000 |
| WO | WO-0015275 A2 | 3/2000 |
| WO | WO-0016848 A1 | 3/2000 |
| WO | WO 00/18330 | 4/2000 |
| WO | WO-00/18445 | 4/2000 |
| WO | WO-0018302 A2 | 4/2000 |
| WO | WO-0018323 A2 | 4/2000 |
| WO | WO-0018325 A1 | 4/2000 |
| WO | WO-0018326 A1 | 4/2000 |
| WO | WO-0018330 A1 | 4/2000 |
| WO | WO-0018331 A2 | 4/2000 |
| WO | WO-0018333 A1 | 4/2000 |
| WO | WO-0018445 A1 | 4/2000 |
| WO | WO-0018462 A2 | 4/2000 |
| WO | WO-0021436 A1 | 4/2000 |
| WO | WO-0021461 A2 | 4/2000 |
| WO | WO-0021463 A1 | 4/2000 |
| WO | WO-0021464 A1 | 4/2000 |
| WO | WO 2000/25702 A1 | 5/2000 |
| WO | WO-0024449 A1 | 5/2000 |
| WO | WO-0025702 A1 | 5/2000 |
| WO | WO-0028922 A1 | 5/2000 |
| WO | WO-0028924 A2 | 5/2000 |
| WO | WO-0033725 A2 | 6/2000 |
| WO | WO-0035376 A1 | 6/2000 |
| WO | WO-0036997 A1 | 6/2000 |
| WO | WO-0041632 A1 | 7/2000 |
| WO | WO-0041633 A1 | 7/2000 |
| WO | WO-0041652 A1 | 7/2000 |
| WO | WO-0043051 A1 | 7/2000 |
| WO | WO-0044211 A1 | 7/2000 |
| WO | WO-0044308 A2 | 8/2000 |
| WO | WO-0044311 A2 | 8/2000 |
| WO | WO-0044313 A1 | 8/2000 |
| WO | WO-0044331 A1 | 8/2000 |
| WO | WO-0045711 A1 | 8/2000 |
| WO | WO-0045874 A1 | 8/2000 |
| WO | WO-0045886 A2 | 8/2000 |
| WO | WO-0047136 A1 | 8/2000 |
| WO | WO-0047139 A1 | 8/2000 |
| WO | WO-0048531 A1 | 8/2000 |
| WO | WO-0049952 A1 | 8/2000 |
| WO | WO-0049954 A2 | 8/2000 |
| WO | WO-0049956 A1 | 8/2000 |
| WO | WO-0049970 A1 | 8/2000 |
| WO | WO-00/53125 | 9/2000 |
| WO | WO-0053122 A1 | 9/2000 |
| WO | WO-0053125 A1 | 9/2000 |
| WO | WO-0054660 A1 | 9/2000 |
| WO | WO-0054661 A1 | 9/2000 |
| WO | WO-0056224 A1 | 9/2000 |
| WO | WO-0056225 A1 | 9/2000 |
| WO | WO-0056387 A1 | 9/2000 |
| WO | WO-00/62714 | 10/2000 |
| WO | WO-0060995 A2 | 10/2000 |
| WO | WO-0062714 A1 | 10/2000 |
| WO | WO-0066007 A1 | 11/2000 |
| WO | WO-0066009 A1 | 11/2000 |
| WO | WO-0066035 A1 | 11/2000 |
| WO | WO-0067661 A2 | 11/2000 |
| WO | WO-0069345 A1 | 11/2000 |
| WO | WO-0069367 A1 | 11/2000 |
| WO | WO-0069504 A1 | 11/2000 |
| WO | WO-0071195 A1 | 11/2000 |
| WO | WO-0078226 A1 | 12/2000 |
| WO | WO-0105331 A1 | 1/2001 |
| WO | WO-0106959 A1 | 2/2001 |
| WO | WO-0108566 A1 | 2/2001 |
| WO | WO-0108596 A1 | 2/2001 |
| WO | WO-0108602 A1 | 2/2001 |
| WO | WO-0110209 A1 | 2/2001 |
| WO | WO-0110320 A1 | 2/2001 |
| WO | WO-0110340 A1 | 2/2001 |
| WO | WO-0110341 A2 | 2/2001 |
| WO | WO-0110343 A1 | 2/2001 |
| WO | WO-0110347 A1 | 2/2001 |
| WO | WO-0110348 A1 | 2/2001 |
| WO | WO-0110349 A1 | 2/2001 |
| WO | WO-0110350 A1 | 2/2001 |
| WO | WO-0117440 A1 | 3/2001 |
| WO | WO-0117456 A1 | 3/2001 |
| WO | WO 2001/35870 A1 | 5/2001 |
| WO | WO-0135864 A1 | 5/2001 |
| WO | WO-0135870 A1 | 5/2001 |
| WO | WO-0136870 A1 | 5/2001 |
| WO | WO 2001/039700 A1 | 6/2001 |
| WO | WO-0139700 A1 | 6/2001 |
| WO | WO-0141679 A1 | 6/2001 |
| WO | WO-0149185 A1 | 7/2001 |
| WO | WO-0149187 A1 | 7/2001 |
| WO | WO-0149213 A2 | 7/2001 |
| WO | WO-0151104 A1 | 7/2001 |
| WO | WO-0154625 A1 | 8/2001 |
| WO | WO-0158503 A1 | 8/2001 |
| WO | WO-0162189 A1 | 8/2001 |
| WO | WO-0047139 A9 | 9/2001 |
| WO | WO-0164137 A1 | 9/2001 |
| WO | WO-0176510 A2 | 10/2001 |
| WO | WO-0182837 A2 | 11/2001 |
| WO | WO-0197715 A1 | 12/2001 |
| WO | WO-0211647 A2 | 2/2002 |
| WO | WO-0219926 A1 | 3/2002 |
| WO | WO-0222054 A1 | 3/2002 |
| WO | WO-0224118 A1 | 3/2002 |
| WO | WO 2002/36048 A1 | 5/2002 |
| WO | WO-0236048 A1 | 5/2002 |
| WO | WO-0241789 A2 | 5/2002 |
| WO | WO-0243620 A1 | 6/2002 |
| WO | WO-0247575 A2 | 6/2002 |
| WO | WO-0249540 A2 | 6/2002 |
| WO | WO 2002/051489 A2 | 7/2002 |
| WO | WO-02051489 A2 | 7/2002 |
| WO | WO-02056798 A2 | 7/2002 |
| WO | WO-02056955 A1 | 7/2002 |
| WO | WO-02058745 A1 | 8/2002 |
| WO | WO-02060509 A1 | 8/2002 |
| WO | WO-02067782 A2 | 9/2002 |
| WO | WO-02069842 A2 | 9/2002 |
| WO | WO-02076349 A1 | 10/2002 |
| WO | WO-02100297 A2 | 12/2002 |
| WO | WO-02100301 A1 | 12/2002 |
| WO | WO-02102286 A1 | 12/2002 |
| WO | WO 2003/003949 A2 | 1/2003 |
| WO | WO-03003943 A2 | 1/2003 |
| WO | WO-03003949 A2 | 1/2003 |
| WO | WO-03007795 A2 | 1/2003 |
| WO | WO 03/013239 | 2/2003 |
| WO | WO 2003/011195 A2 | 2/2003 |
| WO | WO-03009785 A1 | 2/2003 |
| WO | WO-03011195 A2 | 2/2003 |
| WO | WO-03013239 A2 | 2/2003 |
| WO | WO-03015851 A1 | 2/2003 |
| WO | WO-03028592 A1 | 4/2003 |
| WO | WO-03030776 A2 | 4/2003 |
| WO | WO-03032869 A1 | 4/2003 |
| WO | WO-03032870 A1 | 4/2003 |
| WO | WO-03037222 A2 | 5/2003 |
| WO | WO-03037227 A2 | 5/2003 |
| WO | WO-03047460 A2 | 6/2003 |
| WO | WO-03047468 A1 | 6/2003 |
| WO | WO-03047648 A2 | 6/2003 |
| WO | WO-03051231 A2 | 6/2003 |
| WO | WO-03063729 A2 | 8/2003 |
| WO | WO-03079928 A2 | 10/2003 |
| WO | WO-03079932 A2 | 10/2003 |
| WO | WO-03079933 A1 | 10/2003 |
| WO | WO-03088873 A1 | 10/2003 |
| WO | WO 2003/096935 A1 | 11/2003 |
| WO | WO-03015851 B1 | 11/2003 |
| WO | WO-03063729 A3 | 11/2003 |
| WO | WO-03092554 A1 | 11/2003 |

(56) References Cited

FOREIGN PATENT DOCUMENTS

| | | |
|---|---|---|
| WO | WO-03094793 A1 | 11/2003 |
| WO | WO-03094797 A1 | 11/2003 |
| WO | WO-03096932 A1 | 11/2003 |
| WO | WO-03096935 A1 | 11/2003 |
| WO | WO-03101195 A1 | 12/2003 |
| WO | WO-03103949 A1 | 12/2003 |
| WO | WO-03003949 A3 | 1/2004 |
| WO | WO-2004004597 A2 | 1/2004 |
| WO | WO-2004006803 A1 | 1/2004 |
| WO | WO-2004006804 A1 | 1/2004 |
| WO | WO-2004014256 A1 | 2/2004 |
| WO | WO-2004016200 A1 | 2/2004 |
| WO | WO-2004016201 A2 | 2/2004 |
| WO | WO-2004019811 A2 | 3/2004 |
| WO | WO-2004019817 A1 | 3/2004 |
| WO | WO-2004019825 A1 | 3/2004 |
| WO | WO-2004021922 A2 | 3/2004 |
| WO | WO-2004023980 A2 | 3/2004 |
| WO | WO-2004019811 A9 | 4/2004 |
| WO | WO-2004026117 A2 | 4/2004 |
| WO | WO-2004026173 A2 | 4/2004 |
| WO | WO-2004028399 A2 | 4/2004 |
| WO | WO-2004030515 A2 | 4/2004 |
| WO | WO-2004041126 A1 | 5/2004 |
| WO | WO-2004043293 A2 | 5/2004 |
| WO | WO-2004043301 A1 | 5/2004 |
| WO | WO-2004047681 A1 | 6/2004 |
| WO | WO-2004058106 A2 | 7/2004 |
| WO | WO-2004062980 A1 | 7/2004 |
| WO | WO-2004058106 A3 | 8/2004 |
| WO | WO-2004064671 A2 | 8/2004 |
| WO | WO-2004066876 A1 | 8/2004 |
| WO | WO-2004071352 A1 | 8/2004 |
| WO | WO-2004082527 A2 | 9/2004 |
| WO | WO-2004082528 A2 | 9/2004 |
| WO | WO-2004082536 A1 | 9/2004 |
| WO | WO-2004089250 A1 | 10/2004 |
| WO | WO-2004089253 A1 | 10/2004 |
| WO | WO-2004093728 A2 | 11/2004 |
| WO | WO-2004096100 A1 | 11/2004 |
| WO | WO-2004105651 A1 | 12/2004 |
| WO | WO-2005002466 A2 | 1/2005 |
| WO | WO-2005004753 A1 | 1/2005 |
| WO | WO-2005007343 A1 | 1/2005 |
| WO | WO-2005009285 A2 | 2/2005 |
| WO | WO-2005011534 A1 | 2/2005 |
| WO | WO-2005011535 A2 | 2/2005 |
| WO | WO-2005021063 A2 | 3/2005 |
| WO | WO-2005023155 A1 | 3/2005 |
| WO | WO-2005027790 A1 | 3/2005 |
| WO | WO-2005027797 A1 | 3/2005 |
| WO | WO-2005032622 A2 | 4/2005 |
| WO | WO-2005034812 A1 | 4/2005 |
| WO | WO-2005010215 A3 | 5/2005 |
| WO | WO-2005046528 A1 | 5/2005 |
| WO | WO-2005046529 A1 | 5/2005 |
| WO | WO-2005048883 A1 | 6/2005 |
| WO | WO-2005062980 A2 | 7/2005 |
| WO | WO-2005063980 A1 | 7/2005 |
| WO | WO-2005065585 A1 | 7/2005 |
| WO | WO-2005065594 A1 | 7/2005 |
| WO | WO-2005070343 A1 | 8/2005 |
| WO | WO-2005072654 A1 | 8/2005 |
| WO | WO-2005076890 A2 | 8/2005 |
| WO | WO-2005084595 A1 | 9/2005 |
| WO | WO-2005087140 A1 | 9/2005 |
| WO | WO-2005096993 A1 | 10/2005 |
| WO | WO-2005102015 A2 | 11/2005 |
| WO | WO-2005110240 A1 | 11/2005 |
| WO | WO-2005112779 A1 | 12/2005 |
| WO | WO-2006005015 A2 | 1/2006 |
| WO | WO-2006009690 A1 | 1/2006 |
| WO | WO-2006026371 A1 | 3/2006 |
| WO | WO-2006027499 A2 | 3/2006 |
| WO | WO-2005062980 A3 | 5/2006 |
| WO | WO 2006/066327 | 6/2006 |
| WO | WO-2006058163 A2 | 6/2006 |
| WO | WO-2006065949 A2 | 6/2006 |
| WO | WO-2006066327 A1 | 6/2006 |
| WO | WO-2006068944 A2 | 6/2006 |
| WO | WO 2006/076890 | 7/2006 |
| WO | WO-2006070372 A2 | 7/2006 |
| WO | WO-2006076890 A1 | 7/2006 |
| WO | WO-2006083763 A1 | 8/2006 |
| WO | WO-2006086135 A2 | 8/2006 |
| WO | WO-2006086736 A2 | 8/2006 |
| WO | WO-2006089517 A1 | 8/2006 |
| WO | WO-2006093795 A1 | 9/2006 |
| WO | WO-2006102063 A2 | 9/2006 |
| WO | WO-2006108090 A2 | 10/2006 |
| WO | WO-2006118766 A1 | 11/2006 |
| WO | WO-2006124649 A2 | 11/2006 |
| WO | WO-2006127756 A2 | 11/2006 |
| WO | WO-2006127765 A1 | 11/2006 |
| WO | WO-2006129441 A1 | 12/2006 |
| WO | WO-2006132948 A1 | 12/2006 |
| WO | WO-2006133959 A1 | 12/2006 |
| WO | WO-2006138391 A2 | 12/2006 |
| WO | WO-2007009117 A1 | 1/2007 |
| WO | WO-2007009609 A1 | 1/2007 |
| WO | WO-2007013999 A2 | 2/2007 |
| WO | WO-2007033093 A2 | 3/2007 |
| WO | WO-2007035471 A2 | 3/2007 |
| WO | WO-2005102015 A3 | 4/2007 |
| WO | WO-2006138391 A9 | 4/2007 |
| WO | WO-2007044285 A2 | 4/2007 |
| WO | WO-2007047488 A2 | 4/2007 |
| WO | WO-2007047945 A2 | 4/2007 |
| WO | WO 2007/059252 A1 | 5/2007 |
| WO | WO-2007048529 A1 | 5/2007 |
| WO | WO-2007051620 A1 | 5/2007 |
| WO | WO-2007053243 A2 | 5/2007 |
| WO | WO-2007058847 A2 | 5/2007 |
| WO | WO-2006086736 A3 | 6/2007 |
| WO | WO-2007071436 A2 | 6/2007 |
| WO | WO-2007092354 A2 | 8/2007 |
| WO | WO-2007097983 A2 | 8/2007 |
| WO | WO-2007098232 A2 | 8/2007 |
| WO | WO-2007053243 A3 | 9/2007 |
| WO | WO-2007120543 A1 | 10/2007 |
| WO | WO 2007/123956 | 11/2007 |
| WO | WO-2007071436 A3 | 11/2007 |
| WO | WO-2007123658 A1 | 11/2007 |
| WO | WO-2007123956 A2 | 11/2007 |
| WO | WO-2007033093 A3 | 1/2008 |
| WO | WO-2007071436 B1 | 1/2008 |
| WO | WO 2008/031103 A2 | 3/2008 |
| WO | WO-2008028569 A1 | 3/2008 |
| WO | WO-2008035337 A2 | 3/2008 |
| WO | WO 2008/045949 | 4/2008 |
| WO | WO-2008040555 A2 | 4/2008 |
| WO | WO-2008045949 A2 | 4/2008 |
| WO | WO-2008047354 A2 | 4/2008 |
| WO | WO-2008051554 A2 | 5/2008 |
| WO | WO-2008070442 A1 | 6/2008 |
| WO | WO-2008070797 A2 | 6/2008 |
| WO | WO-2008079962 A1 | 7/2008 |
| WO | WO-2008098191 A2 | 8/2008 |
| WO | WO-2008100599 A1 | 8/2008 |
| WO | WO-2008101083 A2 | 8/2008 |
| WO | WO-2008125153 A1 | 10/2008 |
| WO | WO-2008137603 A2 | 11/2008 |
| WO | WO-2008138584 A1 | 11/2008 |
| WO | WO-2008150529 A1 | 12/2008 |
| WO | WO-2009002548 A1 | 12/2008 |
| WO | WO-2009024859 A2 | 2/2009 |
| WO | WO-2009029199 A1 | 3/2009 |
| WO | WO-2009042196 A2 | 4/2009 |
| WO | WO-2009045334 A1 | 4/2009 |
| WO | WO-2009045338 A1 | 4/2009 |
| WO | WO-2009053497 A1 | 4/2009 |
| WO | WO-2009054397 A1 | 4/2009 |
| WO | WO-2007044285 A3 | 5/2009 |
| WO | WO-2009061389 A2 | 5/2009 |

(56) References Cited

FOREIGN PATENT DOCUMENTS

| | | |
|---|---|---|
| WO | WO-2009085206 A2 | 7/2009 |
| WO | WO-2009091509 A1 | 7/2009 |
| WO | WO-2009094188 A2 | 7/2009 |
| WO | WO-2009094501 A1 | 7/2009 |
| WO | WO-2009100198 A2 | 8/2009 |
| WO | WO-2009106545 A1 | 9/2009 |
| WO | WO-2009108615 A1 | 9/2009 |
| WO | WO-2009111241 A2 | 9/2009 |
| WO | WO 2009/155561 A2 | 12/2009 |
| WO | WO-2009149462 A2 | 12/2009 |
| WO | WO 2010/022138 A2 | 2/2010 |
| WO | WO-2010042950 A2 | 4/2010 |
| WO | WO-2010043950 A2 | 4/2010 |
| WO | WO-2010044851 A1 | 4/2010 |
| WO | WO-2010045238 A2 | 4/2010 |
| WO | WO-2010045297 A2 | 4/2010 |
| WO | WO-2010049160 A1 | 5/2010 |
| WO | WO-2010083558 A1 | 7/2010 |
| WO | WO-2010086460 A1 | 8/2010 |
| WO | WO-2010098857 A1 | 9/2010 |
| WO | WO-2010104638 A2 | 9/2010 |
| WO | WO-2010045238 A3 | 10/2010 |
| WO | WO-2010141626 A2 | 12/2010 |
| WO | WO-2011008812 A2 | 1/2011 |
| WO | WO-2011008853 A2 | 1/2011 |
| WO | WO-2011035327 A1 | 3/2011 |
| WO | WO-2011051043 A1 | 5/2011 |
| WO | WO-2011057087 A1 | 5/2011 |
| WO | WO-2011060386 A2 | 5/2011 |
| WO | WO-2011102968 A1 | 8/2011 |
| WO | WO-2011104269 A1 | 9/2011 |
| WO | WO-2011120050 A1 | 9/2011 |
| WO | WO-2011133368 A1 | 10/2011 |
| WO | WO-2011144351 A2 | 11/2011 |
| WO | WO-2011147849 A1 | 12/2011 |
| WO | WO-2012002228 A1 | 1/2012 |
| WO | WO-2012023980 A1 | 2/2012 |
| WO | WO-2012036742 A2 | 3/2012 |
| WO | WO-2012038550 A1 | 3/2012 |
| WO | WO-2012039748 A2 | 3/2012 |
| WO | WO-2012082952 A2 | 6/2012 |
| WO | WO-2012106491 A1 | 8/2012 |
| WO | WO-2012116368 A2 | 8/2012 |
| WO | WO-2012142189 A1 | 10/2012 |
| WO | WO-2012145546 A1 | 10/2012 |
| WO | WO-2012162228 A1 | 11/2012 |
| WO | WO-2013009975 A1 | 1/2013 |
| WO | WO-2013028387 A2 | 2/2013 |
| WO | WO-2013033791 A1 | 3/2013 |
| WO | WO-2013074671 A1 | 5/2013 |
| WO | WO-2013096545 A1 | 6/2013 |
| WO | WO-2013134214 A1 | 9/2013 |
| WO | WO 2014/056644 A1 | 4/2014 |
| WO | WO-2014072439 A1 | 5/2014 |
| WO | WO-2014072439 A9 | 7/2014 |
| WO | WO-2015028209 A1 | 3/2015 |
| WO | WO-2016093877 A1 | 6/2016 |
| WO | WO-2016126511 A2 | 8/2016 |
| WO | WO-2023156879 A1 | 8/2023 |

OTHER PUBLICATIONS

US 8,062,356 B2, 11/2011, Salahieh et al. (withdrawn)
US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
English translation of Aortenklappenbioprothese erfolgreich in der Entwicklung (2 pages).
Screen shots from http://www.fraunhofer.de/presse/filme/2006/index.jsp, 2006 (2 pages).
Liang, Ma, et al., "Double-crowned valved stents for off-pump mitral valve replacement," Eur. J. Cardio-Thoracic Surgery, vol. 28, pp. 194-198 (2005) (5 pages).
Huber, Christoph H., et al. "Direct Access Valve Replacement (DAVR)—are we entering a new era in cardiac surgery?" Eur. J. Cardio-Thoracic Surgery, vol. 29, pp. 380-385 (2006) (6 pages).
File history for German Patent DE 195 46 692 filed Dec. 14, 1995 and patented Jul. 11, 2002 (111 pages).
Klein, Allan L. et al., "Age-related Prevalence of Valvular Regurgitation in Normal Subjects: A Comprehensive Color Flow Examination of 118 Volunteers," J. Am. Soc. Echocardiography, vol. 3, No. 1, pp. 54-63 (1990) (10 pages).
Gummert, J.F. et al., "Cardiac Surgery in Germany During 2007: A Report on Behalf of the German Society for Thoracic and Cardiovascular Surgery," Thorac. Cardiov. Surg., vol. 56, pp. 328-336 (2008) (9 pages).
Gummert, J.F. et al., "Cardiac Surgery in Germany During 2006: A Report on Behalf of the German Society for Thoracic and Cardiovascular Surgery," Thorac. Cardiov. Surg., vol. 55, pp. 343-350 (2007) (8 pages).
Ferrari, M.W. et al., "Transarterial Aortic Valve Replacement with a Self expanding Stent in Pigs," Heart, vol. 90, No. 11, pp. 1326-1331 (2004).
Ferrari, "Entwicklung eines Verfahrens zum transvaskularen Aortenklappenersatz," Habilitationsschrift, Medizinische Fakultät der Friedrich-Schiller-Universität Jena, pp. 49-52, dated Sep. 2003.
Ferrari, "Entwicklung eines Verfahrens zum transvaskularen Aortenklappenersatz," Habilitationsschrift, Medizinische Fakultät der Friedrich-Schiller-Universität Jena, pp. 1-159, dated Sep. 2003.
German National Library, bibliographic information for Ferrari, M., "Entwicklung eines Verfahrens zum transvaskulären Aortenklappenersatz," available at https://www.deutsche-digitale-bibliothek.de/item/U2RQV45RMES4YP6AHEPGN4QPJWAMGROI.
Ahmed S., et al., Silent left coronary artery-cameral fistula: probable cause of myocardial ischemia, American Heart Journal, The C.V. Mosby Company, St. Louis, MO., vol. 104, No. 4, Part 1, Oct. 1982, pp. 869-870.
Akins C.W., et al., "Risk of Reoperative Valve Replacement for Failed Mitral and Aortic Bioprostheses," The Annals of Thoracic Surgery, vol. 65, Jun. 1998, pp. 1545-1552. Retreived from th Internet: URL: http://ats.ctsnetjournals.org/cgi/contenUfull/65/6/1545.
Allen et al., "What are the characteristics of the ideal endovascular graft for abdominal aortic aneurysm exclusion?" J. Endovasc. Surg., vol. 4(2), May 1997, pp. 195-202.
Anabtawi I.N., et al., "Experimental evaluation of myocardial tunnelization as a method of myocardial revascularization," Journal of Thoracic and Cardiovascular Surgery, The C.V. Mosby Company; St. Louis, MO., vol. 58, No. 5, Nov. 1969, pp. 638-646.
Andersen et al., "Transluminal catheter implantation of a new expandable artificial cardiac valve (the stent-valve) in the aorta and the beating heart of closed chest pigs, Abstract", Eur. Heart J., 11 Suppl.: 224a, Jan. 1990.
Andersen et al., "Transluminal implantation of artificial heart valves, Description of a new expandable aortic valve and initial results with implantation by catheter technique in closed chest pigs," Euro. Heart J., vol. 13, May 1992, pp. 704-708.
"Aortenklappenbioprothese erfolgreich in der Entwicklung," May 16, 2003, 1 page.
Archie J.P., et al., "Intramyocardial Pressure: Effect of Preload on Transmural Distribution of Systolic Coronary Blood Flow," The American Journal of Cardiology, vol. 35, USA, Jun. 1975, pp. 904-911.
Atwood et al., "Insertion of Heart Valves by Catheterization", Project Supervised by Prof. S. Muftu of Northeastern University 2001-2002, May 30, 2002, pp. 36-40.
Atwood et al., "Insertion of Heart Valves by Catheterization", The Capstone Design Course Report MIME 1501-1502, Technical Design Report Northeastern University, Nov. 5, 2007, pp. 1-93.
Baba H., et al., "Hemodynamic effects of venous valves in aorta-coronary bypass grafts," The Journal of Thoracic and Cardiovascular Surgery, vol. 71 (5), May 1976, pp. 774-778.
Babaliaros et al., "State of the Art Percutaneous Intervention for the Treatment of Valvular Heart Disease: A Review of the Current

(56) References Cited

OTHER PUBLICATIONS

Technologies and Ongoing Research in the Field of Percutaneous Heart Valve Replacement and Repair," Cardiology 107, Feb. 2007, pp. 87-96.
Bailey., "Percutaneous Expandable Prosthetic Valves, Textbook of Interventional Cardiology", 2d ed. Eric J. Topol, W.B. Saunders Co., vol. 2, pp. 1268-1276. (1994) (Month of publication not available).
Block et al., "Percutaneous Approaches to Valvular Heart Disease," Current Cardiology Reports, vol. 7, Mar. 2005, pp. 108-113.
Blum et al., "Endoluminal Stent—Grafts for Intrarenal Abdominal Aortic Aneurysms." New Engl. J. Med., 336:13-20, Jan. 1997.
Bodnar et al., "Replacement Cardiac Valves R Chapter 13: Extinct Cardiac Valve Prostheses", Pergamon Publishing Corporation, New York: 307-322 (1991). (Month of publication not available).
Bohning A., et al., "The Thebesian Vessels as a Source of Nourishment for the Myocardium," American Journal of Physiology, American Physiological Society, U.S.A., vol. 106, Sep. 1933, pp. 183-200.
Bonhoeffer et al., "Percutaneous Insertion of the Pulmonary Valve," J. Am. Coll. Cardiol., vol. 39, May 15, 2002, pp. 1664-1669.
Bonhoeffer et al., "Percutaneous Mitral Valve Dilatation with the Multi-Track System," Catheterization and Cardiovascular Interventions—Official Journal of the Society for Cardiac Angiograhy & Interventions, United States (Oct. 1999), pp. 178-183.
Bonhoeffer et al., "Percutaneous replacement of pulmonary valve in a right ventricle to pulmonary-artery prosthetic conduit with valve dysfunction", The Lancet, Oct. 21, 2000, vol. 356, pp. 1403-1405.
Bonhoeffer et al., "Transcatheter Implantation of a Bovine Valve in Pulmonary Position: A Lamb Study," Circulation, vol. 102, Aug. 15, 2000, pp. 813-816.
Bonhoeffer P., et al., "Technique and Results of Percutaneous Mitral Valvuloplasty With the Multi-Track System," Journal of Interventional Cadiology, vol. 13, No. 4, United States, Aug. 2000, pp. 263-268.
Boudjemline et al., "Percutaneous Implantation of a Biological Valve in Aoritc Position: Preliminary Results in a Sheep Study," European Heart Journal 22: p. 630 (Sep. 2001).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., Jul. 2002, 23, pp. 1045-1049.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Stent Implantation Combined with a Valve Replacement to Treat Degenerated Right Ventricle to Pulmonary Artery Prosthetic Conduits," European Heart Journal 22: 355 (Sep. 2001).
Boudjemline et al., "Steps Toward Percutaneous Aortic Valve Replacement." Circulation, Feb. 12, 2002, vol. 105, pp. 775-778.
Boudjemline et al., "The Percutaneous Implantable Heart Valve," Progress in Pediatric Cardiology: 89-93, Ireland, Nov. 2001.
Boudjemline Y., et al., "Images in Cardiovascular Medicine, Percutaneous Aortic Valve Replacement in Animals," Circulation, vol. 109: e161, United States, Mar. 16, 2004, 1 page.
Boudjemline Y., et al., "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research, Poland, Mar. 2004, pp. BR61-BR66.
Boudjemline Y., et al., "Off-pump Replacement of the Pulmonary Valve in Large Right Ventricular Outflow Tracts: A Hybrid Approach," Journal of Thoracic and Cardiovascular Surgery, United States, vol. 129, No. 4, Apr. 2005, pp. 831-837.

Boudjemline Y., et al., "Percutaneous Aortic Valve Replacement: Will We Get There?" Heart, British Cardiac Society, England, Dec. 2001, pp. 705-706.
Boudjemline Y., et al., "Percutaneous Closure of a Paravalvular Mitral Regurgitation with Amplatzer and Coil Prostheses," Archives des Maladies du Coeur Et Des Vaisseaux, vol. 95, No. 5, France, May 2002, pp. 483-486.
Boudjemline Y., et al., "Transcatheter Reconstruction of the Right Heart," Cardiology in the Young, England, Jun. 2003, pp. 308-311.
Bruce C.J., et al., "Right-sided Valve Disease Deserves Little More Respect," Circulation, vol. 119, No. 20, May 2009, pp. 2726-2734.
Totaro, et al., Carpentier-Edwards Perimount Magna bioprosthesis: A Stented valve with stentless performance?, Journal of Thoracis and Cardiovascular Surgery, 130(6):1668-1674 (Dec. 2005).
"Cell", Dictionary.com, http://www.dictionary.com/browse/cell, accessed May 11, 2017, pp. 1-11.
Coats L., et al., "The Potential Impact of Percutaneous Pulmonary Valve Stent Implantation on Right Ventricular Outflow Tract Re-Intervention," European Journal of Cardio-Thoracic Surgery, vol. 27, England, Apr. 2005, pp. 536-543.
Cohen H.A., et al., "Alternative Approaches to Coronary Revascularization," Current International Cardiology Reports, Current Science, Inc., U.S.A., vol. 1, Jul. 1999, pp. 138-146.
Commeau P et al., "Percutaneous Balloon Dilatation of calcific aortic Valve Stenosis: Anatomical and Haemodynamic Evaluation," British Heart Journal, vol. 59, Feb. 1988, pp. 227-238.
"Continuous", Collins English Dictionary, accessed Mar. 18, 2014, pp. 1-3.
Couper., "Surgical Aspects of Prosthetic Valve Selection", Overview of Cardiac Surgery for the Cardiologist, Springer-Verlag New York, Inc., Jan. 1994, pp. 131-145.
Cribier et al., "Early Experience with Percutaneous Transcatheter Implantation of Heart Valve Prosthesis for the Treatment of End-Stage Inoperable Patients with Calcific Aortic Stenosis", J. of Am. Coll. of Cardio, Feb. 18, 2004, 43(4), pp. 698-703.
Cribier et al., "Percutaneous Transcatheter Implantation of an Aortic Valve Prosthesis for Calcific Aortic Stenosis: First Human Case Description." Circulation, Dec. 10, 2002, 106: 3006-3008.
Cribier et al., "Percutaneous Transcatheter Implantation of an Aortic Valve Prosthesis for Calcific Aortic Stenosis: First Human Case", Percutaneous Valve Technologies, Inc., Apr. 16, 2002, 16 pages.
Cribier et al., "Percutaneous Transluminal Valvuloplasty of Acquired Aortic Stenosis in Elderly Patients: An Alternative to Valve Replacement?", The Lancet, Jan. 11, 1986, pp. 63-67.
Cribier et al., "Trans-Cathether Implantation of Balloon-Expandable Prosthetic Heart Valves: Early Results in an Animal Model." Circulation [suppl. II] 104(17)II-552 (Oct. 23, 2001).
Cunanan et al., "Tissue Characterization and Calcification Potential of Commercial Bioprosthetic Heart Valves." Ann. Thorac. Surg., May 15, 2001, pp. S417-421.
Cunliffe et al., "Glutaraldehyde Inactivation of Exotic Animal Viruses in Swine Heart Tissue," Applied and Environmental Microbiology, Greenport, New York, vol. 37, No. 5, May 1979, pp. 1044-1046.
Dake et al., "Transluminal Placement of Endovascular Stent-Grafts for the Treatment of Descending Thoracic Aortic Aneurysms." New Engl. J. of Med., vol. 331(26), Dec. 1994, pp. 1729-1734.
Dalby et al., "Non-Surgical Aortic Valve Replacement" Br. J. Cardiol., 10(6):450-452 (Nov. 2003).
Davidson et al., "Percutaneous therapies for valvular heart disease," Cardiovascular Pathology Jan. 15, 2006, pp. 123-129.
Deac, R. et al., "New evolution in mitral physical and surgery: mitral stentless pericardial valve," Ann Thorac Surg. 60(2 Suppl):S433-8 (Aug. 1995).
Dewey et al., "Transapical aortic valve implantation: An Animal Feasibility Study", The annals of thoracic surgery, Feb. 2006, vol. 82, pp. 110-116.
Dhasmana et al., "Factors Associated With Periprosthetic Leakage Following Primary Mitral Valve Replacement: With Special Consideration of Suture Technique." Annals of Thorac. Surg., (Feb. 1983), 35(2), pp. 170-178.
Diethrich, AAA Stent Grafts: Current Developments, J. Invasive Cardiol. 13(5) (May 2001).

(56) References Cited

OTHER PUBLICATIONS

Dolmatch et al., Stent Grafts: Current Clinical Practice (Oct. 2000)—EVT Endograft and Talent Endoprosthesis.
Dotter, "Transluminally-Placed Coilspring Endarterial Tube Grafts," Investigative Radiology, Sep.-Oct. 1969, pp. 329-332.
Emery et al., "Replacement of the Aortic Valve in Patients Under 50 Years of Age: Long-Term Follow-Up of the St. Jude Medical Prosthesis." Ann. Thorac. Surg., Jun. 2003, 75:1815-1819.
EP Search Report dated Aug. 10, 2011 for EP Application No. 06824992.9.
European Search Report for EP Patent Appl. Serial No. 12179049.7 (1257), dated Oct. 30, 2012, 4 pages.
European Search Report for EP Patent Appl. Serial No. 12179075.2 (1257), dated Oct. 29, 2012, 3 pages.
European Search Report for EP Patent Appl. Serial No. 12179141.2 (1257), dated Nov. 2, 2012, 3 pages.
European Search Report for EP Patent Appl. Serial No. 12179146.1 (1257), dated Nov. 7, 2012, 8 pages.
European Search Report for EP Patent Appl. Serial No. 12179330.1 (1257), dated Nov. 22, 2012, 3 pages.
European Search Report for EP Patent Appl. Serial No. 12179338.4 (1257), dated Nov. 2, 2012, 3 pages.
European Search Report for EP Patent Appl. Serial No. 12179339.2 (1257), dated Oct. 29, 2012, 4 pages.
European Search Report for EP Patent Appl. Serial No. 12179914.2 (1257), dated Nov. 7, 2012, 6 pages.
European Search Report for EP Patent Appl. Serial No. 13150337.7 (1257), dated Jul. 9, 2013, 3 pages.
European Search Report for EP Patent Appl. Serial No. 13183134.9 (1651), dated Nov. 19, 2013, 3 pages.
European Search Report for EP Patent Appl. Serial No. 14159630.4 (1651), dated May 22, 2014, 3 pages.
European Search Report for EP Patent Appl. Serial No. 14161991.6 (1651), dated Jun. 3, 2014, 3 pages.
European Search Report for EP Patent Appl. Serial No. 15167832.3 (1651), dated Jul. 23, 2015, 3 pages.
European Search Report for EP Patent Appl. Serial No. 15167847.1 (1651), dated Jul. 23, 2015, 3 pages.
European Search Report for EP Patent Appl. Serial No. 17196833.2, dated Mar. 6, 2018, 4 pages.
European Search Report for EP Patent Appl. Serial No. 18164490.7, dated Sep. 17, 2018 5 pages.
European Search Report from EP Patent Office for EP Application No. 15177718.2, dated Jan. 18, 2016, 4 pages.
European Search Report from EP Patent Office for EP Application No. 15177731.5, dated Apr. 14, 2016, 4 pages.
European Search Report from EP Patent Office for EP Application No. 16151726.3, dated Feb. 25, 2016, 4 pages.
Expert report of Dr. Nigel Buller, non-confidential annex-infringement, dated Jan. 12, 2009, Edwards' United Kingdom action for invalidity, Claim No. HC08CO0934, 83 pages.
Extended European Search Report dated Apr. 11, 2008 in EP Patent Appl. Serial No. 081630410, 5 pages.
Extended European Search Report for Application No. 10183946.2.4-2320 dated Feb. 14, 2012, 7 pages.
Extended European Search Report dated Aug. 9, 2018 in EP Patent Appl. Serial No. 18158901.1 (1113).
Extended European Search Report dated Jun. 12, 2018 in EP Patent Appl. Serial No. 17209326.2 (1113).
Extended European Search Report dated May 16, 2012 in EP Patent Appl. Serial No. 11178135.7 (1257).
Extended European Search Report for Application No. 11178076.3-1257 dated Feb. 29, 2012, 5 pages.
Extended European Search Report from EP Patent Office for EP Application No. 17162616.1, dated Jul. 27, 2017, 7 pages.
Extended European Search Report dated Apr. 9, 2014 in EP Patent Appl. Serial No. 14164683.6.
Extended European Search Report dated May 9, 2013 in EP Patent Appl. Serial No. 130178309.4, 4 pages.
Extended European Search Report dated Aug. 19, 2011 in EP Patent Appl. Serial No. 07827132.7.
Extended European Search Report dated Feb. 27, 2017 in EP Patent Appl. Serial No. 16186773,6 pages.
Extended European Search Report dated Sep. 29, 2014 in EP Patent Appl. Serial No. 14164680, 5 pages.
Extended European Search Report for Application No. 07116242.4-2310 dated Mar. 31, 2008, 10 pages.
Extended European Search Report for Application No. 09154935.2, dated May 29, 2009, 7 pages.
Extended European Search Report for Application No. 10012198 dated Mar. 23, 2011, 7 pages.
Extended European Search Report for Application No. 10168525.3-1257 dated Feb. 3, 2011, 13 pages.
Extended European Search Report for Application No. 11153142.2-1257 dated Aug. 3, 2011, 10 pages.
Extended European Search Report for Application No. 11165093.3-1257 dated Aug. 30, 2011, 6 pages.
Extended European Search Report for Application No. 11178073.0-1257 dated Oct. 14, 2011, 5 pages.
Extended European Search Report for Application No. 11178145.6-1257 dated Feb. 29, 2012, 5 pages.
Extended European Search Report for Application No. 13188858.8-1651 dated Jan. 13, 2014, 6 pages.
Extended European Search Report for Application No. 19195062 dated Jan. 2, 2020, 7 pages.
ExtendedEuropean Search Report for EP Patent Appl. Serial No. 06827630.2 dated Jun. 7, 2010, 5 pages.
Extended European Search Report for EP Patent Appl. Serial No. 07110318.8, dated May 29, 2008, 10 pages.
Extended European Search Report for EP Patent Appl. Serial No. 10163478.0, dated Mar. 22, 2011, 9 pages.
Extended European Search Report for EP Patent Appl. Serial No. 10184842.2, dated Mar. 23, 2011, 7 pages.
Extended European Search Report for EP Patent Appl. Serial No. 11162971.3, dated Jun. 30, 2011, 5 pages.
Extended European Search Report for EP Patent Appl. Serial No. 13163918.9, dated Jul. 24, 2013, 8 pages.
Extended European Search Report for EP Patent Appl. Serial No. 14179639.1, dated Mar. 9, 2015, 7 pages.
Extended European Search Report for EP Patent Appl. Serial No. 16201320.5, dated May 19, 2017, 6 pages.
Extended European Search Report for EP Patent Appl. Serial No. 18200191.7, dated May 6, 2019, 8 pages.
Fawzi et al., U.S. Appl. No. 11/155,309, entitled "Apparatus and methods for intravascular embolic protection", filed Jun. 16, 2005, 51 pages.
Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159.
Ferrari, "Entwicklung eines Verfahrens zum transvaskularen Aortenklappenersatz," Habilitationsschrift, Medizinische Fakultät der Friedrich-Schiller-Universität Jena, Sep. 2003, pp. 49-52.
Ferrari et al., "Percutaneous Transvascular Aortic Valve Replacement with Self-Expanding Stent-Valve Device." Poster from the presentation given at SMIT 2000, 12th International Conference, Sep. 5, 2000.
Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.
Filsoufi F., et al., "Long-term Outcomes of Tricuspid Valve Replacement in the Current Era," Ann. Thorac. Surg., vol. 80, No. 3, Sep. 2005, pp. 845-850.
Fluency Vascular Stent Graft Instructions for Use, May 2014, 20 pages.
Galioto F.M., et al., "Right coronary artery to left ventricle fistula: A case report and discussion," American Heart Journal, The C.V. Mosby Company, St. Louis, MO., vol. 82, No. 1, Jul. 1971, pp. 93-97.
Gardner R.J., et al., "An Experimental Anatomic Study of Indirect Myocardial Revascularization," Journal of Surgical Research, Academic Press, U.S.A., vol. 11, May 1971, pp. 243-247.

(56) References Cited

OTHER PUBLICATIONS

German National Library, "Entwicklung eines Verfahrens zum transvaskulären Aortenklappenersatz," bibliographic information for Ferrari M., Sep. 2004, Retreived from the Internet: URL: https://www.deutsche-digitale-bibliothek.de/item/U2RQV45RMES4YP6AHEPGN4QPJWAMGROI, 3 pages.

Goldman A., et al., Experimental Methods for Producing a Collateral Circulation to the Heart Directly from the Left Ventricle, Journal of Thoracic Surgery, U.S.A., vol. 31, No. 3, Mar. 1956, pp. 364-374.

Gore Excluder Instructions for Use (2002). (Month of publication not available).

Greeenberg, "Abdominal Aortic Endografting: Fixation and Sealing." J. Am. Coll. Surg., Jan. 2002, 194:1:S79-S87.

Grossi A.E. et al., "Impact of Minimally Invasive Valvular Heart Surgery: A Case-Control Study", Ann. Thorac. Surg., Mar. 2001, vol. 71, pp. 807-810.

Gummert J.F. et al., Cardiac Surgery in Germany During 2006: A Report on Behalf of the German Society for Thoracic and Cardiovascular Surgery, Thorac. Cardiov. Surg., vol. 55, Jun. 24, 2007, pp. 343-350.

Gummert J.F. et al., "Cardiac Surgery in Germany During 2007: A Report on Behalf of the German Society for Thoracic and Cardiovascular Surgery," Thorac. Cardiov. Surg., vol. 56, Sep. 2008, pp. 328-336.

Hanzel et al., "Complications of percutaneous aortic valve replacement: experience with the Criber-Edwards.TM. Percutaneous heart valve," EuroIntervention Supplements I (Supplement A):A3-A8, May 19, 2006.

Haug et al., U.S. Appl. No. 12/028,452 entitled "Methods and apparatus for endovascularly replacing a patient's heart valve," filed Feb. 8, 2008, 48 pages.

Haug et al., U.S. Appl. No. 12/492,512 entitled "Everting Heart Valve," filed Jun. 26, 2009, 92 pages.

"Heart Valve Materials—Bovine (cow)", Equine & Porcine Pericardium, Maverick Biosciences Pty Ltd, http://maverickbio.com/biological-medical-device-materials/, Accessed Jan. 7, 2011.

"Heart Valve Materials—Bovine (cow)", Equine & Porcine Pericardium, Maverick Biosciences Pvt. Lt., http://maverickbio.com/biological-medical-device-materials.php?html, 2009. (Month of publication not available).

Heinrich R.S., et al., "Experimental analysis of fluid mechanical energy losses in aortic valve stenosis: importance of pressure recovery", Ann Biomed Eng., Nov.-Dec. 1996, vol. 24(6), pp. 685-694.

Heinrich RS et al., "Valve orifice area alone is an insufficient index of aortic stenosis severity: effects of the proximal and distal geometry on transaortic energy loss", J Heart Valve Dis., Sep. 1999, 8(5): 509-15.

Helmus, "Mechanical and Bioprosthetic Heart Valves in Biomaterials for Artificial Organs." Woodhead Publishing Limited: 114-162 (2011). (Month of publication not available).

Hijazi et al., "Transcatheter Valve Repair", Taylor & Francis, Jan. 2006, pp. 165-186.

Hijazi Z.M., "Transcatheter Valve Replacement: A New Era of Percutaneous Cardiac Intervention Begins", J. of Am. College of Cardio., Nov. 6, 2004, vol. 43, No. 6, pp. 1088-1089.

Hourihan M., et al., "Transcatheter Umbrella Closure of Valvular and Paravalvular Leaks", JACC, Boston, Massachusetts, Nov. 15, 1992, vol. 20, No. 6, pp. 1371-1377.

Huber C.H., et al., "Direct Access Valve Replacement (DAVR)—are we entering a new era in cardiac surgery?" European Journal of Cardio-thoracic Surgery, vol. 29, Jan. 19, 2006, pp. 380-385.

Huber H.C., et al., "Direct-Access Valve Replacement: A Novel Approach for Off-Pump Valve Implantation Using Valved Stents", Journal of the American College of Cardiology, vol. 46, No. 2, Jul. 19, 2005, pp. 366-370.

Huber H.C., et al., "Do Valved Stents Compromise Coronary Flow?", European Journal of Cardio-thoracic Surgery, Jan. 23, 2004, vol. 25; pp. 754-759.

Ing F., "Stents: What's Available to the Pediatric Interventional Cardiologist?" Catheterization and Cardiovascular Interventions, Jun. 2002, 57; pp. 374-386.

International Search Report dated Dec. 29, 2003 in Intl PCT Patent Appl. U.S. Appl. No. PCT/DE2003/002669.

International Search Report and Written Opinion for PCT Application No. PCT/EP2009/052230 dated Jun. 29, 2009, 12 pages.

International Search Report and Written Opinion for PCT Application No. PCT/EP2010/052429 dated Jun. 14, 2010, 12 pages.

International Search Report and Written Opinion for PCT Application No. PCT/EP2011/002524 dated Apr. 23, 2012, 15 pages.

International Search Report and Written Opinion for PCT Application No. PCT/EP2011/052674 dated Jul. 5, 2011, 12 pages.

International Search Report for PCT Application No. PCT/US1999/020736dated Jan. 28, 2000, 3 pages.

International Search Report and Written Opinion for PCT Application No. PCT/EP2009/050762 dated Jun. 23, 2009, 12 pages.

International Search Report & Written Opinionmailed Jul. 18, 2016 for PCT Patent Appl No. PCT/EP2016/059839, 10 pages.

International Search Report and Written Opinion for Appl. No. PCT/EP2016/055783, mailed on May 30, 2016, 15 pages.

International Search Report and Written Opinion for Application No. PCT/EP2013/057431 dated Jul. 26, 2013, 9 pages.

International Search Report and Written Opinion for Application No. PCT/IB2018/050438 mailed Apr. 12, 2018, 11 pages.

International Search Report and Written Opinion for International Application No. PCT/EP2010/063306, dated Nov. 17, 2010, 9 pages.

International Search Report and Written Opinion for PCT Application No. PCT/EP2006/010519 dated Mar. 1, 2007, 13 pages.

International Search Report and Written Opinion for PCT Application No. PCT/US06/36286 dated Jul. 9, 2007, 4 pages.

International Search Report and Written Opinion for PCT Application No. PCT/US2004/041513 dated Jun. 10, 2005, 4 pages.

International Search Report and Written Opinion for PCT Application No. PCT/US2004/043607 dated Mar. 20, 2006, 4 pages.

International Search Report and Written Opinion for PCT Application No. PCT/US2005/020947 dated Oct. 6, 2005, 5 pages.

International Search Report and Written Opinion for PCT Application No. PCT/US2006/038352 dated May 19, 2008, 4 pages.

International Search Report and Written Opinion for PCT Application No. PCT/US2006/043484 dated Jun. 25, 2008, 4 pages.

International Search Report and Written Opinion for PCT Application No. PCT/US2007/003992 dated Jan. 10, 2008, 5 pages.

International Search Report and Written Opinion for PCT Application No. PCT/US2007/02970 dated Oct. 19, 2007, 7 pages.

International Search Report and Written Opinion for PCT Application No. PCT/US2009/060531 dated May 13, 2010, 6 pages.

International Search Report and Written Opinion for PCT/DE2006/000056 dated Jun. 7, 2006, 11 pages.

International Search Report and Written Opinion for PCT/EP2007/061117 dated May 20, 2008, 16 pages.

International Search Report and Written Opinion for PCT/EP2008/003803 dated Aug. 20, 2008, 10 pages.

International Search Report and Written Opinion for PCT/EP2009/055958 dated Oct. 21, 2009, 8 pages.

International Search Report and Written Opinion for PCT/EP2010/056558 dated Oct. 7, 2010, 14 pages.

International Search Report and Written Opinion for PCT/EP2012/067617 dated Dec. 19, 2012, 10 pages.

International Search Report and Written Opinion for PCT/IL2007/001149 dated May 1, 2008, 4 pages.

International Search Report and Written Opinion for PCT/US2011/027730 dated May 25, 2011, 9 pages.

International Search Report and Written Opinion of the International Search Authority for International Application No. PCT/EP2008/064558, date of completion of report is Mar. 18, 2009, 14 pages.

International Search Report for Application No. PCT/DE2001/000837, dated Aug. 7, 2001, 4 pages.

International Search Report for Application No. PCT/EP2006/012455, mailed Sep. 27, 2007, 5 pages.

(56) References Cited

OTHER PUBLICATIONS

International Search Report for Application No. PCT/EP2010/057798, dated Sep. 12, 2010, 6 pages.
International Search Report for Application No. PCT/EP2011/058506, mailed Nov. 3, 2011, 4 pages.
International Search Report for Application No. PCT/EP2011/066677, dated Feb. 17, 2012, 7 pages.
International Search Report for Application No. PCT/EP2012/067617 mailed Dec. 19, 2012, 3 pages.
International Search Report for Application No. PCT/EP2012/067714 dated Dec. 18, 2012, 3 pages.
International Search Report for Application No. PCT/EP2013/073318, dated Apr. 17, 2014, 5 pages.
International Search Report for Application No. PCT/EP2014/065817, mailed Jan. 7, 2015, 6 pages.
International Search Report for Application No. PCT/EP2016/055783, mailed on May 30, 2016, 5 pages.
International Search Report for Application No. PCT/EP2016/058532, dated Jul. 11, 2016, 4 pages.
International Search Report for Application No. PCT/IB2008/002180, dated Apr. 15, 2009, 7 pages.
International Search Report for Application No. PCT/US83/01932 corresponding to WO 84/02266.
International Search Report for PCT/DE2001/000836 dated Jun. 13, 2001, 6 pages.
International Search Report for PCT/EP2006/010023 dated Mar. 30, 2007, 6 pages.
International Search Report for PCT/EP2007/007413, mailed Jan. 28, 2008, 4 pages.
International Search Report for PCT/IB2017/052718, dated Sep. 5, 2017, 4 pages.
Kaiser, et al., "Surgery for Left Ventricle Outflow Obstruction: Aortic Valve Replacement and Myomectomy," Overview of Cardiac Surgery for the Cardiologist, Springer-Verlag New York, Inc., Jan. 1994, pp. 40-45.
Kato et al., "Traumatic Thoracic Aortic Aneurysm: Treatment with Endovascular Stent-Grafts." Radiol., Dec. 1997, 205: 657-662.
Khambadkone, et al., "Percutaneous Implantation of Pulmonary Valves," Expert Review of Cardiovascular Therapy (England), Nov. 2003, pp. 541-548.
Khambadkone, et al., "Percutaneous Pulmonary Valve Implantation: Early and Medium Term Results," Circulation 108 (17 Supplement), Oct. 28, 2003, p. IV-375.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khonsari et al., "Cardiac Surgery: Safeguards and Pitfalls in Operative Technique." 3d ed., 45-74 (Jul. 2003).
Klein A.L., et al., "Age-related Prevalence of Valvular Regurgitation in Normal Subjects: A Comprehensive Color Flow Examination of 118 Volunteers," Journal of the American Society of Echocardiography, vol. 3, No. 1, Jan.-Feb. 1990, pp. 54-63.
Knudsen et al., "Catheter-implanted prosthetic heart valves", Intl J. of Art. Organs, 16(5): 253-262, May 1993.
Kort et al., "Minimally Invasive Aortic Valve Replacement: Echocardiographic and Clinical Results." Am. Heart J., Sep. 2001, vol. 142(3), pp. 476-481.
Kuzela L., et al., "Experimental evaluation of direct transventricular revascularization," Journal of Thoracic and Cardiovascular Surgery, The C.V. Mosby Company, St. Louis, MO., vol. 57, No. 6, Jun. 1969, pp. 770-773.
Laborde et al., "Percutaneous Implantation of the Corevalve Aortic Valve Prosthesis for Patients Presenting High Risk for Surgical Valve Replacement." EuroIntervention: 472-474, Feb. 2006.
Lary B.G., et al., "A method for creating a coronary-myocardial artery," Surgery, The C.V. Mosby Company, St. Louis, MO., vol. 59, No. 6, Jun. 1966, pp. 1061-1064.

Lary BG., et al., "Myocardial Revascularization Experiments Using the Epicardium," Archives of Surgery, American Medical Association, U.S.A., vol. 98, Jan. 1969, pp. 69-72.
Lawrence et al., "Percutaneous Endovascular Graft: Experimental Evaluation", Radiology, May 1987, vol. 163(2), pp. 357-360.
Lee G., et al., "Effects of laser Irradiation delivered by flexible fiberoptic system on the left ventricular internal myocardium," American Heart Journal, The C.V. Mosby Company, St. Louis, MO., vol. 106, No. 3; Sep. 1983, pp. 587-590.
Levi et al., "Future of Interventional Cardiology in Pediactrics." Current Opinion in Cardiol., Mar. 2003, vol. 18, pp. 79-90.
Levinsky L., et al., "The Revival of the Horseshoe Graft (Side-to-Side Saphenous-Vein-to-Aorta Anastomosis)," The Thoracic and Cardiovascular Surgeon, Georg Thieme Publishers, Stuttgart, Germany, vol. 27, No. 5, Oct. 1979, pp. 322-324.
Levy, "*Mycobacterium chelonei* Infection of Porcine Heart Valves." The New England Journal of Medicine, Washington DC, 297(12), Sep. 22, 1977, pp. 667-668.
Lichtenstein et al., "Transapical Transcatheter Aortic Valve Implantation in Humans: Initial Clinical Experience", circulation, American Heart Association vol. 114, Jul. 31, 2006, pp. 591-596.
Lichtenstein, S.V., "Closed heart surgery: Back to the future" The Journal of Thoracic and Cardiovascular Surgery, vol. 131(5), May 2006, pp. 941-943.
Liu et al., "Effect of Fiber Orientation on the Stress Distribution within a Leaflet of a Polymer Composite Heart Valve in be Closed Position", Journal of Biomechanics, Jan. 2007, vol. 4, pp. 1099-1106.
Lonescu et al., "Prevalence and Clinical Significance of Incidental Paraprosthetic Valvar Regurgitation: A prospective study using transesophageal echocardiography." Heart, Oct. 2003, 89:1316-21.
Love S.C. et al., The Autogenous Tissue Heart Valve: Current Status, Journal of Cardiac Surgery, , Mar. 1991, vol. 6(4), pp. 499-507.
Lutter et al., "Percutaneous Aortic Valve Replacement: An Experimental Study. I. Studies on Implantation." J. of Thoracic and Cardio. Surg., Apr. 2002, vol. 123(4), pp. 768-776.
Lutter et al., "Percutaneous Valve Replacement: Current State and Future Prospects," Annals of Thoracic Surgery, Netherlands Dec. 2004, pp. 2199-2206.
Ma L., et al., "Double-crowned valved stents for off-pump mitral valve replacement," European Journal of Cardio-Thoracic Surgery, vol. 28, No. 2, Jun. 13, 2005, pp. 194-198.
Mack, M.J., "Minimally invasive cardiac surgery", Surg Endosc, Mar. 2006, vol. 20, pp. S488-S492.
Magovern et al., "Twenty-five-Year Review of the Magovern-Cromie Sutureless Aortic Valve", Ann. Thorac. Surg., Jan. 1989, vol. 48, pp. S33-S34.
Maraj et al., Evaluation of Hemolysis in Patients with Prosthetic Heart Valves, Clin. Cardiol. vol. 21, Jun. 1998, pp. 387-392.
Marcus RH et al., "Assessment of small-diameter aortic mechanical prostheses: physiological relevance of the Doppler gradient, utility of flow augmentation, and limitations of orifice area estimation," Circulation. Sep. 1, 1998, 98(9), pp. 866-872.
Massimo C., et al., "Myocardial Revascularization by a New Method of Carrying Blood Directly From the Left Ventricular Cavity into the Coronary Circulation," Journal of Thoracic Surgery, U.S.A., vol. 34, No. 2, Aug. 1957, pp. 257-264.
Mckay G. R. et al., "The Mansfield Scientific Aortic Valvuloplasty Registry: Overview of Acute Hemodynamic Results and Procedural Complications." J. Am. Coll. Cardiol, Feb. 1991, 17(2), pp. 485-491.
Medical Industry Today Headline News, "Sales Dive, Losses Soar in 2Q for CardioGenesis," Article #07179808, Article is 560 words long, Medical Data International Inc., U.S.A., Jul. 17, 1998, pp. 1-2.
Medical Industry Today Headline News, "Eclipse Gets OK to Pump Catheter Marketing in Europe," Article #07179802, Article is 349 words long, Medical Data International, Inc., Santa Ana, CA., Jul. 17, 1998, pp. 1-2.
Medtech Insight 7(8), "New Frontiers in Heart Valve Disease" (Jan. 2005).

(56) References Cited

OTHER PUBLICATIONS

Mills N.L., et al., "Valvulotomy of valves in the saphenous vein graft before coronary artery bypass," The Journal of Thoracic and Cardiovascular Surgery, vol. 71 (6), Jun. 1976, pp. 878-879.
Mirich et al., "Percutaneously Placed Endovascular Grafts for Aortic Aneurysms: Feasibility Study", Radiology, Mar. 1989, vol. 170, pp. 1033-1037.
Moazami N et al. "Transluminal Aortic Valve Placement: a Fesibility Study with a Newly Designed Collapsible Aortic Valve", ASAIO Journal, vol. 42, No. 2, Mar.-Apr. 1996.
Moulopoulos et al., "Catheter-Mounted Aortic Valves," Annals of Thoracic Surg., vol. 11, No. 5, May 1971, pp. 423-430.
Munro I., et al., "The possibility of myocardial revascularization by creation of a left ventriculocoronary artery fistula," The Journal of Thoracic and Cardiovascular Surgery, The C.V. Mosby Company, St. Louis, MO., vol. 58, No. 1, Jul. 1969, pp. 25-32.
Nath J., et al., Impact of Tricuspid Regurgitation on Long-term Survival, Journal of the American College of Cardiology, vol. 43, No. 3, Feb. 2004, pp. 405-406.
Nietlispach F., et al., "Current Balloon-Expandable Transcatheter Heart Valve and Delivery Systems", Catheterization and Cardiovascular Interventions, Sep. 2009, vol. 75, pp. 295-300.
Oesterle SN., et al., "Catheter-Based Coronary Bypass: A Development Update," Catheterization and Cardiovascular Interventions, Wiley-Liss, Inc. U.S.A., vol. 58, No. 2, Feb. 2003, pp. 212-218.
Palacios, "Percutaneous Valve Replacement and Repair, Fiction or Reality?," Journal of American College of Cardiology, vol. 44(8), Oct. 2004, pp. 1662-1663.
Palmaz J.C., et al., "Expandable Intrahepatic Portacaval Shunt Stents: Early Experience in the Dog," American Journal of Roentgenology, U.S.A., vol. 145 (4), Oct. 1985, pp. 821-825.
Palmaz J.C., et al., "Expandable Intrahepatic Portacaval Shunt Stents in Dogs with Chronic Portal Hypertension," American Journal of Roentgenology, The American Roentgen Ray Society, U.S.A., vol. 147, Dec. 1986, pp. 1251-1254.
Paniagua et al., "Heart Watch." Texas Heart Institute. Edition: 8 pages, (Spring 2004). (Month of publication not available).
Paniagua et al., "Percutaneous Heart Valve in the Chronic in Vitro Testing Model." Circulation, Sep. 17, 2002, vol. 106: e51-e52.
Parodi J.C., et al., "Transfemoral Intraluminal Graft Implantation for Abdominal Aortic Aneurysms", Ann. Vasc. Surg., vol. 5(6), Nov. 1991, pp. 491-499.
Partial European Search Report dated Feb. 28, 2012 in EP Patent Appl. Serial No. 11178135.7 (1257).
Partial European Search Report for Application No. 10168525.3-1269 dated Sep. 20, 2010, 5 pages.
Partial European Search Report for Application No. 07116242.4-2310 dated Jan. 14, 2008, 5 pages.
Partial European Search Report for Application No. 11153142.2-1257 dated Apr. 4, 2011, 5 pages.
Partial European Search Report for EP Patent Appl. Serial No. 07110318.8, dated Mar. 10, 2008, 6 pages.
Partial European Search Report for EP Patent Appl. Serial No. 10163478.0, dated Nov. 2, 2010, 6 pages.
Partial International Search Report for International Application No. PCT/EP2014/055044, filed Mar. 13, 2014, 7 pages.
Pavcnik D., et al., "Development and Initial Experimental Evaluation of a Prosthetic Aortic Valve for Transcatheter Placement." Radiology, Apr. 1992, vol. 183, pp. 151-154.
Pavcnik et al., "Aortic and venous valve for percutaneous insertion," Min. Invas. Ther. & Allied Technol, Jan. 2000, 9(3/4), pp. 287-292.
Pavcnik et al., "Percutaneous Bioprosthetic Venous Valve: A Long-term Study in Sheep," Jounal of Vascular Surg., vol. 35, No. 3, Mar. 2002, pp. 598-603.
Pawelec-Wojtalk M., "Closure of left ventricle perforation with the use of muscular VSD occluder," European Journal of Cardia-Thoracic Surgery, vol. 27, No. 4, Jan. 2005, pp. 714-716.
Pelton A.R., et al., "Medical Uses of Nitinol", Materials Science Forum, vol. 327-328, Jan. 2000, pp. 63-70.

"Pericardial Heart Valves", Edwards Lifesciences, Cardiovascular Surgery FAQ, http://www.edwards.com/products/cardiovascularsurgeryfaq.htm, Nov. 14, 2010.
Phillips et al., "A Temporary Catheter-Tip Aortic Valve: Hemodynamic Effects on Experimental Acute Aortic Insufficiency", Annals of Thoracic Surg., Feb. 1976, 21(2), pp. 134-136.
Phillips S.J., et al., "Improvement in Forward Coronary Blood Flow by Using a Reversed Saphenous Vein with a Competent Valve," The Annals of Thoracic Surgery, vol. 21 (1), Jan. 1976, pp. 12-15.
Printz et al., "Let the Blood Circulate", Sulzer Tech. Rev. Apr. 1999.
Raillat et al., "Treatment of Iliac Artery Stenosis with the Wallstent Endoprosthesis." AJR, Mar. 1990, vol. 154(3), pp. 613-616.
Remadi et al., "Preliminary results of 130 aortic valve replacements with a new mechanical bileaflet prosthesis: The Edwards MIRA valve," Interactive Cardiovasc. and Thorac. Surg., vol. 2, Mar. 2003, pp. 80-83.
Richter G.M., et al., "Transjugular Intrahepatic Portacaval Stent Shunt: Preliminary Clinical Results," Radiology, The Radiological Society of North America; Oak Brook, IL., vol. 174, No. 3, Part 2, Mar. 1990, pp. 1027-1030.
Rogers J.H., et al., "The Tricuspid Valve: Current Perspective and Evolving Management of Tricuspid Regurgitation," Circulation, vol. 119, No. 20, May 26, 2009, pp. 2718-2725.
Rösch J., et al., "Gianturco-Rosch Expandable Z-Stents in the Treatment of Superior Vena Cava Syndrome," Cardiovasc Intervent Radiol., vol. 15, No. 5, Sep.-Oct. 1992, pp. 319-327.
Ruiz C.E., "Transcatheter Aortic Valve Implantation and Mitral Valve Repair: State of the Art," Pediatric Cardiology, May-Jun. 2005, vol. 26(3), pp. 289-294.
Saliba et al., "Treatment of Obstruction of Prosthetic Conduits by Percutaneous Implantation of Stents," Archives des Maladies du Coeur et des Vaisseaux: 591-596, France, May 1999. English Abstract.
Schurink et al., "Stent Attachment Site—related Endoleakage after Stent Graft Treatment: An in vitro study of the effects of graft size, stent type, and atherosclerotic wall changes", J. Vasc. Surg., vol. 30(4), Oct. 1999, pp. 658-667.
Screen shots from http://www.fraunhofer.de/presse/filme/2006/index.jsp, Aug. 19, 2006, 2 pages.
Search Report dated Oct. 15, 2003 from the European Patent Office for European Patent Application No. EP 02291953.4, 2 pages.
Search Report from the European Patent Office for European Patent Application No. EP 02291954.4, Dec. 2002, 4 pages.
Search Report (Rapport De Recherche) from French Application No. FR 01 10444 (Month of publication not available).
Second Examination Report dated Jan. 10, 2011 in European Application No. EP 02291953.4, 5 pages.
Sochman et al., "Percutaneous Transcatheter Aortic Disc Valve Prosthesis Implantation: A Feasibility Study." Cardiovasc. Intervent. Radiol., Sep. 2000, 23: 384-388.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience." J. Endovasc. Ther., Oct. 2001, 8:457-464.
Stassano, "Mid-term Results of the Valve-on-Valve Technique for Bioprosthetic Failure", European Journal of Cardiothoracic Surgery, Oct. 2000, vol. 18, pp. 453-457.
Stein D.P., et al., "Turbulent blood flow in the ascending aorta of humans with normal and diseased aortic valves", Circulation Research by American Heart Association, vol. 39, Jul. 1976, pp. 58-65.
Steinhoff et al., "Tissue Engineering of Pulmonary Heart Valves on Allogenic Acellular Matrix Conduits." Circulation102 [suppl. III], Nov. 2000, pp. III-50-III-55.
Stuart, "In Heart Valves, A Brave, New Non-Surgical World", Start-Up. Feb. 9-17, 2004.
Supplemental Search Report from EP Patent Office for EP Application No. 04813777.2, dated Aug. 19, 2011.
Supplemental Search Report from EP Patent Office for EP Application No. 04815634.3, dated Aug. 19, 2011.
Supplemental Search Report from EP Patent Office for EP Application No. 05758878.2, dated Oct. 24, 2011.

(56) References Cited

OTHER PUBLICATIONS

Supplementary European Search Report dated Jan. 2, 2012 in EP Patent Appl. Serial No. 09820051.2.
Textbook of Interventional Cardiology, 2d Ed., Chapter 75: Percutaneous Expandable Prosthetic Valves, Jan. 1994.
Thompson et al., "Endoluminal stent grafting of the thoracic aorta: Initial experience with the Gore Excluder," Journal of Vascular Surgery, Jun. 2002, pp. 1163-1170.
Topol, "Percutaneous Expandable Prosthetic Valves." Textbook of Interventional Cardiology, W.B. Saunders Company, 2: 1268-1276, Jan. 1994.
Translation of "Aortenklappenbioprothese erfolgreich in der Entwicklung," original—German language document dated May 16, 2003, 2 pages.
Triennial Review of the National Nanotechnology Initiative: "A Matter of Size", The National Academies Press, Washington DC, V-13, Retrived from the Interent: URL: http://www.nap.edu/catalog/11752/a-matter-of-size-triennial-review-of-the-national-nanotechnology, Mar. 2006, 200 pages.
Tweden K.S., et al., "Ventriculocoronary Artery Bypass (VCAB), a Novel Approach to Myocardial Revascularization," Heart Surgery Forum., Article #2000-4653, vol. 3(1), Feb. 2000, pp. 47-54.
"Surgical Heart Valves", Edwards Lifesciences, Cardiovascular Surgery FAQ, http://www.edwards.com/products/Pages/cardiovascularsurgeryfaq.aspx, visited on Nov. 14, 2010.
Vahanian et al., "Percutaneous Approaches to Valvular Disease", Circulation, Apr. 6, 2004, 109: 1572-1579.
Van Herwerden et al., "Percutaneous Valve Implantation: Back to the Future?", Euro. Heart J., Sep. 2002, 23(18): 1415-1416.
Venture Beat Profiles, Claudio Argento, Jan. 7, 2010, http://venturebeatprofiles.com/person/profile/claudio-argento.
Vossoughi et al., "Stent Graft Update", Dec. 2000, Kononov, Volodos, and Parodi and Palmaz Stents; Hemobahn Stent Graft.
Wakayabashi A., et al., Myocardial Boring for the Ischemic Heart, American Medical Association Publication; International Cardiovascular Society, Fifteenth Scientific Meeting, Atlantic City, NJ, Archives of Surgery, Jun. 16 and 17, 1967, vol. 95, No. 5, Nov. 1967, pp. 743-752.
Walther et al., "Transapical approach for sutureless stent-fixed aortic valve implantation: experimental results", European Journal of Cardiao-thoracic Surgery 29, May 2006, pp. 703-708.
Webb et al., "Percutaneous Aortic Valve Implantation Retrograde from the Femoral Artery", Circulation, American Hea Association, vol. 113, Feb. 6, 2006, pp. 842-850.
Weerasinghe A., et al., "First Redo Heart Valve Replacement: A 10-Year Analysis," European Journal of Cardia-Thoracic Surgery, vol. 99, Feb. 1999, pp. 655-658.
Weyman AB et al., "Aortic Stenosis: Physics and Physiology—What Do the Numbers Really Mean?", Rev Cardiovasc Med. Jan. 2005, vol. 6(1), pp. 23-32.
White et al., "Endoleak as a Complication of Endoluminal Grafting of Abdominal Aortic Aneurysms: Classification, Incidence, Diagnosis, and Management," J. Endovac. Surg., vol. 4, May 1997, pp. 152-168.
Written Opinion for Application No. PCT/EP2006/012455, mailed Sep. 27, 2007, 11 pages.
Written Opinion for Application No. PCT/EP2007/007413, mailed Jan. 28, 2008, 5 pages.
Written Opinion for Application No. PCT/EP2011/058506, mailed Nov. 3, 2011, 5 pages.
Written Opinion for Application No. PCT/EP2014/065817, mailed Jan. 7, 2015, 7 pages.
Written Opinion for PCT/EP2006/010023 dated Mar. 30, 2007, 10 Pages.
Written Opinion for PCT/EP2012/067714 dated Dec. 18, 2012, 5 Pages.
Yonga et al., "Effect of Percutaneous Balloon Mitral Valvotomy on Pulmonary Venous Flow in Severe Mitral Stenosis," East African Medical Journal (Kenya), Jan. 1999, pp. 28-30.
Yonga et al., "Percutaneous Balloon Mitral Valvotomy: Initial Experience in Nairobi Using a New Multi-Track Catheter System," East African Medical Journal (Kenya), Feb. 1999, pp. 71-74.
Yonga et al., "Percutaneous Transluminal Balloon Valvuloplasty for Pulmonary Valve Stenosis: Report on Six Cases," East African Medical Journal (Kenya), Apr. 1994, pp. 232-235.
Yonga G.O., et al., "Percutaneous Transvenous Mitral Commissurotomy in Juvenile Mitral Stenosis", East African Medical Journal, Kenya, Apr. 2003, pp. 172-174.
Yoshioka et al., "Self-Expanding Endovascular Graft: An Experimental Study in Dogs." AJR 151, Oct. 1988, pp. 673-676.
Zemel G., et al., "Percutaneous Transjugular Portosystemic Shunt," The Journal of the American Medical Association, American Medical Association, U.S.A., vol. 266, No. 3, Jul. 17, 1991, pp. 390-393.
Zhou et al., "Self-expandable Valved Stent of Large Size: Off-Bypass Implantation in Pulmonary Position", Eur. J. Cardiothorac, Aug. 2003, 24: 212-216.
Extended EP Search Report dated Sep. 24, 2020 in EP Patent Appl. Serial No. 20165841.6 (JVT-0280).
International Search Report for PCT/EP2016/055783 dated May 30, 2016(5 pages).
International Search Report & Written Opinion dated Feb. 20, 2024 in Int'l PCT Patent Appl. Serial No. PCT/IB2023/037029.

* cited by examiner

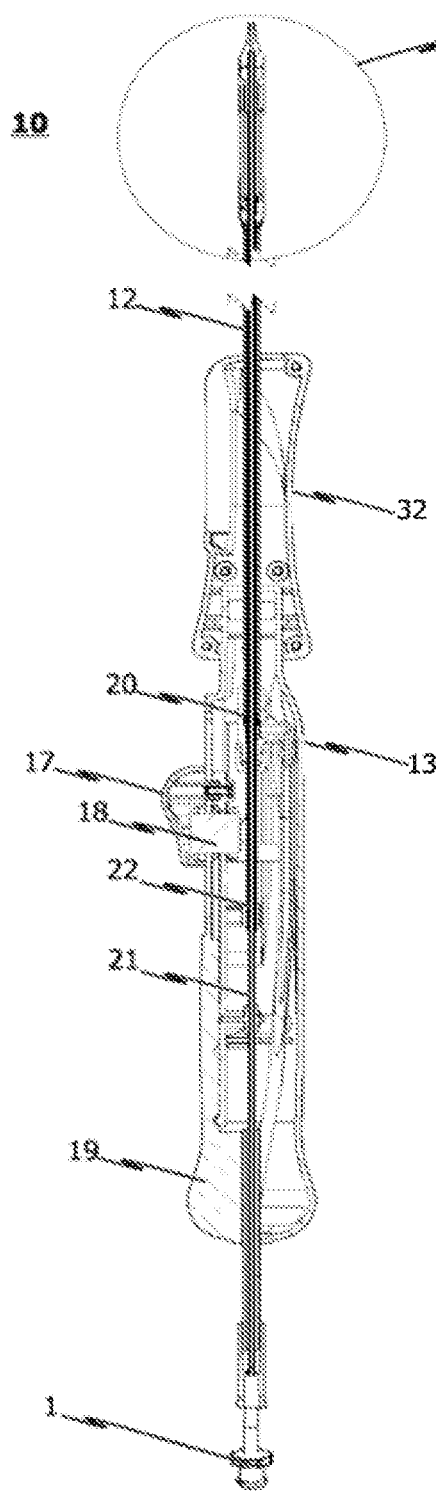
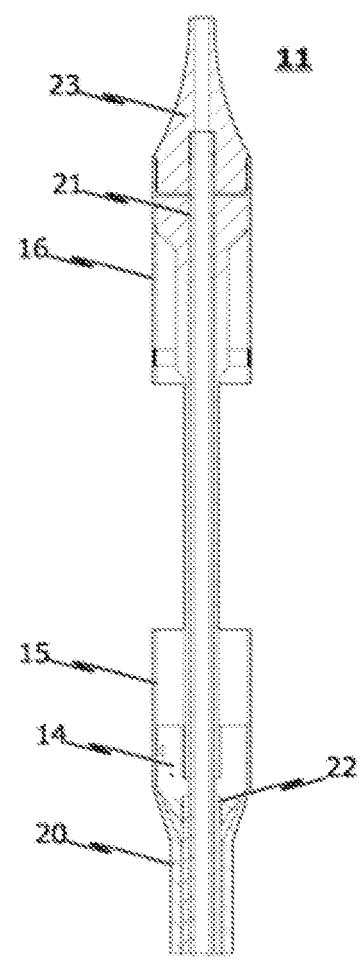
FIG. 2b
FIG. 2c

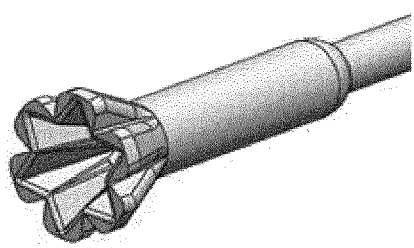
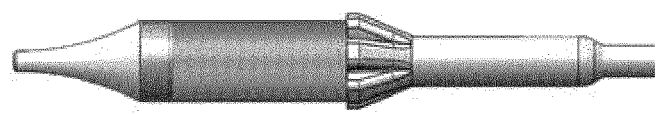
FIG. 16a
FIG. 16b
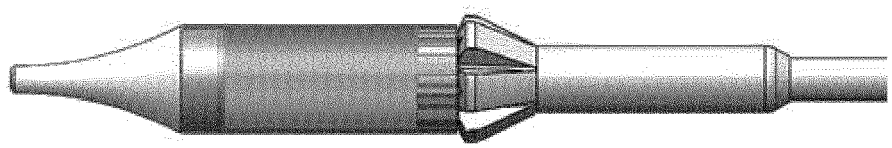
FIG. 17

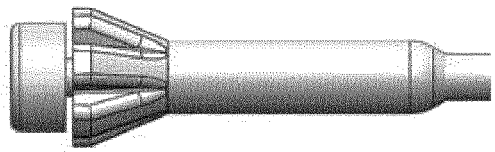
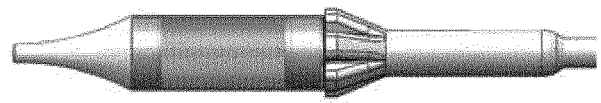
FIG. 18a　　　　　　　　　　FIG. 18b
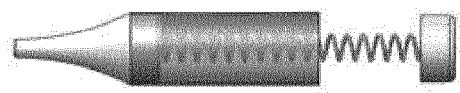
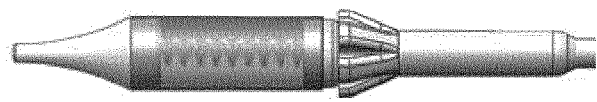
FIG. 19a　　　　　　　　　　FIG. 19b
FIG. 20

HEART VALVE PROSTHESIS DELIVERY SYSTEM AND METHOD FOR DELIVERY OF HEART VALVE PROSTHESIS WITH INTRODUCER SHEATH

This application is a national stage filing under 35 U.S.C. § 371 of International Application No. PCT/EP2016/055783 filed on Mar. 17, 2016, which published in the English language and claims the benefit of priority to U.S. Provisional Application No. 62/136,092 filed on Mar. 20, 2015.

The present disclosure relates to a delivery system, a catheter system and a method for the minimally invasive application of prostheses to an individual in need thereof and a method for loading a prosthesis onto a catheter system and/or a delivery system.

This application is related case of EP13173217.4 & EP13182346.0, U.S. Pat. No. 8,790,395 and US patent publication 2014/0081388A1 (Mar. 20, 2014) all assigned to the instant assignee, the entire disclosures of which are incorporated herein by reference, each as if expressly set forth.

BACKGROUND

The current disclosure relates to the field of medical devices, in particular to prosthesis which are being transplanted into an individual in need thereof in order to re-establish proper body functions by way of minimally invasive methods and means applicable therefor.

Examples of prostheses that are placed by way of minimally invasive methods are stents and heart valves like aortic and mitral heart valves. Heart valves today are applied e.g. by the transapical, transfemoral, or subclavial route. The transapical route is very direct through a cut between the rips of a patient and through the apex of the heart and thus only a short distance has to be passed until the delivery site. The transfemoral route is a very convenient method and widely used because it needs only a cut in the leg of the patient and access to the vasculature.

Usually the prosthesis is applied by way of a delivery system also denoted catheter. The requirements for the catheter by way of transfemoral delivery is more complex as compared with the transapical route because for the delivery of e.g. an aortic heart valve a relatively long distance and bends have to be manoevered through which imply certain difficulties.

One example of such a delivery system is disclosed in EP2387977B1. This patent describes a transfemoral catheter for the delivery of an aortic heart valve. The patent does not disclose nor suggest the embodiments presently disclosed.

Usually the prosthesis has to be loaded in a releasable manner onto the catheter and crimped to a small seize in order be passed through the vasculature of the patient and to be delivered to the implantation site. The different systems known in the prior art use different seizes like 22, 20, or 18 French. Accordingly the prosthesis has to be squeezed together which implies the risk of damaging the pericard material of the valve.

Moreover, the correct positioning is another issue and possibly the capability of the catheter system of repositioning the prosthesis during the course of delivering and applying the prosthesis at the target site and position in the patient. The termination of the procedure after partial release of the prosthesis and complete retrieval of the prosthesis is another advantage which is not possible with many catheter systems of the prior art.

Another issue is the diameter seize of catheter system. The diameter seize of the crimped prosthesis in the catheter for delivery through the vasculature of the patient is critical. Many known systems do not achieve an adequate crimping seize and often the tissue is negatively affected in known systems during the crimping procedure.

Moreover, the crimping of the prosthesis as such represents a challenge. In particular crimping in a manner without damaging, or stretching and/or squeezing the tissue of the prosthesis is often not sufficiently achieved in known systems. Even though immediate damages due to the crimping may not be obvious, often the tissue is still negatively affected by the crimping with a negative impact on the durability of the tissue, e.g. pericard tissue, representing the valve in a heart valve and even the stent component.

Yet another problem in the delivery is the maneuvering of the prosthesis by way of the catheter through the vasculature and its bends. The fact that the vasculature is narrow, and particularly at the aortic entry into the heart a substantive curve with a narrow angle has to be passed through, represents a substantive challenge for such a delivery procedure and device.

Moreover the following has implications for the present disclosure:

Minimally-invasive surgical procedures have evolved substantially since the advent of endovascular technologies and techniques. Embodiments of the present disclosure relate to systems to deliver an endoprosthesis in an implantation site in the heart of a patient. For example, embodiments of the present disclosure relate to systems to deliver and position transcatheter heart valves used in the treatment of a stenosis (narrowing) of a cardiac valve and/or a cardiac valve insufficiency.

Embodiments of the present disclosure also relate to specialized delivery systems for endoprosthetics, including for example, collapsible and expandable prosthetics incorporating a stent which is delivered to the implant site using a specialized catheter and a preshaped sheath.

The expression "narrowing (stenosis) of a cardiac valve and/or cardiac valve insufficiency" is intended to include a functional defect of one or more cardiac valves, which is either genetic or has developed. A cardiac defect of this type might affect each of the four heart valves, although the valves in the left ventricle (aortic and mitral valves) are affected much more often than the right-sided part of the heart (pulmonary and tricuspid valves). The functional defect can result in narrowing (stenosis), inability to close (insufficiency) or a combination of the two (combined vitium). This disclosure relates to delivery systems leveraging an endoprosthesis that includes an expandable stent capable of being implanted transluminally in a patient's body and enlarged radially after being introduced percutaneously for treating heart valve defect, among other indications.

In the current treatment of severe narrowing of a cardiac valve and/or cardiac valve insufficiency, the narrowed or diseased cardiac valve is replaced with an endoprosthesis. Biological or mechanical valves models, which are typically surgically sewn into the cardiac valve bed through an opening in the chest after removal of the diseased cardiac valve, have generally been used for this purpose. Such procedures or operations necessitate the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible valvular prosthesis. Such a self-expandable endoprosthesis can be guided via a catheter system to the implantation site within the heart through an inguinal artery or vein. After reaching the implantation site, the stent can then be unfolded.

However, there is a risk of inexact or incorrect implantation of an endoprosthesis using the solutions described above. Expressed in another way, there is a need for exact positioning and longitudinal alignment of an implanted endoprosthesis. In particular, it is only possible using great skill on the part of the attending surgeon or cardiologist—if at all—to position a stent sufficiently precisely, in both a lateral and longitudinal direction, to ensure that the associated endoprosthesis is located in the correct area of the patient's diseased heart valve to be treated prior to the advent of the instant systems.

On the basis of the problems referenced and outlined above, certain embodiments of the present disclosure address the issue of delivering and positioning a specialized endoprosthesis for treating a narrowed cardiac valve or a cardiac valve insufficiency which realizes optimum positioning accuracy and anchoring of the emplaced device. In addition, the treatment of the narrowed cardiac valve or cardiac valve insufficiency should be by way of a simple procedure to enable routine treatment of narrowed cardiac valve or cardiac valve insufficiency without major stress to the patient.

OBJECTS OF THE DISCLOSURE

One object of certain embodiments of the present disclosure was to provide a catheter system for delivery of a prosthesis, e.g. a heart valve, which is easy to handle. In particular wherein the heart valve can securely be loaded and crimped without negative side effects due to the loading and crimping procedure.

Another object of certain embodiments of the present disclosure is to provide for a catheter and delivery system for a prosthesis designed in a manner in order to facilitate the delivery of the prosthesis to the target site. In particular provide for a system design wherein the maneuvering through the vasculature of a patient is possible without the disadvantages known in the prior art.

Another object of certain embodiments of the present disclosure is to provide for a design wherein the prosthesis can be securely positioned and delivered to the target site with the possibility to terminate the delivery procedure and to retract the prosthesis until a certain procedural time point. Moreover, it is an object of certain embodiments of the present disclosure to enable the free movement of the prosthesis in axial direction and rotational direction.

Another object of certain embodiments of the present disclosure is to provide for a step-wise liberation of the prosthesis in order to place the prosthesis correctly at the target site, enable repositioning in this manner and/or fine tuning of the positioning procedure.

SUMMARY

Embodiments of the present disclosure relate in one aspect to a catheter system comprising i. a steering means; and ii. a delivery means for a heart valve, optionally balloon expandable or self-expandable, wherein the steering means and the delivery means are coaxially and rotationally independently movable.

In another aspect, embodiments of the present disclosure relate to a delivery system for a heart valve comprising i. a steering means; ii. a delivery means for a heart valve and iii. an introducer sheath wherein the steering means, the delivery means and the introducer sheath are coaxially and circumferentially independently movable.

In yet another aspect, embodiments of the present disclosure relate to a method for the delivery of a heart valve to the heart of a patient comprising the steps i. in a first step placing an introducer comprising an introducer sheath into a patient's vasculature; ii. in a second step introducing a catheter system having fixed thereto a self-expanding heart valve through the introducer into the patient's vasculature; iii. in a third step positioning the self-expanding heart valve proximal to the target site in the patient's heart, optionally positioning the heart valve substantially central in the target area; iv. in a fourth step positioning the self-expanding heart valve at the target site; v. in a fifth step partially releasing the self-expanding heart valve from the catheter system; vi. in a sixth step fully releasing the self-expanding heart valve from the catheter system.

In yet another aspect, embodiments of the present disclosure relate to a method of loading a self-expanding heart valve onto a delivery means of a catheter system having an inner shaft, an attachable distal tip, and at least one outer sheath, consisting of compressing the self-expanding heart valve radially and placing the compressed self-expanding heart valve into a tubular retainer, the retainer preventing the self-expanding valve from expanding radially, passing the inner shaft of the delivery system through the central opening of the compressed self-expanding heart valve, attaching the distal tip to the shaft of the delivery system, advancing the outer sheath onto the compressed heart valve to prevent radial expansion of at least part of the heart valve, and removing the tubular retainer from the compressed self-expanding heart valve. In yet another aspect, embodiments of the present disclosure relate to a 2-step deployment procedure of a heart valve.

In yet another aspect, embodiments of the present disclosure relate in particular to the attachment of a heart valve in a catheter or delivery system wherein only the lateral parts of the heart valve are fixed and/or covered by a fixation means of the catheter and wherein essentially the middle part of the heart valve is not being covered.

In yet another aspect, embodiments of the present disclosure relate to a steerable catheter for the delivery of a heart valve.

Briefly stated, transcatheter heart valves are delivered by transapical (TA) and/or transfemoral (TF) delivery systems featuring novel preshaped sheaths and/or steerable catheters to enable emplacement leveraging benefits of proprietary JenaValve® brand of prosthetics.

According to the some embodiment, transcatheter heart valve delivery systems include a Pericardial THV system which comprises a specialized prosthesis; a prosthetic delivery system and separate valve loader.

According to some embodiments, the prosthesis is constructed from porcine pericardial tissue and attached to a self-expanding Nitinol stent scaffold with polyester sutures, having specialized struts and the ability to fit into either transapical or transfemoral catheter delivering devices, as further described, illustrated and claimed below.

According to some embodiments, transapical and/or transfemoral catheter delivery systems are effective to collapsibly house and deliver the scaffold, which has a crown-like design, and works with a pre-shaped sheath and/or steerable catheters, as further described, illustrated and claimed below.

According to some embodiments, the instant systems match with at least three valve sizes, accommodating native valve annulus diameters from at least about 21 to 27 mm.

In accordance with an aspect, the present disclosure provides a catheter system for introducing an expandable heart valve into the body of a patient, the catheter system comprising delivering means for the heart valve.

In some aspects of the present disclosure, the delivering means comprises a catheter tip and a catheter shaft. The catheter tip of the delivery means has a seat portion for accommodating the heart valve to be introduced into the patient's body in its collapsed or crimped state. The catheter tip has further holding means for realisably fixing the heart valve to the catheter tip.

The seat portion of the catheter tip is constituted by a first retaining means and a second retaining means. In some embodiments of the present disclosure, the first retaining means and second retaining means may be constituted by a first sleeve-shaped member and a second sleeve-shaped member.

The first retaining means of the catheter tip serves for reversibly securing a distal end section of the heart valve to the delivery means and, in particular, to the catheter tip of the delivery means. On the other hand, the second retaining means of the catheter tip serves for reversibly securing a proximal end section of the heart valve to the delivery means and, in particular, to the catheter tip of the delivery means.

The first and second retaining means are moveable relative to each other and also relative to the holding means of the catheter tip.

According to some embodiments of the present disclosure, the catheter shaft of the delivery means comprises first force transmitting means and second force transmitting means.

A distal end section of the first force transmitting means is connected or connectable to the first retaining means of the catheter tip and a proximal end section of the first force transmitting means is connected or connectable to a first operating means of a handle of the delivery means. A distal end section of the second force transmitting means is connected or connectable to the second retaining means of the catheter tip and a proximal end section of the second force transmitting means is connected or connectable to a second operating means of the handle of the delivery means.

According to some embodiments of the present disclosure, the handle of the delivery means has at least one first operating means and at least one second operating means with which the catheter tip of the delivery means may be appropriately manipulated so that an expandable heart valve secured to the catheter tip may be released from the catheter tip in steps or in a defined or definable sequence of events.

In accordance with preferred embodiments of the present disclosure, the catheter tip has first and second retaining means—for example in the form of sleeve-shaped members—which may be manipulated with the handle of the delivery means. These retaining means are used for releasably and reversibly securing a distal and proximal end section of the heart valve to the catheter tip.

In some embodiments of the present disclosure, the first retaining means serves for releasably and reversibly securing first functional components of the heart valve, for example retaining hoops of a stent or alternatively positioning hoops of a stent, while the second retaining means serves for releasably and reversibly securing second functional components of the heart valve, for example, positioning hoops of a stent or alternatively for accommodating retaining hoops of a stent.

In relation to the handle of the delivery means, it is preferably provided that, on one hand, the first operating means cooperate with the first retaining means of the catheter tip so that, on actuation of the first operating means, a previously definable longitudinal displacement of the first retaining means may be effected relative to the holding means. On the other hand, the second operating means cooperates with the second retaining means of the catheter tip so that a previously definable longitudinal displacement of the second retaining means may be affected relative to the holding means.

In accordance with some embodiments of the present disclosure, the first and second retaining means only serve for securing the distal and proximal end sections of the heart valve to the catheter tip. In case the first and second retaining means are configured as first and second sleeve-shaped members, these sleeve-shaped members have a length such that a gap is between the first and second sleeve-shaped members when securing the distal and proximal end sections of the heart valve to the catheter tip.

In accordance with some embodiments of the present disclosure, the first force transmitting means of the delivery means is constituted by a first catheter tube defining a first lumen, and the second force transmitting means of the delivery means is constituted by a second catheter tube defining a second lumen. The second catheter tube has a cross-section less than the cross-section of the first catheter tube. The first catheter tube is disposed concentrically and coaxially with the second catheter tube and the second catheter tube is received within the first lumen defined by the first catheter tube.

Contrary to the first and second sleeve-shaped members of the catheter tip, however, the holding means of the catheter tip is not moveable relative to the handle of the delivery means. Rather, the holding means is connected to the handle of the delivery means by using a holding tube having a distal end connected to the holding means and a proximal end connected to a body of the handle of the delivery means. The holding tube has a cross-section less than the cross-section of the first catheter tube. In particular, the first catheter tube is disposed concentrically and coaxially with both, the second catheter tube on the one hand and the holding tube on the other hand.

Preferably, the holding tube has a cross-section less than the cross-section of the first catheter tube and greater than the cross-section of the second catheter tube such that the holding tube is received within the first lumen defined by the first catheter tube and the second catheter tube is received within a passageway defined by the holding tube. The passageway defined by the holding tube has a diameter sufficient to accommodate the second catheter tube such that the second catheter tube is moveable relative to the holding tube.

The second lumen defined by the second catheter tube has a diameter sufficient to accommodate a guide wire. The second catheter tube is made from a rigid material including, for example, nitinol, stainless steel or a rigid plastic material. The material of the distal end section of the second catheter tube may have an increased flexibility compared to the material of the proximal end section in order to allow the distal end section of the catheter shaft to pass the aortic arch during insertion of the catheter tip.

In some embodiments of the present disclosure, the distal end section of the second catheter tube terminates in a soft catheter end tip having an atraumatic shape. The soft catheter end tip is provided with a channel aligned with the second lumen defined by the second catheter tube such that a guide wire accommodated within the second lumen of the second catheter tube may pass through the channel of the soft catheter end tip. The second sleeve-shaped member of the catheter tip is connected to the soft catheter end tip such that the opened end of the second sleeve-shaped member faces in the proximal direction opposite to the direction of the soft catheter end tip and to the second catheter tube.

The holding tube is preferably made of a rigid material, for example, a rigid plastic material, stainless steel or Nitinol. The distal end of the holding tube terminates in the holding means which is also made of a rigid material, for example, a rigid plastic material or stainless steel. The passageway defined by the holding tube is aligned with a channel which passes through the holding means. In this way, the second catheter tube is accommodated in the passageway of the holding tube and the channel of the holding means such as to be moveable relative to the holding tube and the holding means.

The holding tube is provided for connecting the holding means to the handle of the delivery means. For this purpose, the holding tube has a distal end connected to the holding means and a proximal end connected to a body of the handle of the delivery means.

The first catheter tube is preferably made of a bendable but inelastic material. For example, the first catheter tube may be at least partly made of a braided or non-braided catheter tube. Hence, the first catheter tube may have a stiff braid reinforced body similar to the catheter body described in U.S. Pat. No. 4,665,604 which is incorporated herein by reference.

The first catheter tube shall be adapted to transfer compression and tension forces from the first operating means of the handle of the delivery means to the first retaining means of the catheter tip without overly changing of its total length. The distal end of the first catheter tube terminates at a flared section as the transition to the section defining the first retaining means of the catheter tip.

The flared section and the first retaining means may be formed integrally and may be connected to the distal end section of the first catheter tube. Alternatively, the first retaining means and the flared section of the first catheter tube may be all of the same material and originating from the same raw tube prior to a widening process so that the flared section and the first retaining means are the same elements.

In accordance with another aspect of the present disclosure, the catheter system further comprises steering means. The steering means serves for guiding the delivery means and, in particular, the catheter tip of the delivery means when advancing the catheter tip through the patient's vasculature.

In some embodiments of the present disclosure, the steering means comprises a steerable catheter tube having a proximal end section and a distal end section. The proximal end section of the steerable catheter tube is connected or connectable with a handle of the steering means.

The handle of the steering means is provided with operating means, for example in the form of a rotatable knob or wheel, by means of which a flexural link region of the steerable catheter tube can be controlled.

In accordance with other embodiments disclosed herein, the steerable catheter tube of the steering means is provided without any flexural link region, which can be manipulated by corresponding operating means. Rather, in these embodiments, the material of the distal end section of the steerable catheter tube may have an increased flexibility compared to the material of the proximal end section. In this way, the distal end section of the steerable catheter tube may easily pass, for example, the aortic arch during insertion of the steerable catheter tube.

In some embodiments disclosed herein, the handle of the steering means is provided with operating means by means of which a flexural link region of the steerable catheter tube can be controlled, wherein the operating means preferably has a detent device to allow a set deflection of the flexural link region of the steerable catheter tube to be fixed. For example, it is possible to provide a suitable catch mechanism on the operating means, which cooperates with a body of the handle of the steering means. In particular, it is possible for the flexural link region of the steerable catheter tube to be connected to the operating means of the steering means by way of a control wire whereby, on an actuation of the operating means via the control wire a tensile forces is exerted on the flexural link region of the steerable catheter tube, which produces a predefined or predefinable deflection of the flexural link region.

However it is also possible, of course, to choose other embodiments as the operating means of the steering means for deflecting the steerable catheter tube or a flexural link region of the steerable catheter tube, in case the steerable catheter tube is provided with such a flexural link region.

In accordance with some embodiments disclosed herein, the proximal end section of the steerable catheter tube of the steering means terminates in a port section of the steering means or is connected with a port section of the steering means. The port section of the steering means serves for introducing the catheter tip and catheter shaft of the delivery means into the steerable catheter tube. For this purpose, the port section of the steering means has a lumen defining a passageway which extends through the port section, the distal end section of the passageway being aligned with the proximal end section of the steerable catheter tube.

The port section of the steering means is preferably integrated in or connected with the handle of the steering means.

The catheter tip and catheter shaft of the delivery means is introducible (via the port section of the steering means) into the steerable catheter tube. The catheter shaft of the delivery means and particularly the first catheter tube of the catheter shaft of the delivery means is moveable relative to the steerable catheter tube. In particular, the steerable catheter tube terminates proximal to the catheter tip wherein the cross-section of proximal end section of the introducer sheath shall be substantially the same as or slightly larger than the cross-section of the flared section provided at the proximal end of the first catheter tube.

The proximal end section of the steering means and, in particular, the proximal end section of the port section of the steering means is releasably connectable to the handle of the delivery means.

According to an aspect of the present disclosure, the catheter system further comprises an introducer having an introducer sheath. The introducer sheath has a cross-section greater than the cross-section of the steerable catheter tube of the steering means.

The introducer sheath serves as guiding means when introducing the delivery means and/or the steering means and, in particular, the steerable catheter tube of the steering means into the patient's vasculature. In more detail, the introducer sheath defines a passageway through which the catheter tip and catheter shaft of the delivery means and/or the steerable catheter tube of the steering means may be guided to the implantation side within the patient's body.

The introducer sheath has a distal end, a proximal end and a passageway extending there between. The introducer sheath has a length such that the distal end of the introducer sheath terminates proximal to the catheter tip of the delivery system, when the catheter shaft and the catheter tip of the delivery system has been fully introduced into the introducer sheath.

When at least a section of the catheter shaft of the delivery means or at least a section of the steerable catheter tube of the steering means has been introduced into the passageway defined by the introducer sheath, the introducer sheath is disposed concentrically and coaxially with the section of the catheter shaft of the delivery means or the steerable catheter tube of the steering means.

In any case, however, the catheter shaft of the delivery means and/or the steerable catheter tube of the steering means is moveable relative to the introducer sheath. In particular, the introducer sheath terminates proximal to the catheter tip wherein the cross-section of proximal end section of the introducer sheath shall be substantially the same as or slightly larger than the cross-section of the steerable catheter tube.

The proximal end section of the introducer sheath is connected to an introducer port. The introducer port serves for providing access to the introducer sheath of the introducer required for delivering the delivery means or the steerable catheter tube of the steering means into the introducer sheath.

The introducer port may comprise a base member which is configured to be manually fixable to the handle of the delivery means, when the catheter shaft of the delivery means is introduced into the passageway defined by the introducer sheath, or to be manually fixable to the handle of the steering means, when the steerable catheter tube of the steering means is introduced into the passageway defined by the introducer sheath.

In accordance with some embodiments disclosed herein, the introducer port is provided with a sealing arrangement for preventing leakage of fluid, in particular blood, from the introducer, when the introducer sheath is introduced into the patient's vasculature.

In some embodiments disclosed herein, the proximal end section of the introducer sheath terminates in a crimping section distal to the sealing arrangement of the introducer port. The crimping section of the introducer serves for crimping at least a middle section of a heart valve fixed to the catheter tip of the delivery means during the introduction of the catheter tip into the introducer sheath. As already mentioned above, according to embodiments disclosed herein, preferably only the distal and proximal end sections of the heart valve are fixed to the catheter tip of the delivery means by means of the first and second retaining means, wherein no dedicated retaining means is allocated to the middle section of the heart valve between the distal and proximal end sections of the heart valve.

For crimping the middle section of the heart valve during the introduction of the catheter tip into the introducer sheath, the catheter tip passes through the crimping section of the introducer thereby further reducing the diameter of the middle section of the heart valve fixed to the catheter tip. In some embodiments disclosed herein, the crimping section may comprise a conical tubular member having an inner diameter which decreases in the distal direction of the tubular member.

The introducer sheath may be of a thin material such as to allow length deformation of the introducer sheath upon transfer of compression and tension forces. The introducer sheath material, however, shall have sufficient stiffness in order to mechanically avoid kinking of the flexible sections of the distal portion of the catheter shaft during insertion of the catheter tip.

In some embodiments of the present disclosure, the introducer sheath has a pre-shaped, preferably curved, configuration.

An inlet may be provided at a proximal end section of the steering means, the introducer and/or the delivery means for injection of fluids, if necessary. Furthermore, a check valve may be provided at the proximal end section of the introducer sheath to prevent fluid from leaking out of the introducer sheath.

The introducer sheath may have a length sufficient to protect the inner wall of the blood vessel through which the catheter tip passes. In addition, a separate introducer system (not belonging to the catheter system) may be provided. The introducer system then may serve as a portal for passing the complete catheter system from the catheter tip to the catheter shaft into the patient's body and up to the heart.

In addition, the introducer sheath reduces the compression force exerted on the first catheter tube that is inserted through the introducer sheath. This increases manoeuvrability of the steerable catheter tube and the catheter shaft of the delivery means throughout the procedure. A consequence thereof is that any frictional force is reduced. Moreover, moving the catheter tip after it has been advanced through the vascular system of a patient, is greatly improved while at the same time lowering the risk of injury of the patient.

The length of the introducer sheath depends on the length of the catheter shaft of the delivery means and will typically be between about 20 cm and 100 cm. Those skilled in the art will appreciate, however, that all dimensions provided herein are intended as examples only, and that the introducer sheaths and catheter tubes of different dimensions may be substituted for a particular use.

As will be appreciated, the introducer sheath will be of a size, i.e. has an outer diameter, which will permit insertion in a patient's blood vessel (artery or vein) which is used for moving the stent transarterially or via a vein to an insufficient heart valve.

The introducer sheath may be capable of traversing tortuous pathways in the body of the patient without kinking. The introducer sheath may include an inner lubricious liner, an outer polymeric jacket, and a coil reinforcement between the inner and the outer layers. This introducer sheath may provide favourable flexibility without kinking or compression. One or more radiopaque bands or markers may be incorporated within the introducer sheaths material to allow precise location of the introducer sheaths distal end for positioning accuracy. Those skilled in the art will appreciate that other known materials may also be suitable for a particular purpose.

The catheter system is particularly adapted to deliver and implant a heart valve as described for example in the European Patent Application No. 07 110 318 or in the European Patent Application No. 08 151 963. In some embodiments of the present disclosure, a heart valve is accordingly used which comprises a stent and a heart valve prosthesis attached to the stent. The stent exhibits the following:

a first retaining region, to which the heart valve prosthesis can be attached;

an opposing, second retaining region with at least one retaining element, for example in the form of retaining eyes or in the form of retaining heads, whereby at least one retaining element of the stent can be put in releasable engagement with the holding means of the catheter tip of the delivery means;

at least one retaining hoop, to which the heart valve prosthesis can be fastened; and at least one and preferably three positioning hoops, which are designed to engage in pockets of the native heart valve in the implanted state of the stent, thus to enable automatic positioning of the stent in the aorta of the patient.

In particular, a catheter system is disclosed herein, with which an expandable heart valve stent with a heart valve prosthesis attached to this stent can be advanced to the implantation site in a particularly simple way, for example via the aorta of a patient being treated (transarterially or transfemorally). Preferably, during transarterial or transfemoral access by the catheter system, the whole free cross-section available within the aorta is not completely filled up, since the catheter tip provided at the distal end region of the catheter system, in which the stent can be accommodated with the heart valve prosthesis, can be made sufficiently small with respect to its external diameter.

The expandable heart valve stent with the heart valve prosthesis attached to it can be fixed temporarily during implantation in a crimped state to the catheter tip of the delivery means.

The catheter system designed for transarterial or transfemoral access is therefore suitable for inserting a heart valve stent with a heart valve prosthesis attached to it, transarterially or transfemorally into the body of the patient; for example, the catheter tip of the delivery means of the catheter system is inserted via puncture of the A. femoris communis (inguinal artery).

In particular, with the catheter system designed for transarterial or transfemoral access, the catheter shaft of the delivery means may be designed so that it is both kink-resistant and flexible such that a bending radius of up to 4 cm, and preferably up to 3 cm, can be realised, at least at the distal end region of the catheter shaft.

BRIEF DESCRIPTION OF THE DRAWINGS

Various embodiments will be described with reference to the appended drawings below.
Of these:

FIG. 2b: a sectioned side elevation of the delivery means of FIG. 2a;

FIG. 2c: a sectioned side elevation of the catheter tip of the delivery means of FIG. 2a;

FIG. 3b: a sectioned side elevation of the steering means of FIG. 3a;

FIGS. 6a-i: sectioned side elevations of components of the delivery means of FIG. 2a;

FIGS. 16a, b: side views of another embodiment of a device to facilitate the removal of the distal end of a catheter from an introducer sheath or guiding catheter;

FIG. 17: a side view of another embodiment of a device to facilitate the removal of the distal end of a catheter from an introducer sheath or guiding catheter;

FIGS. 18a, b: side views of another embodiment of a device to facilitate the removal of the distal end of a catheter from an introducer sheath or guiding catheter;

FIGS. 19a, b: side views of another embodiment of a device to facilitate the removal of the distal end of a catheter from an introducer sheath or guiding catheter; and FIG. 20: a side view of another embodiment of a device to facilitate the removal of the distal end of a catheter from an introducer sheath or guiding catheter.

DETAILED DESCRIPTION

In the following, exemplary embodiments of the present disclosure will be described in more detail.

Figure 5:
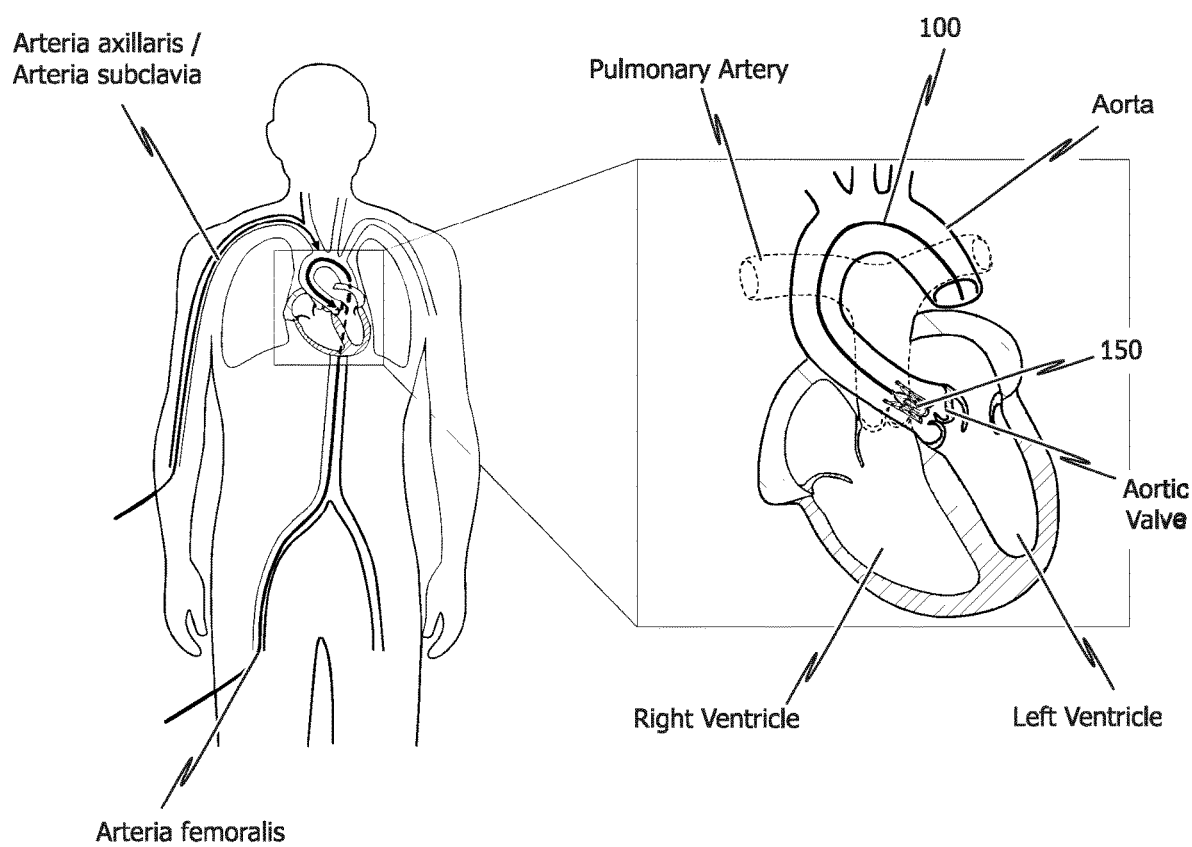
FIG. 5: a schematic view to illustrate a transfemoral/transarterial implantation procedure of a heart valve stent.
Figure 6A:
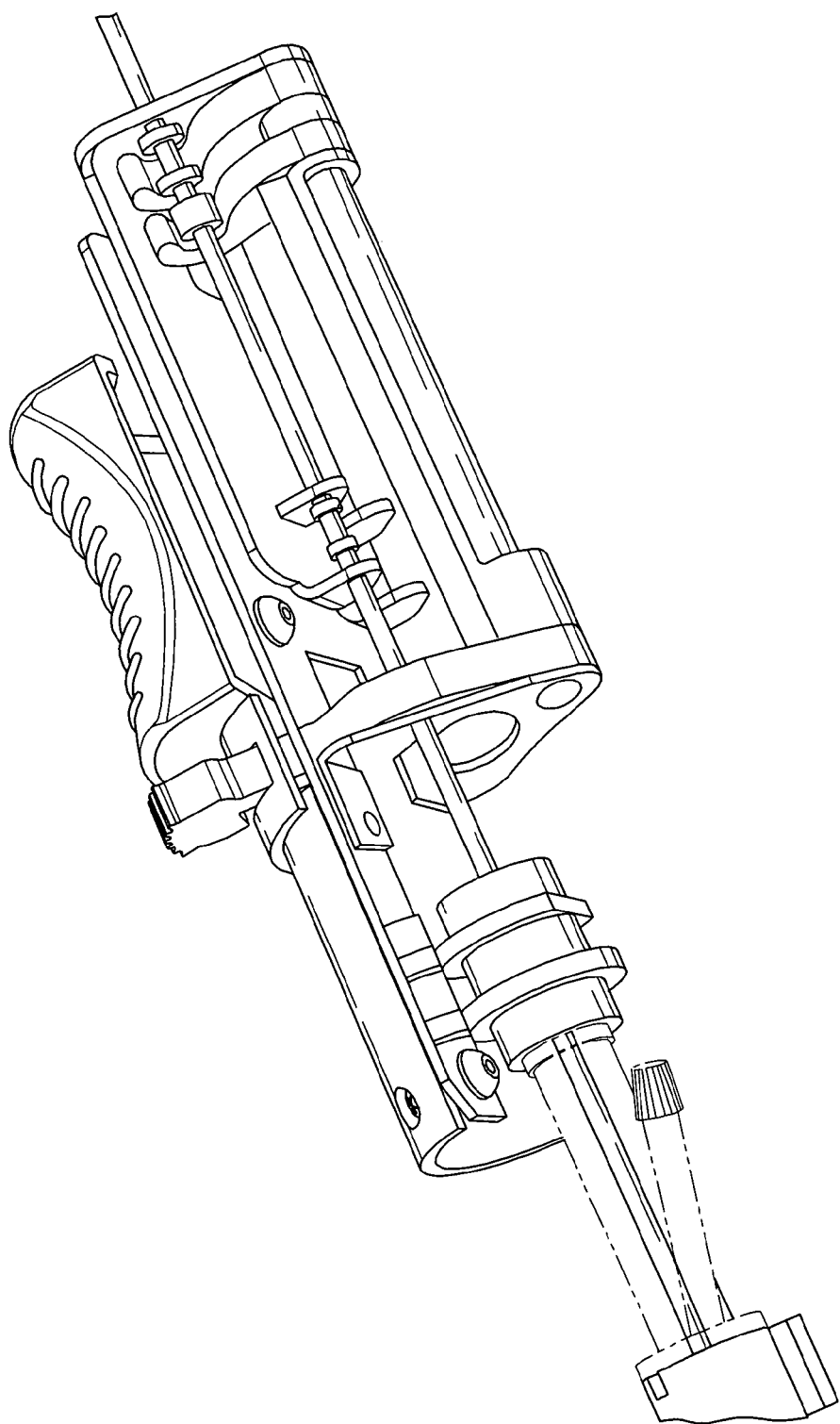
Figure 6B:
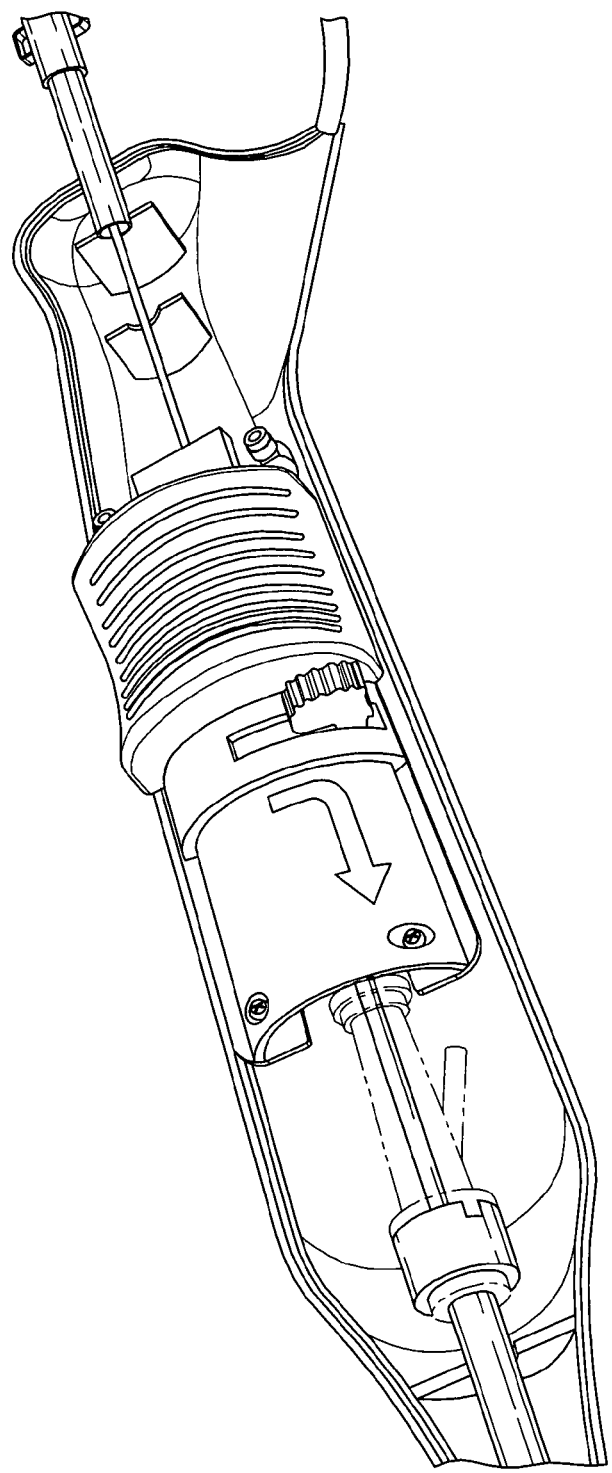
Figure 6C:
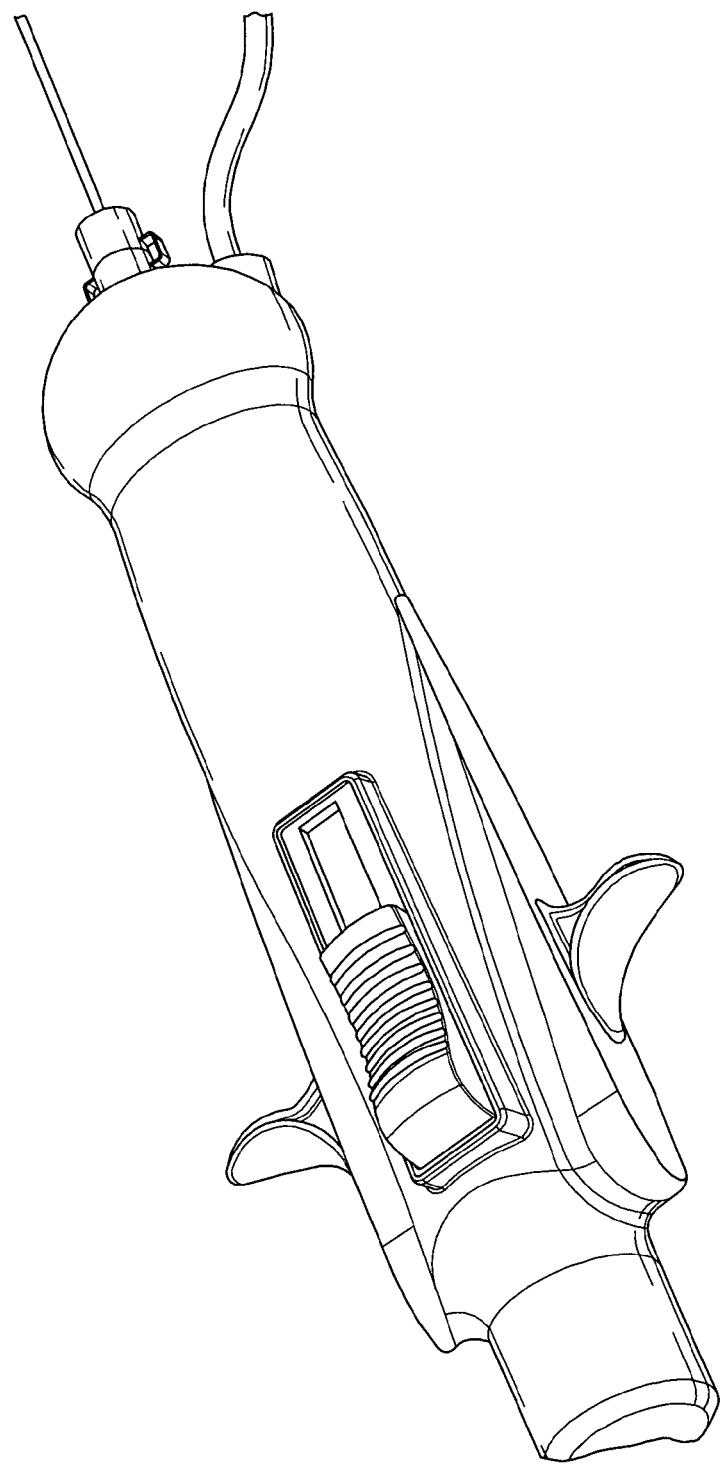
Figure 6D:
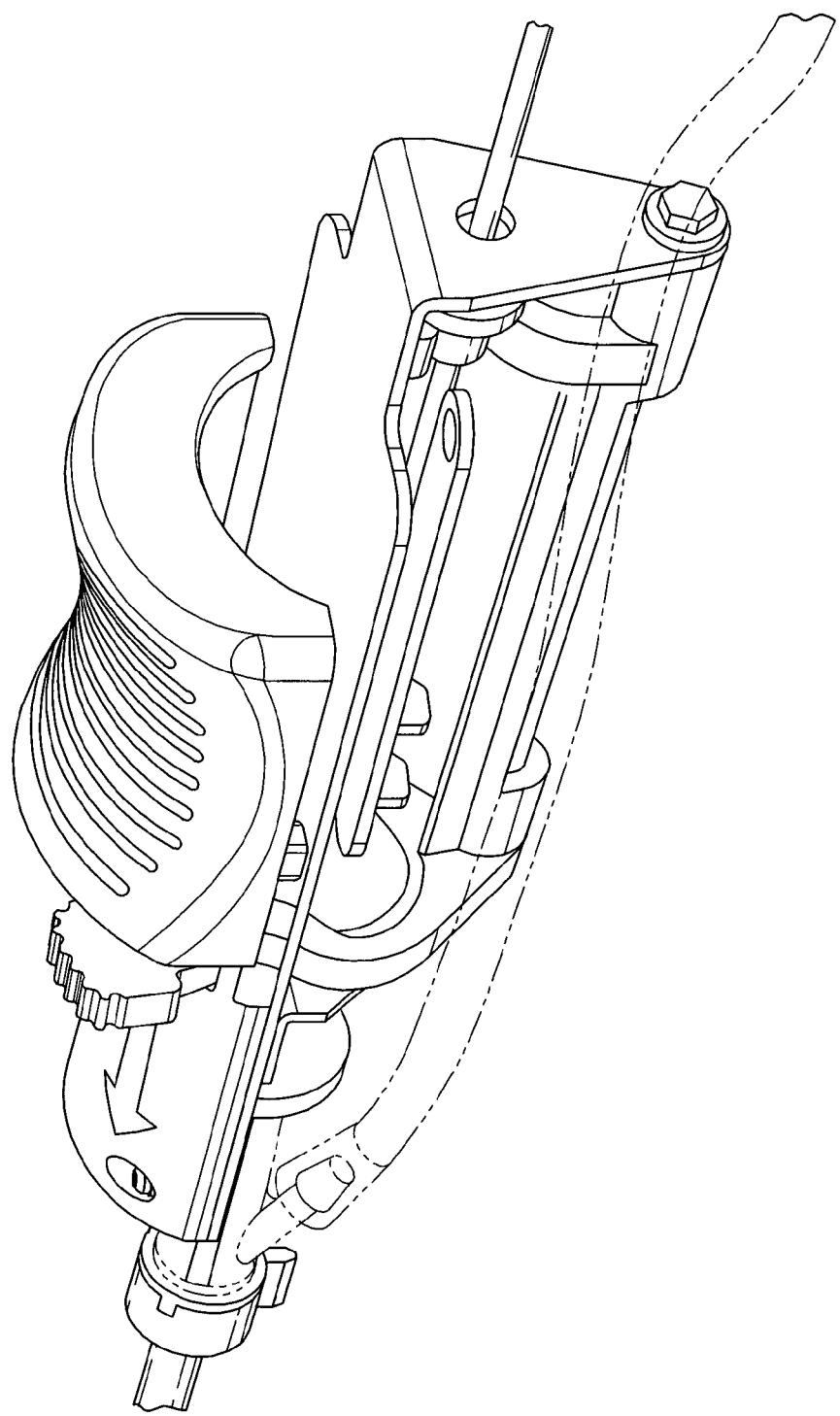
Figure 6E:
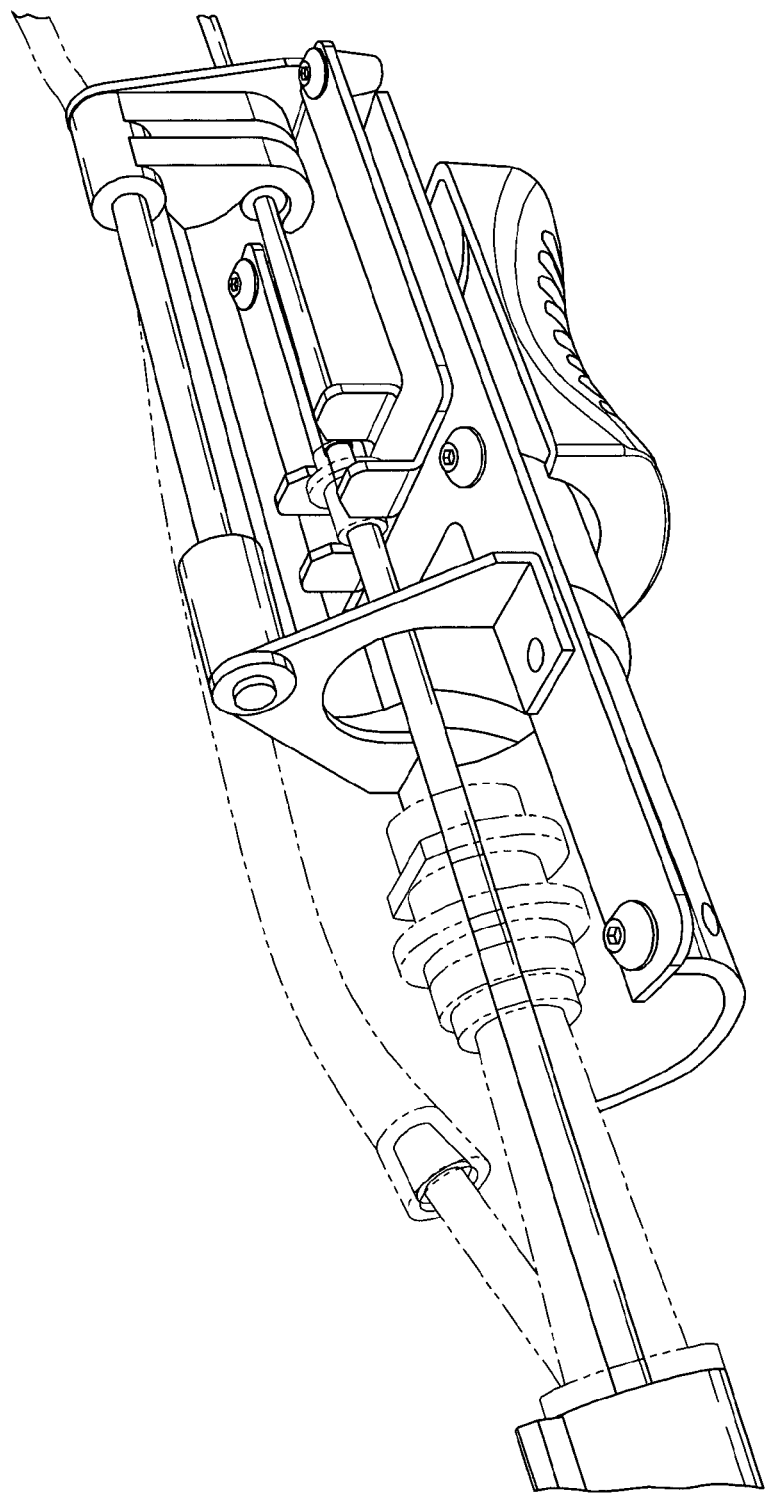
Figure 6F:
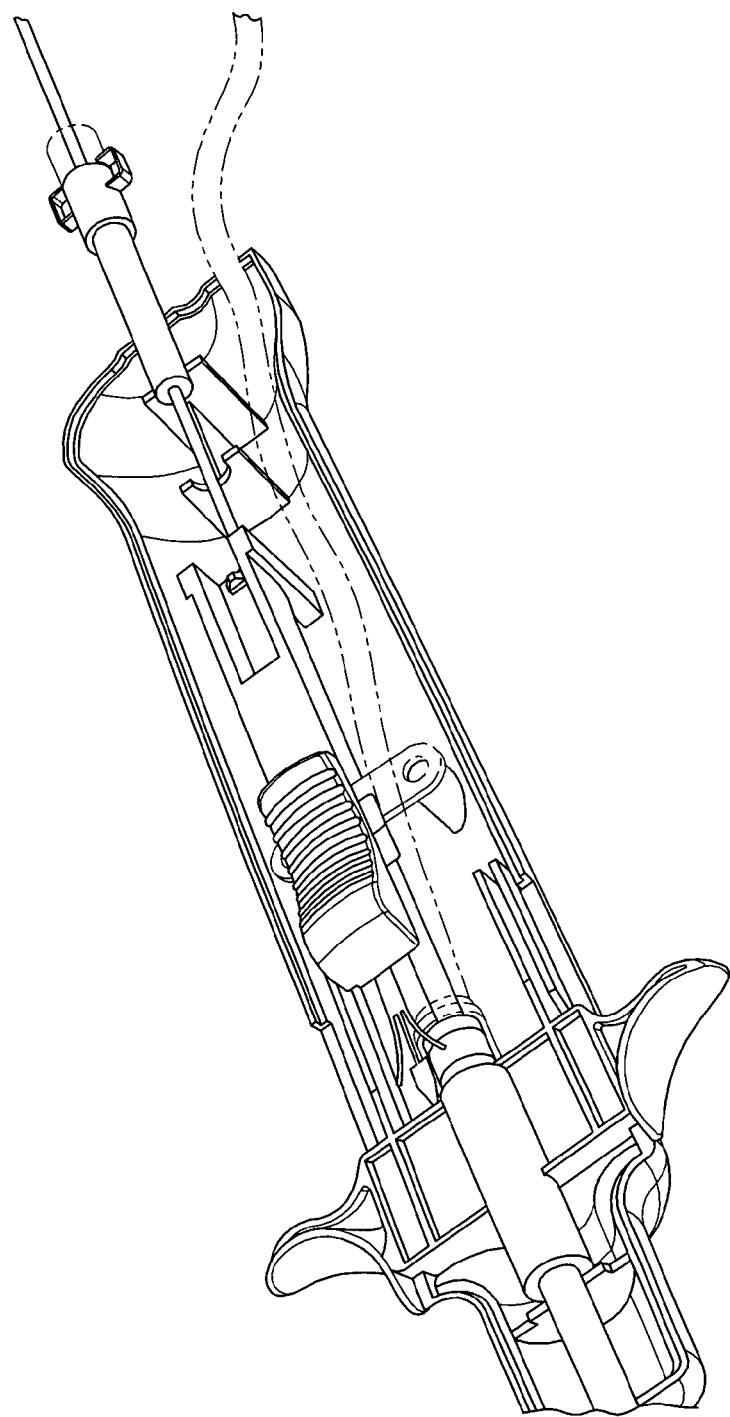
Figure 6G:
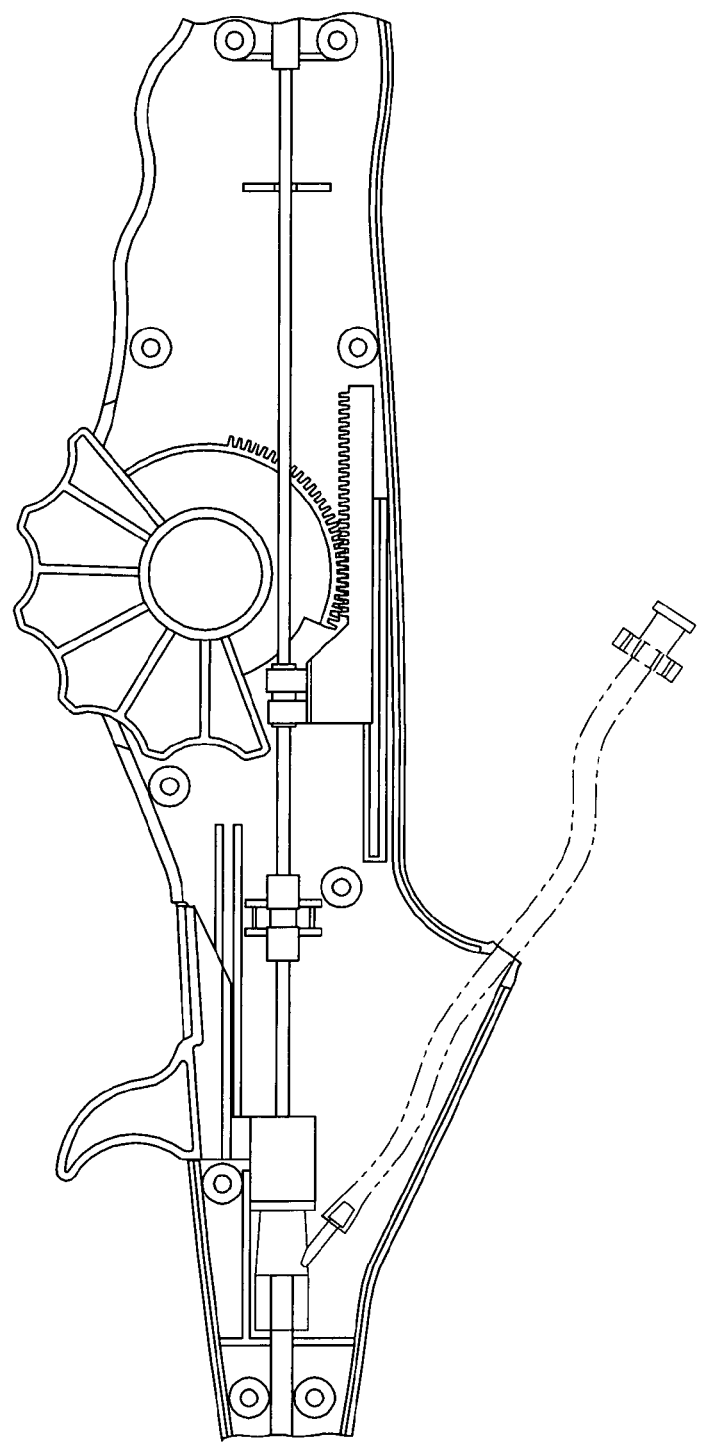
Figure 6H:
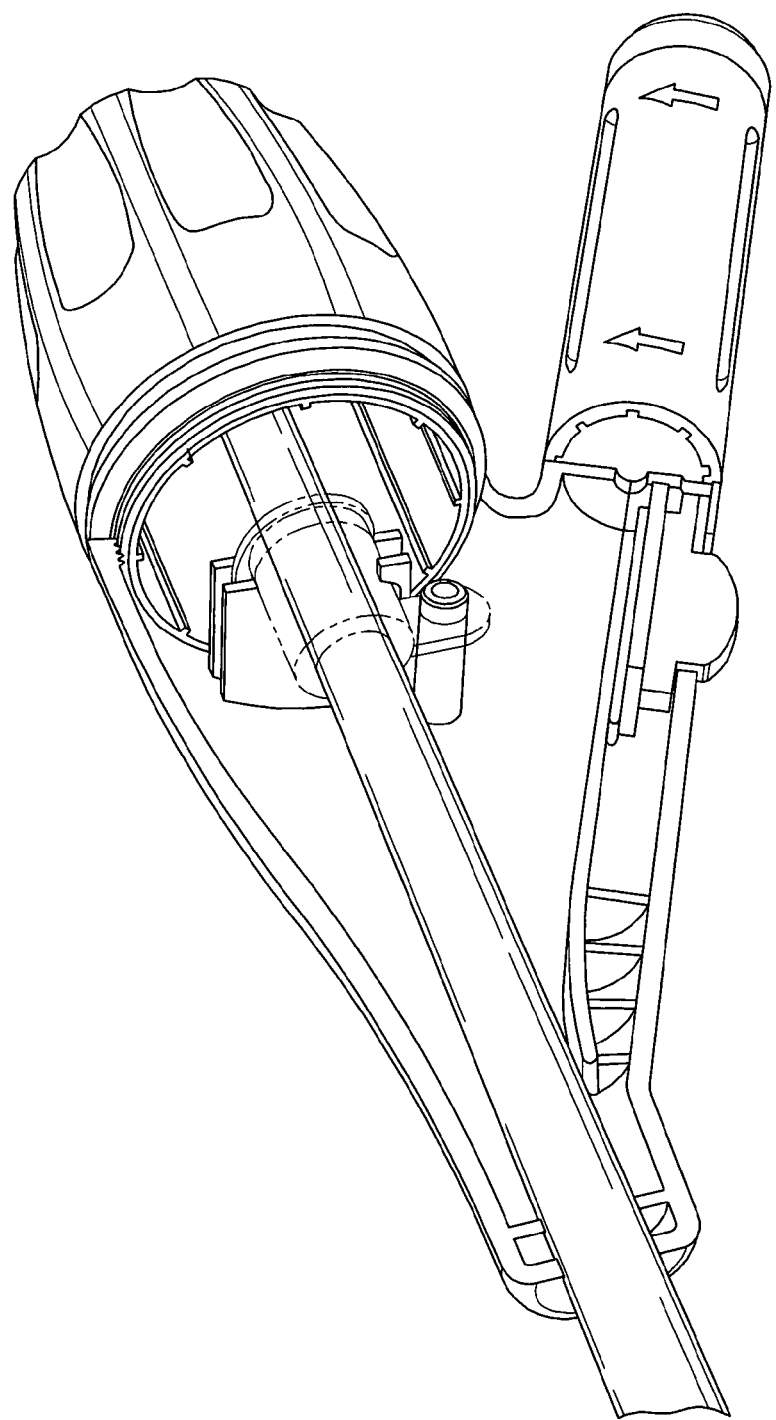
Figure 6I:
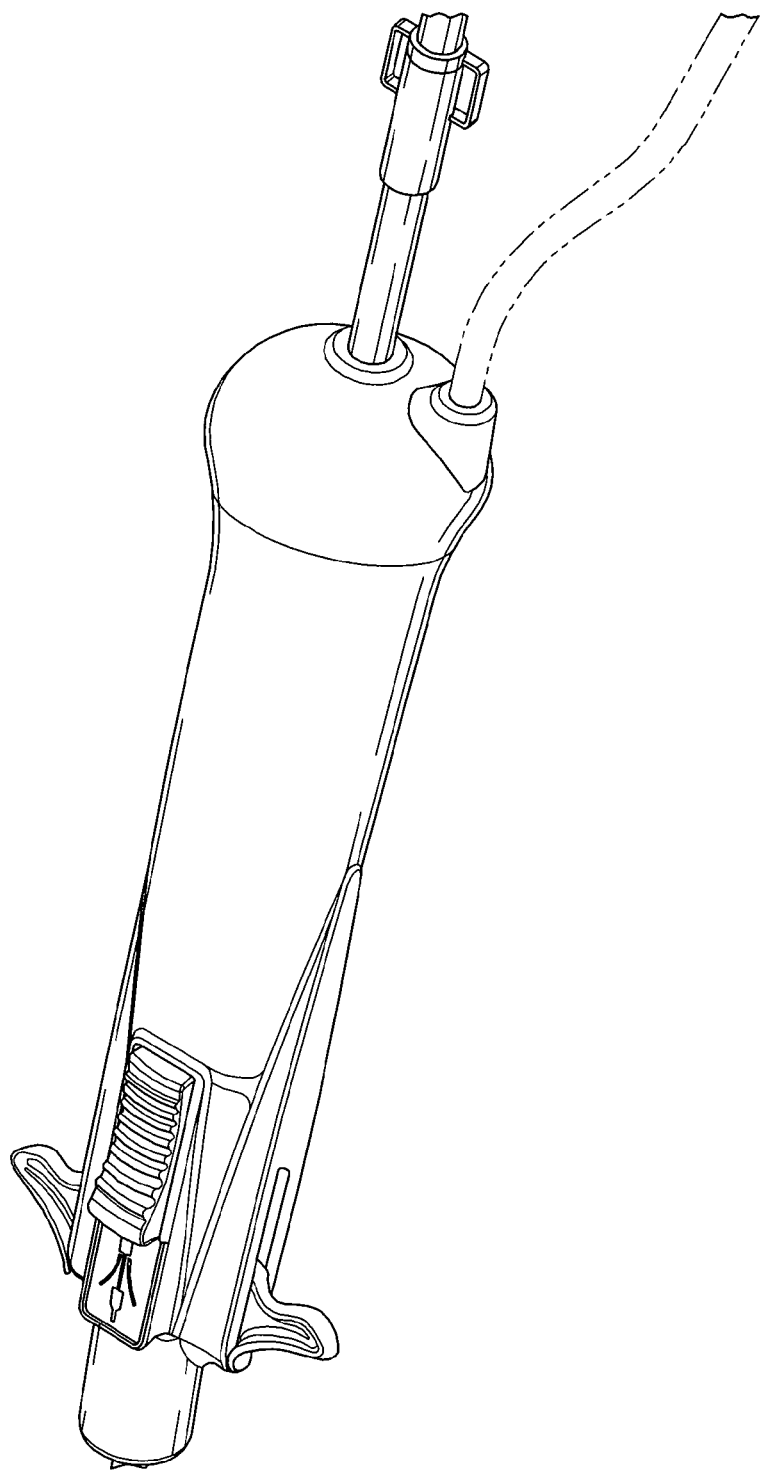

FIG. 5 shows schematically an example of how a transarterial or transfemoral access can be gained to the heart of a patient. In the illustration in accordance with FIG. 5, a heart valve stent 150 is advanced with the aid of a delivery system 100 via the femoral artery to the aortic valve. Embodiments of a delivery system 100, which is suitable for transarterial or transfemoral access, are described in the following.

Figure 1:
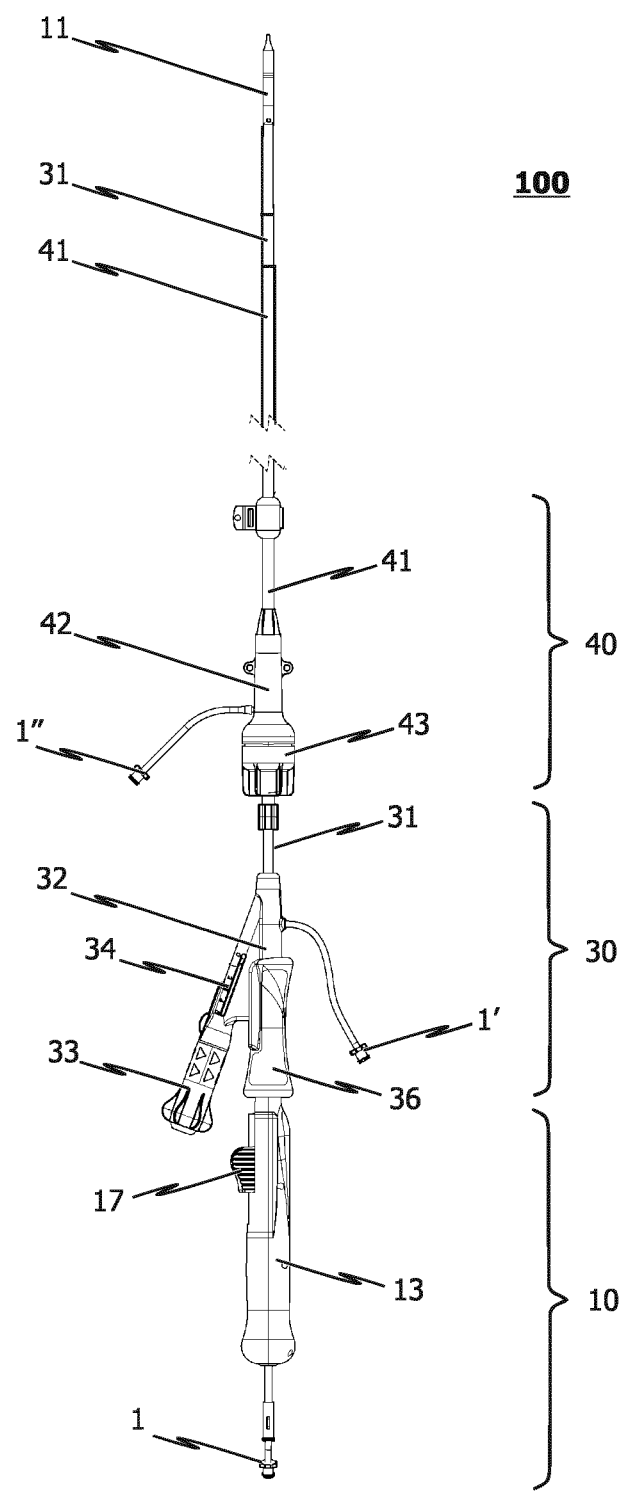
FIG. 1: a side elevation of an embodiment of a delivery system for transfemoral/transarterial insertion of an expandable heart valve.

As depicted, for example, in FIG. 1, the delivery system 100 according to an exemplary embodiment of the present disclosure comprises delivery means 10, steering means 30, and an introducer 40.

The delivery means 10 has a catheter tip 11, a catheter shaft 12, and a handle 13 connected to the proximal end section of the catheter shaft 12. In this regard, reference is also made to FIG. 2a and FIG. 2b.

As illustrated, for example, in FIG. 2c, the catheter tip 11 of the delivery means 10 has a seat portion for accommodating a heart valve to be inserted in its crimped state and holding means 14 for releasably fixing the heart valve to the catheter tip 11.

The delivery means 10 further comprises a catheter shaft 12 for connecting the catheter tip 11 to the handle 13 of the delivery means 10, the distal end section of the catheter shaft 12 being flexible enough such that the catheter tip 11 and the distal end section of the catheter shaft 12 may pass the aortic arch during insertion through the aorta of the patient.

The seat portion of the catheter tip 11 comprises first retaining means 15 and second retaining means 16, the respective cross-sections of the first and second retaining means 15, 16 may be identical to each other. In the exemplary embodiment illustrated in FIG. 2c, the first and second retaining means 15, 16 are configured as sleeve-shaped elements, respectively. The lengths of these sleeve-shaped elements are respectively chosen such that the seat portion of the catheter tip is not totally covered by the sleeve-shaped elements. Rather and as illustrated in FIG. 2c, a middle section of the seat portion of the catheter tip is always uncovered.

The first and second retaining means 15, 16 are movable relative to each other and relative to the holding means 14. For this purpose, first force transmitting means 20 with a distal end section connected to the first retaining means 15 and a proximal end section connected to first operating means 17 of the handle 13 are provided. In addition, second force transmitting means 21 with a distal end section connected to the second retaining means 16 and a proximal end section connected to second operating means 18 of the handle 13 are provided. When manipulating the first and/or second operating means 17, 18 of the handle 13, the first and/or second retaining means 15, 16 may be moved relative to each other and relative to the holding means 14.

As can be seen from FIG. 2b and FIG. 2c, the first force transmitting means 20 may be constituted by a first catheter tube defining a first lumen and the second force transmitting means 21 is constituted by a second catheter tube defining a second lumen. The second catheter tube may have a cross-section less than the cross-section of the first catheter tube. The first catheter tube may be disposed concentrically and coaxially with the second catheter tube and the second catheter tube is received within the first lumen defined by the first catheter tube. Contrary to the first and second retaining means 15, 16 of the catheter tip 11, however, the holding means 14 of the catheter tip 11 are not moveable relative to the handle 13 of the delivery means 10. Rather, the holding means 14 are connected to the body 19 of the handle 13 by using a holding tube 22 having a distal end connected to the holding means 14 and a proximal end connected to a body 19 of the handle 13.

The holding tube 22 may have a cross-section less than the cross-section of the first catheter tube of the first force transmitting means 20. In particular, the first catheter tube of the first force transmitting means 20 may be disposed concentrically and coaxially with both, the second catheter tube of the second force transmitting means 21 on the one hand and the holding tube 22 on the other hand.

In some embodiments, the holding tube 22 has a cross-section less than the cross-section of the first catheter tube and greater than the cross-section of the second catheter tube such that the holding tube 22 is received within the first lumen defined by the first catheter tube and the second catheter tube is received within a passageway defined by the holding tube 22. The passageway defined by the holding tube 22 has a diameter sufficient to accommodate the second catheter tube such that the second catheter tube is moveable relative to the holding tube 22.

The second lumen defined by the second catheter tube has a diameter sufficient to accommodate a guide wire (not shown). The second catheter tube may be made from a rigid material including, for example, Nitinol, stainless steel or a rigid plastic material. The material of the distal end section of the second catheter tube may have an increased flexibility compared to the material of the proximal end section in order to allow the distal end section of the catheter shaft 12 to pass the aortic arch during insertion of the catheter tip 11.

As can been seen, for example, from FIG. 2c, the distal end section of the second catheter tube terminates in a soft catheter end tip 23 having an atraumatic shape. The soft catheter end tip 23 is provided with a channel aligned with the second lumen defined by the second catheter tube such that a guide wire accommodated within the second lumen of the second catheter tube may pass through the channel of the soft catheter end tip. The second retaining means 16 of the catheter tip 11 is connected to the soft catheter end tip 23 such that the opened end of the second retaining means 16 faces in the proximal direction opposite to the direction of the soft catheter end tip 23 and to the second catheter tube.

According to the exemplary embodiments of the present disclosure, the holding tube 22 is made of a rigid material, for example, a rigid plastic material, stainless steel or Nitinol. The distal end of the holding tube 22 terminates in the holding means 14 which is also made of a rigid material, for example, a rigid plastic material or stainless steel. The passageway defined by the holding tube 22 is aligned with a channel which passes through the holding means 14. In this way, the second catheter tube is accommodated in the passageway of the holding tube 22 and the channel of the holding means 14 such as to be moveable relative to the holding tube 22 and the holding means 14.

The first catheter tube of the first force transmitting means 20 is made of a bendable but inelastic material. For example, the first catheter tube may be at least partly made of a braided or non-braided catheter tube. The first catheter tube shall be adapted to transfer compression and tension forces from the first operating means 17 of the handle 13 to the first retaining means 15 of the catheter tip 11 without overly changing its total length. The distal end of the first catheter tube terminates at a flared section as a transition to the section defining the first retaining means 15 of the catheter tip 11.

The flared section and the first retaining means 15 may be formed integrally and may be connected to the distal end section of the first catheter tube. In addition, the flared section may constitute the first retaining means 15 of the catheter tip 11. The first retaining means 15 and the flared section of the first catheter tube may be all of the same material and originating from the same raw tube prior to a widening process so that the flared section and the first retaining means 15 are the same elements.

Referring for example to FIG. 1, the delivery system 100 according to an exemplary embodiment of the present disclosure further comprises steering means 30 for guiding the delivery means 10 and, in particular, the catheter tip 11 of the delivery means 10 when advancing the catheter tip 11 through the patient's vasculature.

Figure 3A:
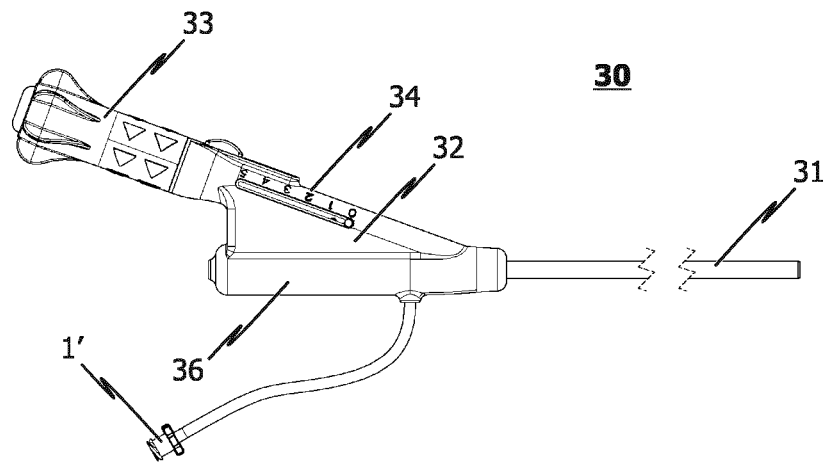
FIG. 3a: a side elevation an embodiment of a steering means of a delivery system in accordance with FIG. 1.
Figure 3B:
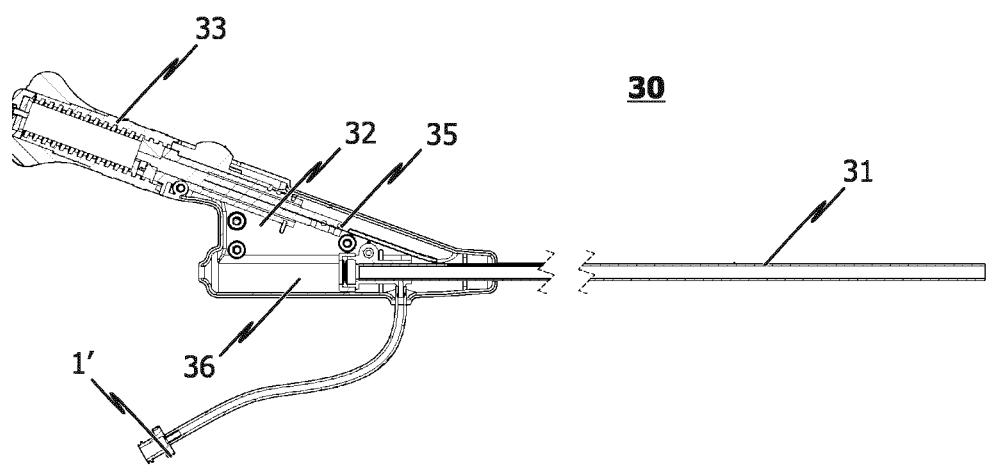

As illustrated in FIGS. 3a-b, the steering means 30 comprises a steerable catheter tube 31 having a proximal end section and a distal end section. The proximal end section of the steerable catheter tube 31 is connected or connectable with a handle 32 of the steering means 30.

The handle 32 of the steering means 30 is provided with operating means 33, for example in the form of a rotatable knob or wheel, by means of which a flexural link region of the steerable catheter tube 31 can be controlled.

As illustrated in FIG. 3a, the handle 32 of the steering means 30 is also provided with indicator means 34 for indicating the degree of deflection applied to the flexural link region of the steerable catheter tube 31 by means of the operating means 33.

Although not explicitly shown in FIG. 3a, in some embodiments, the operating means 33 preferably has a detent device to allow a set deflection of the flexural link region of the steerable catheter tube 31 to be fixed. For example, it is possible to provide a suitable catch mechanism on the operating means 33, which cooperates with a body of the handle 32 of the steering means 30.

As can be seen from FIG. 3b, a control wire 35 is provided, which connects the operating means 34 with the flexural link region of the steerable catheter tube 31. On an actuation of the operating means 33, a tensile forces is exerted via the control wire 35 on the flexural link region of the steerable catheter tube 31, which produces a predefined or predefinable deflection of the flexural link region.

However it is also possible, of course, to choose other embodiments as the operating means 33 of the steering means 30 for deflecting the steerable catheter tube 31 or a flexural link region of the steerable catheter tube 31.

In the exemplary embodiment of the steering means 30 illustrated in FIG. 3b, the proximal end section of the steerable catheter tube 31 of the steering means 30 terminates in a port section 36 of the steering means 30. The port section 36 of the steering means 30 serves for introducing the catheter tip 11 and catheter shaft 12 of the delivery means 10 into the steerable catheter tube 31. For this purpose, the port section 36 of the steering means 30 has a lumen defining a passageway which extends through the port section 36, the distal end section of the passageway being aligned with the proximal end section of the steerable catheter tube 31.

As illustrated in FIG. 1, the catheter tip 11 and catheter shaft 12 of the delivery means 10 is introducible (via the port section 36 of the steering means 30) into the steerable catheter tube 31. The catheter shaft 12 of the delivery means 10 and particularly the first catheter tube of the catheter shaft of the delivery means 10 is moveable relative to the steerable catheter tube 31. In particular, the steerable catheter tube 31 terminates proximal to the catheter tip 11 wherein the cross-section of proximal end section of the introducer sheath shall be substantially the same as or slightly larger than the cross-section of the flared section provided at the proximal end of the first catheter tube.

As illustrated in FIG. 1, the exemplary embodiment of the delivery system 100 is also provided with an introducer 40 having an introducer sheath 41. The introducer sheath 41 has a cross-section greater than the cross-section of the steerable catheter tube 31 of the steering means 30.

The introducer sheath 41 serves as guiding means when introducing the delivery means 10 and/or the steering means 30 and, in particular, the steerable catheter tube 31 of the steering means 30 into the patient's vasculature. In more detail, the introducer sheath 41 defines a passageway through which the catheter tip 11 and catheter shaft 12 of the delivery means 10 and/or the steerable catheter tube 31 of the steering means 30 may be guided to the implantation side within the patient's body.

Figure 4:
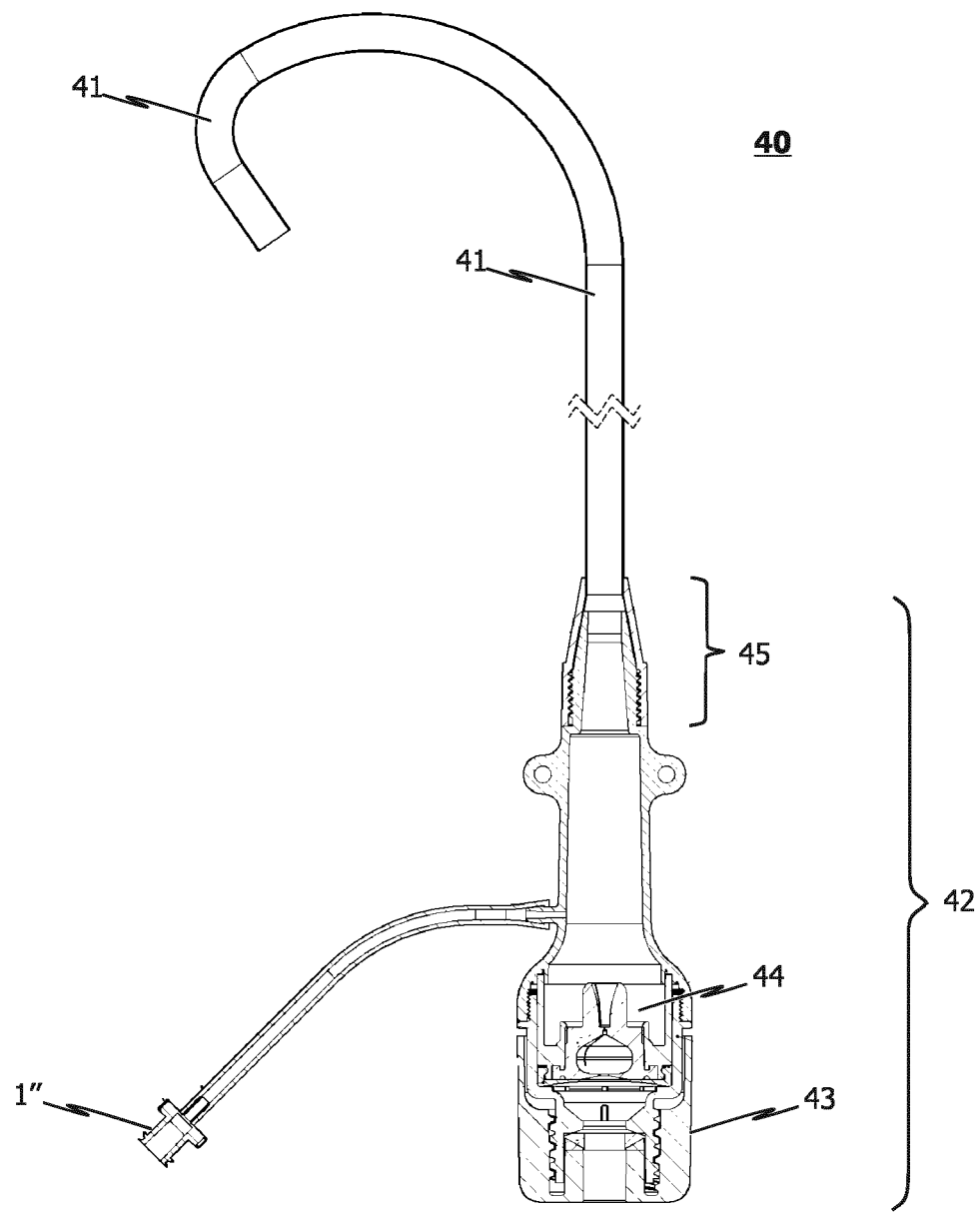
FIG. 4: a sectioned side elevation of an embodiment of an introducer of a delivery system in accordance with FIG. 1.

A sectional-side view of one embodiment of the introducer 40 is illustrated in FIG. 4.

Hence, the introducer sheath 41 has a distal end, a proximal end and a passageway extending there between. The introducer sheath 41 has a length such that the distal end of the introducer sheath 41 terminates proximal to the catheter tip 11 of the delivery system, when the catheter shaft 12 and the catheter tip 11 of the delivery system 100 has been fully introduced into the introducer sheath 41.

When at least a section of the catheter shaft 12 of the delivery means 10 or at least a section of the steerable catheter tube 31 of the steering means 30 has been introduced into the passageway defined by the introducer sheath 41, the introducer sheath 41 is disposed concentrically and coaxially with the section of the catheter shaft 12 of the delivery means 10 or the steerable catheter tube 31 of the steering means 30.

In any case, however, the catheter shaft 12 of the delivery means 10 and/or the steerable catheter tube 31 of the steering means 30 is moveable relative to the introducer sheath 41. In particular, the introducer sheath 41 terminates proximal to the catheter tip 11 wherein the cross-section of proximal end section of the introducer sheath 41 shall be substantially the same as or slightly larger than the cross-section of the steerable catheter tube 31.

The proximal end section of the introducer sheath 41 is connected to an introducer port 42. The introducer port 42 serves for providing access to the introducer sheath 41 of the introducer 40 required for delivering the delivery means 10 or the steerable catheter tube 31 of the steering means 30 into the introducer sheath 41.

The introducer port 42 may comprise a base member 43 which is configured to be manually fixable to the steerable catheter tube 31 is introduced into the passageway defined by the introducer sheath 41, or to be manually fixable to the handle 32 of the steering means 30, when the steerable catheter tube 31 of the steering means 30 is introduced into the passageway defined by the introducer sheath 41.

As can be seen from FIG. 4 the introducer port 42 is provided with a sealing arrangement 44 for preventing leakage of fluid, in particular blood, from the introducer 40, when the introducer sheath 41 is introduced into the patient's vasculature.

Moreover, in the exemplary embodiment of the introducer 40 illustrated in FIG. 4, the proximal end section of the introducer sheath 41 terminates in a crimping section 45 distal to the sealing arrangement 44 of the introducer port 42. The crimping section 45 of the introducer 40 serves for crimping at least a middle section of a heart valve fixed to the catheter tip 11 of the delivery means 10 during the introduction of the catheter tip 11 into the introducer sheath 41. As described with respect to FIG. 2c only the distal and proximal end sections of the heart valve are fixed to the catheter tip 11 of the delivery means 10 by means of the first and second retaining means 15, 16, wherein no dedicated retaining means is allocated to the middle section of the heart valve between the distal and proximal end sections of the heart valve.

For crimping the middle section of the heart valve during the introduction of the catheter tip 11 into the introducer sheath 41, the catheter tip 11 passes through the crimping section 45 of the introducer 40 thereby further reducing the diameter of the middle section of the heart valve fixed to the catheter tip 11. As illustrated in FIG. 4, the crimping section 45 may comprise a conical tubular member having an inner diameter which decreases in the distal direction of the tubular member.

The introducer sheath 41 may be of a thin material such as to allow bending of the introducer sheath 41 in order to follow the tortuous pathway from the femoral artery to the implant site. The introducer sheath 41 material, however, shall have sufficient stiffness in order to mechanically avoid kinking of the flexible sections of the distal portion of the catheter shaft 12 during insertion of the catheter tip 11.

An inlet 1, 1', 1" may be provided at a proximal end sections of the steering means 30, the introducer 40 and/or the delivery means 10 for injection of fluids, if necessary. Furthermore, a check valve may be provided at the proximal end section of the introducer sheath 41 to prevent fluid from leaking out of the introducer sheath 41.

The introducer sheath 41 may have a length sufficient to protect the inner wall of the blood vessel through which the catheter tip 11 passes. In addition, a separate introducer system (not belonging to the catheter system) may be provided. The introducer system then may serve as a portal for passing the complete catheter system from the catheter tip 11 to the catheter shaft 12 into the patient's body and up to the heart.

In addition, the introducer sheath 41 reduces the compression force exerted on the first catheter tube that is inserted through the introducer sheath 41. This increases manoeuvrability of the steerable catheter tube 31 and the catheter shaft 12 of the delivery means 10 throughout the procedure. A consequence thereof is that any frictional force is reduced. Moreover, moving the catheter tip 11 after it has been advanced through the vascular system of a patient, is greatly improved while at the same time lowering the risk of injury of the patient.

As will be appreciated, the introducer sheath 41 will be of a size, i.e. has an outer diameter, which will permit insertion in a patient's blood vessel (artery or vein) which is used for moving the stent transarterially or via a vein to an insufficient heart valve.

Figure 2A:
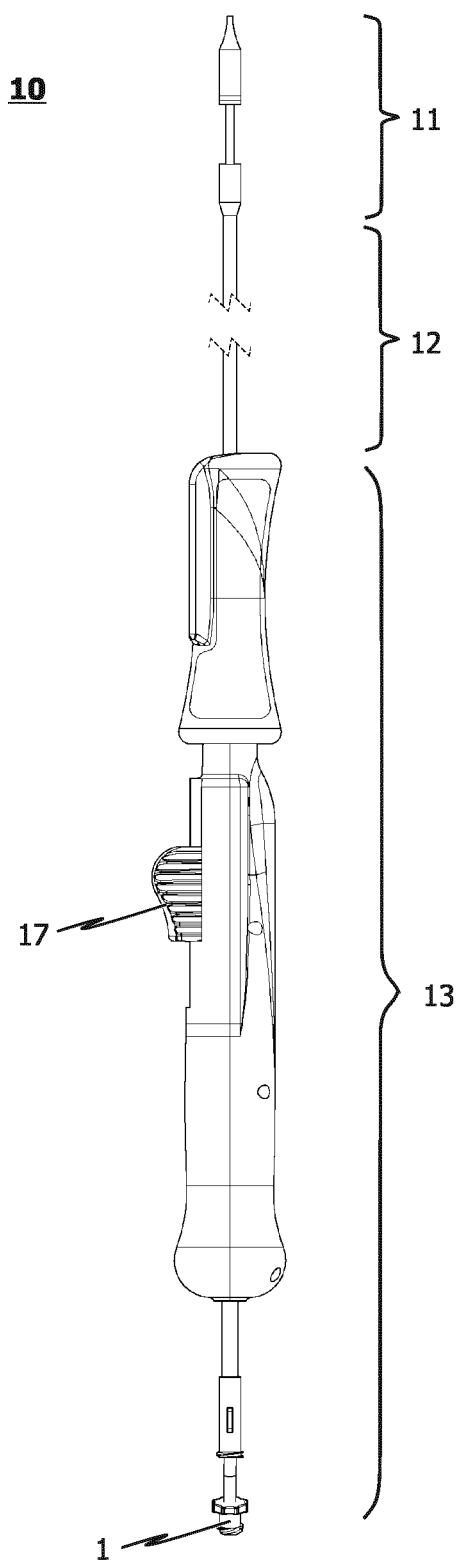
FIG. 2a: a side elevation of an embodiment of a delivery means of a delivery system in accordance with FIG. 1.

The FIGS. 6a to 6i represent sectioned side elevations of components of the delivery means of FIG. 2a.

The FIGS. 7 to 12 represent further embodiments of the present disclosure.

In one aspect, embodiments of the present disclosure relate to a catheter system, comprising:
i) a steering means; and
ii) a delivery means for a heart valve, optionally balloon expandable or self-expandable, wherein the steering means and the delivery means are coaxially and rotationally independently movable.

In an embodiment, said catheter system is compatible with an introducer for intravascular, optionally transfemora (TF), applications or can be modified to be suitable for transapical (TA) delivery of a replacement heart valve. In such a TA system and means the direction in which the heart prosthesis is releaseably connected with the delivery means in turned by 180° compared to the TF application.

In some embodiments, the catheter system according to the present disclosure is made such that the introducer comprises an introducer sheath which extends or is extendable through the vascular duct and optionally proximal to the target site of the heart and optionally wherein the introducer sheath exhibits a crimping section.

The catheter system according to embodiments of the present disclosure may have a first and a second retaining means at the distal end of the catheter system to reversibly secure the heart valve to the delivery means.

Optionally the catheter system according to embodiments of the present disclosure is characterized in that the first retaining means reversibly secures the distal end of the heart valve to the delivery means and the second retaining means reversibly secures the proximal end of the heart valve to the delivery means.

In an embodiment, the mid-section of the heart valve is not covered by a sleeve means. It thus rests flexible in terms of diameter and the tissue is not pressured by way of a crimping procedure that results in tension onto the pericard valve material. In this manner the heart valve is only crimped during the deployment procedure and thus the time during which the replacement heart valve is crimped to its smallest diameter is kept relatively short.

Accordingly, in at least one embodiment of a catheter system according to the present disclosure the diameter of the secured heart valve varies over its length, and preferably the heart valve is compressible over its length to the inner diameter of the introducer sheath.

In at least one embodiment thus the catheter system according to the present disclosure the inner diameter if the introducer sheath can be chosen as required by the respective application and may be less than 24 French, for example, less than 20 French, less than 18 French, and even less than 16 French.

In at least one embodiment the introducer sheath has a pre-shaped, preferably a curved, configuration.

The skilled person will appreciate that materials usually applied in catheter and delivery systems can also be used in embodiments according to the present disclosure. For example, in a catheter system according to an embodiment of the present disclosure the introducer sheath is characterized by a flexible polymer, a hydrophilic coating, a PTFE liner, coil reinforcement and/or braid reinforcement.

The replacement heart valve may be attached with useful meant to the delivery means which are compatible with the other parts of the device. In an embodiment the heart valve is attached to the delivery means by way of holding means wherein the heart valve and the delivery means exhibit complementary shapes. For example, the heart valve may have male connector elements at the distal and proximal end to engage with female connector elements on the delivery means.

In at least one embodiment according to the present disclosure in the catheter system the delivery means and steering means are operated by one or two means, optionally one or two handles. The steering means may exhibit means to deflect the shaft of the delivery catheter from a relaxed configuration into a curved configuration.

In at least one embodiment of the catheter system according to the present disclosure the delivery means and steering means are releasably connectable.

In another aspect, embodiments of the present disclosure relate to a delivery system for a heart valve comprising i. a steering means; ii. a delivery means for a heart valve and iii. an introducer sheath wherein the steering means, the delivery means and the introducer sheath are coaxially and circumferentially independently movable.

In an exemplary embodiment the introducer sheath extends or is extendable through the vascular duct and optionally proximal to the heart.

The different parts and sections of the delivery system may be adapted to each other and made in a way that they are compatible in their constructive and functional characteristics. In at least one embodiment, the steering means, the delivery means and the introducer sheath are at least sectionally, partially or substantially completely arranged coaxially to each other. The steering means, the delivery means and the introducer sheath may be coaxially and rotationally independently movable.

In the delivery system according to some embodiments of the present disclosure, the delivery means and steering means can be simultaneously or independently introducible into the introducer sheath.

In the delivery system according to embodiments of the present disclosure the introducer sheath can exhibit a crimping section for reducing the diameter of the heart valve attached to the delivery means. Such a crimping section has the advantage that the replacement heart valve is only crimped over its entire length to its minimal diameter during the delivery and deployment procedure which leads to less stress impact onto the pericard tissue of the replacement heart valve.

In another aspect, embodiments of the present disclosure relate to a method for the delivery of a heart valve to the heart of a patient comprising the steps i. in a first step placing an introducer comprising an introducer sheath into a patient's vasculature; ii. in a second step introducing a catheter system having fixed thereto a self-expanding or balloon expandable heart valve through the introducer into the patient's vasculature; iii. in a third step positioning the heart valve proximal to the target site in the patient's heart, optionally positioning the heart valve substantially central in the target area; iv. in a fourth step positioning the heart valve at the target site; v. in a fifth step partially releasing the heart valve from the catheter system; vi. in a sixth step fully releasing the heart valve from the catheter system.

In some methods according to embodiments of the present disclosure at least one segment of the self-expanding heart valve is compressed from a first diameter to a second diameter that is smaller than the first diameter when the self-expanding heart valve is passed through the introducer sheath, preferably the crimping section.

In another aspect of embodiments of the present disclosure, at least one segment of the self-expanding heart valve expands from a first diameter to a second diameter that is larger than the first diameter when the self-expanding heart valve exits the distal end of the introducer sheath.

In another aspect, embodiments of the present disclosure relate to a method of loading a self-expanding or balloon expandable heart valve onto a delivery means of a catheter system having at least one shaft and at least one outer sheath and/or is characterized as described above and throughout the specification and comprising or consisting of:
  compressing the heart valve radially and placing the compressed heart valve into a tubular retainer, the retainer preventing the self-expanding valve from expanding radially,
  passing the inner shaft of the delivery system through the central opening of the compressed heart valve,
  attaching the distal tip to the shaft of the delivery system,
  advancing the outer sheath onto the compressed heart valve to prevent radial expansion of at least part of the heart valve, and
  removing the tubular retainer from the compressed self-expanding heart valve.

In the following further alternative and/or exemplary embodiments will be described.

In at least one embodiment the present disclosure relates to a delivery system for a prosthesis, e.g. a heart valve, which consists of or comprises in general three components. The three components each consist of a handle wherein each handle is characterized by additional parts as follows.

A port handle comprises a pre-shaped tubular component which can be introduced through the vasculature, e.g. transfemoral, of a patient starting femoral up to proximal to the heart. This introducer sheath has a length of 50 to 150 cm, such as 100 to 120 cm. The tubular element may have a pre-shaped bent or may be designed in a manner so that it easily bents around the main artery proximal the heart. A balloon device can be introduced through this handle/introducer sheath which represents a first step in the prosthesis delivery procedure. This handle exhibits a twist grip and is positioned at the upper leg and is functional to introduce the other components of the delivery system. The tubular component can be pushed through the port handle or is fixed thereto. The tubular component is made from a compatible polymer material reinforced with wire and may include PTFE or Teflon coated at the inside. The port handle may exhibit a valve or other means for closing the hollow entry tube which serves to introduce the introducer sheath and the catheter component of the system. The inner diameter of the introducer sheath is less than 25 French, such as less than 20 French, less than 18 French or has a diameter of 20, 18 or 16 French.

The introducer sheath can be coupled to the second handle (introducer sheath handle) by way of which one can push the introducer sheath combined with the introducer sheath handle. The introducer sheath handle exhibits a wire of similar means in a manner so that the introducer sheath is steerable. In this manner during the deployment of the prosthesis the introducer sheath can be bent or directed in a defined position which will facilitate the deployment procedure. The first and second handles can exhibit a means to releasable connect them to each other.

A third handle represents the catheter component of the delivery system. It comprises a handle, a catheter shaft, a distal capsule for releasable connecting the prosthesis, a tubing for flushing including a closing means. The handle exhibits control means for connecting the prosthesis and releasing it.

Any component or all components can be introduced by way of a guide wire.

The delivery procedure can follow the steps of opening the femoral vasculature as access and introducing a port and/or a guide wire. The port handle and the introducer sheath is positioned at the upper leg and introduced ascending the aorta. In a next step a balloon device is introduced through the port and the introducer sheath for widening by way of balloon expansion the target site. After this task is performed the balloon device is retrieved. In a next step the catheter is introduced through the introducer sheath. The prosthesis is preloaded onto the catheter at the distal capsule. The prosthesis is connected with its ends at defined mounting positions which represent male/female connections which allow the controlled release of the prosthesis at the target site in a step-wise manner. Accordingly, the prosthesis is connected with the catheter so that the connections represent a small diameter and the prosthesis is otherwise not connected and also not covered by way of a sheath or other covering. Thus the diameter of this middle part of the prosthesis is due to the outward tension of the stent material larger than at the connection sites. An advantage of this design is that a small diameter of the loaded prosthesis can be achieved. In the course of introducing the prosthesis loaded onto the catheter capsule into and through the introducer sheath the prosthesis will be crimped to its final diameter pre-defined by the inner diameter of the introducer sheath. The material design of the introducer sheath facilitates the crimping and also the progression through this sheath.

The prosthesis can now be approached in direction to the target site using the introducer sheath and catheter. Another advantage of the delivery system is that the catheter and the introducer sheath are both coaxially and rotationally independently movable. Moreover, by way of the steering means of the second handle the introducer sheath can be bended and thus facilitate to maneuver the prosthesis through the vasculature to its final target site. Another advantage of a system according to embodiments of the present disclosure is that the catheter handle and the second handle of the introducer sheath with the steering means can be moved and operated independently.

The release procedure can be managed by a reversible two-step process. The release process is initiated once the feelers of the prosthesis are placed inside the cusps of the native aortic valve. In a first step the proximal connecting means is pushed in a forward direction/proximal direction. This will release the proximal end of the prosthesis. The catheter of the prosthesis may exhibit visualization means for better visual control. In a second step, the distal connecting means may be retracted or pulled back by way of a control means on the catheter handle to release the distal end of the prosthesis and disconnect the entire prosthesis from the catheter. The control means can be designed as independent means for each connecting means or in a connected manner.

Thus the advantages of embodiments of the present disclosure are that the loading and in particular crimping of the prosthesis is achieved by way of the introducer sheath and thus the crimping procedure is combined with the introduction of the prosthesis into the vasculature which facilitates the process. This implies the advantage that a separate cover means to crimp the prosthesis beforehand is not necessary with the effect and additional advantage that the tissue of the prosthesis is more smoothly and less vigorously crimped. This implies a lower risk of damages to the tissue. Moreover, the crimping procedure is facilitated and the middle part of the prosthesis which is usually the thickest part of a valve prosthesis needs not be crimped by a special device or by hand. Another advantage is the steering mechanism independent from the catheter handle. The extension of the port by way of the introducer sheath for the delivery of heart prosthesis is novel and has the advantages as above described.

A further advantage is that the bending can be managed independently from the delivery capsule. Thus all parts like port, handles, capsule, steerable means and prosthesis are all independently movable and coaxially and rotationally movable which facilitates the deployment of the prosthesis at the target site. Moreover, the prosthesis may be deployed by a two-step procedure and is repositionable. The procedure may also be aborted during the delivery procedure.

The combination of the different components of the delivery system may help to achieve certain advantages and superior delivery and deployment results in a simple and safe manner.

The release of the heart valve prosthesis from the delivery means can occur in a 2-step deployment way.

The skilled person will appreciate that the catheter system, the delivery system, the method for loading and the method for the delivery of the heart valve to the heart may be combined with suitable devices and methods or steps to prepare the target site in the heart for the deployment of the replacement heart valve prosthesis. Accordingly, a balloon device or balloon system can be applied before the delivery of the replacement heart valve to expand the target site within the heart. This system may be introduced by way of the port and/or introducer sheath according to embodiments of the present disclosure which exhibits the advantage that the port and introducer sheath can be positioned in the patient's vasculator entrance femorally and only one access is necessary to perform the dilatation of the target site by way of balloon expansion. After the balloon device is retrieved the replacement prosthesis can be applied as described above.

Parts and devices that are introduced can be guided by a guide wire known in the art and made from materials as usually applied in the field.

It can be advantageous if the tip of the catheter device is made of a soft or semi firm material and/or which is bendable in order to easily pass through the vasculator of the patient. Known materials can be used for such a flexible tip.

It is emphasized that the combination of the introducer sheath with the delivery catheter part according to embodiments of the present disclosure does not only simplify the loading and delivery procedure but an advantage is also that less layers of heart valve prosthesis coverage is needed and thus the diameter and crimping diameter can be reduced or/and the forces applied to the prosthesis is influenced in an advantageous manner. Thus less impact as compared in conventional devices and loading procedures can be expected which implies the advantage of less damage and a longer lifespan of the replacement heart valve.

In view of the particular construction characteristics of various catheters and delivery devices according to embodiments of the present disclosure one can denote two steps to the delivery procedure. The first step being the placement and the port, introducer sheath and loading of the replacement heart valve and the second step the deployment of the heart valve to the target site. The deployment as such is in turn a two-step sequence of steps with a first release step of part of the replacement heart valve and in a second step the final and complete release and final positioning of the replacement heart valve at the target site. In between these steps a retrieval of the replacement heart valve is still possible and offers the option of repositioning and complete retrieval and stop of the deployment procedure.

In accordance with an aspect, the present disclosure provides a catheter system for introducing an expandable heart valve into the body of a patient, the catheter system comprising delivering means for the heart valve.

In some aspects of the present disclosure, the delivering means comprises a catheter tip and a catheter shaft. The catheter tip of the delivery means has a seat portion for accommodating the heart valve to be introduced into the patient's body in its collapsed or crimped state. The catheter tip has further holding means for realisably fixing the heart valve to the catheter tip.

The seat portion of the catheter tip is constituted by a first retaining means and a second retaining means. In some embodiments of the present disclosure, the first retaining means and second retaining means may be constituted by a first sleeve-shaped member and a second sleeve-shaped member.

The first retaining means of the catheter tip serves for reversibly securing a distal end section of the heart valve to the delivery means and, in particular, to the catheter tip of the delivery means. On the other hand, the second retaining means of the catheter tip serves for reversibly securing a proximal end section of the heart valve to the delivery means and, in particular, to the catheter tip of the delivery means.

The first and second retaining means are moveable relative to each other and also relative to the holding means of the catheter tip.

According to some embodiments of the present disclosure, the catheter shaft of the delivery means comprises first force transmitting means and second force transmitting means.

A distal end section of the first force transmitting means is connected or connectable to the first retaining means of the catheter tip and a proximal end section of the first force transmitting means is connected or connectable to a first operating means of a handle of the delivery means. A distal end section of the second force transmitting means is connected or connectable to the second retaining means of the catheter tip and a proximal end section of the second force transmitting means is connected or connectable to a second operating means of the handle of the delivery means.

According to some embodiments of the present disclosure, the handle of the delivery means has at least one first operating means and at least one second operating means with which the catheter tip of the delivery means may be appropriately manipulated so that an expandable heart valve secured to the catheter tip may be released from the catheter tip in steps or in a defined or definable sequence of events.

In accordance with some embodiments of the present disclosure, the catheter tip has first and second retaining means—for example in the form of sleeve-shaped members—which may be manipulated with the handle of the delivery means. These retaining means are used for releasably and reversibly securing a distal and proximal end section of the heart valve to the catheter tip.

In some embodiments of the present disclosure, the first retaining means serves for releasably and reversibly securing first functional components of the heart valve, for example retaining hoops of a stent or alternatively positioning hoops of a stent, while the second retaining means serves for releasably and reversibly securing second functional components of the heart valve, for example, positioning hoops of a stent or alternatively for accommodating retaining hoops of a stent.

In relation to the handle of the delivery means, in some embodiments it is preferably provided that, on one hand, the first operating means cooperate with the first retaining means of the catheter tip so that, on actuation of the first operating means, a previously definable longitudinal displacement of the first retaining means may be effected relative to the holding means. On the other hand, the second operating means cooperates with the second retaining means of the catheter tip so that a previously definable longitudinal displacement of the second retaining means may be affected relative to the holding means.

In accordance with some embodiments of the present disclosure, the first and second retaining means only serve for securing the distal and proximal end sections of the heart valve to the catheter tip. In case the first and second retaining means are configured as first and second sleeve-shaped members, these sleeve-shaped members have a length such that a gap is between the first and second sleeve-shaped members when securing the distal and proximal end sections of the heart valve to the catheter tip.

In accordance with some embodiments of the present disclosure, the first force transmitting means of the delivery means is constituted by a first catheter tube defining a first lumen, and the second force transmitting means of the delivery means is constituted by a second catheter tube defining a second lumen. The second catheter tube has a cross-section less than the cross-section of the first catheter tube. The first catheter tube is disposed concentrically and coaxially with the second catheter tube and the second catheter tube is received within the first lumen defined by the first catheter tube.

Contrary to the first and second sleeve-shaped members of the catheter tip, however, the holding means of the catheter tip is not moveable relative to the handle of the delivery means. Rather, the holding means is connected to the handle of the delivery means by using a holding tube having a distal end connected to the holding means and a proximal end connected to a body of the handle of the delivery means. The holding tube has a cross-section less than the cross-section of the first catheter tube. In particular, the first catheter tube is disposed concentrically and coaxially with both, the second catheter tube on the one hand and the holding tube on the other hand.

In some embodiments, the holding tube has a cross-section less than the cross-section of the first catheter tube and greater than the cross-section of the second catheter tube such that the holding tube is received within the first lumen defined by the first catheter tube and the second catheter tube is received within a passageway defined by the holding tube. The passageway defined by the holding tube has a diameter sufficient to accommodate the second catheter tube such that the second catheter tube is moveable relative to the holding tube.

The second lumen defined by the second catheter tube has a diameter sufficient to accommodate a guide wire. The second catheter tube is made from a rigid material including, for example, nitinol, stainless steel or a rigid plastic material. The material of the distal end section of the second catheter tube may have an increased flexibility compared to the material of the proximal end section in order to allow the distal end section of the catheter shaft to pass the aortic arch during insertion of the catheter tip.

In some embodiments of the present disclosure, the distal end section of the second catheter tube terminates in a soft catheter end tip having an atraumatic shape. The soft catheter end tip is provided with a channel aligned with the second lumen defined by the second catheter tube such that a guide wire accommodated within the second lumen of the second catheter tube may pass through the channel of the soft catheter end tip. The second sleeve-shaped member of the catheter tip is connected to the soft catheter end tip such that the opened end of the second sleeve-shaped member faces in the proximal direction opposite to the direction of the soft catheter end tip and to the second catheter tube.

In some embodiments, the holding tube is made of a rigid material, for example, a rigid plastic material, stainless steel or Nitinol. The distal end of the holding tube terminates in the holding means which is also made of a rigid material, for example, a rigid plastic material or stainless steel. The passageway defined by the holding tube is aligned with a channel which passes through the holding means. In this way, the second catheter tube is accommodated in the passageway of the holding tube and the channel of the holding means such as to be moveable relative to the holding tube and the holding means.

The holding tube is provided for connecting the holding means to the handle of the delivery means. For this purpose, the holding tube has a distal end connected to the holding means and a proximal end connected to a body of the handle of the delivery means.

In some embodiments, the first catheter tube is preferably made of a bendable but axially rigid material. For example, the first catheter tube may be at least partly made of a braided or non-braided catheter tube. Hence, the first catheter tube may have a stiff braid reinforced body similar to the catheter body described in U.S. Pat. No. 4,665,604 which is incorporated herein by reference.

The first catheter tube shall be adapted to transfer compression and tension forces from the first operating means of the handle of the delivery means to the first retaining means of the catheter tip without overly changing of its total length. The distal end of the first catheter tube terminates at a flared section as the transition to the section defining the first retaining means of the catheter tip.

The flared section and the first retaining means may be formed integrally and may be connected to the distal end section of the first catheter tube.

Alternatively, the first retaining means and the flared section of the first catheter tube may be all of the same material and originating from the same raw tube prior to a widening process so that the flared section and the first retaining means are the same elements.

In accordance with another aspect of the present disclosure, the catheter system further comprises steering means. The steering means for guiding the delivery means and, in particular, the catheter tip of the delivery means when advancing the catheter tip through the patient's vasculature.

In some embodiments of the present disclosure, the steering means comprises a steerable catheter tube having a proximal end section and a distal end section. The proximal end section of the steerable catheter tube is connected or connectable with a handle of the steering means.

The handle of the steering means is provided with operating means, for example in the form of a rotatable knob or wheel, by means of which a flexural link region of the steerable catheter tube can be controlled.

In accordance with other embodiments disclosed herein, the material of the distal end section of the steerable catheter tube may have an increased flexibility compared to the material of the proximal end section. In this way, the distal end section of the steerable catheter tube may easily pass, for example, the aortic arch during insertion of the steerable catheter tube.

In some embodiments disclosed herein, the handle of the steering means is provided with operating means by means of which a flexural link region of the steerable catheter tube can be controlled, wherein the operating means preferably has a detent device to allow a set deflection of the flexural link region of the steerable catheter tube to be fixed. For example, it is possible to provide a suitable catch mechanism on the operating means, which cooperates with a body of the handle of the steering means. In particular, it is possible for the flexural link region of the steerable catheter tube to be connected to the operating means of the steering means by way of a control wire whereby, on an actuation of the operating means via the control wire a tensile forces is exerted on the flexural link region of the steerable catheter tube, which produces a predefined or predefinable deflection of the flexural link region.

However it is also possible, of course, to choose other embodiments as the operating means of the steering means for deflecting the steerable catheter tube or a flexural link region of the steerable catheter tube, in case the steerable catheter tube is provided with such a flexural link region.

In accordance with some embodiments disclosed herein, the proximal end section of the steerable catheter tube of the steering means terminates in a port section of the steering means or is connected with a port section of the steering means. The port section of the steering means serves for introducing the catheter tip and catheter shaft of the delivery means into the steerable catheter tube. For this purpose, the port section of the steering means has a lumen defining a passageway which extends through the port section, the distal end section of the passageway being aligned with the proximal end section of the steerable catheter tube.

In some embodiments, the port section of the steering means is preferably integrated in or connected with the handle of the steering means.

The catheter tip and catheter shaft of the delivery means is introducible (via the port section of the steering means) into the steerable catheter tube. The catheter shaft of the delivery means and particularly the first catheter tube of the catheter shaft of the delivery means is moveable relative to the steerable catheter tube. In particular, the steerable catheter tube terminates proximal to the catheter tip wherein the cross-section of proximal end section of the introducer sheath shall be substantially the same as or slightly larger than the cross-section of the flared section provided at the proximal end of the first catheter tube.

The proximal end section of the steering means and, in particular, the proximal end section of the port section of the steering means is releasably connectable to the handle of the delivery means.

According to an aspect of the present disclosure, the catheter system further comprises an introducer having an introducer sheath. The introducer sheath has a cross-section greater than the cross-section of the steerable catheter tube of the steering means.

The introducer sheath serves as guiding means when introducing the delivery means and/or the steering means and, in particular, the steerable catheter tube of the steering means into the patient's vasculature. In more detail, the introducer sheath defines a passageway through which the catheter tip and catheter shaft of the delivery means and/or the steerable catheter tube of the steering means may be guided to the implantation side within the patient's body.

The introducer sheath has a distal end, a proximal end and a passageway extending there between. The introducer sheath has a length such that the distal end of the introducer sheath terminates proximal to the catheter tip of the delivery system, when the catheter shaft and the catheter tip of the delivery system has been fully introduced into the introducer sheath.

When at least a section of the catheter shaft of the delivery means or at least a section of the steerable catheter tube of the steering means has been introduced into the passageway defined by the introducer sheath, the introducer sheath is disposed concentrically and coaxially with the section of the catheter shaft of the delivery means or the steerable catheter tube of the steering means.

In any case, however, the catheter shaft of the delivery means and/or the steerable catheter tube of the steering means is moveable relative to the introducer sheath. In particular, the introducer sheath terminates proximal to the catheter tip wherein the cross-section of proximal end section of the introducer sheath shall be substantially the same as or slightly larger than the cross-section of the steerable catheter tube.

The proximal end section of the introducer sheath is connected to an introducer port. The introducer port serves for providing access to the introducer sheath of the introducer required for delivering the delivery means or the steerable catheter tube of the steering means into the introducer sheath.

The introducer port may comprise a base member which is configured to be manually fixable to the handle of the delivery means, when the catheter shaft of the delivery means is introduced into the passageway defined by the introducer sheath, or to be manually fixable to the handle of the steering means, when the steerable catheter tube of the steering means is introduced into the passageway defined by the introducer sheath.

In accordance with some embodiments disclosed herein, the introducer port is provided with a sealing arrangement for preventing leakage of fluid, in particular blood, from the introducer, when the introducer sheath is introduced into the patient's vasculature.

In some embodiments disclosed herein, the proximal end section of the introducer sheath terminates in a crimping section distal to the sealing arrangement of the introducer port. The crimping section of the introducer serves for crimping at least a middle section of a heart valve fixed to the catheter tip of the delivery means during the introduction of the catheter tip into the introducer sheath. As already mentioned above, according to embodiments disclosed herein, preferably only the distal and proximal end sections of the heart valve are fixed to the catheter tip of the delivery means by means of the first and second retaining means, wherein no dedicated retaining means is allocated to the middle section of the heart valve between the distal and proximal end sections of the heart valve.

For crimping the middle section of the heart valve during the introduction of the catheter tip into the introducer sheath, the catheter tip passes through the crimping section of the introducer thereby further reducing the diameter of the middle section of the heart valve fixed to the catheter tip. In some embodiments disclosed herein, the crimping section may comprise a conical tubular member having an inner diameter which decreases in the distal direction of the tubular member.

The introducer sheath may be of a thin material such as to allow length deformation of the introducer sheath upon transfer of compression and tension forces. The introducer sheath material, however, shall have sufficient stiffness in order to mechanically avoid kinking of the flexible sections of the distal portion of the catheter shaft during insertion of the catheter tip.

In some embodiments of the present disclosure, the introducer sheath has a pre-shaped, preferably curved, configuration.

An inlet may be provided at a proximal end section of the steering means, the introducer and/or the delivery means for injection of fluids, if necessary. Furthermore, a check valve may be provided at the proximal end section of the introducer sheath to prevent fluid from leaking out of the introducer sheath.

The introducer sheath may have a length sufficient to protect the inner wall of the blood vessel through which the catheter tip passes. In addition, a separate introducer system (not belonging to the catheter system) may be provided. The introducer system then may serve as a portal for passing the complete catheter system from the catheter tip to the catheter shaft into the patient's body and up to the heart.

In addition, the introducer sheath reduces the compression force exerted on the first catheter tube that is inserted through the introducer sheath. This increases manoeuvrability of the steerable catheter tube and the catheter shaft of the delivery means throughout the procedure. A consequence thereof is that any frictional force is reduced. Moreover, moving the catheter tip after it has been advanced through the vascular system of a patient, is greatly improved while at the same time lowering the risk of injury of the patient.

The length of the introducer sheath depends on the length of the catheter shaft of the delivery means and will typically be between about 20 cm to 60 cm for transaortic (TA) access and 80 cm to 150 cm for transfemoral (TF) access. Those skilled in the art will appreciate, however, that all dimensions provided herein are intended as examples only, and that the introducer sheaths and catheter tubes of different dimensions may be substituted for a particular use.

As will be appreciated, the introducer sheath will be of a size, i.e. has an outer diameter, which will permit insertion in a patient's blood vessel (artery or vein) which is used for moving the stent transarterially or via a vein to an insufficient heart valve.

The introducer sheath may be capable of traversing tortuous pathways in the body of the patient without kinking. The introducer sheath may include an inner lubricious liner, an outer polymeric jacket, and a coil reinforcement between the inner and the outer layers. This introducer sheath may provide favourable flexibility without kinking or compression. One or more radiopaque bands or markers may be incorporated within the introducer sheaths material to allow precise location of the introducer sheaths distal end for positioning accuracy. Those skilled in the art will appreciate that other known materials may also be suitable for a particular purpose.

The catheter system is particularly adapted to deliver and implant a heart valve as described for example in the European Patent Application No. 07 110 318 or in the European Patent Application No. 08 151 963. In some embodiments of the present disclosure, a heart valve is accordingly used which comprises a stent and a heart valve prosthesis attached to the stent. The stent exhibits the following:

a first retaining region, to which the heart valve prosthesis can be attached;

an opposing, second retaining region with at least one retaining element, for example in the form of retaining eyes or in the form of retaining heads, whereby at least one retaining element of the stent can be put in releasable engagement with the holding means of the catheter tip of the delivery means;

at least one retaining hoop, to which the heart valve prosthesis can be fastened; and at least one and, in some embodiments, preferably three positioning hoops, which are designed to engage in pockets of the native heart valve in the implanted state of the stent, thus to enable automatic positioning of the stent in the aorta of the patient.

In particular, a catheter system is disclosed herein, with which an expandable heart valve stent with a heart valve prosthesis attached to this stent can be advanced to the implantation site in a particularly simple way, for example via the aorta of a patient being treated (transarterially or transfemorally). In some embodiments, during transarterial or transfemoral access by the catheter system, the whole free cross-section available within the aorta is not completely filled up, since the catheter tip provided at the distal end region of the catheter system, in which the stent can be accommodated with the heart valve prosthesis, can be made sufficiently small with respect to its external diameter.

The expandable heart valve stent with the heart valve prosthesis attached to it can be fixed temporarily during implantation in a crimped state to the catheter tip of the delivery means.

The catheter system designed for transarterial or transfemoral access is therefore suitable for inserting a heart valve stent with a heart valve prosthesis attached to it, transarterially or transfemorally into the body of the patient; for example, the catheter tip of the delivery means of the catheter system is inserted via puncture of the A. femoris communis (inguinal artery).

In particular, with the catheter system designed for transarterial or transfemoral access, the catheter shaft of the delivery means may be designed so that it is both kink-resistant and flexible such that a bending radius of up to 4 cm, e.g., up to 3 cm, can be realised, at least at the distal end region of the catheter shaft.

Exemplary embodiments will be described with reference to the appended drawings below.

In the following section, additional alternative and/or exemplary aspects of the present disclosure will be illustrated:

1. An improved system for delivering a self-expanding implant to an implant site within a blood vessel of a patient consisting of an introducer sheath and a delivery catheter,
the introducer sheath extending from outside of the body of the patient to the vicinity of the implant site,
the delivery catheter having a first and a second retaining means at the distal end of the delivery catheter to reversibly secure the implant to the delivery catheter,
the first retaining means reversibly secures the distal end of the self-expanding implant to the delivery catheter and the second retaining means reversibly secures the proximal end of the self-expanding implant to the delivery catheter,
wherein the delivery catheter is passed through the introducer sheath to deliver the self-expanding implant to the implant site, and
the central segment of the self-expanding implant is compressed from a first diameter to a second diameter that is smaller than the first diameter when the self-expanding implant is passed through the introducer sheath.

2. The system of aspect 1, wherein the implant is at least one of a stent, a stent graft, and a heart valve prosthesis.

3. The system of aspect 1, wherein the implant has male connector elements at the distal and proximal end to engage with female connector elements on the delivery catheter.

4. The system of aspect 3, where the male connector elements are eyelets and the female elements are recesses in the delivery catheter.

5. The system of aspect 1, wherein the introducer sheath has a hemostasis valve at the proximal end.

6. The system of aspect 1, wherein the retaining means consists of axially moveable sheaths that at least partially restrict radial expansion of the implant.

7. A process for delivering a self-expanding implant to an implant site within a blood vessel, comprising in combination:
inserting an introducer sheath from outside the body through an opening in the body into a blood vessel;
placing the distal end of the introducer sheath in the vicinity of the implant site;
reversibly securing the distal end and the proximal end of the self-expanding implant to the distal end of a delivery catheter;
inserting the delivery catheter with the self-expanding implant secured to the delivery catheter into the introducer sheath wherein the central segment of the self-expanding implant is compressed from a first diameter to a second diameter when inserted into the introducer sheath;
advancing the delivery catheter through the introducer sheath until the self-expanding implant exits the distal end of the introducer sheath; and releasing the distal end and the proximal end of the self-expanding implant from the delivery catheter at the implant site.

8. A system for delivering an implant to an implant site within a blood vessel of a patient consisting of an introducer sheath, a delivery catheter, and a biasing member, wherein
the introducer sheath extends from outside of the body of the patient to the vicinity of the implant site;
the delivery catheter has retaining means to reversibly retain an implant at the distal end of the delivery catheter;
the biasing member has means to deflect the shaft of the delivery catheter from a relaxed configuration into a curved configuration;
wherein the delivery catheter is passed through the introducer sheath to deliver the implant to the implant site; and,
the biasing member is axially and rotationally moveable inside the introducer sheath with respect to the introducer sheath and the delivery catheter.

9. The system of aspect 8, wherein the implant is a self-expanding or balloon expandable heart valve prosthesis.

10. The system of aspect 9, wherein the implant site is the native aortic or mitral valve.

11. The system of any one of the aspects herein, wherein the introducer sheath has a pre-shaped curved configuration.

12. A system for maneuvering an implant to an implant site within a blood vessel of a patient consisting of an introducer sheath, a delivery catheter, and a biasing member, which comprises, in combination:
the delivery catheter having retaining means to reversibly retain an implant at the distal end of the delivery catheter;
the biasing member having means to deflect the shaft of the delivery catheter from a relaxed configuration into a curved configuration;
the delivery catheter is inserted into the introducer sheath and is axially and rotationally moveable within the introducer sheath; and
the biasing member is inserted into the introducer sheath and is axially and rotationally moveable within the introducer sheath and is axially and rotationally moveable with respect to the delivery catheter.

13. A method of positioning an implant toward a target site within a blood vessel, comprising, the steps of:
inserting an introducer sheath from outside the body through an opening in the body into a blood vessel;
placing the distal end of the introducer sheath in the vicinity of the implant site;
reversibly securing the implant to the distal end of a delivery catheter;
placing a biasing member having means to actively deflect the shaft of the delivery system from a relaxed configuration into a curved configuration onto the shaft of the delivery system;
inserting the delivery catheter with the implant and biasing member into the introducer sheath;
advancing the delivery catheter through the introducer sheath until the implant exits the distal end of the introducer sheath;
adjusting the axially and rotationally position of the biasing member within the introducer sheath;
activating the biasing member to deflect the shaft of the delivery system into a desired bend configuration;
adjusting the axially position of the delivery system to place the implant at the target site; and
releasing the implant from the delivery system.

14. A method of loading a self-expanding heart valve onto a delivery catheter having an inner shaft, an attachable distal tip, and at least one outer sheath, comprising:
compressing the self-expanding heart valve radially and placing the compressed self-expanding heart valve into a tubular retainer, the retainer preventing the self-expanding valve from expanding radially;
passing the inner shaft of the delivery system through the central opening of the compressed self-expanding heart valve;

attaching the distal tip to the inner shaft of the delivery system;

advancing the outer sheath onto the compressed heart valve to prevent radial expansion of at least part of the heart valve; and removing the tubular retainer from the compressed self-expanding heart valve.

15. A catheter system comprising in combination: i. a steering means; and ii. a delivery means for a heart valve, optionally balloon expandable or self-expandable, wherein the steering means and the delivery means are coaxially and rotationally independently movable.

16. Catheter system according to aspect 15, wherein said system is compatible with an introducer for intravascular, optionally transfemoral, applications.

17. Catheter system according to aspect 16, wherein the introducer comprises an introducer sheath which extends or is extendable through the vascular duct and optionally proximal to the target site of the heart.

18. Catheter system according to aspect 15 or 16 having a first and a second retaining mean at the distal end of the catheter system to reversibly secure the heart valve to the delivery means.

19. Catheter system according to aspect 18 wherein the first retaining mean reversibly secures the distal end of the heart valve to the delivery means and the second retaining mean reversibly secures the proximal end of the heart valve to the delivery means.

20. Catheter system according to any of the preceding aspects wherein the heart valve is compressible to the inner diameter of the introducer sheath.

21. Catheter system according to aspect 20, wherein the inner diameter if the introducer sheath is less than 24 french, preferably less than 20 french, more preferably less than 18 french and even more preferably less than 16 french.

22. Catheter system according to any of the preceding aspects wherein the introducer sheath has a pre-shaped curved configuration.

23. Catheter system wherein the heart valve has male connector elements at the distal and proximal end to engage with female connector elements on the delivery means.

24. Catheter system wherein the delivery means and steering means are operated by one or two means, optionally one or two handles in operative relationship to the pre-shaped introducer sheath.

25. Catheter system according to aspect 15, wherein the steering means have means to deflect the shaft of the delivery catheter from a relaxed configuration into a curved configuration.

26. A delivery system for a heart valve comprising i. a steering means; ii. a delivery means for a heart valve and iii. a introducer sheath wherein the steering means, the delivery means and the introducer sheath are coaxially and circumferentially independently movable.

27. Delivery system according to aspect 28, wherein the introducer sheath extends or is extendable through the vascular duct and optionally proximal to the heart.

28. A method for the delivery of a heart valve to the heart of a patient comprising the steps of: i. in a first step placing an introducer comprising an introducer sheath into a patient's vasculature; ii. in a second step introducing a catheter system having fixed thereto a self-expanding heart valve through the introducer into the patient's vasculature; iii. in a third step positioning the self-expanding heart valve proximal to the target site in the patient's heart, optionally positioning the heart valve substantially central in the target area; iv. in a fourth step positioning the self-expanding heart valve at the target site; v. in a fifth step partially releasing the self-expanding heart valve from the catheter system; vi. in a sixth step fully releasing the self-expanding heart valve from the catheter system.

29. The method according to aspect 31, wherein the self-expanding heart valve is compressed from a first diameter to a second diameter that is smaller than the first diameter when the self-expanding heart valve is passed through the introducer sheath.

30. A method of loading a self-expanding heart valve onto a delivery means of a catheter system having an inner shaft, an attachable distal tip, and at least one outer sheath, consisting of:

compressing the self-expanding heart valve radially and placing the compressed self-expanding heart valve into a tubular retainer, the retainer preventing the self-expanding valve from expanding radially;

passing the inner shaft of the delivery system through the central opening of the compressed self-expanding heart valve;

attaching the distal tip to the inner shaft of the delivery system;

advancing the outer sheath onto the compressed heart valve to prevent radial expansion of at least part of the heart valve; and removing the tubular retainer from the compressed self-expanding heart valve.

31. A system for delivering a self-expanding implant to an implant site within a blood vessel of a patient consisting of an introducer sheath and a delivery catheter, further comprising:

the introducer sheath extending from outside of the body of the patient to the vicinity of the implant site;

the delivery catheter having a first and a second retaining mean at the distal end of the delivery catheter to reversibly secure the implant to the delivery catheter;

the first retaining mean reversibly secures the distal end of the self-expanding implant to the delivery catheter and the second retaining mean reversibly secures the proximal end of the self-expanding implant to the delivery catheter;

wherein the delivery catheter is passed through the introducer sheath to deliver the self-expanding implant to the implant site; and the central segment of the self-expanding implant is compressed from a first diameter to a second diameter that is smaller than the first diameter when self-expanding implant is passed through the introducer sheath.

32. The system of aspect 35, wherein the implant is a stent, a stent graft, or a heart valve prosthesis.

33. The system of aspect 35, wherein the implant has male connector elements at the distal and proximal end to engage with female connector elements on the delivery catheter.

34. The system of aspect 37, where the male connector elements are eyelets and the female elements are recesses in the delivery catheter.

35. The system of aspect 35, wherein the introducer sheath has a hemostasis valve at the proximal end.

36. The system of aspect 35, wherein the retaining means consists of axially moveable sheaths that at least partially restrict radial expansion of the implant.

37. A method of delivering a self-expanding implant to an implant site within a blood vessel consisting of:

inserting an introducer sheath from outside the body through an opening in the body into a blood vessel;

placing the distal end of the introducer sheath in the vicinity of the implant site;

reversibly securing the distal end and the proximal end of the self-expanding implant to the distal end of a delivery catheter;

inserting the delivery catheter with the self-expanding secured to the delivery catheter into the introducer sheath wherein the central segment of the self-expanding implant is compressed from a first diameter to a second diameter when inserted into the introducer sheath;

advancing the delivery catheter through the introducer sheath until the self-expanding implant exits the distal end of the introducer sheath; and releasing the distal end and the proximal end of the self-expanding implant from the delivery catheter at the implant site.

38. A system for delivering an implant to an implant site within a blood vessel of a patient consisting of an introducer sheath, a delivery catheter, and a biasing member, wherein:

the introducer sheath extending from outside of the body of the patient to the vicinity of the implant site;

the delivery catheter having retaining means to reversibly retain an implant at the distal end of the delivery catheter;

the biasing member having means to deflect the shaft of the delivery catheter from a relaxed configuration into a curved configuration;

wherein the delivery catheter is passed through the introducer sheath to deliver the implant to the implant site; and, the biasing member is axially and rotationally moveable inside the introducer sheath with respect to the introducer sheath and the delivery catheter.

39. A system of aspect 38, wherein the implant is a self-expanding or balloon expandable heart valve prosthesis.

40. A system of aspect 38, wherein the implant site is the native aortic or mitral valve.

41. A system of aspect 39, wherein the introducer sheath has a pre-shaped curved configuration.

42. A system for maneuvering an implant to an implant site within a blood vessel of a patient consisting of an introducer sheath, a delivery catheter, and a biasing member, whereby:

the delivery catheter having retaining means to reversibly retain an implant at the distal end of the delivery catheter;

the biasing member having means to deflect the shaft of the delivery catheter from a relaxed configuration into a curved configuration;

the delivery catheter is inserted into the introducer sheath and is axially and rotationally moveable within the introducer sheath; and the biasing member is inserted into the introducer sheath and is axially and rotationally moveable within the introducer sheath and is axially and rotationally moveable with respect to the delivery catheter.

A method of positioning an implant toward a target site within a blood vessel consisting of inserting an introducer sheath from outside the body through an opening in the body into a blood vessel, wherein emplacement is achieved by:

placing the distal end of the introducer sheath in the vicinity of the implant site;

reversibly securing the implant to the distal end of a delivery catheter; placing a biasing member having means to actively deflect the shaft of the delivery system from a relaxed configuration into a curved configuration onto the shaft of the delivery system;

inserting the delivery catheter with the implant and biasing member into the introducer sheath; and advancing the delivery catheter through the introducer sheath until the implant exits the distal end of the introducer sheath.

43. A method of loading a self-expanding heart valve onto a delivery catheter having an inner shaft, an attachable distal tip, and at least one outer sheath, consisting of:

compressing the self-expanding heart valve radially and placing the compressed self-expanding heart valve into a tubular retainer, the retainer preventing the self-expanding valve from expanding radially;

passing the inner shaft of the delivery system through the central opening of the compressed self-expanding heart valve;

attaching the distal tip to the inner shaft of the delivery system;

advancing the outer sheath onto the compressed heart valve to prevent radial expansion of at least part of the heart valve;

removing the tubular retainer from the compressed self-expanding heart valve;

adjusting the axially and rotationally position of the biasing member within the introducer sheath;

activating the biasing member to deflect the shaft of the delivery system into a desired bend configuration;

adjusting the axially position of the delivery system to place the implant at the target site; and releasing the implant from the delivery system.

44. Novel enhanced transcatheter heart valve delivery systems, comprising, in combination:

at least a specialized prosthetic;
a prosthetic delivery system; and
at least a valve loader.

45. The system of aspect 44, or any preceding aspects, further comprising a computer interface having a processor.

46. The system of aspect 45, or any preceding aspects, wherein the processor interfaces with imaging and/or sensing modalities.

47. The system of aspect 46, or any preceding aspects, wherein transapical and/or transfemoral delivery systems emplacement is confirmed by the processor, imaging or sensors and a data stream showing the same is captured, stored and/or transmitted wirelessly.

The embodiments as described in this section above can be combined with the embodiments and with each of the features as depicted in the claims and/or as described above herein.

In particular all aspects 1 to 47 as depicted above and the features contained therein can be combined with the disclosure and in particular with each of the features contained in the attached claims forming part of the disclosure of this application.

The following details will describe and illustrate the above listed alternative and/or exemplary embodiments and wherein the below terms and definitions are to be applied to said aspects 1 to 47: the instant disclosure includes an improved bioproshtetic valve which is indicated for patients with high-grade symptomatic aortic valve stenosis and patients with significant aortic valve regurgitation, who require aortic valve replacement, for whom open heart surgery is associated with increased surgical mortality or patients who are otherwise considered inoperable (e.g. porcelain aorta, chest deformation). Examples of the systems for delivery are described below as proprietary disclosures and ostensively patentable subject matters as offered for consideration.

The system consists of three main components: the Valve Prosthesis, the Delivery System and a separate Valve Loader. Each component comes packaged separately.

The valve prosthesis may be constructed from porcine pericardial tissue that is attached to a self-expanding Nitinol stent scaffold using polyester sutures. The scaffold has a crown design that can collapse to fit inside either a transapical or transfemoral catheter delivery device. The valve prosthesis is available in three valve sizes (23 mm, 25 mm and 27 mm) that accommodate native valve annulus diameters ranging from at least about 21 to 27 mm as indicated in Table 2. The valve comes packaged in a polypropylene jar with glutaraldehyde to maintain sterility. The valve is maintained in the deployed dimensional configuration in the jar with the aid of Polyoxymethylene Ring.

Figure 9:
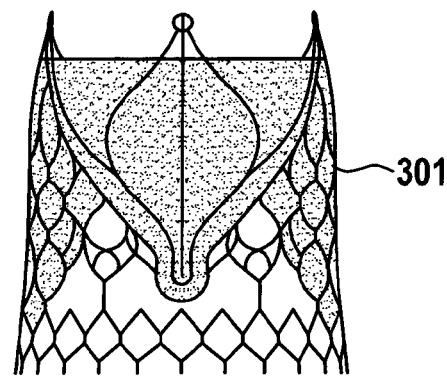
FIG. 9: a schematic of the JenaValve® brand of prosthetic, and an actual view of the same.
Figure 9:
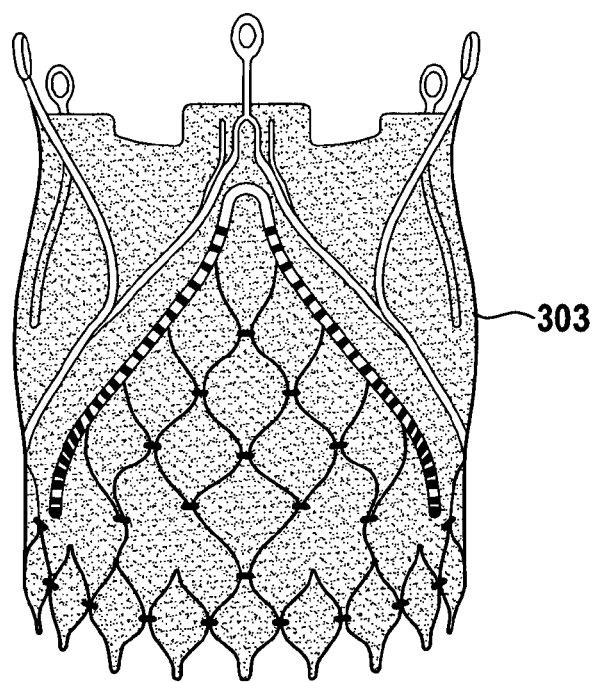
Figure 10:
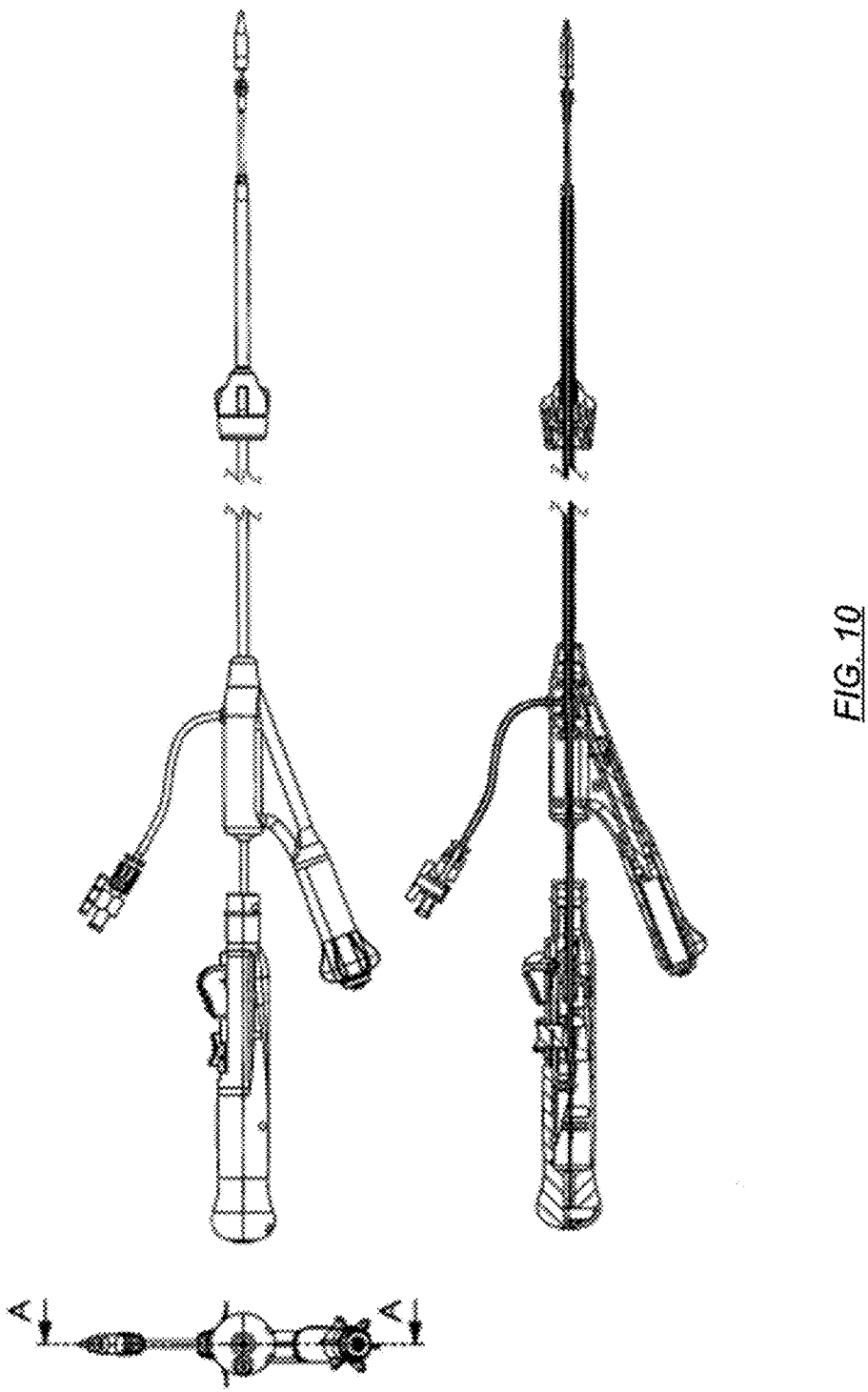
FIG. 10: a depiction of the TF delivery system.
Figure 11:
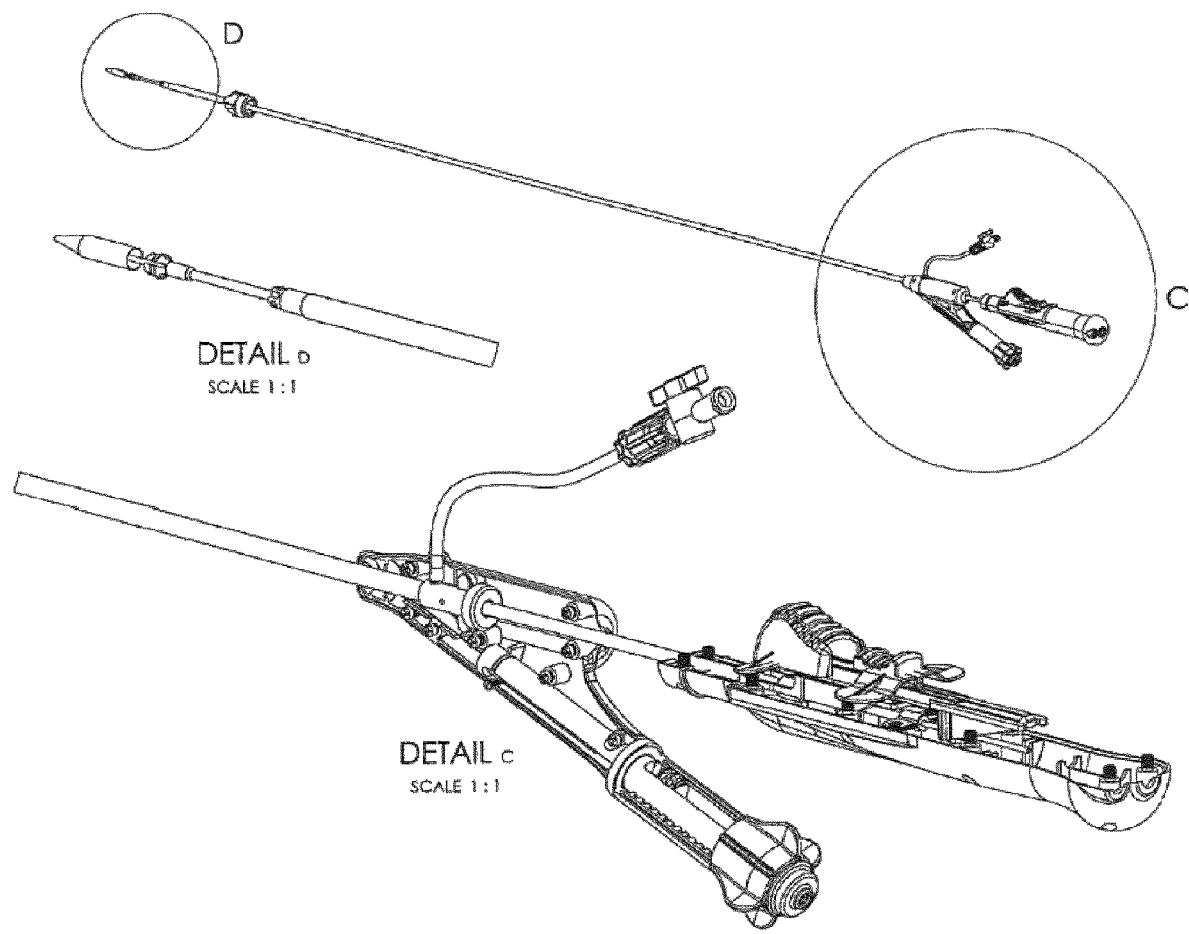
FIG. 11 another view of the TF delivery system.
Figure 12:
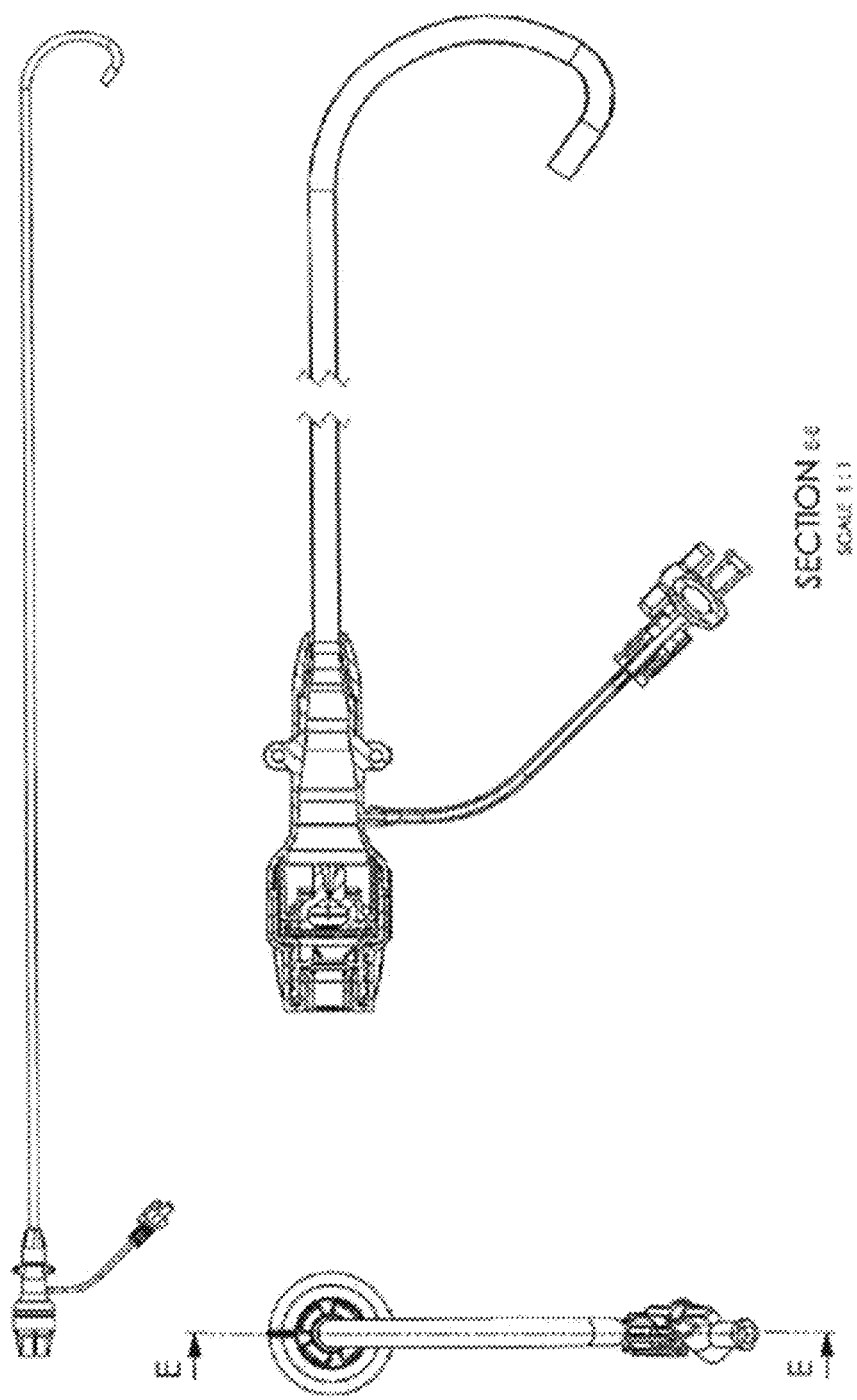
FIG. 12 an additional view illustrating a pre-shaped sheath, according to the instant disclosure.

The valve prosthesis may be constructed from porcine pericardial tissue for the leaflets (or cusps) and the skirt. A glutaraldehyde fixation process is used to cross-link and stabilize the collagen structure of the porcine pericardial tissue. The valve leaflets are formed by joining three tissue panels together and attaching them to the metallic stent scaffold using polyester sutures. The prosthesis is sterilized using a solution based sterilization process and then placed in a glutaraldehyde storage solution until ready for implantation. The following sections provide details on each of the structural elements of the prosthesis and a dimensional summary is provided, to demonstrate how the systems of the instant disclosure improve over, and are technically distinct from any known prior art. FIG. 9 shows this device.

Stent Scaffold:

The stent scaffold is produced in three different diameters to accommodate the final intended annular diameter of the valve. The nitinol scaffold has a larger diameter than the final dimension of the valve to ensure a constant outward force on the native valve annulus to avoid any valve movement. In addition, the height of the stent scaffold is also increased with increasing valve size. The outward force of the prosthesis, coupled with the unique fixation feature provided by the clipping mechanism of the feelers, mitigates the known risk of valve movement that has been identified with currently marketed TAVR products.

According to the instant disclosure, in embodiments, the nitinol structure is laser cut from a single tube (OD 7 mm and ID 6 mm). The nitinol is etched in a diamond pattern in the "rhombi" section of the scaffold. The stent scaffold consists of three sets of rails that provide attachment for the leaflet side of the pericardial tissue. It also consists of a nitinol structure below the rail termed as the onion region for pericardial skirt tissue attachment. The stent scaffold additionally consists of nitinol support structures termed as feelers that enable the valve to attach directly to the native valve leaflets for implantation. The stent scaffold may contain eyelets on at least on end of the stent that engage with the delivery system to secure the crimped valve to the delivery system.

Pericardial Tissue:

The pericardial tissue is obtained from a vendor that supplies porcine tissue for a variety of medical implants. As described above, the pericardial tissue is used for the prosthetic valve leaflets, for the valve skirt that provides a seal onto the native valve and for the feeler cover to protect the native tissue from potential damage. The tissue is attached to the nitinol stent scaffold with standard surgical polyester suture material. A 6-0 suture is used to sew the pericardial material to the commissure tabs and the rhombi of nitinol. A 5-0 suture is used to sew the pericardial material to the rails and of the nitinol scaffold.

Fabric Tabs:

The commissure posts and feelers each have a PET fabric tab (pledget) sewn in place using standard surgical polyester 6-0 suture material. The fabric tabs at the commissure are in place to provide structural support during valve assembly and the fabric tabs on feelers covering the pericardial tissue are in place to protect the native tissue from potential damage that may be caused by the nitinol metal.

Valve Implantation Concept

At the outflow section of the valve prosthesis, the self-expanding Nitinol stent scaffold includes three eyelets designed to align with the corresponding recesses at the crown of the delivery system. These mating structures ensure a firm attachment of the prosthesis to the delivery system during the complete course of deployment during implantation. Additional eyelets may be placed on the inflow section of the valve.

According to the instant disclosure, the prosthesis also contains three positional "feelers" that spread apart during delivery of the prosthesis. The feelers are placed in the sinus region behind and at the base of the native leaflets to provide correct positioning with a fixed depth of implant relative to the native leaflet. For enhanced fluoroscopic visualization during the procedure the feelers contain radiopaque markers made of tantalum. The feelers are protected by a small patch of pericardial tissue and fabric sutured to the ends. The Nitinol stent struts at the base of the prosthesis, along with the feelers, provide a securing mechanism of the prosthesis to the native valve leaflets. The inflow of the valve is composed of 24 diamond shaped struts forming a ring that provides the radial strength and seal to securely anchor the valve in position to the native annulus and minimize the paravalvular leakage after implantation.

The rail provides the margin of attachment for the valve leaflets and divides the leaflet and skirt region of the pericardial tissue. The rail is formed in a scalloped shape to mimic the natural shape of a native aortic valve and is designed to allow for commissure deflection which transfers the bulk of the loads from the tissue to the stent to prolong the durability of the prosthesis. The skirt seals the prosthesis to the native annulus.

The instant disclosure contemplates using a transfermoral (TF) delivery system, whereby a prosthetic valve can be inserted via transfemoral delivery using a specially designed catheter system. The approach is to implant the aortic valve prosthesis via transfemoral access using general or local anaesthesia. The TF delivery system is comprised of two catheters: Introducer sheath assembly and a main deployment delivery system.

According to certain embodiments of the instant disclosure, the femoral-iliac vessel will be punctured and the introducer sheath assembly (pre-shaped sheath and introducer) will be inserted into the femoral artery and the tip of the pre-shaped sheath will be positioned in the ascending aorta approximately 2 cm to 4 cm above the native valve. Once in place, the dilator is removed and the pre-shaped sheath is left in position.

The pre-shaped sheath has a generally straight segment to conform to the pathway from the femoral artery to the descending thoracic aorta, and a curved segment to follow the pathway over the arch of the aorta to the aortic valve.

The total length of the introducer sheath may be 100 cm to 150 cm. The length of the curved segment may be 15 cm to 30 cm. The radius of curvature of the curved segment may be 3 cm to 15 cm, such as 5 cm to 8 cm. The bend angle from the straight segment to the tip of the sheath maybe 90 degrees to 270 degrees, such as 150 degrees to 210 degrees.

The pre-shaped sheath may be made from flexible polymer material such as PEBAX or Nylon. The wall of the sheath may be reinforced with metal braids or metal coils. The inner wall of the sheath may be lined with PTFE to reduce friction forces. The pre-shaped sheath may have a hydrophilic coating.

A dilator with an atraumatic tip is inserted into the pre-shaped sheath for insertion into the femoral artery and advancement to the aortic valve. The dilator has a guidewire lumen to accommodate a guidewire. The dilator may be pre-shaped. The dilator may be straight. In some embodiments, it may be preferable that the dilator is straight and when inserted into the pre-shaped sheath substantially straightens the curved segment of the pre-shaped sheath for insertion into the femoral artery and passage through the iliac artery and abdominal and descending aorta.

The valve prosthesis is placed into the main delivery system. The inflow segment of the valve prosthesis is restrained by a first sheath. The outflow segment of the valve prosthesis is retrained by a second sheath. The mid-section of the valve prosthesis including the feelers is unconstrained. The first and the second sheath are respectively connected to first and second actuators at the handle of the delivery system. Moving the first actuator distally (toward the tip of the delivery system) moves the first sheath distally and releases the inflow segment of the valve prosthesis. Moving the second actuator proximally (away from the tip of the delivery system) moves the second sheath proximally and releases the outflow segment of the valve prosthesis from the delivery system.

A steerable catheter is mounted on the shaft of the delivery system. The steerable catheter has a handle with a mechanism to deflect the distal segment of the steerable catheter. The mechanism allows for deflection of the steerable catheter by at least 90 degrees from the straight configuration, such as by at least 180 degrees from the straight configuration. Deflecting the steerable catheter will result in a corresponding deflection of the shaft of the delivery system. The steerable catheter is coaxially placed onto the shaft of the delivery system and can move axially and rotationally with respect to the shaft of the delivery system. By rotating the steerable catheter and moving it axially, the location and direction of deflection of the shaft of the delivery system can be selected.

The delivery system with the steerable catheter mounted on the shaft of the delivery system is inserted into the pre-shaped sheath. As the partially crimped valve prosthesis passes into the pre-shaped sheath, the unconstrained mid-section of the valve prosthesis is compressed. The compression of the mid-section of the valve prosthesis may be facilitated by a funnel-shaped inlet into the pre-shaped sheath. Alternatively, a temporary transfer sheath may be placed over the mid-section of the valve prosthesis that compresses the mid-section of the valve prosthesis for insertion into the pre-shaped sheath. The compressed valve prosthesis is advanced through the pre-shaped sheath by pushing the shaft of the delivery system into the pre-shaped sheath.

The distal tip of the pre-shaped sheath is placed in the ascending aorta distal to native aortic valve. When the valve prosthesis exits the distal end of the pre-shaped sheath, the mid-section of the valve prosthesis including the feelers expands. Using the pre-shaped sheath to compress the section of the valve prosthesis for delivery to the native aortic valve, eliminates the need for a separate mechanism to un-sheath the mid-section of the valve prosthesis for release of the feelers.

To place the feelers into the native cusps, it is advantageous to center the valve prosthesis in the aortic root. This can be accomplished by deflecting and rotating the steerable catheter. The point of deflection can be altered by moving the steerable catheter axially along the shaft of the delivery system. Thus, the distal segment of the delivery system can be shaped by the steerable catheter to follow the pathway of the aorta of an individual patient. In some patients the ascending aorta is as short as 3-5 cm. In some patients the ascending aorta is as long as 15-20 cm. In some patients the aortic arch is curved less than 180 degrees. In some patients the aortic arch is curved more than 270 degrees. The degree of deflection of the delivery system can be controlled by the degree of deflection of the steerable catheter. The location of the deflecting region of the delivery system can be controlled by the axial location of the steerable catheter on the delivery system shaft. The direction of deflection of the delivery system can be controlled by the rotational positing of the steerable catheter on the shaft of the delivery system.

An advantage of the pre-shaped sheath is that it deflects the distal end of the delivery system in the general direction of the aortic valve without the use of the steerable catheter. This reduces the bending forces that the steerable catheter has to apply to the shaft of the delivery system to deflect the tip of the delivery system into the final position. Axial movement of the pre-shaped sheath with respect to the delivery system can also be used to adjust the deflection of the shaft of the delivery system. The pre-shaped sheath protects the aortic wall during manipulation of the delivery system and steerable catheter.

Once the distal end of the delivery system is centered in the aortic root with use of the steerable catheter, positioning of the feelers into the native cusps is accomplished by rotationally aligning the feelers with the cusps of the native aortic valve and advancing the valve prosthesis into the aortic annulus. Rotational and axial movement of the valve prosthesis is controlled by axial and rotational movement of the delivery system within the steerable catheter.

Once the feelers are positioned in the native cusps, the valve prosthesis is released by sequentially unsheathing the inflow segment and the outflow segment of the valve prosthesis. Release of the inflow segment of the valve prosthesis anchors the valve prosthesis in the aortic annulus and captures the native leaflets between the feelers and the stent scaffold of the valve prosthesis. Release of the outflow segment of the valve prosthesis disconnects the valve prosthesis from the delivery system.

Alternatively, the outflow segment of the valve prosthesis may be released before the inflow segment of the valve prosthesis. In some cases, it may be preferred to release the inflow segment of the valve prosthesis simultaneously with the outflow segment of the valve prosthesis.

In at least one aspect of the present disclosure, the valve prosthesis may be pre-mounted onto the delivery system by the manufacturer. The mid-section of the valve prosthesis containing the leaflets is unconstrained. The pericardial leaflets located in the mid-section of the valve prosthesis are not compressed avoiding long-term compression damage to the leaflets during shipping and storage. The distal segment including the including the valve prosthesis may be detachable from the shaft of the delivery system. The detached distal segment with the valve prosthesis may be stored separately from the remainder of the delivery system. The distal segment of the delivery system with the mounted partially crimped valve prosthesis may be stored in liquid to avoid de-hydration of the leaflet tissue. Prior to use, the distal segment of the delivery system is connected to the shaft of the delivery system. The connection mechanism used to attach the distal end of the delivery system to the shaft of the delivery system may be in form of male-female thread, magnets, crimping, or bonding.

In another aspect of the present disclosure, the valve prosthesis may have eyelets on at least one end of the stent scaffold to engage the valve prosthesis with the delivery system. The eyelets may sit in recesses in the body of the delivery system. A sheath retains the eyelets in the recesses. By securing the eyelets in the delivery system "melon-seeding" or premature deployment of the self-expanding stent scaffold from the delivery system is prevented. As long as the eyelets are covered by the sheath the valve prosthesis will not deploy. The advantage of this arrangement is that a large segment of the midsection of the valve prosthesis can be un-restrained to allow for full release of the feelers and to minimize compression of the tissue leaflets. Furthermore, the sheaths covering the inflow and outflow segment of the valve prosthesis only require limited travel to release the eyelets in order to disconnect the valve prosthesis from the delivery system.

In another aspect of the present disclosure, the length of the un-restrained midsection of the valve prosthesis is at least 50% of the total length of the valve prosthesis. In another aspect of the present disclosure, the length of the inflow segment of the valve prosthesis restrained by the distal sheath is less than 20% of the length of the valve prosthesis. In another aspect of the present disclosure, the length of the outflow segment of the valve prosthesis restrained by the proximal sheath is less than 20% of the length of the valve prosthesis.

Figure 7:
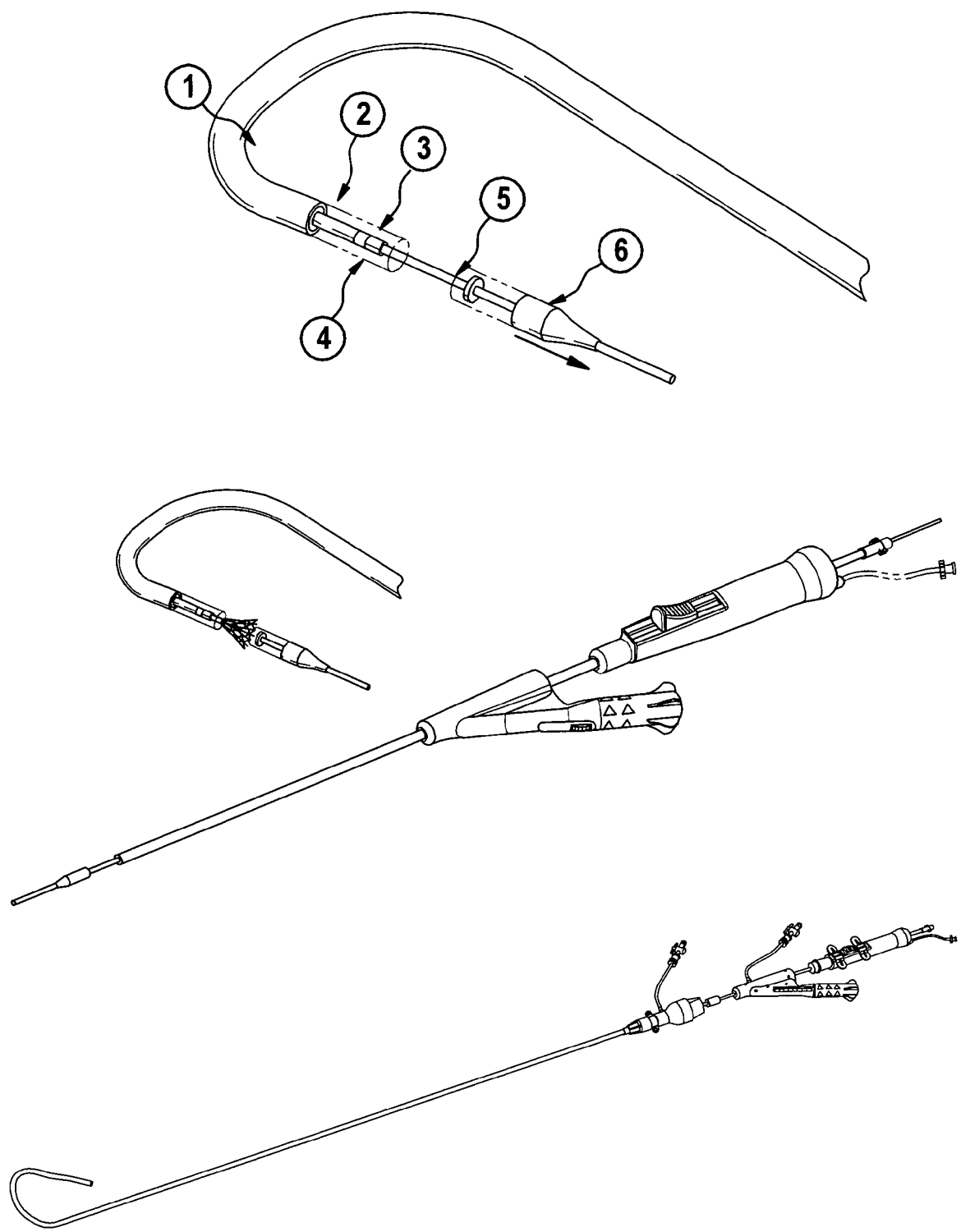
FIG. 7: a plan view of a full system for TF transcatheter heart valve delivery, according to the instant disclosure.

An embodiment of a delivery system according to the present disclosure is represented in FIG. 7. The reference numerals used in FIG. 7 are as follows:

Main Delivery System Distal Assembly:

| ITEM NUMBER | COMPONENT DESCRIPTION | MATERIAL |
| --- | --- | --- |
| 1 | Pre-Shaped Introducer Sheath | Multi Durometer pebax material (55D + 72D) SS 304 V coil reinforced SS 304 V braid reinforced PTFE Liner |
| 2 | Steerable Catheter | Multidurometer pebax 72D + 55D + 25D 304SS coil, braid wire and pull wire |
| 3 | Stentholder tubing | Multidurometer pebax 55D + Nylon Ultem or polyimide stentholder PTFE Liner 304SS coil, braid wire |
| 4 | Outer Shaft | PTFE Liner Multidurometer pebax 72D + 35D 304SS braid wire Plt/Ir marker band |
| 5 | Guidewire tubing/Rhombi Support | Pebax, Polyurethane, Polyimide |
| 6 | Rhombi Sleeve | Nylon 304SS braid Plt/Ir marker band |

Figure 8:
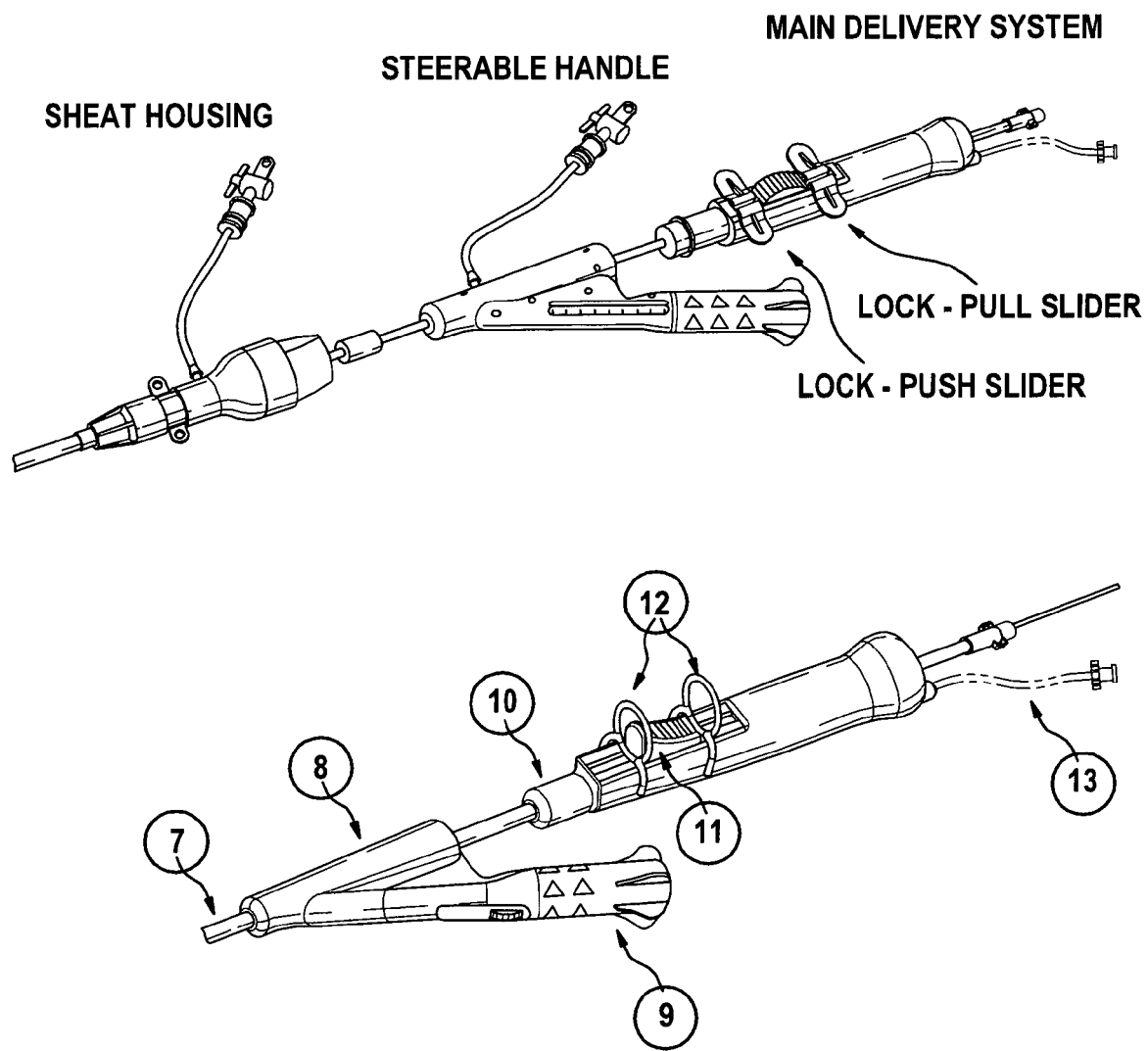
FIG. 8: a close up of the system of FIG. 1, according to the instant disclosure.

An embodiment of a handle assembly of the delivery system according to the present disclosure is represented in FIG. 8. The reference numerals used in FIG. 8 are as follows:

Main Delivery System Distal Assembly:

| ITEM NUMBER | COMPONENT DESCRIPTION | MATERIAL |
| --- | --- | --- |
| 7 | Shaft of Steerable Sheath | PTFE Liner Multidurometer pebax 72D + 35D 304SS braid wire Plt/Ir marker band Stainless steel flat wire |
| 8 | Housing of Steerable Sheath | ABS, Polycarbonate |
| 9 | Steerable Rotational Actuator | ABS, Polycarbonate, stainless steel |
| 10 | Delivery System Handle | ABS, Polycarbonate |
| 11 | Push-pull Actuator | ABS, Polycarbonate |
| 12 | Safety Locks | Nylon ABS, Polycarbonate |
| 13 | Flush Port | Polyurethane tubing |

The final crimping of the prosthesis is assisted by two loading tubes which allows securing the prosthesis with the outer shaft by distal movement. It is EO-sterilized and for single use only. It should be noted that the TF Valve Loader will utilize the same principle of operation as outlined for the TA Valve Loader.

The present disclosure further relates to a device to facilitate the removal of the distal end of a catheter from an introducer sheath or guiding catheter. Delivery catheters for stents or transcatheter heart valves, for example, may have a split capsule which contains the implant. After the implant is released from the catheter, the open end of the split capsule may be difficult to retract back into the opening of an introducer sheath or guiding catheter within a vessel.

This aspect of the present disclosure provides a tapered insertion device to channel the capsule back into the inner diameter of the introducer sheath or guiding catheter for removal from the body. The device may be static or self-expanding. The device may also include a step to support the implant.

Figure 13A:
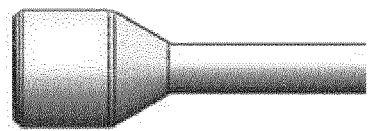
FIGS. 13a, b: side views of an embodiment of a device to facilitate the removal of the distal end of a catheter from an introducer sheath or guiding catheter.
Figure 13B:
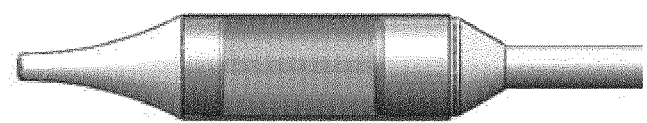

In one embodiment, the device comprises a tapered cylinder that is automatically exposed when capsule is actuated, thereby closing the capsule with a tapered tip. In this regard, reference is made to FIGS. 13*a*, *b*. In more detail, FIG. 13*a* shows one embodiment of the tapered device, and FIG. 13*b* shows the tapered device with capsule.

Figure 14A:
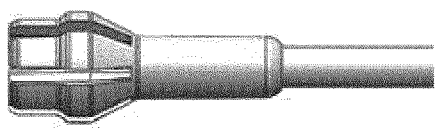
FIGS. 14a, b: side views of another embodiment of a device to facilitate the removal of the distal end of a catheter from an introducer sheath or guiding catheter.
Figure 14B:
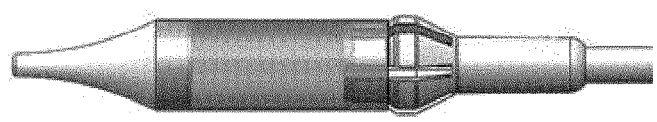

In one embodiment (cf. FIGS. 14*a*, *b*), the device is self-collapsing, allowing for the device to expand to a larger outer diameter than the capsule when exposed. There is also a straight section on the distal end of the self-collapsing device designed to keep the capsule concentric with the device. The device may be a single piece made from thermoplastic polymer or made from multiple pieces assembled together. In more detail, FIG. 14*a* shows one embodiment of the self-collapsing device, and FIG. 14*b* shows the self-collapsing device with capsule.

Figure 15:
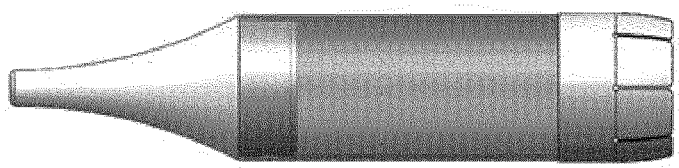
FIG. 15: a side view of another embodiment of a device to facilitate the removal of the distal end of a catheter from an introducer sheath or guiding catheter.

In another embodiment (cf. FIG. 15), the device is incorporated into the capsule and collapses after implant is released from capsule. The device may be made from a single piece of thermoplastic polymer and may contain slits or living hinges. Collapsing of the device may also be mechanically actuated by the user. In more detail, FIG. 15 shows one embodiment of the collapsing capsule.

In another embodiment (cf. FIGS. 16*a*, *b*), the device is self-expanding. The device is made from thermoplastic polymer with living hinges that allow the device to compress to a smaller diameter that will fit inside the capsule when not in use. When the capsule is opened, the device expands back to its original diameter, larger than the capsule diameter. The self-expanding device is tapered to facilitate entry into the introducer sheath or guiding catheter. FIGS. 16*a, b* show the device with a step to support the inner diameter of the implant. In more detail, FIG. 16*a* shows one embodiment of the self-collapsing device, and FIG. 16*b* shows the self-collapsing device with capsule.

In another embodiment (cf. FIG. 17), the self-expanding device comprises fingers under the capsule to keep the capsule concentric with the device. In more detail, FIG. 17 shows one embodiment of the self-collapsing device with centralizing members.

In another embodiment (cf. FIGS. 18*a, b*), the self-expanding device comprises a stabilizer element distal to the self-expanding wedges. The stabilizer maintains the capsule's concentricity with the device. The profile of the stabilizer may vary. In more detail, FIG. 18*a* shows one embodiment of the self-expanding device with stabilizer, and FIG. 18*b* shows the self-expanding device with stabilizer and capsule.

In another embodiment (cf. FIGS. 19*a, b*), the stabilizer is retractably attached to the inside of the capsule. A spring may be used to actuate the stabilizer. The stabilizer pushes up again the self-expanding device to keep the capsule concentric with the device. The profile of the stabilizer may vary. In more detail, FIG. 19*a* shows one embodiment of the self-expanding device with stabilizer, and FIG. 19*b* shows the self-expanding device with stabilizer and capsule.

In another embodiment (cf. FIG. 20), the stabilizer and spring may work without the self-expanding device. The stabilizer may have a tapered or conical shape to facilitate entry into the introducer sheath or guiding catheter. In more detail, FIG. 20 shows one embodiment of the self-actuated device in capsule.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate embodiments of the present disclosure and does not pose a limitation on the scope of the present disclosure otherwise claimed. No language in the specification should be construed as indicating any non-claimed element essential to the practice of embodiments of the present disclosure.

Groupings of alternative elements or embodiments of the present disclosure described herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out embodiments of the present disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the present disclosure described herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

LIST OF REFERENCE NUMBERS

100 delivery means
11 catheter tip
12 catheter shaft
13 handle
14 holding means 15 first retaining means
16 second retaining means
17 first operating means
18 second operating means
19 body of handle
20 first force transmitting means
21 second force transmitting means
22 holding tube
23 catheter end tip
30 steering meens
31 steering catheter tube
32 handle
33 operating means
34 indicator means
35 control wire
36 post section
40 introducer
41 introducer sheath
42 introducer port
43 base member
44 sealing arrangement
45 crimping section

The invention claimed is:

1. A catheter system comprising:
a delivery catheter configured to deliver a prosthetic heart valve, the delivery catheter having a proximal end and a distal end, and comprising a tip at the distal end that includes a first sleeve and a second sleeve movable relative to each other in a proximal-distal direction, wherein the second sleeve is proximal to the first sleeve, and the first sleeve has an open end facing in a proximal direction, and wherein a middle section of the tip is uncovered when the first sleeve is in a proximal-most position while the second sleeve is in a distal-most position, the delivery catheter having a holder disposed in the second sleeve;
an introducer comprising a sheath;
a steering catheter configured to be deflected to steer the delivery catheter; and
an integrated handle comprising a delivery handle portion and a steering handle portion comprising a housing, the housing of the steering handle portion sized and configured to receive the delivery handle portion, the integrated handle configured to control movement of the delivery catheter and the steering catheter, independently;
an actuator movably coupled to the delivery handle portion and configured to move with respect to the delivery handle portion to manipulate the first sleeve and the second sleeve relative to the holder while the delivery handle portion is received by the housing of the steering handle portion,
wherein the steering catheter is fixedly connected to the steering handle portion and the delivery catheter is fixedly connected to the delivery handle portion, and
wherein the steering catheter and the delivery catheter are selectively coaxially and rotationally independently movable.

2. The catheter system according to claim 1, wherein the steering catheter comprises a control wire to deflect the steering catheter to steer the delivery catheter.

3. The catheter system according to claim 1, wherein the sheath is extendable through a vascular duct and comprises a crimping section.

4. The catheter system according to claim 1, further comprising the prosthetic heart valve, wherein the first sleeve secures a distal end of the prosthetic heart valve to the delivery catheter and the second sleeve secures a proximal end of the prosthetic heart valve to the delivery catheter, and wherein at least a portion of the prosthetic heart valve is disposed in the middle section of the tip and not covered by the first sleeve or the second sleeve prior to movement of either the first sleeve or the second sleeve during deployment of the prosthetic heart valve.

5. The catheter system according to claim 4, wherein a diameter of the prosthetic heart valve varies over a length of the prosthetic heart valve when the prosthetic heart valve is secured to the delivery catheter.

6. The catheter system according to claim 4, wherein the delivery catheter comprises a holding tube, and the prosthetic heart valve is secured to the delivery catheter by the holding tube.

7. The catheter system according to claim 6, wherein the distal end or the proximal end of the prosthetic heart valve comprises a male connector, and the delivery catheter comprises a female connector complimentary to the male connector of the prosthetic heart valve.

8. The catheter system according to claim 1, wherein an inner diameter of the sheath is less than 24 French.

9. The catheter system according to claim 1, wherein the sheath has a pre-shaped, curved configuration.

10. The catheter system according to claim 1, wherein the sheath comprises a flexible polymer, a hydrophilic coating, a PTFE liner, coil reinforcement, braid reinforcement, or a combination thereof.

11. The catheter system according to claim 1, wherein the delivery handle portion comprises a first handle configured to control movement of the delivery catheter and the steering handle portion comprises a second handle configured to control movement of the steering catheter.

12. The catheter system according to claim 11, wherein the second handle of the steering catheter comprises a second actuator to deflect a shaft of the delivery catheter from a relaxed configuration into a curved configuration.

13. The catheter system according to claim 1, wherein the steering catheter, the delivery catheter, and the sheath are circumferentially independently movable when the steering catheter and the delivery catheter are simultaneously disposed in the sheath.

14. The catheter system according to claim 1, wherein the delivery catheter and the steering catheter are simultaneously introducible into the sheath.

15. A catheter system comprising:
a delivery catheter configured to deliver a prosthetic heart valve, the delivery catheter having a proximal end and a distal end, and comprising a tip at the distal end that includes a first sleeve and a second sleeve movable relative to each other in a proximal-distal direction, wherein the second sleeve is proximal to the first sleeve, and the first sleeve has an open end facing in a proximal direction, the delivery catheter having a holder disposed in the second sleeve;
a steering catheter configured to be deflected to steer the delivery catheter;
an introducer comprising a crimping section proximal to a sheath, the crimping section having an inner diameter that decreases in a distal direction; and
an integrated handle comprising a delivery handle portion fixedly connected to the delivery catheter and a steering handle portion comprising a housing fixedly connected to the steering catheter, the housing of the steering handle portion sized and configured to receive the delivery handle portion, the integrated handle configured to control movement of the delivery catheter and the steering catheter, independently;

an actuator movably coupled to the delivery handle portion and configured to move with respect to the delivery handle portion to manipulate the first sleeve and the second sleeve relative to the holder while the delivery handle portion is received by the housing of the steering handle portion, wherein the delivery catheter and the steering catheter are simultaneously introducible into the crimping section of the introducer; and wherein the steering catheter, the delivery catheter, and the sheath are rotationally independently movable when the steering catheter and the delivery catheter are simultaneously disposed in the sheath.

16. The catheter system according to claim 15, wherein a middle section of the tip is uncovered when the first sleeve is in a proximal-most position while the second sleeve is in a distal-most position.

17. The catheter system according to claim 16, further comprising the prosthetic heart valve, wherein the first sleeve secures a distal end of the prosthetic heart valve to the delivery catheter and the second sleeve secures a proximal end of the prosthetic heart valve to the delivery catheter, and wherein at least a portion of the prosthetic heart valve is disposed in the middle section of the tip.

18. The catheter system according to claim 17, wherein at least one of the distal end or the proximal end of the prosthetic heart valve comprises a first connector, and the delivery catheter comprises a second connector complimentary to the first connector.

19. The catheter system according to claim 18, wherein the first connector comprises eyelets, and the second connector comprises recesses.

20. The catheter system according to claim 17, wherein a central segment of the prosthetic heart valve is compressed from a first diameter to a second diameter smaller than the first diameter when the delivery catheter passes through the crimping section.

21. The catheter system according to claim 15, wherein a proximal end of the sheath comprises a hemostasis valve.

* * * * *